(12) United States Patent
Girijavallabhan et al.

(10) Patent No.: US 9,777,035 B2
(45) Date of Patent: Oct. 3, 2017

(54) 4'-SUBSTITUTED NUCLEOSIDE REVERSE TRANSCRIPTASE INHIBITORS

(71) Applicant: Merck Sharp & Dohme Corp., Rahway, NJ (US)

(72) Inventors: Vinay M. Girijavallabhan, Whippany, NJ (US); David B. Olsen, Lansdale, PA (US); Zhibo Zhang, Beijing (CN); Jianmin Fu, Beijing (CN); Bing-Yu Tang, Beijing (CN)

(73) Assignee: MERCK SHARP & DOHME CORP., Rahway, NJ (US)

( * ) Notice: Subject to any disclaimer, the term of this patent is extended or adjusted under 35 U.S.C. 154(b) by 10 days.

(21) Appl. No.: 14/669,398

(22) Filed: Mar. 26, 2015

(65) Prior Publication Data
US 2015/0274767 A1    Oct. 1, 2015

(30) Foreign Application Priority Data
Mar. 28, 2014 (WO) ................ PCT/CN2014/074294

(51) Int. Cl.
| | | |
|---|---|---|
| A61K 31/7064 | (2006.01) |
| A61K 45/06 | (2006.01) |
| C07H 19/12 | (2006.01) |
| C07H 19/14 | (2006.01) |
| C07H 19/06 | (2006.01) |
| C07D 487/04 | (2006.01) |

(52) U.S. Cl.
CPC ......... C07H 19/14 (2013.01); A61K 31/7064 (2013.01); A61K 45/06 (2013.01); C07D 487/04 (2013.01); C07H 19/06 (2013.01); C07H 19/12 (2013.01)

(58) Field of Classification Search
None
See application file for complete search history.

(56) References Cited

U.S. PATENT DOCUMENTS

| | | |
|---|---|---|
| 6,333,315 B1 | 12/2001 | Ohrui et al. |
| 6,403,568 B1 | 6/2002 | Ohrui et al. |
| 7,339,053 B2 | 3/2008 | Kohgo et al. |
| 7,625,877 B2 | 12/2009 | Kohgo et al. |
| 7,879,815 B2 | 2/2011 | MacCoss et al. |
| 8,039,614 B2 | 10/2011 | Kohgo et al. |
| 8,835,615 B2 | 9/2014 | Chang |
| 2004/0229839 A1 | 11/2004 | Babu et al. |
| 2010/0234584 A1* | 9/2010 | Chang ................. C07H 19/06 536/27.11 |
| 2011/0171192 A1 | 7/2011 | Tomiyama et al. |

FOREIGN PATENT DOCUMENTS

| | | |
|---|---|---|
| EP | 2177527 A1 | 4/2010 |
| WO | 9110671 A1 | 7/1991 |
| WO | 9521184 A1 | 8/1995 |
| WO | 9816184 A2 | 4/1998 |
| WO | 02100354 A2 | 12/2002 |
| WO | 03061576 A2 | 7/2003 |
| WO | 03099840 A1 | 12/2003 |
| WO | 2004106356 A1 | 12/2004 |
| WO | 2008048981 A2 | 4/2008 |
| WO | 2008082602 A2 | 7/2008 |
| WO | 2008089105 A2 | 7/2008 |
| WO | 2009009951 A1 | 1/2009 |
| WO | 2009067409 A1 | 5/2009 |
| WO | 2009132123 A1 | 10/2009 |
| WO | 2009132135 A1 | 10/2009 |
| WO | 2010002877 A2 | 1/2010 |
| WO | 2010026153 A1 | 3/2010 |
| WO | 2010027005 A1 | 3/2010 |
| WO | 2010036407 A2 | 4/2010 |
| WO | 2010075549 A2 | 7/2010 |
| WO | 2010084115 A2 | 7/2010 |
| WO | 2010108140 A1 | 9/2010 |
| WO | 2011005860 A2 | 1/2011 |
| WO | 2011075517 A1 | 6/2011 |
| WO | 2012012776 A1 | 1/2012 |
| WO | 2012037038 A1 | 3/2012 |
| WO | 2013138236 A1 | 9/2013 |
| WO | 2015069939 A1 | 5/2015 |

OTHER PUBLICATIONS

Serajuddin, Abu T.M., Solid Dispersion of Poorly Water-Soluble Drugs: Early Promises, Subsequent Problems, and Recent Breakthroughs, J. Pharm Sci., 1999, 1058-1066, vol. 88, No. 10.

Beaumont, et al, Design Of Ester Prodrugs To Enhance Oral Absorption of Poorly Permeable Compounds: Challenges To The Discovery Scientist, Current Drug Metabolism, 2003, 461-485, vol. 4.

Bobeck et al., Advances in nucleoside monophosphate prodrugs as anti-HCV agents, Antiviral Therapy, 2010, 935-950, 15.

Furman et al., Nucleoside analog inhibitors of hepatitis C viral replication: recent advances, challenges and trends, Future Medicinal Chemistry, 2009, 1429-1452, 1.

(Continued)

*Primary Examiner* — Layla Berry
(74) *Attorney, Agent, or Firm* — Carol S. Quagliato; Catherine D. Fitch

(57) ABSTRACT

The present invention is directed to 4'-substituted nucleoside derivatives of Formula I

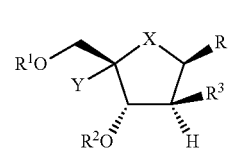

and their use in the inhibition of HIV reverse transcriptase, the prophylaxis of infection by HIV, the treatment of infection by HIV, and the prophylaxis, treatment, and delay in the onset or progression of AIDS and/or ARC.

59 Claims, No Drawings

(56) References Cited

OTHER PUBLICATIONS

Hale, et al., Phosphorylated Morpholine Acetal Human Neurokinin-1 Receptor Antagonists As Water-Soluble Prodrugs, J. Med. Chem, 2000, 1234-1241, vol. 43.

Haraguchi et al,. "Synthesis of 4'-Ethynyl-2'-Deoxy-4'-Thioribonucleosides and Discovery of a Highly Potent and Less Toxic NRTI", ACS Medicinal Chemistry Letters, 2011, pp. 692-697, vol. 2, No. 9, WO.

Kesisoglou, F. et al., "Nanosizing—Oral Formulation Development and Biopharmaceutical Evaluation", Advanced Drug Delivery Reviews, 2007, pp. 631-644, vol. 59, US.

Kodama, et al., "4'-Ethynyl Nucleoside Analogs: Potent Inhibitors Of Multidrug-Resistant Human Immunodeficiency Virus Variants In Vitro", Antimicrobial Agents and Chemotherapy, American Society For Microbiology, 2001, pp. 1539-1546, vol. 45, No. 5.

Larsen, et al., Design and Application Of Prodrugs, Textbook of Drug Design and Discovery, 3rd Ed, 2002, 410-458, Chapter 14, US.

Erion, M., "Liver-Targeted Drug Delivery Using HepDirect Prodrugs", Metabsis Therapeutics, Inc., La Jolla, U.S.A., Jul. 6-10, 2008, pp. 7-12, 17th International Symposium on Microsomes and drug Oxidations, Saratoga Springs (NY, USA), US.

Krogsgaard-Larsen, et al., "Design and Appplcation of Prodrugs", Drug Design and Discovery, 2002, pp. 461-485, 4d Edition, vol. 4, US.

Higuchi, T. and Stell, V., Pro-drugs as NovelDelivery Systems (1987) 14 of the A.C.S. Symposium Series.

Wu, et al., Nanosizing—Oral Formulation Developement and Biopharmaceutical Evaluation, Adv. Drug Delivery, 2007, 631-644, vol. 59, No. 7.

Mehellou, Y., "Phosphoramidate Prodrugs Deliver with Potency Against Hepatitis C Virus", Chem. Med. Chem., 2010, pp. 1841-1842, vol. 5.

International Search Report and Written Opinion of the International Searching Authority, PCT/CN2014/074294—International Filing Date Mar. 28, 2014.

International Search Report and Written Opinion of the International Searching Authority—PCT/US2015/022621—Mar. 3, 2015.

Kohgo, Satoru, et al.,, "Design, Efficient Synthesis, and Anti-HIV Activity of 4'-C-Cyano- and 4'-C-Ethynyl-2'-Deoxy Purine Nucleosides", Nucleosides, Nucleotides & Nucleic Acids, 2004, pp. 671-690, vol. 23, No. 4.

Kohgo, Satoru, et al.,, "Synthesis of 4'-C-Ethynyl and 4'-C-Cyano Purine Nucleosides from Natural Nucleosides and Their Anti-HIV Activity", Nucleosides, Nucleotides & Nucleic Acids, 2003, pp. 887-889, vol. 22, Nos. 5-8.

Ohrui, Hiroshi, "4'-C-Ethynyl-2'-Deoxynucleosides", Modified Nucleosides: In Biochemistry, Biotechnology and Medicine, 2008, pp. 425-431.

Gupta, M., et al., "Adenosine Deaminase in Nucleoside Synthesis. A Review", Collect. Czech. Chem. Commun., 2006, pp. 769-787, vol. 71, No. 6.

Kirby, K, et al., "Effects of Substitutions at the 4' and 2 Positions on the Bioactivity of 4'-Ethynyl-2-Fluoro-2'- Deoxyadenosine", Antimicrobial Agents and Chemotherapy, 2013, pp. 6254-6264, vol. 57, No. 12.

Marongiu, M., et al., "Enhancement of the Anti-HIV-1 Activity of ddAdo by Coformycin, EHNA and Deaza-EHNA Derivatives", Microbiologica, 1995, pp. 359-370, vol. 18.

Obara, T., et al, "New Neplanocin Analogues. 7. Synthesis and Antiviral Activity of 2-Halo Derivatives of Neplanocin A1", Journal of Medicial Chemistry, 1996, pp. 3847-3852, vol. 39, No. 19.

Shuto, S., et al., "New Neplanocin Analogues. IV. 2-Fluoroneplanocin A: An Adenosine Deaminase-Resistant Equivalent of Neplanocin A1", Chem.Pharm. Bull, 1994, pp. 1688-1690, vol. 42, No. 8.

Cristalli, G., et al., "Adenosine Deaminase Inhibitors. Synthesis and Biological Activity of Deaza Analogues of erythro-9-(2-Hydroxy-3-nonyl)adenine", Journal of Medicial Chemistry, 1988, pp. 390-393, vol. 31.

\* cited by examiner

4'-SUBSTITUTED NUCLEOSIDE REVERSE TRANSCRIPTASE INHIBITORS

BACKGROUND OF THE INVENTION

The retrovirus designated human immunodeficiency virus (HIV), particularly the strains known as HIV type-1 (HIV-1) and type-2 (HIV-2), have been etiologically linked to the immunosuppressive disease known as acquired immunodeficiency syndrome (AIDS). HIV seropositive individuals are initially asymptomatic but typically develop AIDS related complex (ARC) followed by AIDS. Affected individuals exhibit severe immunosuppression which makes them highly susceptible to debilitating and ultimately fatal opportunistic infections. Replication of HIV by a host cell requires integration of the viral genome into the host cell's DNA. Since HIV is a retrovirus, the HIV replication cycle requires transcription of the viral RNA genome into DNA via an enzyme known as reverse transcriptase (RT).

Reverse transcriptase has three known enzymatic functions: The enzyme acts as an RNA-dependent DNA polymerase, as a ribonuclease, and as a DNA-dependent DNA polymerase. In its role as an RNA-dependent DNA polymerase, RT transcribes a single-stranded DNA copy of the viral RNA. As a ribonuclease, RT destroys the original viral RNA and frees the DNA just produced from the original RNA. And as a DNA-dependent DNA polymerase, RT makes a second, complementary DNA strand using the first DNA strand as a template. The two strands form double-stranded DNA, which is integrated into the host cell's genome by the integrase enzyme.

It is known that compounds that inhibit enzymatic functions of HIV RT will inhibit HIV replication in infected cells. These compounds are useful in the prophylaxis or treatment of HIV infection in humans. Among the compounds approved for use in treating HIV infection and AIDS are nucleoside RT inhibitors (NRTI) such as 3'-azido-3'-deoxythymidine (AZT), 2',3'-dideoxyinosine (ddI), 2',3'-dideoxycytidine (ddC), d4T, 3TC, abacavir, emtricitabine, and tenofovir disoproxil fumarate, as well as non-nucleoside RT inhibitors (nNRTI) such as nevirapine, delavirdine, and efavirenz.

While each of the foregoing drugs is effective in treating HIV infection and AIDS, there remains a need to develop additional HIV antiviral drugs including additional RT inhibitors. A particular problem is the development of mutant HIV strains that are resistant to the known inhibitors. The use of anti-retrovirals to treat AIDS often leads to viruses that are less sensitive to the inhibitors. This resistance is typically the result of mutations that occur in the reverse transcriptase segment of the pol gene. The continued use of antiviral compounds to prevent HIV infection will inevitably result in the emergence of new resistant strains of HIV. Accordingly, there is a continuing need for new RT inhibitors that are effective against mutant HIV strains.

SUMMARY OF THE INVENTION

The present invention is directed to 4'-substituted nucleoside derivatives and their use in the inhibition of HIV reverse transcriptase, the prophylaxis of infection by HIV, the treatment of infection by HIV, and the prophylaxis, treatment, and delay in the onset or progression of AIDS and/or ARC.

DETAILED DESCRIPTION OF THE INVENTION

The present invention is directed to compounds having structural Formula I:

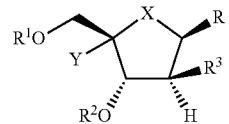

or a pharmaceutically acceptable salt thereof, wherein:

R is

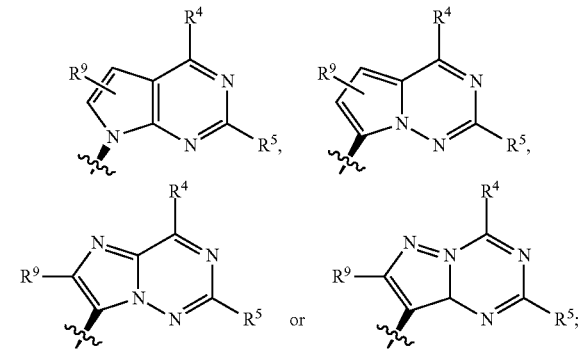

X is O, S, $CH_2$ or $CF_2$;
Y is —C≡C—$R^8$ or —C≡N;
$R^1$ is —H, —C(O)$R^6$, —C(O)O$R^6$, —C(O)N($R^6$)$_2$,

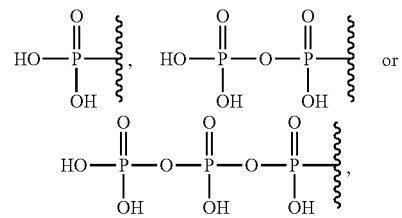

or a pro-drug modification of the mono-, di- or triphosphate;
$R^2$ is —H, —C(O)$R^{6a}$, —C(O)O$R^{6a}$ or —C(O)N($R^{6a}$)$_2$;
$R^3$ is —H, —F, or —OH;
$R^4$ is —H, —$C_1$-$C_6$ alkyl, —$C_2$-$C_6$ alkenyl, —$C_2$-$C_6$ alkynyl, —$C_1$-$C_6$ haloalkyl, —$C_3$-$C_7$ cycloalkyl, 5- or 6-membered monocyclic heteroaryl, a 9- or 10-membered bicyclic heteroaryl, halo, —CN, —$NO_2$, —N($R^X$)$_2$, —NH($C_1$-$C_6$alkylene)-(5- or 6-membered monocyclic heteroaryl), —NH($C_1$-$C_6$ alkylene)-(9- or 10-membered bicyclic heteroaryl), aryl, —NHC(O)O$R^{6b}$, —N(C(O)O$R^{6b}$)$_2$, —NHC(O)N($R^{6b}$)$_2$, or —NHC(O)$R^{6b}$, wherein each of said —$C_1$-$C_6$ alkyl group, said —$C_2$-$C_6$ alkenyl group or said —$C_2$-$C_6$ alkynyl group can be optionally substituted with halo;
$R^5$ is —H, —$C_1$-$C_6$ alkyl, —$C_2$-$C_6$ alkenyl, —$C_2$-$C_6$ alkynyl, —$C_1$-$C_6$ haloalkyl, —$C_3$-$C_7$ cycloalkyl, 5- or 6-membered monocyclic heteroaryl, a 9- or 10-membered bicyclic heteroaryl, halo, —O$R^X$, —CN, —$NO_2$, —N($R^X$)$_2$, —NH($C_1$-$C_6$alkylene)-(5- or 6-membered monocyclic heteroaryl), —NH($C_1$-$C_6$ alkylene)-(9- or 10-membered bicyclic heteroaryl), aryl, —NHC(O)O$R^{6b}$, —N(C(O)O$R^{6b}$)$_2$, —NHC(O)N($R^{6b}$)$_2$, or —NHC(O)$R^{6b}$, wherein each of said —$C_1$-$C_6$ alkyl group, said —$C_2$-$C_6$ alkenyl group or said —$C_2$-$C_6$ alkynyl group can be optionally substituted with halo;

$R^6$, $R^{6a}$ and $R^{6b}$ are each independently selected at each occurrence from —H, —$C_1$-$C_6$ alkyl, —$C_1$-$C_6$ haloalkyl, —($C_1$-$C_3$ alkylene)$_m$-($C_3$-$C_7$ cycloalkyl), —($C_1$-$C_3$ alkylene)$_m$-(aryl), —($C_1$-$C_3$ alkylene)$_m$-(4 to 7-membered heterocycloalkyl), —($C_1$-$C_3$ alkylene)$_m$-(5- or 6-membered monocyclic heteroaryl) or —($C_1$-$C_3$ alkylene)$_m$-(9- or 10-membered bicyclic heteroaryl), wherein each of said —$C_1$-$C_6$ alkyl, said $C_3$-$C_7$ cycloalkyl group, said aryl group, said 4 to 7-membered heterocycloalkyl group, said -(5- or 6-membered monocyclic heteroaryl group or said 9- or 10-membered bicyclic heteroaryl group can be optionally substituted with $R^7$;

m is an integer selected from 0 (zero) or 1;

$R^7$ represents from one to five substituent groups, each independently selected from —$C_1$-$C_6$alkyl, $C_2$-$C_6$ alkenyl, $C_2$-$C_6$ alkynyl, $C_1$-$C_6$ haloalkyl, aryl, or a 5-6-member heteroaryl;

$R^8$ is —H, —$C_1$-$C_6$ alkyl, —$C_1$-$C_6$ haloalkyl, —$C_3$-$C_7$ cycloalkyl, aryl, 5- or 6-membered monocyclic heteroaryl or 9- or 10-membered bicyclic heteroaryl;

$R^9$ is —H, halo, —$C_1$-$C_6$ alkyl, —$C_1$-$C_6$ haloalkyl, —CN, —$OR^Y$ or —$N(R^Y)_2$;

$R^X$ is independently selected at each occurrence from —H, —$C_1$-$C_6$ alkyl, —$C_1$-$C_6$ haloalkyl, aryl, or 5- or 6-membered monocyclic heteroaryl;

or when either or both of $R^4$ or $R^5$ is —$N(R^X)_2$, each $R^X$ may optionally be joined together with the nitrogen to which they are both attached to form a 5- or 6-membered monocyclic heteroaryl or 9- or 10-membered bicyclic heteroaryl; and $R^Y$ is —H, —$C_1$-$C_6$ alkyl or —$C_1$-$C_6$ haloalkyl;

with the proviso that when X is O, Y is —C≡CH or —C≡N, $R^1$ is —H, $R^2$ is —H, $R^4$ is —$NH_2$, $R^5$ is —H, —F, or —OH and $R^9$ is —F, then $R^3$ is not —F.

In an embodiment of this invention referred to herein as Formula Ia are compounds of Formula I, or a pharmaceutically acceptable salt thereof, wherein R is

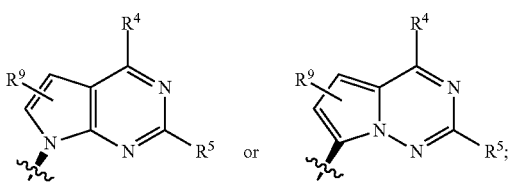

and all other variables therein ($R^1$, $R^2$, X, Y, etc.) are as defined in Formula I.

In an embodiment of this invention are compounds of Formula I having structural Formula II or a pharmaceutically acceptable salt thereof:

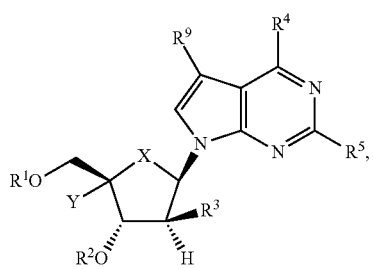

II wherein all variables therein ($R^1$, $R^2$, X, Y, etc.) are as defined in Formula I.

In another embodiment of this invention are compounds of Formula I having structural Formula III or a pharmaceutically acceptable salt thereof:

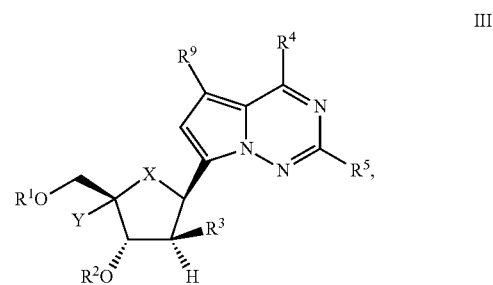

III wherein all variables therein ($R^1$, $R^2$, X, Y, etc.) are as defined in Formula I.

In another embodiment of this invention are compounds of Formula I having structural Formula IV or a pharmaceutically acceptable salt thereof:

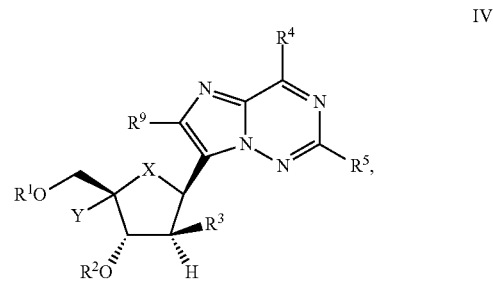

IV wherein all variables therein ($R^1$, $R^2$, X, Y, etc.) are as defined in Formula I.

In another embodiment of this invention are compounds of Formula I having structural Formula V or a pharmaceutically acceptable salt thereof:

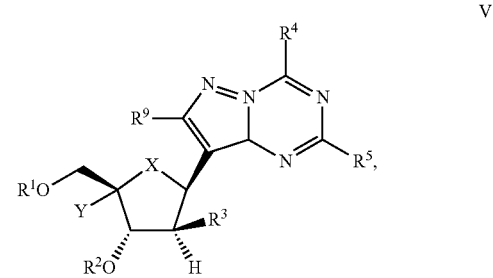

V wherein all variables therein ($R^1$, $R^2$, X, Y, etc.) are as defined in Formula I.

In an embodiment of this invention referred to herein as Embodiment A are compounds of Formula I, Ia, II, III, IV or V, or a pharmaceutically acceptable salt thereof, wherein:

X is O, S, CH$_2$ or CF$_2$;
Y is —C≡C—R$^8$ or —C≡N;
R$^1$ is —H or

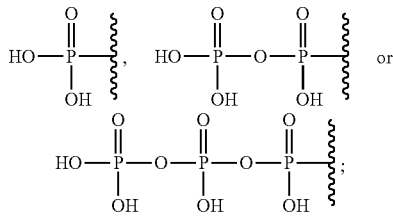

R$^2$ is —H;
R$^3$ is —H, —F, or —OH;
R$^4$ is —H, —C$_1$-C$_6$ alkyl, —C$_2$-C$_6$ alkenyl, —C$_2$-C$_6$ alkynyl, —C$_1$-C$_6$ haloalkyl, —C$_3$-C$_7$ cycloalkyl, 5- or 6-membered monocyclic heteroaryl, a 9- or 10-membered bicyclic heteroaryl, halo, —CN, —NO$_2$, —N(R$^X$)$_2$, —NH(C$_1$-C$_6$alkylene)-(5- or 6-membered monocyclic heteroaryl), —NH(C$_1$-C$_6$ alkylene)-(9- or 10-membered bicyclic heteroaryl), aryl, —NHC(O)OR$^{6b}$, —N(C(O)OR$^{6b}$)$_2$, —NHC(O)N(R$^{6b}$)$_2$, or —NHC(O)R$^{6b}$, wherein each of said —C$_1$-C$_6$ alkyl group, said —C$_2$-C$_6$ alkenyl group or said —C$_2$-C$_6$ alkynyl group can be optionally substituted with halo;
R$^5$ is —H, —C$_1$-C$_6$ alkyl, —C$_2$-C$_6$ alkenyl, —C$_2$-C$_6$ alkynyl, —C$_1$-C$_6$ haloalkyl, —C$_3$-C$_7$ cycloalkyl, a 5- or 6-membered monocyclic heteroaryl, a 9- or 10-membered bicyclic heteroaryl, halo, —OR$^X$, —CN, —NO$_2$, —N(R$^X$)$_2$, —NH(C$_1$-C$_6$alkylene)-(5- or 6-membered monocyclic heteroaryl), —NH(C$_1$-C$_6$ alkylene)-(9- or 10-membered bicyclic heteroaryl) or aryl, wherein each of said —C$_1$-C$_6$ alkyl group, said —C$_2$-C$_6$ alkenyl group or said —C$_2$-C$_6$ alkynyl group can be optionally substituted with halo;
R$^8$ is —H, —C$_1$-C$_6$ alkyl, —C$_1$-C$_6$ haloalkyl, —C$_3$-C$_7$ cycloalkyl, aryl, 5- or 6-membered monocyclic heteroaryl or 9- or 10-membered bicyclic heteroaryl;
R$^9$ is —H, halo, —C$_1$-C$_6$ alkyl, —C$_1$-C$_6$ haloalkyl, —CN, —OR$^Y$, or —N(R$^Y$)$_2$;
R$^X$ is independently selected at each occurrence from —H, —C$_1$-C$_6$ alkyl, —C$_1$-C$_6$ haloalkyl, aryl, or 5- or 6-membered monocyclic heteroaryl;
or when either or both of R$^4$ or R$^5$ is —N(R$^X$)$_2$, each R$^X$ may optionally be joined together with the nitrogen to which they are both attached to form a 5- or 6-membered monocyclic heteroaryl or 9- or 10-membered bicyclic heteroaryl; and
R$^Y$ is —H, —C$_1$-C$_6$ alkyl or —C$_1$-C$_6$ haloalkyl;
and all other variables, e.g., R$^6$, R$^{6a}$, R$^{6b}$, m, etc., are as defined in Formula I.

In classes of Embodiment A are compounds of Formula I, Ia, II, III, IV or V, or a pharmaceutically acceptable salt thereof, wherein:
R$^1$ is —H:
or R$^1$ is

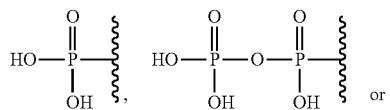

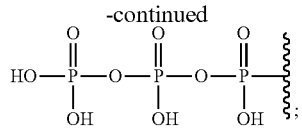

or R$^1$ is

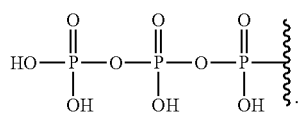 [SMILES: *P(=O)(O)OP(=O)(O)OP(=O)(O)O]

In an embodiment of this invention referred to herein as Embodiment B are compounds of Formula I, Ia, II, III, IV or V, or a pharmaceutically acceptable salt thereof, wherein:
R$^1$ is —H, —C(O)R$^6$, —C(O)OR$^6$ or —C(O)N(R$^6$)$_2$,

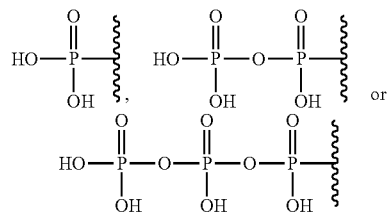

or a pro-drug modification of the mono-, di- or triphosphate;
R$^2$ is —H, —C(O)R$^{6a}$, —C(O)OR$^{6a}$ or —C(O)N(R$^{6a}$)$_2$; and
R$^4$ is —H, —C$_1$-C$_6$ alkyl, —C$_2$-C$_6$ alkenyl, —C$_2$-C$_6$ alkynyl, —C$_1$-C$_6$ haloalkyl, —C$_3$-C$_7$ cycloalkyl, 5- or 6-membered monocyclic heteroaryl, a 9- or 10-membered bicyclic heteroaryl, halo, —CN, —NO$_2$, —N(R$^X$)$_2$, —NH(C$_1$-C$_6$alkylene)-(5- or 6-membered monocyclic heteroaryl), —NH(C$_1$-C$_6$ alkylene)-(9- or 10-membered bicyclic heteroaryl), aryl, —NHC(O)OR$^{6b}$, —N(C(O)OR$^{6b}$)$_2$, —NHC(O)N(R$^{6b}$)$_2$, or —NHC(O)R$^{6b}$, wherein each of said —C$_1$-C$_6$ alkyl group, said —C$_2$-C$_6$ alkenyl group or said —C$_2$-C$_6$ alkynyl group can be optionally substituted with halo;
R$^5$ is —H, —C$_1$-C$_6$ alkyl, —C$_2$-C$_6$ alkenyl, —C$_2$-C$_6$ alkynyl, —C$_1$-C$_6$ haloalkyl, —C$_3$-C$_7$ cycloalkyl, 5- or 6-membered monocyclic heteroaryl, a 9- or 10-membered bicyclic heteroaryl, halo, —OR$^X$, —CN, —NO$_2$, —N(R$^X$)$_2$, —NH(C$_1$-C$_6$alkylene)-(5- or 6-membered monocyclic heteroaryl), —NH(C$_1$-C$_6$ alkylene)-(9- or 10-membered bicyclic heteroaryl), aryl, —NHC(O)OR$^{6b}$, —N(C(O)OR$^{6b}$)$_2$, —NHC(O)N(R$^{6b}$)$_2$, or —NHC(O)R$^{6b}$, wherein each of said —C$_1$-C$_6$ alkyl group, said —C$_2$-C$_6$ alkenyl group or said —C$_2$-C$_6$ alkynyl group can be optionally substituted with halo;
provided that one or more of R$^1$, R$^2$, R$^4$ or R$^5$ is selected as follows:
R$^1$ is —C(O)R$^6$, —C(O)OR$^6$, —C(O)N(R$^6$)$_2$ or a pro-drug modification of the mono-, di- or triphosphate; and/or
R$^2$ is —C(O)R$^{6a}$, —C(O)OR$^{6a}$ or —C(O)N(R$^{6a}$)$_2$; and/or
R$^4$ is —NHC(O)OR$^{6b}$, —N(C(O)OR$^{6b}$)$_2$, —NHC(O)N(R$^{6b}$)$_2$, or —NHC(O)R$^{6b}$; and/or
R$^5$ is —NHC(O)OR$^{6b}$, —N(C(O)OR$^{6b}$)$_2$, —NHC(O)N(R$^{6b}$)$_2$, or —NHC(O)R$^{6b}$;
and all other variables, e.g., X, Y, R$^3$, R$^6$, R$^{6a}$, R$^{6b}$, m, R$^7$, R$^8$, R$^9$, R$^X$, and R$^Y$, are as defined in Formula I.

In another embodiment of this invention, referred to as Embodiment C, are compounds of Formula I, Ia, II, III, IV or V, or a pharmaceutically acceptable salt thereof, wherein:
X is O;
Y is —C≡CH or —C≡N;
$R^1$ is —H, —C(O)$R^6$, —C(O)O$R^6$, —C(O)N($R^6$)$_2$,

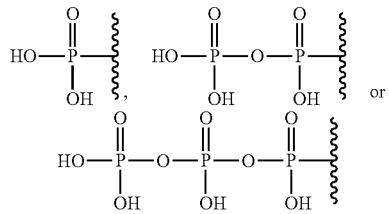

or a pro-drug modification of the mono-, di- or triphosphate;
$R^2$ is H, —C(O)$R^{6a}$, —C(O)O$R^{6a}$ or —C(O)N($R^{6a}$)$_2$, or particularly it is —H;
$R^3$ is —H, or —OH; or particularly $R^3$ is —H;
$R^4$ is —N($R^X$)$_2$, —NHC(O)O$R^{6b}$ or —NHC(O)N($R^{6b}$)$_2$; or particularly $R^4$ is —N($R^X$)$_2$;
$R^5$ is —H, halo, —$C_1$-$C_6$ alkyl, —O$R^X$ or —N($R^X$)$_2$; and particularly $R^5$ is —H, —Cl, —F or —NH$_2$;
$R^6$, $R^{6a}$, and $R^{6b}$ are each independently selected at each occurrence from —H, —$C_1$-$C_6$ alkyl, —$C_1$-$C_6$ haloalkyl, aryl (preferably phenyl), or a 5- or 6-membered monocyclic heteroaryl, wherein $R^6$, $R^{6a}$, and $R^{6b}$ are each optionally substituted with $R^7$;
$R^7$ is —$C_1$-$C_6$ alkyl, aryl (preferably phenyl) or 5-6 member monocyclic heteroaryl;
$R^8$ is —H;
$R^9$ is —H, halo, —$C_1$-$C_3$ alkyl, —$C_1$-$C_3$ haloalkyl, —CN, —O$R^Y$, or —N($R^Y$)$_2$, and particularly it is —H, —F, —Cl, —I, —Br or —CH$_3$;
$R^X$ is independently selected at each occurrence from —H, —$C_1$-$C_6$ alkyl, —$C_1$-$C_6$ haloalkyl, aryl, or 5- or 6-membered monocyclic heteroaryl;
or when either or both of $R^4$ or $R^5$ is —N($R^X$)$_2$, each $R^X$ may optionally be joined together with the nitrogen to which they are both attached to form a 5- or 6-membered monocyclic heteroaryl or 9- or 10-membered bicyclic heteroaryl; and
$R^Y$ is —H, —$C_1$-$C_6$ alkyl or —$C_1$-$C_6$ haloalkyl.

In another embodiment of this invention, referred to as Embodiment D, are compounds of Formula I, Ia, II, III, IV or V, or a pharmaceutically acceptable salt thereof, wherein:
X is O;
Y is —C≡CH or —C≡N;
$R^1$ is —H,

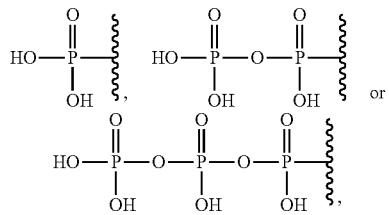

or a pro-drug modification of the mono-, di- or triphosphate;
$R^2$ is —H;
$R^3$ is —H;
$R^4$ is —NH$_2$;
$R^5$ is —H, —Cl, —F or —NH$_2$;
$R^8$ is —H; and
$R^9$ is —H, —F, —Cl, —I, —Br, or —CH$_3$.

In another embodiment of this invention are compounds of Formula I, Ia, II, III, IV or V, or Embodiment A or B, or a pharmaceutically acceptable salt thereof wherein
X is O.

In another embodiment of this invention are compounds of Formula I, Ia, II, III, IV or V, or Embodiment A or B, or a pharmaceutically acceptable salt thereof wherein
Y is —C≡C—$R^8$. In another embodiment are compounds of Formula I, Ia, II, III, IV or V, or Embodiment A, B, C or D, or a pharmaceutically acceptable salt thereof wherein Y is —C≡CH.

In another embodiment of this invention are compounds of Formula I, Ia, II, III, IV or V, or Embodiment A, B, C or D, or a pharmaceutically acceptable salt thereof, wherein Y is —C≡N.

In other embodiments of this invention are compounds of Formula I, Ia, II, III, IV or V, or Embodiment B or C, or a pharmaceutically acceptable salt thereof, wherein:
$R^1$ is —H, —C(O)$R^6$, —C(O)O$R^6$, —C(O)N($R^6$)$_2$, or a pro-drug modification of

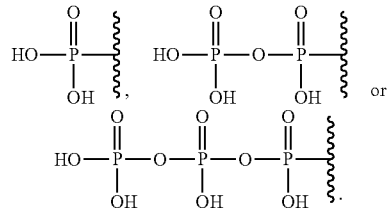

In other embodiments of this invention are compounds of Formula I, Ia, II, III, IV or V, or Embodiment A, B, C or D, or a pharmaceutically acceptable salt thereof, wherein
(a) $R^1$ is —H; or
(b) $R^1$ is

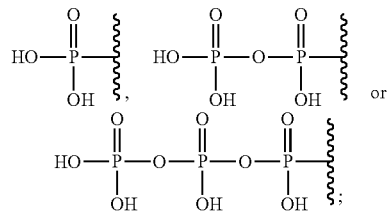

or
(c) $R^1$ is

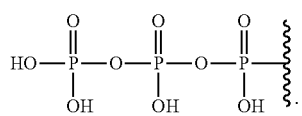

In other embodiments of this invention are compounds of Formula I, Ia, II, III, IV or V, or Embodiment B, C or D, or a pharmaceutically acceptable salt thereof, wherein:

(a) $R^1$ is —H or

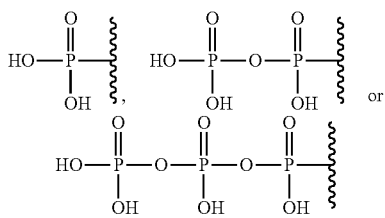

or a pro-drug modification of the mono-, di- or triphosphate;
or (b) $R^1$ is

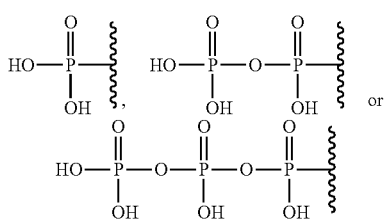

or a pro-drug modification of the mono-, di- or triphosphate;
or (c) $R^1$ is

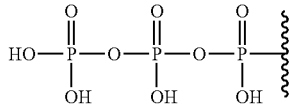 [SMILES: *P(=O)(O)OP(=O)(O)OP(=O)(O)O]

or a pro-drug modification of the triphosphate;
or (d) $R^1$ is a pro-drug modification of

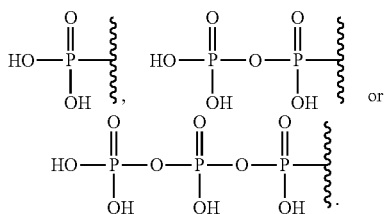

In another embodiment of this invention are compounds of Formula I, Ia, II, III, IV or V, or Embodiment B or C, or a pharmaceutically acceptable salt thereof, wherein $R^1$ is —H, —C(O)$R^6$, —C(O)O$R^6$, or —C(O)N($R^6$)$_2$, or a pro-drug modification of the mono-, di- or triphosphate. In a class thereof, $R^1$ is —C(O)$R^6$, —C(O)O$R^6$, or —C(O)N($R^6$)$_2$, or a pro-drug modification of the mono-, di- or triphosphate.

In other embodiments of this invention are compounds of Formula I, Ia, II, III, IV or V, or Embodiment B or C, or a pharmaceutically acceptable salt thereof, wherein:
$R^2$ is —H, —C(O)$R^{6a}$, —C(O)O$R^{6a}$ or —C(O)N($R^{6a}$)$_2$;
or $R^2$ is —C(O)$R^{6a}$, —C(O)O$R^{6a}$ or —C(O)N($R^{6a}$)$_2$;
or $R^2$ is —H.

In another embodiment of this invention are compounds of Formula I, Ia, II, III, IV or V, or Embodiment A, B or C, or a pharmaceutically acceptable salt thereof, wherein $R^3$ is —H or —OH. In a further embodiment are compounds of Formula I, Ia, II, III, IV or V, or Embodiment A, B or C, or a pharmaceutically acceptable salt thereof, wherein $R^3$ is —H.

In another embodiment of this invention are compounds of Formula I, Ia, II, III, IV or V, or Embodiment A or B, or a pharmaceutically acceptable salt thereof, wherein $R^4$ is —N($R^X$)$_2$, —NHC(O)O$R^{6b}$, —N(C(O)O$R^{6b}$)$_2$, —NHC(O)N($R^{6b}$)$_2$, or —NHC(O)$R^{6b}$; and particularly $R^4$ is —N($R^X$)$_2$. More particularly $R^4$ is —NH$_2$.

In other embodiments of this invention are compounds of Formula I, Ia, II, III, IV or V, or Embodiment B, or a pharmaceutically acceptable salt thereof, wherein:
$R^5$ is —H, halo, —C$_1$-C$_6$ alkyl, —O$R^X$, —N($R^X$)$_2$, —NHC(O)O$R^{6b}$, —N(C(O)O$R^{6b}$)$_2$, —NHC(O)N($R^{6b}$)$_2$, or —NHC(O)$R^{6b}$;
or $R^5$ is —NHC(O)O$R^{6b}$, —N(C(O)O$R^{6b}$)$_2$, —NHC(O)N($R^{6b}$)$_2$, or —NHC(O)$R^{6b}$;
or $R^5$ is —H, halo (preferably —F or —CO, —C$_1$-C$_6$ alkyl, —O$R^X$ or —N($R^X$)$_2$;
or $R^5$ is —H, —Cl, —F or —NH$_2$.

In other embodiments of this invention are compounds of Embodiment A or B, or a pharmaceutically acceptable salt thereof, wherein:
$R^5$ is —H, halo (preferably —F or —CO, —C$_1$-C$_6$ alkyl, —O$R^X$ or —N($R^X$)$_2$;
or $R^5$ is —H, —Cl, —F or —NH$_2$.

In another embodiment of this invention are compounds of Formula I, Ia, II, III, IV or V, or Embodiment B, or a pharmaceutically acceptable salt thereof, wherein $R^6$, $R^{6a}$ and $R^{6b}$ are each independently selected at each occurrence from —H, —C$_1$-C$_6$ alkyl, —C$_1$-C$_6$ haloalkyl, aryl (preferably phenyl), or a 5- or 6-membered monocyclic heteroaryl.

In another embodiment of this invention are compounds of Embodiment A, or a pharmaceutically acceptable salt thereof, wherein $R^{6b}$ is selected at each occurrence from —H, —C$_1$-C$_6$ alkyl, —C$_1$-C$_6$ haloalkyl, aryl (preferably phenyl), or a 5- or 6-membered monocyclic heteroaryl.

In another embodiment of this invention are compounds of Formula I, Ia, II, III, IV or V, or Embodiment A or B, or a pharmaceutically acceptable salt thereof, wherein $R^7$ is —C$_1$-C$_6$ alkyl, aryl (preferably phenyl) or 5-6 member monocyclic heteroaryl.

In another embodiment of this invention are compounds of Formula I, Ia, II, III, IV or V, or Embodiment A or B, or a pharmaceutically acceptable salt thereof, wherein $R^8$ is —H.

In another embodiment of this invention are compounds of Formula I, Ia, II, III, IV or V, or Embodiment A or B, or a pharmaceutically acceptable salt thereof, wherein $R^9$ is —H, halo, —C$_1$-C$_3$ alkyl, —C$_1$-C$_3$ haloalkyl, —CN, —O$R^Y$, or —N($R^Y$)$_2$; and particularly it is —H, —F, —Cl, —I, —Br or —CH$_3$.

All structural Formulas, embodiments and classes thereof described herein include the pharmaceutically acceptable salts of the compounds defined therein. Reference to the compounds of Formula I herein encompasses the compounds of each of Formulas I, Ia, II III, IV or V, and all embodiments and classes thereof. Reference to the compounds of this invention as those of a specific formula or embodiment, e.g., Formula I, Ia, II III, IV or V, or embodiments thereof, or any other generic structural formula or specific compound described or claimed herein, is intended to encompass the specific compound or compounds falling within the scope of the Formula or embodiment, including salts thereof, particularly pharmaceutically acceptable salts, solvates (including hydrates) of such compounds and solvated salt forms thereof, where such forms are possible, unless specified otherwise.

The present invention includes each of the Examples described herein, and pharmaceutically acceptable salts thereof. The invention also encompasses pharmaceutical compositions comprising an effective amount of a compound of the invention or a pharmaceutically acceptable salt thereof, and a pharmaceutically acceptable carrier.

As used herein, the term "alkyl" refers to a monovalent straight or branched chain, saturated aliphatic hydrocarbon radical having a number of carbon atoms in the specified range. Thus, for example, "$C_{1-6}$ alkyl" (or "$C_1$-$C_6$ alkyl") refers to any of the hexyl alkyl and pentyl alkyl isomers as well as n-, iso-, sec- and t-butyl, n- and iso-propyl, ethyl and methyl. As another example, "$C_{1-4}$ alkyl" refers to n-, iso-, sec- and t-butyl, n- and iso-propyl, ethyl and methyl.

The term "alkenyl" refers to a monovalent straight or branched chain aliphatic hydrocarbon radical containing one carbon-carbon double bond and having a number of carbon atoms in the specified range. Thus, for example, "$C_{2-6}$ alkenyl" (or "$C_2$-$C_6$ alkenyl") refers to all of the hexenyl and pentenyl isomers as well as 1-butenyl, 2-butenyl, 3-butenyl, isobutenyl, 1-propenyl, 2-propenyl, and ethenyl (or vinyl).

The term "alkynyl" refers to a monovalent straight or branched chain aliphatic hydrocarbon radical containing one carbon-carbon triple bond and having a number of carbon atoms in the specified range. Thus, for example, "$C_{2-6}$ alkynyl" (or "$C_2$-$C_6$ alkynyl") refers to all of the hexynyl and pentynyl isomers as well as 1-butynyl, 2-butynyl, 3-butynyl, 1-propynyl, 2-propynyl, and ethynyl.

The term "alkylene" refers to any divalent linear or branched chain aliphatic hydrocarbon radical having a number of carbon atoms in the specified range. Thus, for example, "—$C_{1-6}$ alkylene-" refers to any of the $C_1$ to $C_6$ linear or branched alkylenes, and "—$C_{1-3}$ alkylene-" refers to any of the $C_1$ to $C_3$ linear or branched alkylenes. A particular class of alkylenes includes —(CH$_2$)$_{1-3}$—, —(CH$_2$)$_{2-3}$—, —(CH$_2$)$_{1-2}$—, and —CH$_2$—, —CH(CH$_3$)—, and —C(CH$_3$)$_2$—.

The term "cycloalkyl" refers to any monocyclic ring of an alkane having a number of carbon atoms in the specified range. Thus, for example, "$C_{3-7}$ cycloalkyl" (or "$C_3$-$C_7$ cycloalkyl") refers to cyclopropyl, cyclobutyl, cyclopentyl, cyclohexyl, and cycloheptyl. A particular class of interest for compounds of Formula I and embodiments thereof is $C_{3-6}$ cycloalkyl.

The term "halogen" (or "halo") refers to fluorine, chlorine, bromine and iodine (alternatively referred to as fluoro, chloro, bromo, and iodo). A particular class of interest for compounds of Formula I and embodiments thereof is each of fluoro of chloro.

The term "haloalkyl" refers to an alkyl group as defined above in which one or more of the hydrogen atoms have been replaced with halo (i.e., —F, —Cl, —Br and/or —I). Thus, for example, "$C_{1-6}$ haloalkyl" (or "$C_1$-$C_6$ haloalkyl") refers to a $C_1$ to $C_6$ linear or branched alkyl group as defined above with one or more halo substituents. The term "fluoroalkyl" has an analogous meaning except that the halogen substituents are restricted to fluoro. Suitable fluoroalkyls include the series (CH$_2$)$_{0-4}$CF$_3$ (i.e., trifluoromethyl, 2,2,2-trifluoroethyl, 3,3,3-trifluoro-n-propyl, etc.). A fluoroalkyl of particular interest is CF$_3$.

The term "C(O)" refers to carbonyl. The terms "S(O)$_2$" and "SO$_2$" each refer to sulfonyl. The term "S(O)" refers to sulfinyl.

The term "aryl" (or "$C_6$-$C_{10}$ aryl") refers to (i) phenyl, or (ii) 9- or 10-membered bicyclic, fused carbocyclic ring systems in which at least one ring is aromatic. Suitable aryls include, for example, phenyl, naphthyl, tetrahydronaphthyl (tetralinyl), or indenyl. In a particular class of compounds of Formula I and embodiments thereof, aryl is phenyl or naphthyl, and more particularly aryl is phenyl.

The term "heteroaryl" refers to (i) a 5- or 6-membered heteroaromatic ring containing from 1 to 4 heteroatoms independently selected from N, O and S, wherein each N is optionally in the form of an oxide to the extent chemically possible, (ii) a 9- or 10-membered bicyclic fused ring system, wherein the fused ring system contains from 1 to 6 heteroatoms independently selected from N, O and S, wherein each ring in the fused ring system contains zero, one, or more than one heteroatom, and at least one ring is aromatic, and each N is optionally in the form of an oxide to the extent chemically possible, and each S in a ring which is not aromatic is optionally S(O) or S(O)$_2$. Suitable 5- and 6-membered heteroaromatic rings include, for example, pyridyl, pyrrolyl, pyrazinyl, pyrimidinyl, pyridazinyl, triazinyl, thienyl, furanyl, imidazolyl, pyrazolyl, triazolyl triazolyl (i.e., 1,2,3-triazolyl or 1,2,4-triazolyl), tetrazolyl, oxazolyl, isooxazolyl, oxadiazolyl (i.e., the 1,2,3-, 1,2,4-, 1,2,5-(furazanyl), or 1,3,4-isomer), oxatriazolyl, thiazolyl, isothiazolyl, and thiadiazolyl. Suitable 9- and 10-membered heterobicyclic, fused ring systems include, for example, benzofuranyl, indolyl, indazolyl, naphthyridinyl, isobenzofuranyl, benzopiperidinyl, benzisoxazolyl, benzoxazolyl, chromenyl, quinolinyl, isoquinolinyl, cinnolinyl, quinazolinyl, tetrahydroquinolinyl, tetrahydroisoquinolinyl, isoindolyl, benzodioxolyl (e.g., benzo-1,3-dioxolyl:

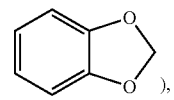), benzopiperidinyl, benzisoxazolyl, benzoxazolyl, chromanyl, isochromanyl, benzothienyl, benzofuranyl, imidazo[1,2-a]pyridinyl, benzotriazolyl, dihydroindolyl, dihydroisoindolyl, indazolyl, indolinyl quinoxalinyl, quinazolinyl, 2,3-dihydrobenzofuranyl, and 2,3-dihydrobenzo-1,4-dioxinyl (i.e., 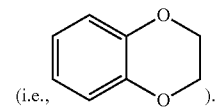).

It is understood that the specific rings and ring systems suitable for use in the present invention are not limited to those listed in the preceding paragraphs. These rings and ring systems are merely representative. Unless expressly stated to the contrary in a particular context, any of the various cyclic rings and ring systems described herein may be attached to the rest of the compound at any ring atom (i.e., any carbon atom or any heteroatom) provided that the attachment is chemically allowed and a stable compound results.

Unless expressly depicted or described otherwise, a variable depicted in a structural formula with a "floating" bond attached to a ring, such as $R^9$ in Formula I, is permitted to be a substituent (alternatively, $R^9$ may be —H) on any available carbon or nitrogen atom in the ring to which the variable is attached.

When a moiety is noted as being "optionally substituted" in Formula I or any embodiment thereof, it means that Formula I or the embodiment thereof encompasses both compounds that are substituted with the noted substituent (or substituents) on the moiety and compounds that do not contain the noted substituent (or substituents) on the moiety (i.e., wherein the moiety is unsubstituted). As one example, when $R^4$ is a $—C_1-C_6$ alkyl group that can be optionally substituted with halo, then $R^4$ can be $—C_1-C_6$ alkyl or $—C_1-C_6$ haloalkyl.

When any variable (e.g., $R^7$, $R^X$, $R^Y$) occurs more than one time in any constituent or in Formula I or in any other formula depicting and describing compounds of the present invention, its definition on each occurrence is independent of its definition at every other occurrence. Also, combinations of substituents and/or variables are permissible only if such combinations result in stable compounds.

Unless expressly stated to the contrary, substitution by a named substituent is permitted on any atom in a ring (e.g., cycloalkyl, aryl, or heteroaryl) provided such ring substitution is chemically allowed and results in a stable compound.

Unless expressly stated to the contrary, all ranges cited herein are inclusive. For example, a heteroaromatic ring described as containing from "1 to 4 heteroatoms" means the ring can contain 1, 2, 3 or 4 heteroatoms. It is also to be understood that any range cited herein includes within its scope all of the sub-ranges within that range. Thus, for example, a heterocyclic ring described as containing from "1 to 4 heteroatoms" is intended to include as aspects thereof, heterocyclic rings containing 2 to 4 heteroatoms, 3 or 4 heteroatoms, 1 to 3 heteroatoms, 2 or 3 heteroatoms, 1 or 2 heteroatoms, 1 heteroatom, 2 heteroatoms, 3 heteroatoms, or 4 heteroatoms. As another example, an aryl or heteroaryl described as optionally substituted with $R^7$, wherein $R^7$ is "from 1 to 5 substituent groups" is intended to include as aspects thereof, the aryl or heteroaryl substituted with 1 to 5 substituents, 2 to 5 substituents, 3 to 5 substituents, 4 to 5 substituents, 5 substituents, 1 to 4 substituents, 2 to 4 substituents, 3 to 4 substituents, 4 substituents, 1 to 3 substituents, 2 to 3 substituents, 3 substituents, 1 to 2 substituents, 2 substituents, and 1 substituent.

In Embodiment B, "one or more of $R^1$, $R^2$, $R^4$ or $R^5$ is selected as follows" includes only one of $R^1$, $R^2$, $R^4$ or $R^5$ as being defined as in the proviso, or any combination of more than one of $R^1$, $R^2$, $R^4$ and/or $R^5$ each being defined as in the proviso. For example, the following combinations of variables may be defined as in the proviso of Embodiment B: $R^1$ and $R^2$; $R^1$ and $R^4$; $R^1$ and $R^5$; $R^2$ and $R^4$; $R^2$ and $R^5$; $R^4$ and $R^5$; $R^1$, $R^2$ and $R^4$; $R^1$, $R^2$ and $R^5$; $R^1$, $R^4$ and $R^5$; $R^2$, $R^4$ and $R^5$; or $R^1$, $R^2$, $R^4$ and $R^5$.

As would be recognized by one of ordinary skill in the art, certain of the compounds of the present invention can exist as tautomers. All tautomeric forms of these compounds, whether isolated individually or in mixtures, are within the scope of the present invention. For example, in instances where an —OH substituent is permitted on a heteroaromatic ring and keto-enol tautomerism is possible, it is understood that the substituent might in fact be present, in whole or in part, in the oxo (=O) form.

A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject). The compounds of the present invention are limited to stable compounds embraced by Formula I and its embodiments.

The compounds of Formula I may have one or more chiral (asymmetric) centers. The present invention encompasses all stereoisomeric forms of the compounds of Formula I. Centers of asymmetry that are present in the compounds of Formula I can all independently of one another have (R) or (S) configuration. When bonds to a chiral carbon are depicted as straight lines in the structural Formulas of the invention, or when a compound name is recited without an (R) or (S) chiral designation for a chiral carbon, it is understood that both the (R) and (S) configurations of each such chiral carbon, and hence each enantiomer or diastereomer and mixtures thereof, are embraced within the Formula or by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or it can be done on a final racemic product. Absolute stereochemistry may be determined by X-ray crystallography of crystalline products or crystalline intermediates which are derivatized, if necessary, with a reagent containing a stereogenic center of known configuration. Alternatively, absolute stereochemistry may be determined by Vibrational Circular Dichroism (VCD) spectroscopy analysis. The present invention includes all such isomers, as well as salts, solvates (which includes hydrates) and solvated salts of such racemates, enantiomers, diastereomers and tautomers and mixtures thereof.

The atoms in a compound of Formula I may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

The compounds can be administered in the form of pharmaceutically acceptable salts. The term "pharmaceutically acceptable salt" refers to a salt which is not biologically or otherwise undesirable (e.g., is neither toxic nor otherwise deleterious to the recipient thereof).

When the compounds of Formula I contain one or more acidic or basic groups the invention also includes the corresponding pharmaceutically acceptable salts. Thus, the compounds of Formula I which contain acidic groups (e.g., —COOH or a phenolic group) can be used according to the invention as, for example but not limited to, alkali metal salts, alkaline earth metal salts or as ammonium salts. Examples of such salts include but are not limited to sodium salts, potassium salts, calcium salts, magnesium salts or salts with ammonia or organic amines such as, for example, ethylamine, ethanolamine, triethanolamine or amino acids. Compounds of Formula I which contain one or more basic groups, i.e. groups which can be protonated, can be used according to the invention in the form of their acid addition salts with inorganic or organic acids as, for example but not limited to, salts with hydrogen chloride, hydrogen bromide, phosphoric acid, sulfuric acid, nitric acid, benzenesulfonic acid, methanesulfonic acid, p-toluenesulfonic acid, naphthalenedisulfonic acids, oxalic acid, acetic acid, trifluoroacetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, etc. If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of pharmaceutically acceptable salts.

Another embodiment of the present invention is a compound of Formula I wherein the compound or its salt is in a substantially pure form. As used herein "substantially pure" means suitably at least about 60 wt. %, typically at least about 70 wt. %, preferably at least about 80 wt. %, more preferably at least about 90 wt. % (e.g., from about 90 wt. % to about 99 wt. %), even more preferably at least about 95 wt. % (e.g., from about 95 wt. % to about 99 wt. %, or from about 98 wt. % to 100 wt. %), and most preferably at least about 99 wt. % (e.g., 100 wt. %) of a product containing a compound of Formula I or its salt (e.g., the product isolated from a reaction mixture affording the compound or salt) consists of the compound or salt. The level of purity of the compounds and salts can be determined using a standard method of analysis such as thin layer chromatography, gel electrophoresis, high performance liquid chromatography, and/or mass spectrometry. If more than one method of analysis is employed and the methods provide experimentally significant differences in the level of purity determined, then the method providing the highest purity level governs. A compound or salt of 100% purity is one which is free of detectable impurities as determined by a standard method of analysis. With respect to a compound of the invention which has one or more asymmetric centers and can occur as mixtures of stereoisomers, a substantially pure compound can be either a substantially pure mixture of the stereoisomers or a substantially pure individual diastereomer or enantiomer.

Furthermore, compounds of the present invention may exist in amorphous form and/or one or more crystalline forms, and as such all amorphous and crystalline forms and mixtures thereof of the compounds of Formula I are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with unsolvated and anhydrous forms.

It is understood that a compound of Formula I (or any embodiment thereof and pharmaceutically acceptable salts thereof) wherein, for example, $R^1$ is —H, —C(O)$R^6$, —C(O)O$R^6$, —C(O)N($R^6$)$_2$, or a pro-drug modification of the mono-, di- or triphosphate, may be converted intracellularly/in vivo by one or more mechanisms (e.g., enzyme-catalyzed chemical reactions) to the corresponding nucleoside 5' triphosphate (i.e., wherein $R^1$ is —P(O)(OH)—O—P(O)(OH)—O—P(O)(OH)$_2$). While not wishing to be bound by any particular theory, the nucleoside 5'triphosphate is generally understood to be responsible for inhibiting the HIV RT enzyme and for the resulting antiviral activity after administration of the compound of Formula I to a subject.

Accordingly, prodrugs of the compounds of the invention are contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" herein means a compound (e.g., a drug precursor), which may be in the form of a pharmaceutically acceptable salt, that is transformed intracellularly/in vivo to provide a 4'-substituted Nucleoside Derivative which is an inhibitor of HIV reverse transcriptase. A nucleoside 5'triphosphate is an example of a 4'-substituted Nucleoside Derivative. The in vivo transformation may occur by various mechanisms, e.g., an enzyme-catalyzed chemical reaction, a metabolic chemical reaction, and/or a spontaneous chemical reaction (e.g., solvolysis), such as, for example, through hydrolysis in blood. This invention encompasses any prodrugs which convert, due to intracellular/in vivo conversion, to a 4'-substituted Nucleoside Derivative of a compound of Formula I which is an inhibitor of HIV reverse transcriptase. For example, 4'-substituted Nucleoside Derivatives of Formula I include, but are not limited to, compounds of Formula I wherein:

a) $R^1$ is —P(O)(OH)—O—P(O)(OH)—O—P(O)(OH)$_2$;

b) $R^1$ is —P(O)(OH)—O—P(O)(OH)—O—P(O)(OH)$_2$, and $R^2$ is —H; and/or c) $R^1$ is —P(O)(OH)—O—P(O)(OH)—O—P(O)(OH)$_2$, $R^2$ is —H, $R^4$ is —NH$_2$ and $R^5$ is —H or —NH$_2$.

Prodrugs of compounds of Formula I can exhibit enhanced solubility, absorption, and/or lipophilicity compared to the compounds per se, thereby resulting in increased bioavailability and efficacy. When the compound contains, for example, a hydroxy group, the prodrug can be a derivative of the hydroxy group such as an ester (—OC(O)R), a carbonate ester (—OC(O)OR), a phosphate ester (—O—P(=O)(OH)$_2$), an ether (—OR), or a mono-phosphate prodrug such as a phosphoramidate (can be converted in vivo to the corresponding nucleoside monophosphate).

For example, if a compound of Formula I contains an alcohol functional group, a prodrug can be formed by the replacement of one or more of the hydrogen atoms of the alcohol groups with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino($C_1$-$C_4$)alkyl, α-amino($C_1$-$C_4$)alkylene-aryl, arylacyl and α-aminoacyl, or α-aminoacyl-α-aminoacyl, where each α-aminoacyl group is independently selected from the naturally occurring L-amino acids, or glycosyl (the radical resulting from the removal of a hydroxyl group of the hemiacetal form of a carbohydrate).

The term "pro-drug modification of the mono-, di- or triphosphate" as used herein includes, but is not limited to, 5'-alcohol-derived prodrugs such as —P(O)(—O—$C_1$-$C_6$alkyl)$_2$; —P(O)(—NH-(α-aminoacyl group))(—O-aryl), known as "McGuigan" type prodrugs; —P(O)(—O—($C_1$-$C_6$ alkylene)-S-acyl)(-NH-arylalkyl); S-acyl-2-thioethyl (SATE) prodrugs; a cyclic phosphate ester that forms a bridge between two ribose hydroxyl groups, such as:

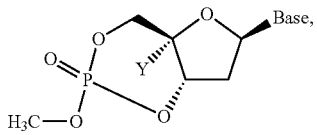

wherein the cyclic phosphate ester forms a bridge between the 3'-OH group and 5'-OH groups; and those described in U.S. Pat. No. 7,879,815; International Publication Nos. WO2005/003047, WO2008/082602, WO2010/0081628, WO2010/075517 and WO2010/075549; Mehellou, Chem. Med. Chem., 5:1841-1842 (2005); Bobeck et al., Antiviral Therapy 15:935-950 (2010); Furman et al., Future Medicinal Chemistry, 1:1429-1452 (2009); and Erion, Microsomes and Drug Oxidations, Proceedings of the International Symposium, 17th, Saratoga Springs, N.Y., United States, Jul. 6-10, 2008, 7-12 (2008).

If a 4'-substituted derivative incorporates an amine functional group, a prodrug can be formed by the replacement of a hydrogen atom in the amine group with a group such as, for example, R-carbonyl-, RO-carbonyl-, NRR'-carbonyl-wherein R and R' are each independently ($C_1$-$C_{10}$)alkyl, ($C_3$-$C_7$)cycloalkyl, benzyl, a natural α-aminoacyl, —C(OH)C(O)O$Y^1$ wherein $Y^1$ is H, ($C_1$-$C_6$)alkyl or benzyl, —C(O$Y^2$)$Y^3$ wherein $Y^2$ is ($C_1$-$C_4$)alkyl and $Y^3$ is ($C_1$-$C_6$)alkyl; carboxy($C_1$-$C_6$)alkyl; amino($C_1$-$C_4$)alkyl or mono-N— or di-N,N—($C_1$-$C_6$)alkylaminoalkyl; —C($Y^4$)$Y^5$ wherein $Y^4$ is H or methyl and $Y^5$ is mono-N— or di-N,N—($C_1$-$C_6$)alkylamino morpholino; piperidin-1-yl or pyrrolidin-1-yl, and the like.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (e.g., methyl, ethyl, n-propyl, isopropyl, t-butyl, sec-butyl or n-butyl), alkoxyalkyl (e.g., methoxymethyl), aryl (e.g., benzyl), aryloxyalkyl (for example, phenoxymethyl), aryl (e.g., phenyl optionally substituted with, for example, halogen, $C_{1-4}$alkyl, —O—($C_{1-4}$alkyl) or amino); (2) sulfonate esters, such as alkyl- or aralkylsulfonyl (for example, methanesulfonyl); (3) amino acid esters (e.g., L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

If a 4'-substituted deoxyribose derivative contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$)alkyl, and the like.

Other examples include the following: when the compound of Formula I, contains a carboxylic acid group, the prodrug can be an ester or an amide, and when the compound of Formula I contains a primary amino group or another suitable nitrogen that can be derivatized, the prodrug can be an amide, carbamate, urea, imine, or a Mannich base. Conventional procedures for the selection and preparation of suitable prodrug derivatives are described, for example, in Design of Prodrugs, edited by H. Bundgaard, Elsevier, 1985; J. J. Hale et al., J. Med. Chem. 2000, vol. 43, pp. 1234-1241; C. S. Larsen and J. Ostergaard, "Design and application of prodrugs" in: Textbook of Drug Design and Discovery, 3rd edition, edited by C. S. Larsen, 2002, pp. 410-458; and Beaumont et al., Current Drug Metabolism 2003, vol. 4, pp. 461-458; the disclosures of each of which are incorporated herein by reference in their entireties.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof which include any combination of stereoisomer, tautomer, solvate, hydrate, salt and/or physical forms of said pro-drugs, where such forms are possible unless specified otherwise.

The invention also encompasses methods for the treatment or prophylaxis of infection by HIV, for the inhibition of HIV reverse transcriptase, for the treatment, prophylaxis, or delay in the onset of AIDS in a subject in need thereof, which comprises administering to the subject an effective amount of a compound of the invention or a pharmaceutically acceptable salt thereof.

The invention also encompasses a compound of the invention, or a pharmaceutically acceptable salt thereof, for use in the preparation of a medicament for the treatment or prophylaxis of infection by HIV, for the inhibition of HIV reverse transcriptase, or for the treatment, prophylaxis, or delay in the onset of AIDS in a subject in need thereof.

The invention also encompasses a pharmaceutical composition comprising an effective amount of a compound of the invention, or a pharmaceutically acceptable salt thereof, and a pharmaceutically acceptable carrier and further comprising an effective amount of an additional anti-HIV agent selected from the group consisting of HIV antiviral agents, immunomodulators, and anti-infective agents. Within this embodiment, the anti-HIV agent is an antiviral selected from the group consisting of HIV protease inhibitors, HIV reverse transcriptase inhibitors, HIV integrase inhibitors, HIV fusion inhibitors, HIV entry inhibitors, and HIV maturation inhibitors.

Compounds of Formula Ia, II, III, IV or V, each form a subset of the compounds included in Formula I. Any description above or which follows that refers to a compound of Formula I also applies to a compound of each of Formula Ia, II, III, IV or V, and each embodiment thereof.

Other embodiments of the present invention include the following:

(a) A pharmaceutical composition comprising an effective amount of a compound of Formula I as defined above, or a prodrug or pharmaceutically acceptable salt thereof, and a pharmaceutically acceptable carrier.

(b) A pharmaceutical composition which comprises the product prepared by combining (e.g., mixing) an effective amount of a compound of Formula I as defined above, or a prodrug or pharmaceutically acceptable salt thereof, and a pharmaceutically acceptable carrier.

(c) The pharmaceutical composition of (a) or (b), further comprising an effective amount of one or more an anti-HIV agents selected from the group consisting of HIV antiviral agents, immunomodulators, and anti-infective agents.

(d) The pharmaceutical composition of (c), wherein the anti-HIV agent is selected from one or more of an antiviral selected from the group consisting of HIV protease inhibitors, nucleoside HIV reverse transcriptase inhibitors, non-nucleoside HIV reverse transcriptase inhibitors, HIV integrase inhibitors, HIV fusion inhibitors, HIV entry inhibitors and HIV maturation inhibitors.

(e) A combination which is (i) a compound of Formula I as defined above, or a prodrug or pharmaceutically acceptable salt thereof, and (ii) an anti-HIV agent selected from the group consisting of HIV antiviral agents, immunomodulators, and anti-infective agents; wherein the compound and the anti-HIV agent are each employed in an amount that renders the combination effective for inhibition of HIV reverse transcriptase, for treatment or prophylaxis of infection by HIV, or for treatment, prophylaxis of, or delay in the onset or progression of AIDS.

(f) The combination of (e), wherein the anti-HIV agent is an antiviral selected from the group consisting of HIV protease inhibitors, nucleoside HIV reverse transcriptase inhibitors, non-nucleoside HIV reverse transcriptase inhibitors, HIV integrase inhibitors, HIV fusion inhibitors, HIV entry inhibitors and HIV maturation inhibitors.

(g) A method for the inhibition of HIV reverse transcriptase in a subject in need thereof which comprises administering to the subject an effective amount of a compound of Formula I or a prodrug or pharmaceutically acceptable salt thereof.

(h) A method for the prophylaxis or treatment of infection by HIV (e.g., HIV-1) in a subject in need thereof which comprises administering to the subject an effective amount of a compound of Formula I or a prodrug or pharmaceutically acceptable salt thereof.

(i) The method of (h), wherein the compound of Formula I is administered in combination with an effective amount of at least one other HIV antiviral selected from the group consisting of HIV protease inhibitors, HIV integrase inhibitors, non-nucleoside HIV reverse transcriptase inhibitors, nucleoside HIV reverse transcriptase inhibitors, HIV fusion inhibitors, HIV entry inhibitors and HIV maturation inhibitors.

(j) A method for the prophylaxis, treatment or delay in the onset or progression of AIDS in a subject in need thereof which comprises administering to the subject an effective amount of a compound of Formula I or a prodrug or pharmaceutically acceptable salt thereof.

(k) The method of (j), wherein the compound is administered in combination with an effective amount of at least one other HIV antiviral selected from the group consisting of HIV protease inhibitors, HIV integrase inhibitors, non-nucleoside HIV reverse transcriptase inhibitors, nucleoside HIV reverse transcriptase inhibitors, HIV fusion inhibitors, HIV entry inhibitors and HIV maturation inhibitors.

(l) A method for the inhibition of HIV reverse transcriptase in a subject in need thereof which comprises administering to the subject the pharmaceutical composition of (a), (b), (c) or (d) or the combination of (e) or (f).

(m) A method for the prophylaxis or treatment of infection by HIV (e.g., HIV-1) in a subject in need thereof which comprises administering to the subject the pharmaceutical composition of (a), (b), (c) or (d) or the combination of (e) or (f).

(n) A method for the prophylaxis, treatment, or delay in the onset or progression of AIDS in a subject in need thereof which comprises administering to the subject the pharmaceutical composition of (a), (b), (c) or (d) or the combination of (e) or (f).

The present invention also includes a compound of Formula I or pharmaceutically acceptable salt thereof, (i) for use in, (ii) for use as a medicament for, or (iii) for use in the preparation of a medicament for: (a) therapy (e.g., of the human body), (b) medicine, (c) inhibition of HIV reverse transcriptase, (d) treatment or prophylaxis of infection by HIV, or (e) treatment, prophylaxis of, or delay in the onset or progression of AIDS. In these uses, the compounds of the present invention can optionally be employed in combination with one or more anti-HIV agents selected from HIV antiviral agents, anti-infective agents, and immunomodulators.

Additional embodiments of the invention include the pharmaceutical compositions, combinations and methods set forth in (a)-(n) above and the uses (i)(a)-(e) through (iii)(a)-(e) set forth in the preceding paragraph, wherein the compound of the present invention employed therein is a compound of one of the embodiments, aspects, classes, sub-classes, or features described above. In all of these embodiments etc., the compound may optionally be used in the form of a prodrug or pharmaceutically acceptable salt or pharmaceutically acceptable salt of a prodrug.

Additional embodiments of the present invention include each of the pharmaceutical compositions, combinations, methods and uses set forth in the preceding paragraphs, wherein the compound of the present invention or its salt employed therein is substantially pure. With respect to a pharmaceutical composition comprising a compound of Formula I or its prodrug or salt and a pharmaceutically acceptable carrier and optionally one or more excipients, it is understood that the term "substantially pure" is in reference to a compound of Formula I or its prodrug and/or salt per se.

Still additional embodiments of the present invention include the pharmaceutical compositions, combinations and methods set forth in (a)-(n) above and the uses (i)(a)-(e) through (iii)(a)-(e) set forth above, wherein the HIV of interest is HIV-1. Thus, for example, in the pharmaceutical composition (d), the compound of Formula I is employed in an amount effective against HIV-1 and the anti-HIV agent is an HIV-1 antiviral selected from the group consisting of HIV-1 protease inhibitors, HIV-1 reverse transcriptase inhibitors, HIV-1 integrase inhibitors, HIV-1 fusion inhibitors and HIV-1 entry inhibitors. The compounds of Formula I may also be useful agents against HIV-2.

The term "administration" and variants thereof (e.g., "administering" a compound) in reference to a compound of Formula I means providing the compound to the individual in need of treatment or prophylaxis and includes both self-administration and administration to the patient by another person. When a compound or a prodrug thereof is provided in combination with one or more other active agents (e.g., antiviral agents useful for treating or prophylaxis of HIV infection or AIDS), "administration" and its variants are each understood to include provision of the compound or prodrug and other agents at the same time or at different times. When the agents of a combination are administered at the same time, they can be administered together in a single composition or they can be administered separately.

As used herein, the term "composition" is intended to encompass a product comprising the specified ingredients, as well as any product which results from combining the specified ingredients. Ingredients suitable for inclusion in a pharmaceutical composition are pharmaceutically acceptable ingredients, which means the ingredients must be compatible with each other and not deleterious to the recipient thereof. By "pharmaceutically acceptable" is meant that the ingredients of the pharmaceutical composition must be compatible with each other and not deleterious to the recipient thereof.

The term "subject" as used herein refers to an animal, preferably a mammal, most preferably a human, who has been the object of treatment, observation or experiment.

The term "effective amount" as used herein means an amount sufficient to inhibit HIV reverse transcriptase, inhibit HIV replication, exert a prophylactic effect, and/or a exert a therapeutic effect after administration. One embodiment of "effective amount" is a "therapeutically effective amount" which is an amount of a compound that is effective for inhibiting HIV reverse transcriptase, inhibiting HIV replication (either of the foregoing which may also be referred to herein as an "inhibition effective amount"), treating HIV infection, treating AIDS, delaying the onset of AIDS, and/or slowing progression of AIDS in a patient. Another embodiment of "effective amount" is a "prophylactically effective amount" which is an amount of the compound that is effective for prophylaxis of HIV infection or prophylaxis of AIDS in a patient. It is understood that an effective amount can simultaneously be both a therapeutically effective amount, e.g., for treatment of HIV infection, and a prophylactically effective amount, e.g., for prevention or reduction of risk for developing AIDS. When the compound of Formula I is administered as a salt, reference to an amount of the compound is to the free form (i.e., the non-salt form) of the compound.

In the method of the present invention (i.e., inhibiting HIV reverse transcriptase, treating or prophylaxis of HIV infection, inhibiting HIV replication, treating or prophylaxis of AIDS, delaying the onset of AIDS, or delaying or slowing progression of AIDS), the compounds of this invention, optionally in the form of a salt, can be administered by means that produces contact of the active agent with the agent's site of action. They can be administered by conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered orally, parenterally (including subcutaneous injections, intravenous, intramuscular, intrasternal injection or infusion techniques), by inhalation spray, or rectally, in the form of a unit dosage of a pharmaceutical composition containing an effective amount of the compound and conventional non-toxic pharmaceutically acceptable carriers, adjuvants and vehicles, any of which administration methods can be provided as a single dose, once-daily, or less frequently such as once weekly or once monthly in, for example but not limited to, the dosage ranges and amounts described below. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose. Further description of methods suitable for use in preparing pharmaceutical compositions for use in the present invention and of ingredients suitable for use in said compositions is provided in *Remington's Pharmaceutical Sciences,* 18th edition, edited by A. R. Gennaro, Mack Publishing Co., 1990 and in *Remington—The Science and Practice of Pharmacy,* 22nd Edition, published by Pharmaceutical Press and Philadelphia College of Pharmacy at University of the Sciences, 2012, ISBN 978 0 85711-062-6 and prior editions.

Formulations of compounds described by Formula I that result in drug supersaturation and/or rapid dissolution may be utilized to facilitate oral drug absorption. Formulation approaches to cause drug supersaturation and/or rapid dissolution include, but are not limited to, nanoparticulate systems, amorphous systems, solid solutions, solid dispersions, and lipid systems. Such formulation approaches and techniques for preparing them are well known in the art. For example, solid dispersions can be prepared using excipients and processes as described in reviews (e.g., A.T.M. Serajuddin, J Pharm Sci, 88:10, pp. 1058-1066 (1999)). Nanoparticulate systems based on both attrition and direct synthesis have also been described in reviews such as Wu et al (F. Kesisoglou, S. Panmai, Y. Wu, Advanced Drug Delivery Reviews, 59:7 pp. 631-644 (2007)).

The compounds of Formula I, and pharmaceutically acceptable salts thereof, are HIV reverse transcriptase inhibitors. The compounds are useful for inhibiting HIV reverse transcriptase and for inhibiting HIV replication in vitro and in vivo. More particularly, the compounds of Formula I inhibit the polymerase function of HIV-1 reverse transcriptase. The testing of compounds of the Examples of the invention in the assay set forth in the RT Polymerase Assay below, illustrates the ability of compounds of the invention to inhibit the RNA-dependent DNA polymerase activity of HIV-1 reverse transcriptase. The compounds of Formula I may also be useful agents against HIV-2.

The compounds of Formula I can be administered in a dosage range of 0.001 to 1000 mg/kg of mammal (e.g., human) body weight per day, or at other time intervals as appropriate, in a single dose or in divided doses. One example of a dosage range is 0.01 to 500 mg/kg body weight per day, or at other time intervals as appropriate, administered orally or via other routes of administration in a single dose or in divided doses. Another example of a dosage range is 0.1 to 100 mg/kg body weight per day, or at other time intervals as appropriate, administered orally or via other routes of administration in single or divided doses. For oral (e.g., tablets or capsules) or other routes of administration, the compositions can be provided containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy. In some cases, depending on the potency of the compound or the individual response, it may be necessary to deviate upwards or downwards from the given dose. Compounds of the invention can be administered as a single dose, once-daily, or less frequently such as once weekly or once monthly in, for example but not limited to, the dosage ranges and amounts noted above. Furthermore, the compound may be formulated for immediate or modified release such as extended or controlled release.

As noted above, the present invention is also directed to use of a compound of Formula I with one or more anti-HIV agents. An "anti-HIV agent" is any agent which is directly or indirectly effective in the inhibition of HIV, the treatment or prophylaxis of HIV infection, and/or the treatment, prophylaxis or delay in the onset or progression of AIDS. It is understood that an anti-HIV agent is effective in treating, preventing, or delaying the onset or progression of HIV infection or AIDS and/or diseases or conditions arising therefrom or associated therewith. For example, the compounds of this invention may be effectively administered, whether at periods of pre-exposure and/or post-exposure, in combination with effective amounts of one or more anti-HIV agents selected from HIV antiviral agents, imunomodulators, antiinfectives, or vaccines useful for treating HIV infection or AIDS. Suitable HIV antivirals for use in combination with the compounds of the present invention include, for example, those listed in Table 1 as follows:

TABLE 1

Antiviral Agents for Treating HIV infection or AIDS

| Name | Type |
| --- | --- |
| abacavir, ABC, Ziagen ® | nRTI |
| abacavir + lamivudine, Epzicom ® | nRTI |
| abacavir + lamivudine + zidovudine, Trizivir ® | nRTI |
| amprenavir, Agenerase ® | PI |
| atazanavir, Reyataz ® | PI |
| AZT, zidovudine, azidothymidine, Retrovir ® | nRTI |
| capravirine | nnRTI |
| darunavir, Prezista ® | PI |

TABLE 1-continued

Antiviral Agents for Treating HIV infection or AIDS

| Name | Type |
| --- | --- |
| ddC, zalcitabine, dideoxycytidine, Hivid ® | nRTI |
| ddI, didanosine, dideoxyinosine, Videx ® | nRTI |
| ddI (enteric coated), Videx EC ® | nRTI |
| delavirdine, DLV, Rescriptor ® | nnRTI |
| dolutegravir, Tivicay ® | InI |
| doravirine, MK-1439 | nnRTI |
| efavirenz, EFV, Sustiva ®, Stocrin ® | nnRTI |
| efavirenz + emtricitabine + tenofovir DF, Atripla ® | nnRTI + nRTI |
| EFdA (4'-ethynyl-2-fluoro-2'-deoxyadenosine) | nRTI |
| Elvitegravir | InI |
| emtricitabine, FTC, Emtriva ® | nRTI |
| emtricitabine + tenofovir DF, Truvada ® | nRTI |
| emvirine, Coactinon ® | nnRTI |
| enfuvirtide, Fuzeon ® | FI |
| enteric coated didanosine, Videx EC ® | nRTI |
| etravirine, TMC-125 | nnRTI |
| fosamprenavir calcium, Lexiva ® | PI |
| indinavir, Crixivan ® | PI |
| lamivudine, 3TC, Epivir ® | nRTI |
| lamivudine + zidovudine, Combivir ® | nRTI |
| lopinavir | PI |
| lopinavir + ritonavir, Kaletra ® | PI |
| maraviroc, Selzentry ® | EI |
| nelfinavir, Viracept ® | PI |
| nevirapine, NVP, Viramune ® | nnRTI |
| PPF-100 (also known as PL-462) (Ambrilia) | PI |
| raltegravir, MK-0518, Isentress ™ | InI |
| Rilpivirine | nnRTI |
| ritonavir, Norvir ® | PI |
| saquinavir, Invirase ®, Fortovase ® | PI |
| stavudine, d4T, didehydrodeoxythymidine, Zerit ® | nRTI |
| tenofovir DF (DF = disoproxil fumarate), TDF, Viread ® | nRTI |
| Tenofovir, hexadecyloxypropyl (CMX-157) | nRTI |
| Tenofovir alafenamide fumarate (GS-7340) | nRTI |
| tipranavir, Aptivus ® | PI |
| vicriviroc | EI |

EI = entry inhibitor;
FI = fusion inhibitor;
InI = integrase inhibitor;
PI = protease inhibitor;
nRTI = nucleoside reverse transcriptase inhibitor;
nnRTI = non-nucleoside reverse transcriptase inhibitor.
Some of the drugs listed in the table are used in a salt form; e.g., abacavir sulfate, delavirdine mesylate, indinavir sulfate, atazanavir sulfate, nelfinavir mesylate, saquinavir mesylate.

It is understood that the scope of combinations of the compounds of this invention with anti-HIV agents is not limited to the HIV antivirals listed in Table A, but includes in principle any combination with any pharmaceutical composition useful for the treatment or prophylaxis of AIDS. The HIV antiviral agents and other agents will typically be employed in these combinations in their conventional dosage ranges and regimens as reported in the art, including, for example, the dosages described in the Physicians' Desk Reference, Thomson PDR, Thomson PDR, 57th edition (2003), the 58th edition (2004), or the 59th edition (2005) and the current Physicians' Desk Reference (68th ed.). (2014), Montvale, N.J.: PDR Network. The dosage ranges for a compound of the invention in these combinations can be the same as those set forth above.

The compounds of this invention are also useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV reverse transcriptase, e.g., by competitive inhibition.

Abbreviations and acronyms employed herein include the following:

| | |
|---|---|
| ACN = acetonitrile | aq = aqueous |
| AcOH = acetic acid | AIBN = azobisisobutyronitrile |
| CHAPS = 3-((3-Cholamidopropyl)dimethylammonio)-1-Propanesulfonic | m-CPBA = 3-chloroperbenzoic acid |
| | Me = methyl |
| CSH = Charge Surface Hybrid | MeOH = methanol |
| DAST = (diethylamino)sulfur trifluoride | Me-THF = 2-methyltetrahydrofuran |
| DCE = 1,2-dichloroethane | min = minute |
| DCM = dichloromethane | MHz = megahertz |
| DEAD = diethyl azodicarboxylate | mL or ml = milliliter |
| DIBAL-H = diisobutylaluminum hydride | mol = moles |
| DIPEA = diisopropylethylamine | mmol = millimoles |
| DMF = N,N-dimethylformamide | NaH = sodium hydride |
| Dess-Martin periodinane = 1,1,1-Triacetoxy-1,1-dihydro-1,2-benziodoxol-3(1H)-one | NBS = N-bromosuccinimide |
| | NIS—N-iodosuccinimide |
| DMAP = 4-dimethylaminopyridine | NHS = normal human serum |
| DMSO = dimethyl sulfoxide | NMP = N-methyl-2-pyrrolidinone |
| EDTA = ethylenediaminetetraacetic acid | NMR = nuclear magnetic resonance |
| EtOAc = ethyl acetate | NTP = nucleoside triphosphate |
| EA = ethyl acetate | dNTP = 2'-deoxy nucleoside triphosphate |
| EGTA = ethylene glycol tetraacetic acid | PBS = phosphate buffered saline |
| EtOH = ethanol | PE, pet. ether = petroleum ether |
| FBS = fetal bovine serum | Ppm = parts per million |
| HIV = human immunodeficiency virus | PPTS = 4-toluenesulfonic acid |
| HPLC = high performance liquid chromatography | r.t. = room temperature |
| hr = hour | RT = reverse transcriptase |
| h = hour | TBAF = tetrabutylammonium fluoride |
| Hz = hertz | t-BuOH = tert-butanol |
| IBX = 2-iodoxybenzoic acid | TEA = triethylamine |
| LCAP = liquid chromatography area percent | THF = tetrahydrofuran |
| | TFA = trifluoroacetic acid |
| LCMS or LC-MS = liquid chromatography-mass spectroscopy | TLC = thin layer chromatography |
| L = liter | TBS-Cl = t-butyldimethylsilyl chloride |
| LDA = lithium diisopropylamide | TBDMS-Cl = t-butyldimethylsilyl chloride |
| LiHMDS = lithium hexamethyldisilazide | TMSCl = trimethylsilyl chloride |

Compounds of the invention can be prepared by methods well known in the art of organic chemistry. See, for example, J. March, '*Advanced Organic Chemistry*' 6th Edition, John Wiley and Sons. During synthetic sequences it may be necessary and/or desirable to protect sensitive or reactive groups on any of the molecules concerned. This is achieved by means of conventional protecting groups, such as those described in T. W. Greene and P. G. M. Wutts '*Protective Groups in Organic Synthesis*' 4th Edition, John Wiley and Sons. The protective groups are optionally removed at a convenient subsequent stage using methods well known in the art.

The compounds of the present invention can be readily prepared according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above.

Scheme 1

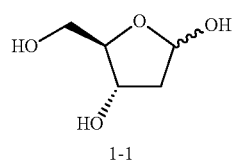

1-1

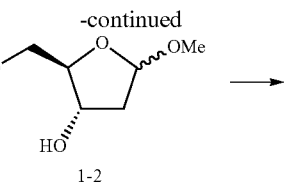

1-2

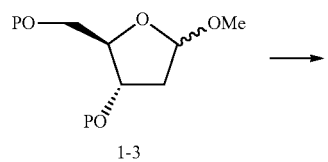

1-3

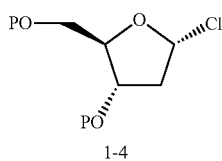

1-4

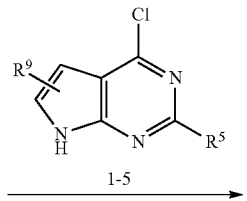

1-5

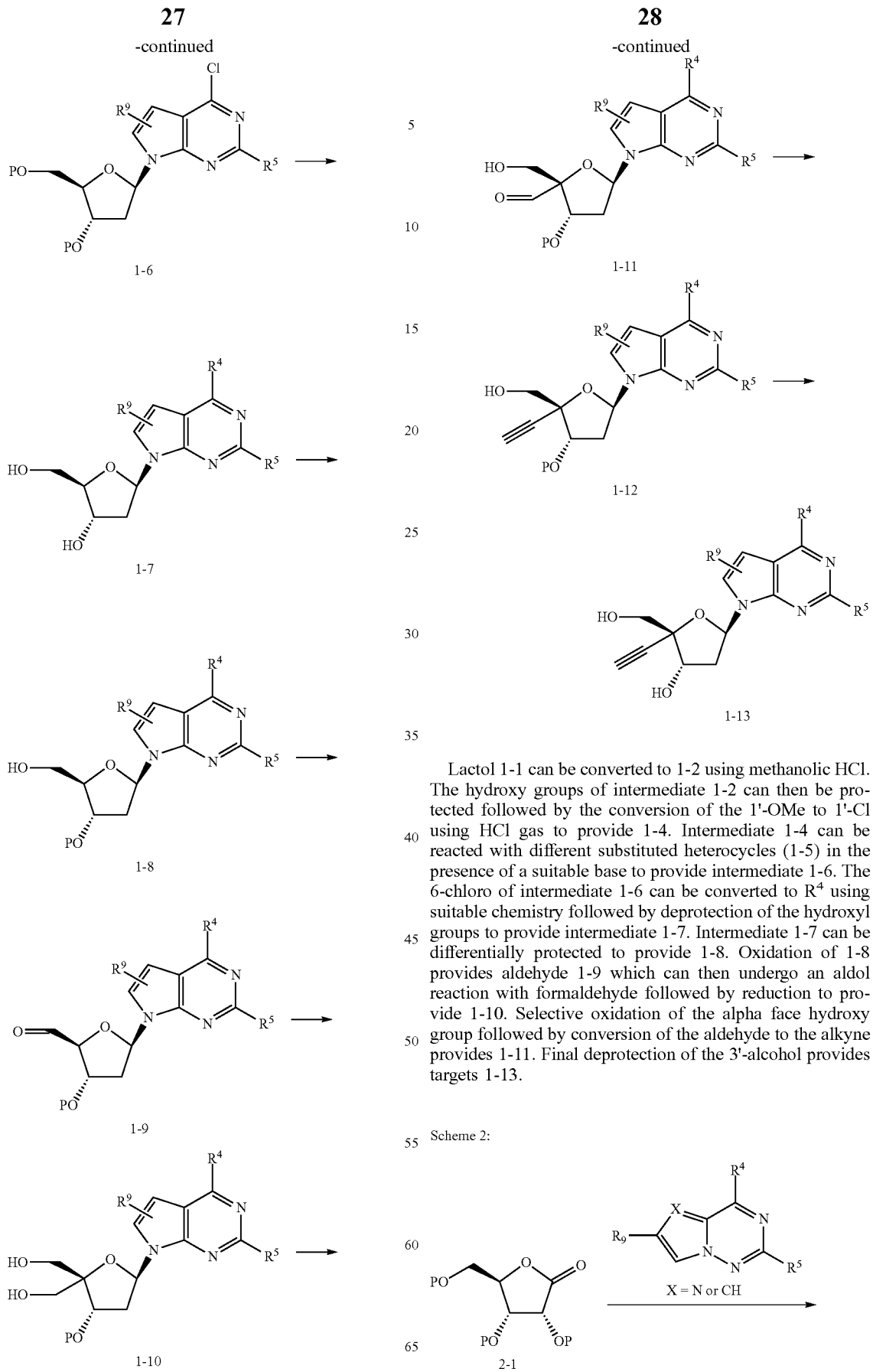

Lactol 1-1 can be converted to 1-2 using methanolic HCl. The hydroxy groups of intermediate 1-2 can then be protected followed by the conversion of the 1'-OMe to 1'-Cl using HCl gas to provide 1-4. Intermediate 1-4 can be reacted with different substituted heterocycles (1-5) in the presence of a suitable base to provide intermediate 1-6. The 6-chloro of intermediate 1-6 can be converted to $R^4$ using suitable chemistry followed by deprotection of the hydroxyl groups to provide intermediate 1-7. Intermediate 1-7 can be differentially protected to provide 1-8. Oxidation of 1-8 provides aldehyde 1-9 which can then undergo an aldol reaction with formaldehyde followed by reduction to provide 1-10. Selective oxidation of the alpha face hydroxy group followed by conversion of the aldehyde to the alkyne provides 1-11. Final deprotection of the 3'-alcohol provides targets 1-13.

Scheme 2:

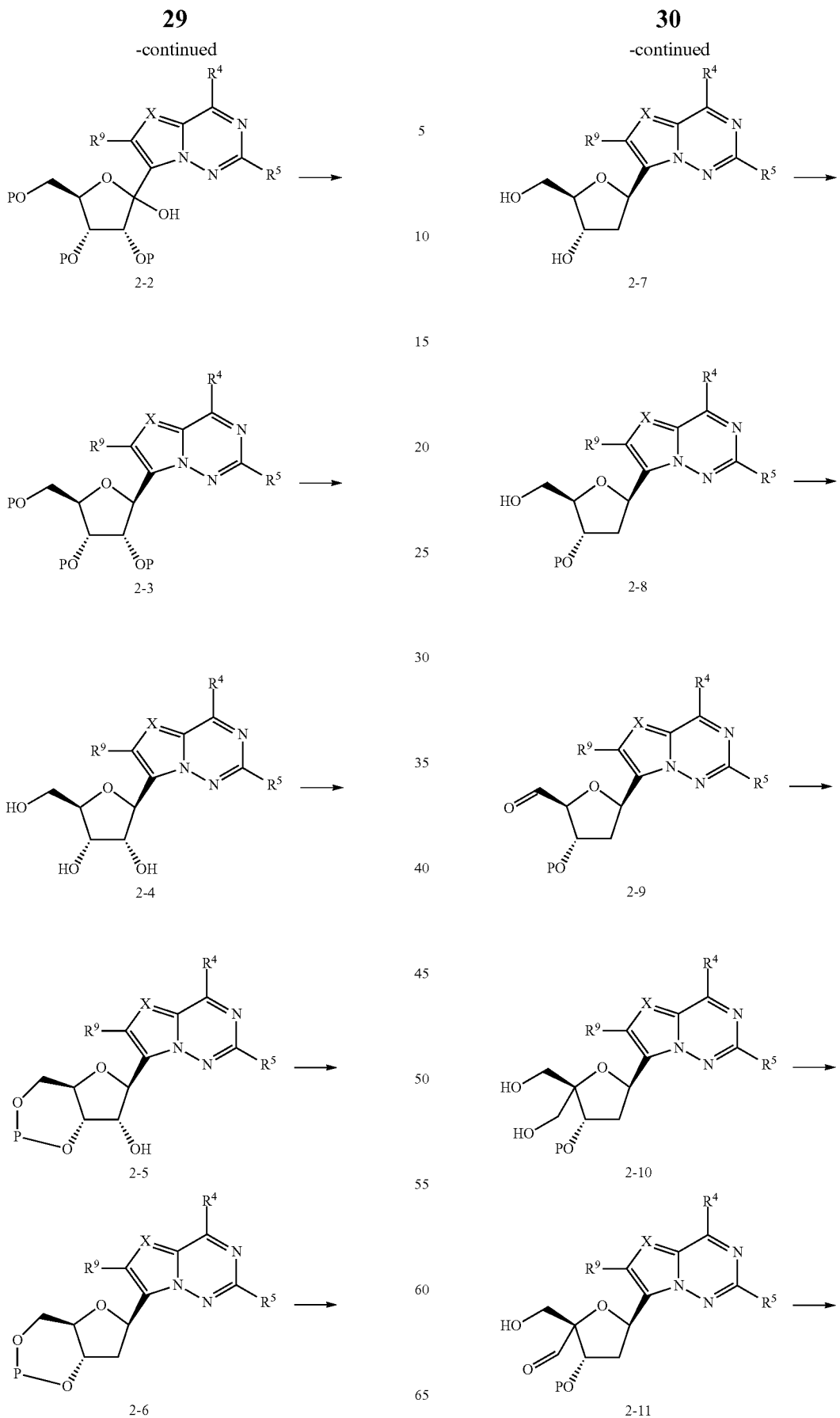

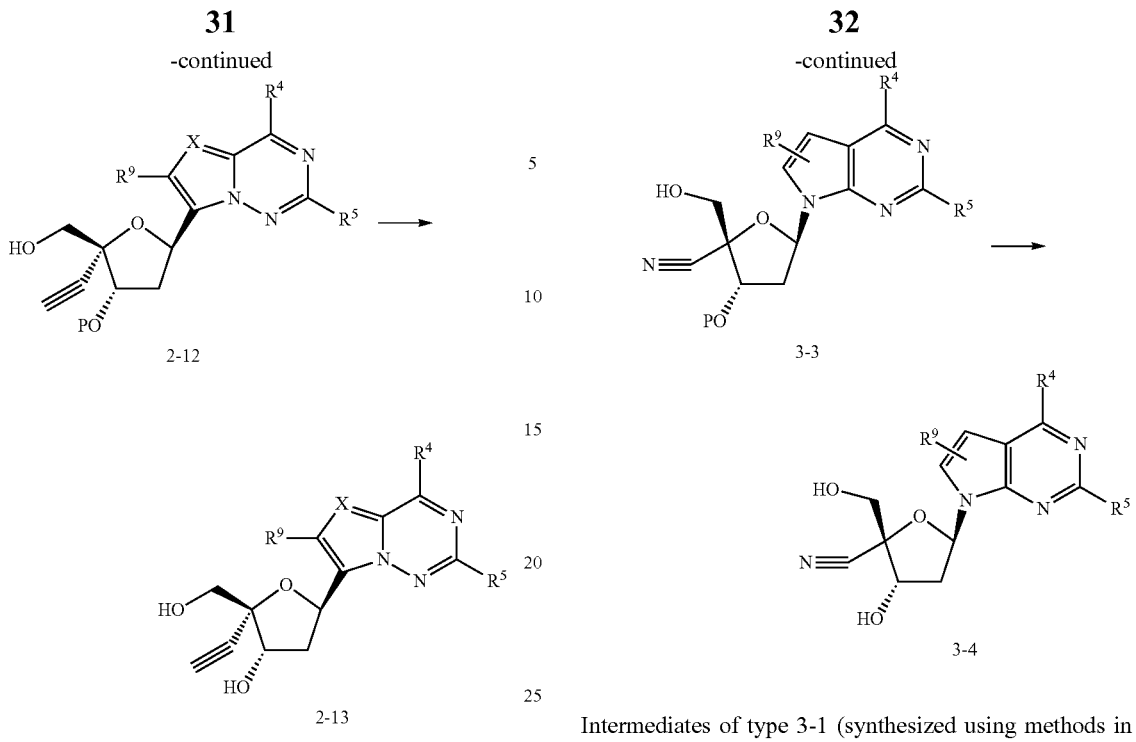

Lactone 2-1 can be treated with the anion of different heterocycles to provide intermediates of type 2-2. Intermediate 2-2 can be converted to 2-3 by treatment with acid in the presence of silanes. Deprotection of 2-3 followed by differential protection of the 3' and 5' hydroxyls provides 2-5. Deoxygenation of 2-5 provides 2-6 which can then be deprotected followed by differential protection to provide 2-8. Oxidation of the terminal alcohol to 2-9 followed by aldol reaction with formaldehyde and reduction provides the 2-10. Selective oxidation of the alpha face alcohol provides aldehyde 2-11 which can then be converted to the acetylene 2-12. Global deprotection affords 2-13.

Intermediates of type 3-1 (synthesized using methods in scheme 1) are converted to oximes of type 3-2. Dehydration of the oxime leads to compounds 3-3 which can undergo final deprotection to provide targets 3-4.

Scheme 4:

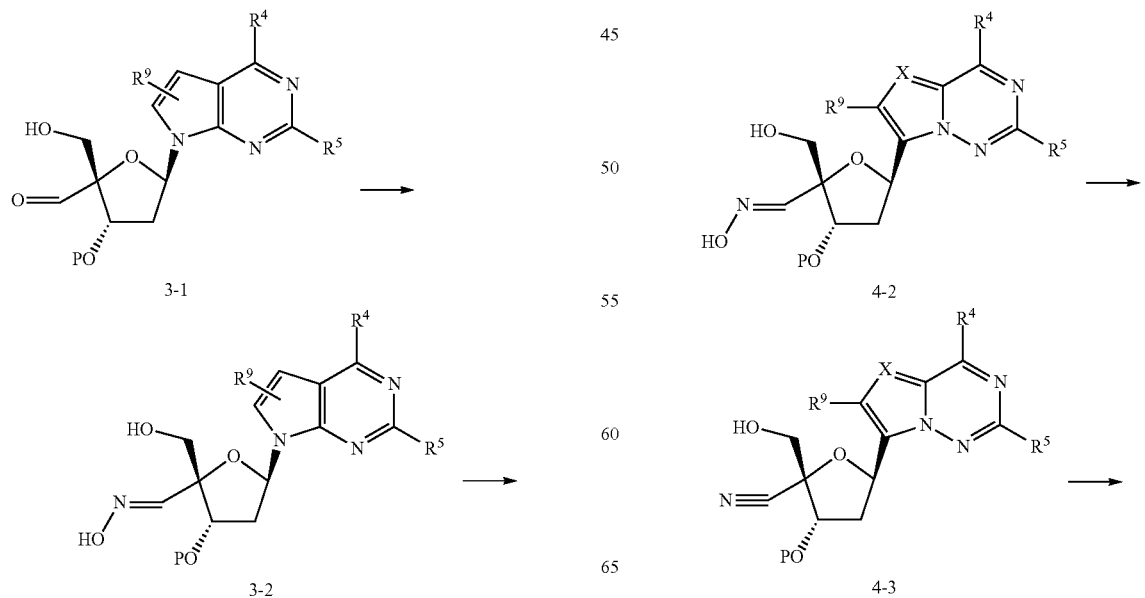

Scheme 3:

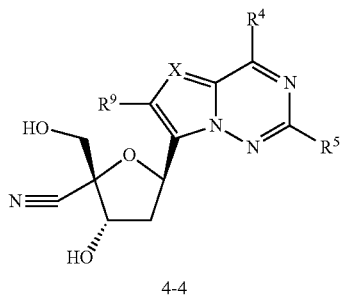

4-4

X = CH or N

Intermediates of type 4-1 (synthesized using methods in scheme 2) are converted to oximes of type 4-2. Dehydration of the oxime leads to compounds 4-3 which can undergo final deprotection to provide targets 4-4.

Scheme 5:

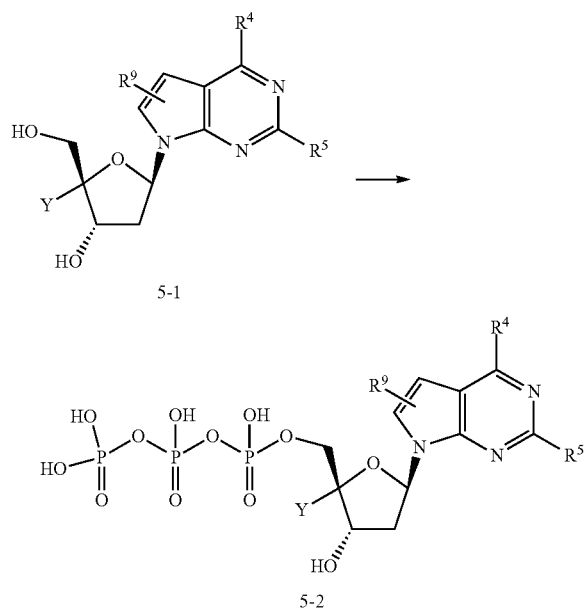

Intermediates of type 5-1 (Synthesized using methods from previous schemes) can be converted to the triphosphates 5-2 using literature known methods.

Scheme 6:

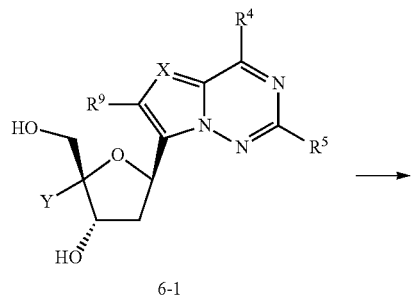

6-1

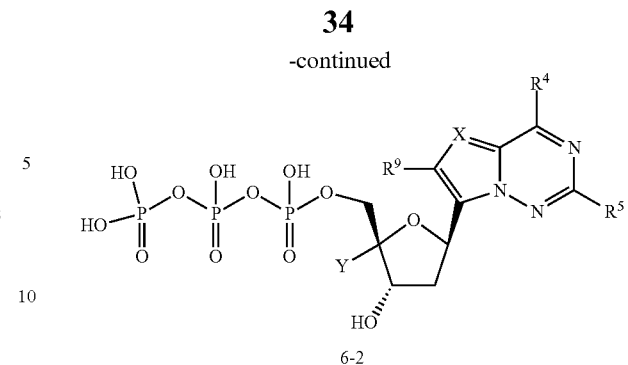

6-2

Intermediates of type 6-1 (Synthesized using methods from previous schemes) can be converted to the triphosphates 6-2 using literature known methods.

General Chemical Procedures:

All reagents were either purchased from common commercial sources or synthesized according to literature procedures beginning from commercial reagents. Commercial reagents were used without further purification. Unless otherwise indicated, percent is percent by weight given the component and the total weight of the composition, temperature is in ° C. or is at ambient temperature and pressure is at or near atmospheric. $^1$H NMR spectra were obtained on a Varian VNMR System 400 (400 MHz) and are reported as ppm downfield from Me$_4$Si with number of protons, multiplicities, and coupling const=ants in Hertz indicated parenthetically. Where LC/MS data are presented, analyses was performed using an Agilent 6110A MSD or an Applied Biosystems API-100 mass spectrometer. The parent ion is given. Preparative HPLC was performed on a Waters preparative HPLC system fitted with a Waters Xselect. C18 column, typically using gradient elution with water/acetonitrile containing 0.075% trifluoro acetic acid. Flash column chromatography was performed using pre-packed normal phase silica from Biotage, Inc. or bulk silica from Fisher Scientific. Unless otherwise indicated, column chromatography was performed using a gradient elution of petroleum ether/ethyl acetate, from petroleum ether 100% to 100% ethyl acetate. The term "room temperature" in the examples refers to the ambient temperature which was typically in the range of about 20° C. to about 26° C.

Intermediate A (2R,3S,5R)-5-chloro-2-(((4-methylbenzoyl)oxy)methyl)tetrahydrofuran-3-yl 4-methylbenzoate Intermediate A

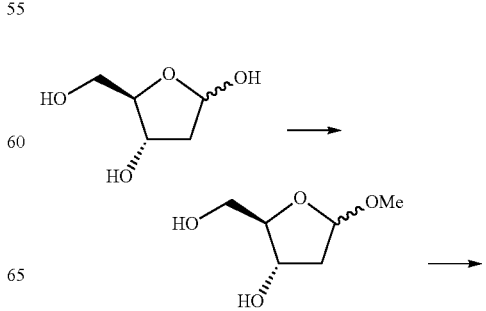

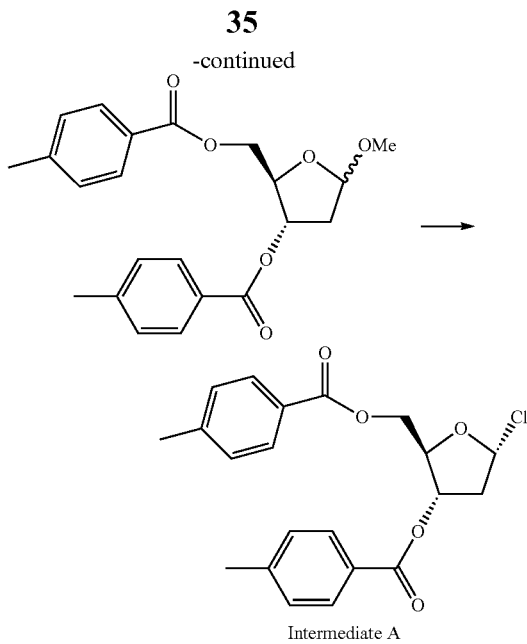

Intermediate A

Step 1: Synthesis of (2R,3S)-2-(hydroxymethyl)-5-methoxytetrahydrofuran-3-ol To a stirred solution of (4S,5R)-5-(hydroxymethyl)tetrahydrofuran-2,4-diol (7.0 g, 52.2 mmol) in anhydrous methanol (105 mL) under argon atmosphere, was added acetyl chloride (0.614 g, 7.83 mmol) dropwise with stirring at 0° C. over 5 minutes and the resulting mixture was stirred at 0° C. for 3 hours. Then solid sodium bicarbonate was added to neutralize the reaction mixture. The organic phase was collected by filtration and then concentrated under reduced pressure to give a residue as syrup. The residue was purified by silica gel (100-200 mesh) chromatography with dichloromethane/methanol (20/1) to give the title compound. $^1$H-NMR: (300 MHz, CDCl$_3$, ppm): δ 4.98-5.04 (m, 1H), 4.21-4.23 (m, 0.4H), 4.07-4.09 (m, 0.6H), 3.83-3.89 (m, 1H), 3.50-3.66 (m, 2H), 3.27-3.32 (m, 3H), 2.23-2.29 (m, 0.6H), 2.08-2.12 (m, 0.4H), 1.98-2.03 (m, 0.4H), 1.77-1.83 (m, 0.6H).

Step 2: Synthesis of (2R,3S)-5-methoxy-2-(((4-methylbenzoyl)oxy)methyl)tetrahydrofuran-3-yl 4-methylbenzoate To a stirred solution of (2R,3S)-2-(hydroxymethyl)-5-methoxytetrahydrofuran-3-ol (6.5 g, 43.9 mmol) in dry pyridine (45 mL) under argon atmosphere, was added 4-methylbenzoyl chloride (20.35 g, 132 mmol) dropwise at 0° C. over period of 15 minutes. The resulting mixture was gradually warmed to 30° C. and then stirred for 16 hours. The resulting solution was concentrated under reduced pressure. The resulting residue was diluted with ethyl acetate (400 mL), and then washed with aqueous hydrogen chloride (1 mol/L, 2×100 mL), saturated aqueous sodium bicarbonate (2×100 mL) and brine (100 mL) respectively. The organic phase was collected, dried over anhydrous sodium sulfate, filtered and concentrated under reduced pressure. The residue was purified by silica gel (100-200 mesh) chromatography with petroleum ether/ethyl acetate (20:1) to give the title compound. $^1$H-NMR: (300 MHz, CDCl$_3$, ppm): δ 7.90-7.99 (m, 4H), 7.20-7.26 (m, 4H), 5.58-5.61 (m, 0.47H), 5.39-5.42 (m, 0.55H), 5.18-5.24 (m, 1H), 4.46-4.65 (m, 3H), 3.43 (s, 1.61H), 3.36 (s, 1.33H), 2.52-2.60 (m, 1H), 2.17-2.43 (m, 7H).

Step 3: (2R,3S,5R)-5-chloro-2-(((4-methylbenzoyl)oxy)methyl)tetrahydrofuran-3-yl 4-methylbenzoate Intermediate A To a stirred solution of (2R,3S)-5-methoxy-2-(((4-methylbenzoyl)oxy)methyl)tetrahydrofuran-3-yl 4-methylbenzoate (4.0 g, 10.41 mmol) in anhydrous diethyl ether (20 mL) in a 100 mL three necked round-bottom flask, was introduced HCl (g). The product was gradually precipitated out over period of 40 min at 0° C. The solid was filtered and washed with dry diethyl ether (3×20 mL), dried under high vacuum for 2 hours to give Intermediate A as a solid. $^1$H-NMR: (300 MHz, CDCl$_3$, ppm): δ 7.96 (d, J=9.0 Hz, 2H), 7.90 (d, J=8.1 Hz, 2H), 7.19-7.27 (m, 4H), 6.47 (d, J=5.1 Hz, 1H), 5.54-5.58 (m, 1H), 4.85 (dd, J=3.3 Hz, J=7.2 Hz, 1H), 4.68 (dd, J=3.3 Hz, J=12.0 Hz, 1H), 4.59 (dd, J=4.2 Hz, J=12.0 Hz, 1H), 2.83-2.92 (m, 1H), 2.74 (d, J=15.0 Hz, 1H), 2.42 (d, J=3.6 Hz, 6H).

Example 1

Synthesis of (2R,3S,5R)-5-(4-amino-7H-pyrrolo[2,3-d]pyrimidin-7-yl)-2-ethynyl-2-(hydroxymethyl)tetrahydrofuran-3-ol (1)

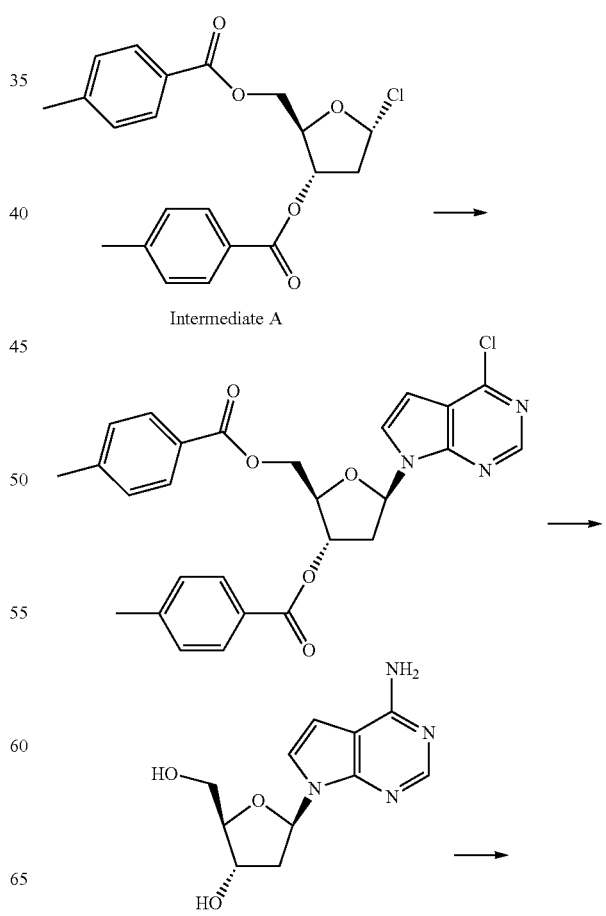

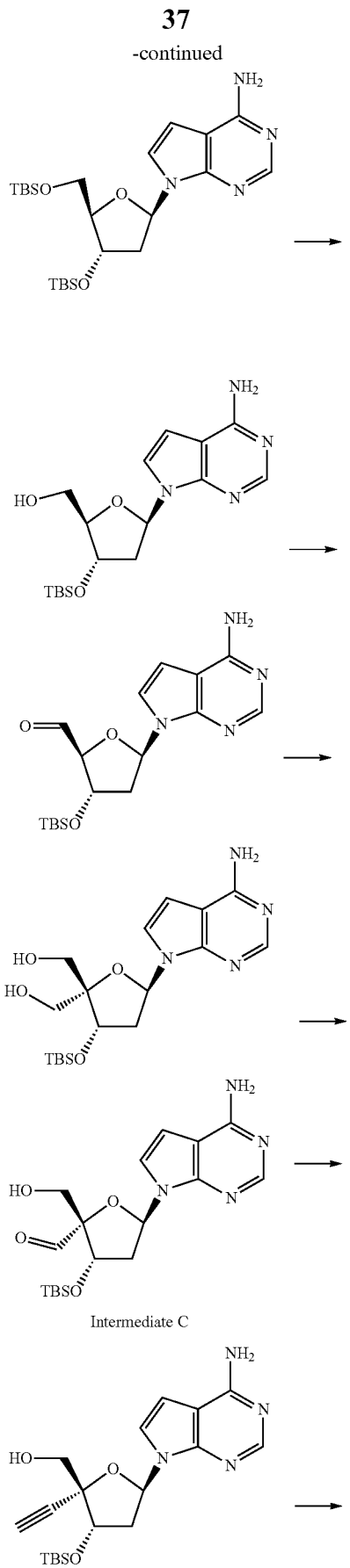

Intermediate C

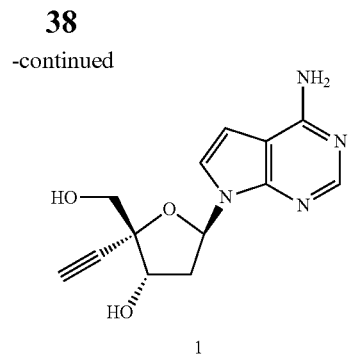

Step 1: Synthesis of (2R,3S,5R)-5-(4-chloro-7H-pyrrolo[2,3-d]pyrimidin-7-yl)-2-(((4-methylbenzoyl)oxy)methyl)tetrahydrofuran-3-yl 4-methylbenzoate To a suspension of sodium hydride (60% dispersion in mineral oil, 0.272 g, 6.79 mmol) in anhydrous acetonitrile (50 ml) under argon atmosphere in a 250 ml three necked round-bottom flask, was added 4-chloro-7H-pyrrolo[2,3-d]pyrimidine (0.948 g, 6.17 mmol) and the mixture was stirred at ambient temperature for 30 minutes. (2R,3S,5R)-5-chloro-2-(((4-methylbenzoyl)oxy)methyl)tetrahydrofuran-3-yl 4-methylbenzoate (2.4 g, 6.17 mmol) was added in portions with stirring. The reaction mixture was heated to 50° C. and stirred for 2 hours. The reaction progress was monitored by TLC & LCMS. Evaporation of the reaction mixture gave an oily residue, which was purified by silica-gel chromatography with ethyl acetate/petroleum ether (1:6, v/v) to give the title compound. $^1$H-NMR: (300 MHz, CDCl$_3$, ppm): δ 8.64 (s, 1H), 7.98 (d, J=8.1 Hz, 2H), 7.92 (d, J=8.1 Hz, 2H), 7.43 (d, J=3.6 Hz, 1H), 7.20-7.30 (m, 4H), 6.82 (dd, J=5.7 Hz, J=8.1 Hz, 1H), 6.60 (d, J=3.9 Hz, 1H), 4.60-4.76 (m, 3H), 2.86-2.96 (m, 1H), 2.74-2.82 (m, 1H), 2.43 (d, J=5.4 Hz, 6H). LC-MS: (ES, m/z): 506.43 [M+H]$^+$.

Step 2: Synthesis of (2R,3S,5R)-5-(4-amino-7H-pyrrolo[2,3-d]pyrimidin-7-yl)-2-(hydroxymethyl)tetrahydrofuran-3-ol (2R,3S,5R)-5-(4-chloro-7H-pyrrolo[2,3-d]pyrimidin-7-yl)-2-(((4-methylbenzoyl)oxy)methyl)tetrahydrofuran-3-yl 4-methylbenzoate (2.18 g, 4.31 mmol) was added to an 80 ml steel bomb and it was cooled down to −40° C. To this was added isopropanolic ammonia (saturated at −40° C., 60 ml). After the mixture was stirred at 90° C. and for 15 hours, it was cooled down to room temperature and concentrated under vacuum. The residue was purified by silica gel column chromatography with dichloromethane/methanol (4/1) to give the title compound. $^1$H-NMR: (400 MHz, d$_6$-DMSO, ppm): δ 8.04 (s, 1H), 7.34 (d, J=3.6 Hz, 1H), 7.04 (br, 2H), 6.58 (d, J=3.6 Hz, 1H), 6.48 (dd, J=6.0 Hz, J=8.0 Hz, 1H), 5.24 (d, J=3.6 Hz, 1H), 5.16 (t, J=4.2 Hz, 1H), 4.34 (d, J=2.0 Hz, 1H), 3.82 (dd, J=4.0 Hz, J=6.4 Hz, 1H), 3.48-3.58 (m, 2H), 2.48-2.54 (m, 1H), 2.13-2.17 (m, 1H).

Step 3: Synthesis of 7-((2R,4S,5R)-4-((tert-butyldimethylsilyl)oxy)-5-(((tert-butyldimethylsilyl)oxy)methyl)tetrahydrofuran-2-yl)-7H-pyrrolo[2,3-d]pyrimidin-4-amine (2R,3S,5R)-5-(4-amino-7H-pyrrolo[2,3-d]pyrimidin-7-yl)-2-(hydroxymethyl)tetrahydrofuran-3-ol (950 mg, 3.796 mmol) and imidazole (775.4 mg, 11.388 mmol) were added into a 25 mL round bottom flask under argon atmosphere. To the flask was injected anhydrous DMF (8 mL), followed by the addition of t-butyldimethylsilyl chloride (1716.4 mg, 11.388 mmol). After the mixture was stirred at 25° C. for 3 hours, it was diluted with ethyl acetate (40 mL), washed with water (20 mL×2), aqueous NaHCO$_3$ (saturated, 20 mL×2) and brine (20 mL×2) respectively. The organic layer was collected and dried over anhydrous Na$_2$SO$_4$, filtered and concentrated under reduced pressure to give crude product. The crude product was then purified by silica gel chromatography with ethyl acetate/petroleum ether (35% to 42% ethyl acetate in petroleum ether) to give the title compound. $^1$H-NMR: (300 MHz, CDCl$_3$, ppm): δ 8.32 (s, 1H), 7.32 (d, J=3.9 Hz, 1H), 6.69 (t, J=6.6 Hz, 1H), 6.39 (d, J=3.6 Hz, 1H), 5.29 (br, 2H), 4.56-4.61 (m, 1H), 3.96 (dd, J=3.5 Hz, J=7.0 Hz, 1H), 3.74-3.84 (m, 2H), 2.42-2.51 (m, 1H), 2.30-2.38 (m, 1H), 0.92 (d, J=4.2 Hz, 18H), 0.08-0.1 (m, 12H). LC-MS: (ES, m/z): 497.71 [M+H]$^+$.

Step 4: Synthesis of ((2R,3S,5R)-5-(4-amino-7H-pyrrolo[2,3-d]pyrimidin-7-yl)-3-((tert-butyldimethylsilyl)oxy)tetrahydrofuran-2-yl)methanol To a stirred solution of 7-((2R,4S,5R)-4-((tert-butyldimethylsilyl)oxy)-5-(((tert-butyldimethylsilyl)oxy)methyl)tetrahydrofuran-2-yl)-7H-pyrrolo[2,3-d]pyrimidin-4-amine (1.2 g, 2.506 mmol) in THF (24 mL), was added a pre-cooled solution of trifluoroacetic acid/water (1/2, v/v, 9 mL) dropwise at 0° C. over period of 10 minutes. The resulting mixture was stirred at 0° C. for 4 hours and then co-evaporated with toluene below 25° C. for three times to give a syrup. The crude product was purified by silica gel column chromatography with ethyl acetate/dichloromethane (1/1) to give the title compound. $^1$H-NMR: (300 MHz, d$_6$-DMSO, ppm): δ 8.03 (s, 1H), 7.34 (d, J=3.9 Hz, 1H), 7.03 (brs, 2H), 6.58 (d, J=3.6 Hz, 1H), 6.46 (dd, J=5.7 Hz, 1H), 5.19 (t, J=5.7 Hz, 1H), 4.51-4.53 (m, 1H), 3.79-3.83 (m, 1H), 3.47-3.57 (m, 2H), 2.55-2.64 (m, 1H), 2.10-2.17 (m, 1H), 0.9 (s, 9H), 0.11 (s, 6H).

Step 5: Synthesis of (2S,3S,5R)-5-(4-amino-7H-pyrrolo[2,3-d]pyrimidin-7-yl)-3-((tert-butyldimethylsilyl)oxy)tetrahydrofuran-2-carbaldehyde To a stirred solution of ((2R,3S,5R)-5-(4-amino-7H-pyrrolo[2,3-d]pyrimidin-7-yl)-3-((tert-butyldimethylsilyl)oxy)tetrahydrofuran-2-yl)methanol (100 mg, 0.274 mmol) in anhydrous acetonitrile (10 mL) under argon atmosphere in a 25 mL round-bottom flask, was added 2-Iodoxybenzoic acid (230 mg, 0.823 mmol). The resulting mixture was refluxed for 0.5 hours and then cooled down to room temperature. The solids were filtered out and the filtrate was concentrated under reduced pressure to give the title compound, which was used to the next reaction step directly without further purification. LC-MS: (ES, m/z): 363.20 [M+H]$^+$, 381.20 [M+H+H$_2$O]$^+$.

Step 6: Synthesis of ((4S,5R)-5-(4-amino-7H-pyrrolo[2,3-d]pyrimidin-7-yl)-3-((tert-butyldimethylsilyl)oxy)tetrahydrofuran-2,2-diyl)dimethanol To a stirred solution of (2S,3S,5R)-5-(4-amino-7H-pyrrolo[2,3-d]pyrimidin-7-yl)-3-((tert-butyldimethylsilyl)oxy)tetrahydrofuran-2-carbaldehyde (100 mg, 0.276 mmol, crude) in 1,4-Dioxane (1 mL), was added formaldehyde solution (0.3 mL, 4.00 mmol), followed by the addition of sodium hydroxide solution (0.3 mL, 0.600 mmol, 2 M) dropwise in 1 minute. The resulting mixture was stirred at 25° C. for 3 hours. After the reaction completed, the reaction mixture was neutralized by addition of acetic acid, diluted with ethyl acetate and washed successively with water, saturated aqueous NaHCO$_3$ and brine, dried over Na$_2$SO$_4$ and evaporated under reduced pressure. The residue was re-dissolved in anhydrous ethanol (2 mL) and added sodium borohydride (20.87 mg, 0.552 mmol) in portions at 0° C. After stirring for 1 hour at 25° C., the reaction mixture was neutralized by addition of acetic acid, diluted with chloroform (20 mL), washed with water and brine. The organic layer was dried over Na$_2$SO$_4$, and evaporated under reduced pressure. The residue was purified by preparative-TLC with dichloromethane/methanol (20/1) to give the title compound. $^1$H-NMR: (300 MHz, d$_6$-DMSO, ppm): δ 8.03 (s, 1H), 7.37 (d, J=3.6 Hz, 1H), 7.02 (brs, 2H), 6.57 (d, J=3.6 Hz, 1H), 6.50 (dd, J=5.7 Hz, J=8.1 Hz, 1H), 5.12 (dd, J=5.1 Hz, J=6.3 Hz, 1H), 4.59-4.60 (m, 1H), 4.38 (dd, J=5.1 Hz, J=6.3 Hz, 1H), 3.46-3.61 (m, 4H), 2.70-2.75 (m, 1H), 2.13-2.20 (m, 1H), 0.90 (s, 9H), 0.09 (s, 6H). LC-MS: (ES, m/z): 395.20 [M+H]$^+$.

Step 7: Synthesis of (2R,3S,5R)-5-(4-amino-7H-pyrrolo[2,3-d]pyrimidin-7-yl)-3-((tert-butyldimethylsilyl)oxy)-2-(hydroxymethyl)tetrahydrofuran-2-carbaldehyde To a stirred solution of ((3S,5R)-5-(4-amino-7H-pyrrolo[2,3-d]pyrimidin-7-yl)-3-((tert-butyldimethylsilyl)oxy)tetrahydrofuran-2,2-diyl)dimethanol (100 mg, 0.253 mmol) in anhydrous acetonitrile (20 mL) under argon atmosphere, was added 2-Iodoxybenzoic acid (284 mg, 1.014 mmol). The resulting mixture was stirred at 30° C. for 36 hours. LCMS indicated that little part of started diol-nucleoside was left, and target compound was the major product. The mixture was filtered, washed with dichloromethane. The filtrate was collected and concentrated under reduced pressure to give the title compound, which was used to the next reaction step directly without further purification. LC-MS: (ES, m/z): 393.28 [M+H]$^+$.

Step 8: Synthesis of ((2R,3S,5R)-5-(4-amino-7H-pyrrolo[2,3-d]pyrimidin-7-yl)-3-((tert-butyldimethylsilyl)oxy)-2-ethynyltetrahydrofuran-2-yl)methanol To a stirred solution of (2R,3S,5R)-5-(4-amino-7H-pyrrolo[2,3-d]pyrimidin-7-yl)-3-((tert-butyldimethylsilyl)oxy)-2-(hydroxymethyl)tetrahydrofuran-2-carbaldehyde (100 mg, 0.248 mmol, crude) in anhydrous methanol (10 mL) under argon atmosphere, was added potassium carbonate (68.04 mg, 0.492 mmol). The mixture was cooled down to 0° C., then dimethyl (1-diazo-2-oxopropyl)phosphonate (94.56 mg, 0.492 mmol) was added dropwise in 2 minutes. After the resulting mixture was stirred at 25° C. overnight, it was concentrated under reduced pressure. The residue was purified by preparative-TLC (methanol/dichloromethane=1/15) to give the title compound. $^1$H-NMR: (300 MHz, CDCl$_3$, ppm): δ 8.24 (s, 1H), 7.04 (d, J=3.6 Hz, 1H), 6.35 (d, J=3.6 Hz, 1H), 6.31 (dd, J=5.7 Hz, J=9.3 Hz, 1H), 5.48 (br, 2H), 4.73 (d, J=4.2 Hz, 1H), 4.03 (d, J=12.6 Hz, 1H), 3.80 (d, J=12.3 Hz, 1H), 3.13-3.23 (m, 1H), 2.58 (s, 1H), 2.22-2.28 (m, 1H), 0.95 (s, 9H), 0.15 (d, J=7.2 Hz, 6H).

Step 9: Synthesis of (2R,3S,5R)-5-(4-amino-7H-pyrrolo[2,3-d]pyrimidin-7-yl)-2-ethynyl-2-(hydroxymethyl)tetrahydrofuran-3-ol To a stirred solution of ((2R,3S,5R)-5-(4-amino-7H-pyrrolo[2,3-d]pyrimidin-7-yl)-3-((tert-butyldimethylsilyl)oxy)-

2-ethynyltetrahydrofuran-2-yl)methanol (60 mg, 0.154 mmol) in anhydrous THF (2 mL) under argon atmosphere, was added 1M tetrabutylammonium fluoride THF solution (0.309 mL, 0.309 mmol) dropwise in 1 minute at ambient temperature. The resulting solution was stirred at this temperature for 2 hours. The reaction progress was monitored by TLC. Upon the started nucleoside was all consumed, the mixture was concentrated under reduced pressure. The residue was purified by preparative-TLC (methanol/dichloromethane=1/9) to give crude title compound that was further purified by preparative-HPLC with the following conditions: (1#-Pre-HPLC-011(Waters)): Column, X-select CSH Column, 19*150 mm, 5um; mobile phase, water with 10 mmol ammonium bicarbonate and acetonitrile (5% acetonitrile up to 20% in 7.5 min, up to 95% in 2 min); Detector, UV 254 & 220 nm to give compound 1 as a solid. $^1$H-NMR: (300 MHz, $d_6$-DMSO, ppm): δ 8.05 (s, 1H), 7.31 (d, J=3.6 Hz, 1H), 7.03 (brs, 2H), 6.58 (d, J=3.6 Hz, 1H), 6.50 (t, J=6.3 Hz, 1H), 5.40-5.49 (m, 2H), 4.49 (dd, J=6.0 Hz, J=11.4 Hz, 1H), 3.51-3.66 (m, 2H), 3.46 (s, 1H), 2.55-2.59 (m, 1H), 2.28-2.39 (m, 1H). LC-MS: (ES, m/z): 275.20 [M+H]$^+$.

Example 2

Synthesis of (2R,3S,5R)-5-(4-amino-5-fluoro-7H-pyrrolo[2,3-d]pyrimidin-7-yl)-2-ethynyl-2-(hydroxymethyl)tetrahydrofuran-3-ol (2)

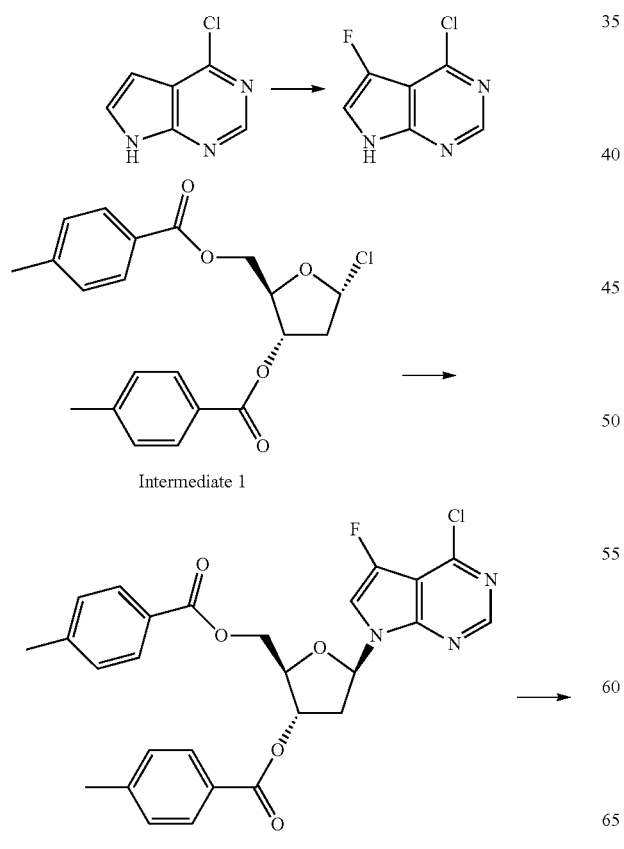

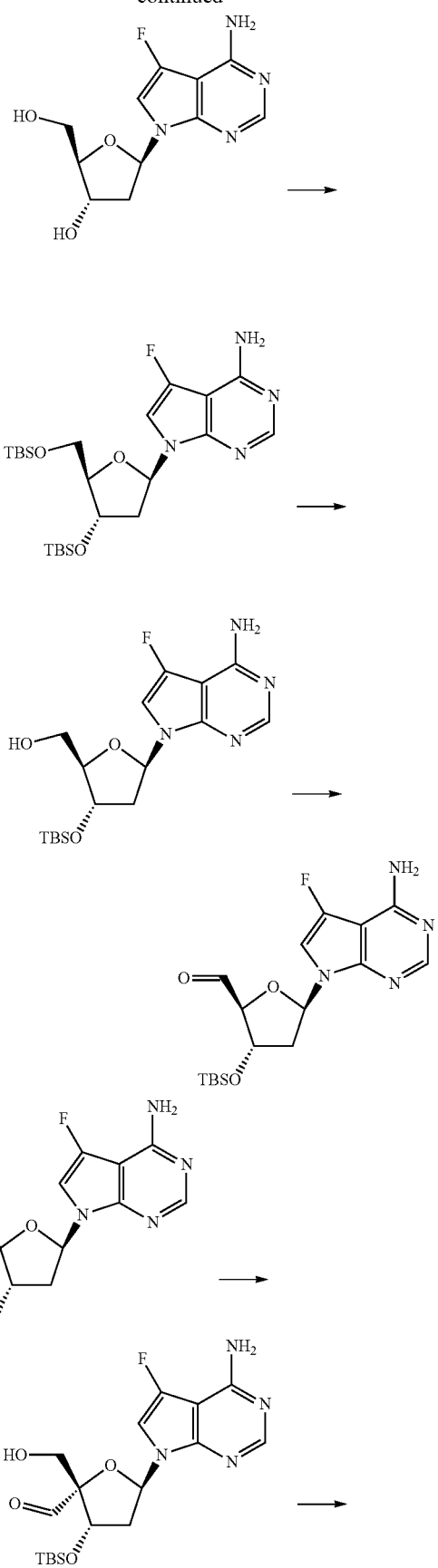

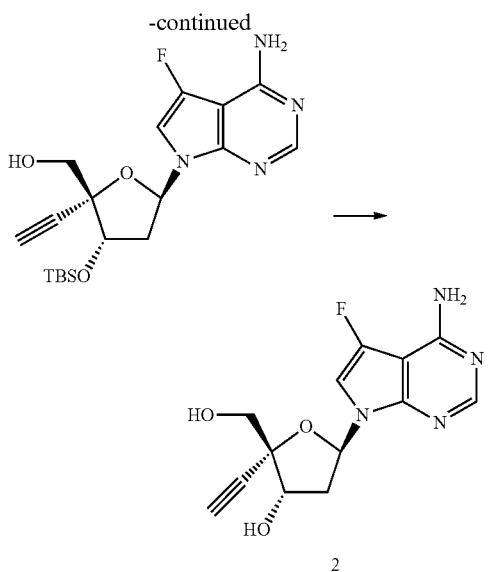

Step 1: Synthesis of 4-chloro-5-fluoro-7H-pyrrolo[2,3-d]pyrimidine 4-chloro-7H-pyrrolo[2,3-d]pyrimidine (5 g, 32.6 mmol) and SELECTFLUOR® (1-chloromethyl-4-fluoro-1,4-diazoniabicyclo[2.2.2]octane bis(tetrafluoroborate)) (17.30 g, 48.8 mmol) were placed in a 500 mL round-bottom flask under argon atmosphere. To the above was added dry acetonitrile (150 mL) and dry acetic acid (50 mL). The mixture was heated at 70° C. and stirred for 16 hours. After cooling down to room temperature, the solvents were removed under reduced pressure and the residue was co-evaporated with toluene. The crude solid was dissolved in a mixture of dichloromethane/ethyl acetate (1:1) and filtered through a pad of silica gel. The combined organic phases were evaporated under reduced pressure. The crude product was then purified by silica gel chromatography with dichloromethane/ethyl acetate (5:1) to give the title compound. $^1$H-NMR: (400 MHz, $d_6$-DMSO, ppm): δ 12.48 (brs, 1H), 8.62 (s, 1H), 7.71 (t, J=2.6 Hz, 1H). F-NMR: (376 MHz, $d_6$-DMSO, ppm): δ −170.76 (s, 1F). LC-MS: (ES, m/z): 172.00 [M+H]$^+$.

Step 2: Synthesis of (2R,3S,5R)-5-(4-chloro-5-fluoro-7H-pyrrolo[2,3-d]pyrimidin-7-yl)-2-(((4-methylbenzoyl)oxy)methyl)tetrahydrofuran-3-yl 4-methylbenzoate To a suspension of sodium hydride 60% dispersion in mineral oil (0.177 g, 4.41 mmol) in anhydrous acetonitrile (40 mL) under argon atmosphere, was added 4-chloro-5-fluoro-7H-pyrrolo[2,3-d]pyrimidine (0.688 g, 4.01 mmol) in portions and the mixture was stirred at ambient temperature for 30 minutes. Then Intermediate A (1.56 g, 4.01 mmol) was added in portions. After the reaction mixture was heated to 50° C. and stirred for 2 hours, the volatile was removed under reduced pressure, the residue of was then purified by silica gel chromatography with ethyl acetate/petroleum ether (1/1) to give the title compound. $^1$H-NMR: (300 MHz, CDCl$_3$, ppm): δ 8.62-8.68 (m, 1H), 7.91-7.99 (m, 4H), 7.26-7.29 (m, 4H), 7.16-7.18 (m, 2H), 6.84-6.88 (m, 1H), 5.74-5.76 (m, 1H), 4.60-4.74 (m, 3H), 2.74-2.79 (m, 2H), 2.43-2.46 (m, 6H). LC-MS: (ES, m/z): 524.30 [M+H]$^+$.

Step 3: Synthesis of (2R,3S,5R)-5-(4-amino-5-fluoro-7H-pyrrolo[2,3-d]pyrimidin-7-yl)-2-(hydroxymethyl)tetrahydrofuran-3-ol To an 80 mL steel bomb, was added (2R,3S,5R)-5-(4-chloro-5-fluoro-7H-pyrrolo[2,3-d]pyrimidin-7-yl)-2-(((4-methylbenzoyl)oxy)methyl)tetrahydrofuran-3-yl 4-methylbenzoate (2.0 g, 3.82 mmol). The medium was cooled to −40° C. To this was added ammonia saturated i-PrOH (60 mL). After the mixture was heated to 80° C. and stirred for 18 hours, the resulting mixture was concentrated under reduced pressure. The residue was purified by silica gel chromatography with dichloromethane/methanol (5/1) to give the title compound. $^1$H-NMR: (400 MHz, $d_6$-DMSO, ppm): δ 8.06 (s, 1H), 7.33 (d, J=2.0 Hz, 1H), 6.99 (brs, 2H), 6.54 (t, J=6.0 Hz, 1H), 5.24 (d, J=4.4 Hz, 1H), 4.99 (t, J=5.6 Hz, 1H), 4.30-4.33 (m, 1H), 3.78-3.81 (m, 1H), 3.47-3.56 (m, 2H), 2.37-2.44 (m, 1H), 2.12-2.17 (m, 1H). F-NMR: (376 MHz, $d_6$-DMSO, ppm): δ −167.49 (s, 1F).

Step 4: Synthesis of 7-((2R,4S,5R)-4-((tert-butyldimethylsilyl)oxy)-5-(((tert-butyldimethylsilyl)oxy)methyl)tetrahydrofuran-2-yl)-5-fluoro-7H-pyrrolo[2,3-d]pyrimidin-4-amine (2R,3S,5R)-5-(4-amino-5-fluoro-7H-pyrrolo[2,3-d]pyrimidin-7-yl)-2-(hydroxymethyl)tetrahydrofuran-3-ol (538 mg, 2.006 mmol) and imidazole (819 mg, 12.03 mmol) were added into a 25 mL round-bottom flask under argon atmosphere. To this was added dry DMF (5 mL), followed by the addition of tert-butylchlorodimethylsilane (1209 mg, 8.02 mmol) in portions. The resulting mixture was stirred at 25° C. for 3 hours. The reaction progress was monitored by TLC and LCMS. After the reaction completed, the mixture was diluted with ethyl acetate (40 mL), washed with water (20 mL×2), saturated aqueous NaHCO$_3$ (20 mL×2) and brine (20 mL×2) respectively. The organic layer was collected, dried over anhydrous Na$_2$SO$_4$ and concentrated under reduced pressure. The crude product was then purified by silica gel chromatography with ethyl acetate/petroleum ether (28% to 41% ethyl acetate in petroleum ether) to give the title compound. $^1$H-NMR: (300 MHz, $d_6$-DMSO, ppm): δ 8.07 (s, 1H), 7.27 (s, 1H), 6.99 (brs, 2H), 6.54 (t, J=6.0 Hz, 1H), 4.49 (s, 1H), 3.60-3.78 (m, 3H), 2.51-2.53 (m, 1H), 2.16-2.20 (m, 1H), 0.88 (d, J=4.2 Hz, 18H), 0.11 (s, 6H), 0.04 (s, 6H). LC-MS: (ES, m/z): 497.71 [M+H]$^+$.

Step 5: Synthesis of ((2R,3S,5R)-5-(4-amino-5-fluoro-7H-pyrrolo[2,3-d]pyrimidin-7-yl)-3-((tert-butyldimethylsilyl)oxy)tetrahydrofuran-2-yl)methanol To a stirred solution of 7-((2R,4S,5R)-4-((tert-butyldimethylsilyl)oxy)-5-(((tert-butyldimethylsilyl)oxy)methyl)tetrahydrofuran-2-yl)-5-fluoro-7H-pyrrolo[2,3-d]pyrimidin-4-amine (900 mg, 1.812 mmol) in THF (12 mL) was added aqueous trifluoroacetic acid (trifluoroacetic acid/water=1/1, v/v, 6 mL) dropwise with stirring at 0° C. in 10 minutes. The resulting mixture was stirred at 0° C. The reaction progress was monitored by TLC. After the reaction was completed, the resulting mixture was co-evaporated with toluene (50 mL×3) under vacuum while the temperature maintained below 25° C. to remove the volatiles. The residue was purified by silica gel chromatography with ethyl acetate/petroleum ether (52% to 58% ethyl acetate in petroleum ether) to give the title compound. $^1$H-NMR: (300 MHz, $d_6$-DMSO, ppm): δ 8.07 (s, 1H), 7.34 (s, 1H), 6.99 (brs, 2H), 6.53 (t, J=6.9 Hz, 1H), 5.04 (t, J=5.6 Hz, 1H), 4.47-4.51 (m, 1H), 3.76-3.79 (m, 1H), 3.44-3.57 (m, 2H), 2.45-2.51 (m, 1H), 2.11-2.16 (m, 1H), 0.90 (s, 9H), 0.11 (s, 6H). LC-MS: (ES, m/z): 383.26 [M+H]$^+$.

Step 6: Synthesis of (2S,3S,5R)-5-(4-amino-5-fluoro-7H-pyrrolo[2,3-d]pyrimidin-7-yl)-3-((tert-butyldimethylsilyl)oxy)tetrahydrofuran-2-carbaldehyde To a stirred solution of ((2R,3S,5R)-5-(4-amino-5-fluoro-7H-pyrrolo[2,3-d]pyrimidin-7-yl)-3-((tert-butyldimethylsilyl)oxy)tetrahydrofuran-2-yl)methanol (360 mg, 0.941 mmol) in anhydrous acetonitrile (12 mL) under argon, was added 2-iodoxybenzoic acid (791 mg, 2.82 mmol). The resulting mixture was refluxed for 35 minutes. The reaction was cooled down to room temperature, and the solids were filtered out. The filtration was collected and then concentrated under vacuum to give the title compound, which was used to the next reaction step directly without further purification.

Step 7: Synthesis of ((4S,5R)-5-(4-amino-5-fluoro-7H-pyrrolo[2,3-d]pyrimidin-7-yl)-3-((tert-butyldimethylsilyl)oxy)tetrahydrofuran-2,2-diyl)dimethanol To a stirred solution of (2S,3S,5R)-5-(4-amino-5-fluoro-7H-pyrrolo[2,3-d]pyrimidin-7-yl)-3-((tert-butyldimethylsilyl)oxy)tetrahydrofuran-2-carbaldehyde (400 mg, 1.051 mmol, crude) in 1,4-dioxane (4 mL), was added formaldehyde solution (1.2 mL, 16.01 mmol), followed by the addition of sodium hydroxide solution (1.2 mL, 2 M, 2.400 mmol) dropwise over 5 minutes. The resulting mixture was stirred at 25° C. for 3 hours, and then the reaction mixture was neutralized by addition of acetic acid. The resulting mixture was diluted with ethyl acetate, washed successively with water, saturated aqueous NaHCO$_3$ and brine. The organic phase was dried over Na$_2$SO$_4$ and evaporated under reduced pressure. The residue was dissolved in ethanol (10 mL) and sodium borohydride was added (80 mg, 2.103 mmol) in portions at 0° C. After stirring for 1 hour at 25° C., the reaction mixture was neutralized by addition of acetic acid and then diluted with chloroform and washed successively with water and brine. The organic layer was dried over Na$_2$SO$_4$ and evaporated under reduced pressure. The residue was purified by silica gel chromatography with dichloromethane/methanol (30/1) to give the title compound. $^1$H-NMR: (300 MHz, d$_6$-DMSO, ppm): δ 8.06 (s, 1H), 7.36 (s, 1H), 6.99 (brs, 2H), 6.57 (t, J=3.6 Hz, 1H), 4.99 (t, J=4.8 Hz, 1H), 4.55-4.59 (m, 1H), 4.39 (t, J=5.1 Hz, 1H), 3.45-3.55 (m, 4H), 2.57-2.65 (m, 1H), 2.17-2.20 (m, 1H), 0.90 (s, 9H), 0.09 (s, 6H).

Step 8: Synthesis of (2R,3S,5R)-5-(4-amino-5-fluoro-7H-pyrrolo[2,3-d]pyrimidin-7-yl)-3-((tert-butyldimethylsilyl)oxy)-2-(hydroxymethyl)tetrahydrofuran-2-carbaldehyde To a stirred solution of ((3S,5R)-5-(4-amino-5-fluoro-7H-pyrrolo[2,3-d]pyrimidin-7-yl)-3-((tert-butyldimethylsilyl)oxy)tetrahydrofuran-2,2-diyl)dimethanol (120 mg, 0.291 mmol) in anhydrous acetonitrile (8 mL) under argon atmosphere, was added 2-iodoxybenzoic acid (326 mg, 1.164 mmol). The resulting mixture was stirred at 30° C. for 24 hours and then filtered and washed with dichloromethane. The filtrate was collected and concentrated under reduced pressure to give the title compound, which was used in the next reaction step directly without further purification. LC-MS: (ES, m/z): 411.43 [M+H]$^+$.

Step 9: Synthesis of ((2R,3S,5R)-5-(4-amino-5-fluoro-7H-pyrrolo[2,3-d]pyrimidin-7-yl)-3-((tert-butyldimethylsilyl)oxy)-2-ethynyltetrahydrofuran-2-yl)methanol To a stirred solution of (2R,3S,5R)-5-(4-amino-5-fluoro-7H-pyrrolo[2,3-d]pyrimidin-7-yl)-3-((tert-butyldimethylsilyl)oxy)-2-(hydroxymethyl)tetrahydrofuran-2-carbaldehyde (110 mg, 0.268 mmol, crude) in anhydrous methanol (8 mL) under argon, was added potassium carbonate (111 mg, 0.804 mmol). The mixture was cooled down to 0° C., then dimethyl (1-diazo-2-oxopropyl)phosphonate (154 mg, 0.804 mmol) was added dropwise over 1 minute. After the mixture was stirred at 25° C. overnight, the resulting mixture was concentrated under vacuum, and then purified by preparative-TLC (methanol/dichloromethane=1/15) to give the title compound. $^1$H-NMR: (300 MHz, d$_6$-DMSO, ppm): δ 8.07 (s, 1H), 7.34 (s, 1H), 7.03 (br, 2H), 6.56 (t, J=6.3 Hz, 1H), 5.43 (t, J=6.0 Hz, 1H), 4.61 (t, J=5.4 Hz, 1H), 3.58-3.67 (m, 1H), 3.49-3.53 (m, 1H), 3.47 (s, 1H), 2.52-2.61 (m, 1H), 2.23-2.31 (m, 1H), 0.91 (s, 9H), 0.11 (d, J=2.4 Hz, 6H). LC-MS: (ES, m/z): 407.30 [M+H]$^+$.

Step 10: Synthesis of (2R,3S,5R)-5-(4-amino-5-fluoro-7H-pyrrolo[2,3-d]pyrimidin-7-yl)-2-ethynyl-2-(hydroxymethyl)tetrahydrofuran-3-ol To a stirred solution of ((2R,3S,5R)-5-(4-amino-5-fluoro-7H-pyrrolo[2,3-d]pyrimidin-7-yl)-3-((tert-butyldimethylsilyl)oxy)-2-ethynyltetrahydrofuran-2-yl)methanol (40 mg, 0.098 mmol) in anhydrous THF (2 mL) under argon atmosphere, was added TBAF/THF solution (0.118 mL, 0.118 mmol) dropwise with stirring over 1 minute at room temperature and the resulting solution was stirred at this temperature for 2 hours. After the reaction completed, the resulting mixture was concentrated under vacuum, and the residue was purified by preparative-TLC (methanol/dichloromethane=1/10) to give crude product (28 mg). The crude product was further purified by preparative-HPLC with the following conditions: (1#-Pre-HPLC-011(Waters)): Column, X-select CSH Column, 19*150 mm, 5um; mobile phase, water with 10 mmol ammonium bicarbonate and acetonitrile (5% acetonitrile up to 35% in 7.5 min, up to 95% in 2 min); Detector, UV 254 & 220 nm. The product-containing fractions were collected and lyophilized to give compound 2 as a solid. $^1$H-NMR: (400 MHz, d$_6$-DMSO, ppm): ε8.07 (s, 1H), 7.30 (d, J=1.6 Hz, 1H), 7.02 (br, 2H), 6.55 (t, J=5.8 Hz, 1H), 6.05 (br, 1H), 5.31-5.45 (m, 1H), 4.46 (t, J=6.6 Hz, 1H), 3.58 (dd, J=11.8 Hz, J=29.4 Hz, 2H), 3.47 (s, 1H), 2.44-2.51 (m, 1H), 2.29-2.36 (m, 1H). F-NMR: (376 MHz, d$_6$-DMSO, ppm): δ −167.23 (s, 1F). LC-MS: (ES, m/z): 293.10 [M+H]$^+$, 315.10 [M+Na]$^+$.

Example 3

Synthesis of (2R,3S,5R)-5-(4-amino-5-methyl-7H-pyrrolo[2,3-d]pyrimidin-7-yl)-2-ethynyl-2-(hydroxymethyl)tetrahydrofuran-3-ol (3)

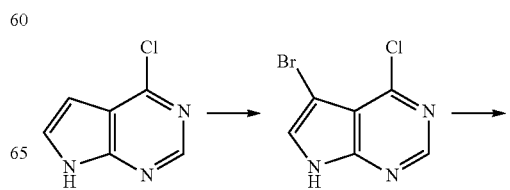

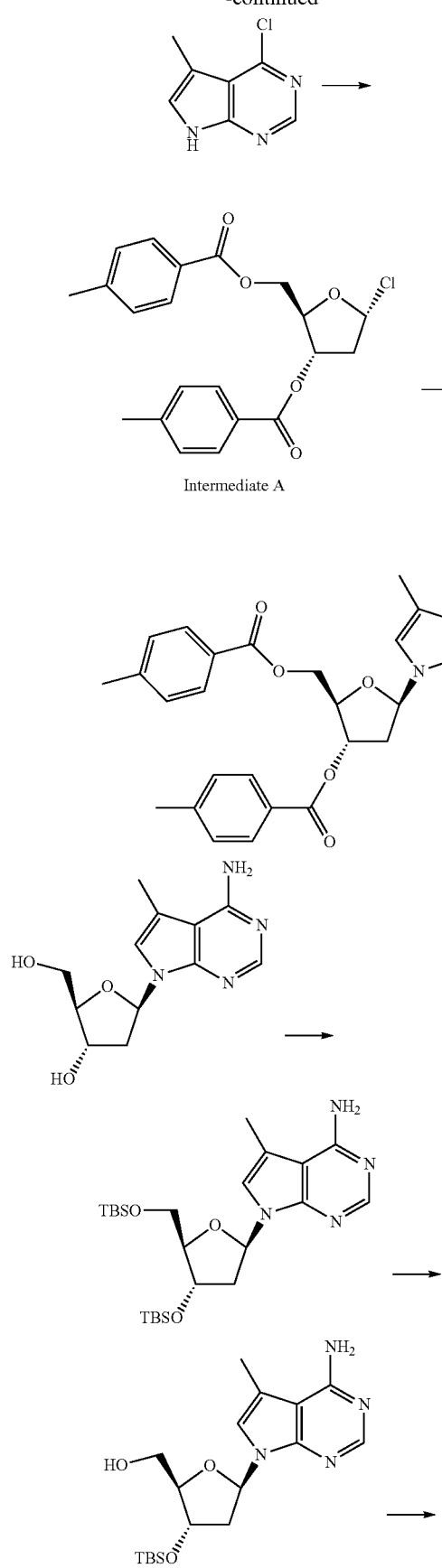
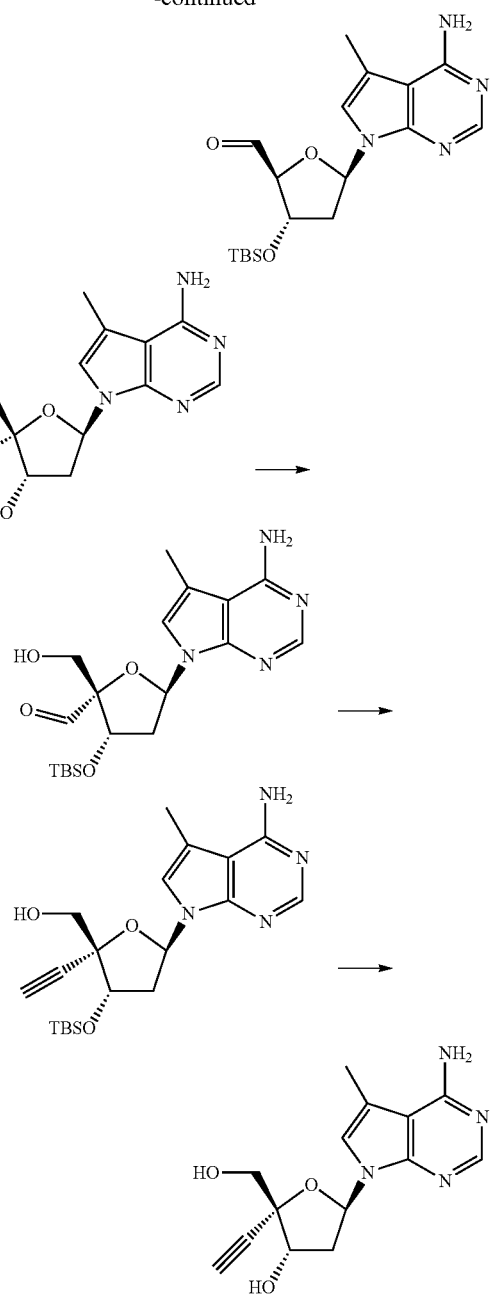

Step 1:
5-bromo-4-chloro-7H-pyrrolo[2,3-d]pyrimidine 4-chloro-7H-pyrrolo[2,3-d]pyrimidine (1 g, 6.51 mmol) was suspended in dry DCM (20 mL) followed by the addition of NBS (N-bromosuccinimide) (1.275 g, 7.16 mmol) at ambient temperature under argon atmosphere. The mixture was heated to reflux and stirred 16 hours. Upon the started deaza-pyrimidine was all consumed, the mixture was cooled to ambient temperature and maintained for 30 min. The precipitated was collected by filtration, washed with DCM (2×20 mL), dried under vacuum to give the title compound. LC-MS: (ES, m/z): 233.90 [M+H]⁺. ¹H-NMR: (300 MHz, d₆-DMSO, ppm): δ 12.98 (brs, 1H), 8.64 (s, 1H), 7.96 (s, 1H).

Step 2: Synthesis of 4-chloro-5-methyl-7H-pyrrolo[2,3-d]pyrimidine 5-bromo-4-chloro-7H-pyrrolo[2,3-d]pyrimidine (232 mg, 0.998 mmol) was dissolved in dry THF (10 mL) and cooled to −78° C. under argon atmosphere. To this was added n-butyllithium hexanes solution (2.5 M, 0.88 mL, 2.196 mmol) dropwise with stirring in 5 minutes. The mixture was stirred for about 40 minutes followed by the addition of iodomethane (212 mg, 1.497 mmol). The solution was then warmed slowly to room temperature in 2 hours. Water (2 mL) was added to quench the reaction. The volatile was removed in vacuo below 40° C. to yield a slurry. The slurry was re-dissolved in EtOAc (50 mL) and washed with water (2×15 mL) and brine (20 mL). The organic layer was collected, dried over anhydrous Na₂SO₄, filtered and the filtrate was concentrated in vacuo to yield a powder that was re-crystallized from MeOH to afford the title compound. LC-MS: (ES, m/z): 168.00 [M+H]⁺. ¹H-NMR: (300 MHz, d₆-DMSO, ppm): δ 12.22 (brs, 1H), 8.51 (s, 1H), 7.43 (s, 1H), 2.41 (d, J=0.90 Hz, 1H).

Step 3: Synthesis of (2R,3S,5R)-5-(4-chloro-5-methyl-7H-pyrrolo[2,3-d]pyrimidin-7-yl)-2-(((4-methylbenzoyl)oxy)methyl)tetrahydrofuran-3-yl 4-methylbenzoate To a stirred suspension of sodium hydride (60% dispersion in oil, 0.453 g, 11.32 mmol) in anhydrous ACN (50 mL) was added 4-chloro-5-methyl-7H-pyrrolo[2,3-d]pyrimidine (1.724 g, 10.29 mmol) in portions under argon atmosphere and the mixture was stirred at 25° C. for 30 minutes. To the resulted clear solution was added Intermediate A (4.0 g, 10.29 mmol) portionwise at 25° C. The resulting mixture was heated to 50° C. and stirred for 3 hours. The reaction progress was monitored by TLC. The mixture was concentrated under vacuum gave a solid, which was purified by silica-gel column chromatography using ethyl acetate/petrol ether (1:6, v/v) to give the title compound. LC-MS: (ES, m/z): 520.25 [M+H]⁺. ¹H-NMR: (300 MHz, CDCl₃, ppm): δ 8.55 (s, 1H), 7.90-7.99 (m, 4H), 7.20-7.30 (m, 4H), 7.11 (s, 1H), 6.81 (dd, J=6.0 Hz, J=8.4 Hz, 1H), 5.76 (dd, J=1.5 Hz, J=3.6 Hz, 1H), 4.73-4.79 (m, 1H), 4.54-4.64 (m, 2H), 2.79-2.88 (m, 1H), 2.68-2.75 (m, 1H), 2.43 (d, J=3.0 Hz, 6H), 2.33 (d, J=0.9 Hz, 3H).

Step 4: Synthesis of (2R,3S,5R)-5-(4-amino-5-methyl-7H-pyrrolo[2,3-d]pyrimidin-7-yl)-2-(hydroxymethyl)tetrahydrofuran-3-ol To a 150 mL steel bomb was placed (2R,3S,5R)-5-(4-chloro-5-methyl-7H-pyrrolo[2,3-d]pyrimidin-7-yl)-2-(((4-methylbenzoyl)oxy)methyl)tetrahydrofuran-3-yl 4-methylbenzoate (4.5 g, 7.79 mmol). The medium was cooled to −40° C. To this was added 2-propanolic ammonia (1-PrOH/Liquid NH₃=1/1, v/v, 120 mL). The bomb was sealed and the mixture was heated to 90° C. and stirred for 40 hours. Upon the reaction was complete, the mixture was cooled to 0° C. and concentrated under vacuum. The residue was purified by silica gel column chromatography using DCM/MeOH (4/1) to give the title compound. LC-MS: (ES, m/z): 265.10 [M+H]⁺. ¹H-NMR: (300 MHz, d₆-DMSO, ppm): δ 8.00 (s, 1H), 7.08 (s, 1H), 6.58 (brs, 2H), 6.45 (dd, J=6.0 Hz, J=8.1 Hz, 1H), 5.21 (d, J=3.3 Hz, 1H), 5.05 (t, J=5.1 Hz, 1H), 4.32-4.36 (m, 1H), 3.78 (d, J=2.1 Hz, 1H), 3.44-3.57 (m, 2H), 2.39-2.51 (m, 1H), 2.33 (s, 3H), 2.06-2.13 (m, 3H).

Step 5: Synthesis of 7-((2R,4S,5R)-4-((tert-butyldimethylsilyl)oxy)-5-(((tert-butyldimethylsilyl)oxy)methyl)tetrahydrofuran-2-yl)-5-methyl-7H-pyrrolo[2,3-d]pyrimidin-4-amine To a stirred solution of (2R,3S,5R)-5-(4-amino-5-methyl-7H-pyrrolo[2,3-d]pyrimidin-7-yl)-2-(hydroxymethyl)tetrahydrofuran-3-ol (1.7 g, 6.43 mmol) and 1H-imidazole (1.752 g, 25.7 mmol) in dry DMF (10 mL) was added tert-butylchlorodimethylsilane (2.91 g, 19.30 mmol) with stirring at 25° C. under argon atmosphere. The resulting mixture was stirred at 25° C. for 3 hours and then diluted with ethyl acetate (100 mL), washed with water (2×30 mL), aqueous NaHCO₃ (saturated, 2×30 mL) and brine (30 mL) respectively. The organic layer was collected and dried over anhydrous Na2SO4, filtered and concentrated under vacuum to give crude product. The crude product was then purified by silica gel column chromatography using ethyl acetate/petroleum ether (28% to 41% EA in PE) to give the title compound. LC-MS: (ES, m/z): 493.30 [M+H]⁺. ¹H-NMR: (300 MHz, CDCl₃, ppm): δ 8.24 (s, 1H), 7.02 (s, 1H), 6.67 (dd, J=6.3 Hz, J=7.2 Hz, 1H), 5.37 (br, 2H), 4.54-4.57 (m, 1H), 3.94 (dd, J=3.3 Hz, J=6.3 Hz, 1H), 3.72-3.82 (m, 2H), 2.37-2.46 (m, 4H), 2.25-2.32 (m, 1H), 0.91 (2s, 18H), 0.10 (s, 12H).

Step 6: Synthesis of ((2R,3S,5R)-5-(4-amino-5-methyl-7H-pyrrolo[2,3-d]pyrimidin-7-yl)-3-(tert-butyldimethylsilyl)tetrahydrofuran-2-yl)methanol To a stirred solution of 7-((2R,4S,5R)-4-(tert-butyldimethylsilyl)-5-((tert-butyldimethylsilyl)methyl)tetrahydrofuran-2-yl)-5-methyl-7H-pyrrolo[2,3-d]pyrimidin-4-amine (2.5 g, 5.07 mmol) in THF (30 mL) was added a pre-cooled solution of trifluoroacetic acid/water (1/1, v/v, 15 mL) dropwise with stirring at 0° C. in 10 minutes. The resulting mixture was stirred at 0° C. for 3 hours. The reaction progress was monitored by TLC. The resulting solution was co-evaporated with toluene (3×100 mL) while maintaining the inner temperature below 25° C. The resulting crude product was then purified by silica gel column chromatography using ethyl acetate/petroleum ether (50% to 58% EA in PE) to give the title compound. LC-MS: (ES, m/z): 493.30 [M+H]⁺. ¹H-NMR: (300 MHz, CD₃OD, ppm): δ 8.18 (s, 1H), 7.41 (s, 1H), 6.59 (dd, J=6.0 Hz, J=7.8 Hz, 1H), 4.56-4.60 (m, 1H), 3.93 (dd, J=3.9 Hz, J=6.6 Hz, 1H), 3.65-3.70 (m, 2H), 2.45-2.54 (m, 1H), 2.42 (d, J=0.9 Hz, 3H), 2.23-2.31 (m, 1H), 0.91 (s, 9H), 0.11 (s, 6H).

Step 7: Synthesis of (2R,3S,5R)-5-(4-amino-5-methyl-7H-pyrrolo[2,3-d]pyrimidin-7-yl)-3-(tert-butyldimethylsilyl)tetrahydrofuran-2-carbaldehyde To a stirred suspension of ((2R,3S,5R)-5-(4-amino-5-methyl-7H-pyrrolo[2,3-d]pyrimidin-7-yl)-3-(tert-butyldimethylsilyl)tetrahydrofuran-2-yl)methanol (600 mg, 1.585 mmol) in anhydrous ACN (12 mL) was added IBX (888 mg, 3.17 mmol) under argon atmosphere. The mixture was heated to reflux and stirred for 55 minutes. The reaction progress was monitored by LCMS. The mixture was cooled to room temperature, and the solids were filtered out. The filtration was collected and then concentrated under vacuum to give the title compound, which was used to the next reaction step directly without further purification. LC-MS: (ES, m/z): 377.15 [M+H]+, 409.15 [M+H+MeOH]+.

Step 8: Synthesis of ((4S,5R)-5-(4-amino-5-methyl-7H-pyrrolo[2,3-d]pyrimidin-7-yl)-3-(tert-butyldimethylsilyl)tetrahydrofuran-2,2-diyl)dimethanol To a stirred solution of (2R,3S,5R)-5-(4-amino-5-methyl-7H-pyrrolo[2,3-d]pyrimidin-7-yl)-3-(tert-butyldimethylsilyl)tetrahydrofuran-2-carbaldehyde (420 mg, crude) in 1,4-Dioxane (12 mL) and water (3 mL) in a 50 mL round-bottom flask, was added aqueous formaldehyde (37% w/w, 6 mL) followed by the addition of sodium hydroxide solution (2 N, 6 mL, 0.12 mmol) dropwise in 2 minutes. The resulting mixture was stirred at 25° C. for 3 hours. Upon the started nucleoside-aldehyde was all consumed, the reaction mixture was neutralized by the addition of AcOH (about 0.8 mL). The resulting mixture was diluted with AcOEt (50 mL) and washed successively with water (30 mL), saturated aqueous NaHCO₃ (20 mL) and brine (20 mL). The organic layer was dried over anhydrous Na₂SO₄, filtered and concentrated under vacuum. The residue was re-dissolved in anhydrous EtOH (8 mL) and added sodium borohydride (84.4 mg, 2.23 mmol) in portions at 0° C. After stirring for 1 hour at 25° C., the reaction mixture was neutralized by addition of AcOH. The mixture was concentrated under vacuum, partitioned between CHCl₃ (50 mL) and water (30 mL). The aqueous layer was re-extracted with CHCl₃ (2×20 mL). The combined organic layer was washed successively with water and brine, dried over anhydrous Na₂SO₄, filtered and concentrated under vacuum. The residue was purified by purified by silica gel column chromatography using dichloromethane/methanol (5.5% MeOH in DCM) to give the title compound. LC-MS: (ES, m/z): 409.35 [M+H]+, 431.35 [M+Na]+. ¹H-NMR: (300 MHz, d₆-DMSO, ppm): δ 8.00 (s, 1H), 7.11 (s, 1H), 6.56 (br, 2H), 6.48 (dd, J=6.0 Hz, J=8.4 Hz, 1H), 6.45-6.47 (m, 1H), 5.02 (t, J=5.5 Hz, 1H), 4.58 (t, J=2.7 Hz, 1H), 4.35 (dd, J=4.5 Hz, J=6.3 Hz, 1H), 3.42-3.60 (m, 4H), 2.58-2.63 (m, 1H), 2.34 (s, 3H), 2.09-2.16 (m, 1H), 0.90 (s, 9H), 0.09 (s, 6H).

Step 9: Synthesis of (2R,3S,5R)-5-(4-amino-5-methyl-7H-pyrrolo[2,3-d]pyrimidin-7-yl)-3-((tert-butyldimethylsilyl)oxy)-2-(hydroxymethyl)tetrahydrofuran-2-carbaldehyde ((3S,5R)-5-(4-amino-5-methyl-7H-pyrrolo[2,3-d]pyrimidin-7-yl)-3-((tert-butyldimethylsilyl)oxy)tetrahydrofuran-2,2-diyl)dimethanol (140 mg, 0.343 mmol) was suspended in dry ACN (15 mL) under argon atmosphere followed by the addition of 2-iodylbenzoic acid (240 mg, 0.857 mmol). The mixture was stirred at 30° C. for 20 hours. The solid was filtered out, washed with CHCl₃ (2×20 mL). The combined filtrate was concentrated under vacuum to afford the title compound, which was used to the next reaction step directly without further purification. LC-MS: (ES, m/z): 407.25 [M+H]+.

Step 10: Synthesis of ((2R,3S,5R)-5-(4-amino-5-methyl-7H-pyrrolo[2,3-d]pyrimidin-7-yl)-3-((tert-butyldimethylsilyl)oxy)-2-ethynyltetrahydrofuran-2-yl)methanol To a stirred solution of (2R,3S,5R)-5-(4-amino-5-methyl-7H-pyrrolo[2,3-d]pyrimidin-7-yl)-3-((tert-butyldimethylsilyl)oxy)-2-(hydroxymethyl)tetrahydrofuran-2-carbaldehyde (120 mg, 0.236 mmol, crude) in dry MeOH (15 mL) was added K₂CO₃ (82 mg, 0.590 mmol) at 0° C. under argon atmosphere, followed by the addition of a solution of dimethyl (1-diazo-2-oxopropyl)phosphonate (91 mg, 0.472 mmol) in MeOH (2 mL) dropwise with stirring at 0° C. in 2 minutes. The resulting mixture was gradually warmed to 25° C. and stirred for 16 hours. The mixture was concentrated under vacuum. The residue was purified by flash silica gel column chromatography using ethyl acetate/petroleum ether (30%-50% EA in PE) to afford the title compound. LC-MS: (ES, m/z): 403.25 [M+H]+. ¹H-NMR: (300 MHz, d₆-DMSO, ppm): δ 8.01 (s, 1H), 7.07 (s, 1H), 6.60 (br, 2H), 6.49 (dd, J=6.0 Hz, J=7.2 Hz, 1H), 5.48 (t, J=5.7 Hz, 1H), 4.62 (t, J=5.7 Hz, 1H), 3.57-3.68 (m, 1H), 3.48-3.52 (m, 1H), 3.45 (s, 1H), 2.49-2.62 (m, 1H), 2.33 (s, 3H), 2.21-2.31 (m, 1H), 0.91 (s, 9H), 0.12 (d, J=6.0 Hz, 6H).

Step 11: Synthesis of (2R,3S,5R)-5-(4-amino-5-methyl-7H-pyrrolo[2,3-d]pyrimidin-7-yl)-2-ethynyl-2-(hydroxymethyl)tetrahydrofuran-3-ol (3)

To a stirred solution of ((2R,3S,5R)-5-(4-amino-5-methyl-7H-pyrrolo[2,3-d]pyrimidin-7-yl)-3-((tert-butyldimethylsilyl)oxy)-2-ethynyltetrahydrofuran-2-yl)methanol (27 mg, 0.067 mmol) in dry THF (1 mL) was added tetra-butylammonium fluoride THF solution (1.0 M, 0.067 mL, 0.067 mmol) dropwise with stirring at 0° C. The resulting mixture was stirred at 25° C. for 30 minutes. The reaction progress was monitored by TLC. The resulting solution was concentrated under vacuum. The crude product was purified by preparative-HPLC with the following conditions (1#-Pre-HPLC-011(Waters)): Column, XBridge™ C18 Column, 19*150 mm, 5um; mobile phase, water with 10 mmol ammonium bicarbonate and acetonitrile (30% acetonitrile up to 70% in 10 min, up to 95% in 2 min, down to 5% in 1.5 min); Flow rate: 20 mL/min; Detector, UV 254&220 nm. The product-containing fractions were collected and lyophilized to give the title compound. LC-MS: (ES, m/z): 289.05 [M+H]+. ¹H-NMR: (300 MHz, d₆-DMSO, ppm): ε 8.00 (s, 1H), 7.06 (s, 1H), 6.58 (br, 2H), 6.48 (t, J=6.60 Hz, 1H), 5.45 (d, J=5.1 Hz, 1H), 5.38 (t, J=6.0 Hz, 1H), 4.46 (q, J=5.4 Hz, 1H), 3.50-3.64 (m, 2H), 3.44 (s, 1H), 2.44-2.54 (m, 1H), 2.33 (s, 3H), 2.24-2.32 (m, 1H).

Example 4

Synthesis of (2R,3S,5R)-5-(4-amino-2-chloro-7H-pyrrolo[2,3-d]pyrimidin-7-yl)-2-ethynyl-2-(hydroxymethyl)tetrahydrofuran-3-ol (4)

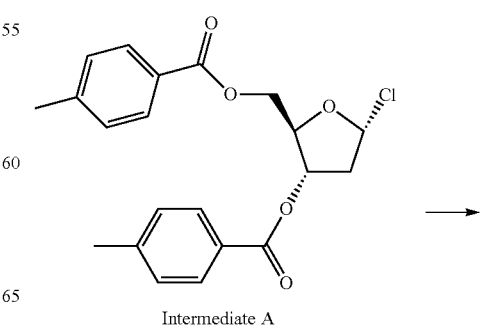

Intermediate A

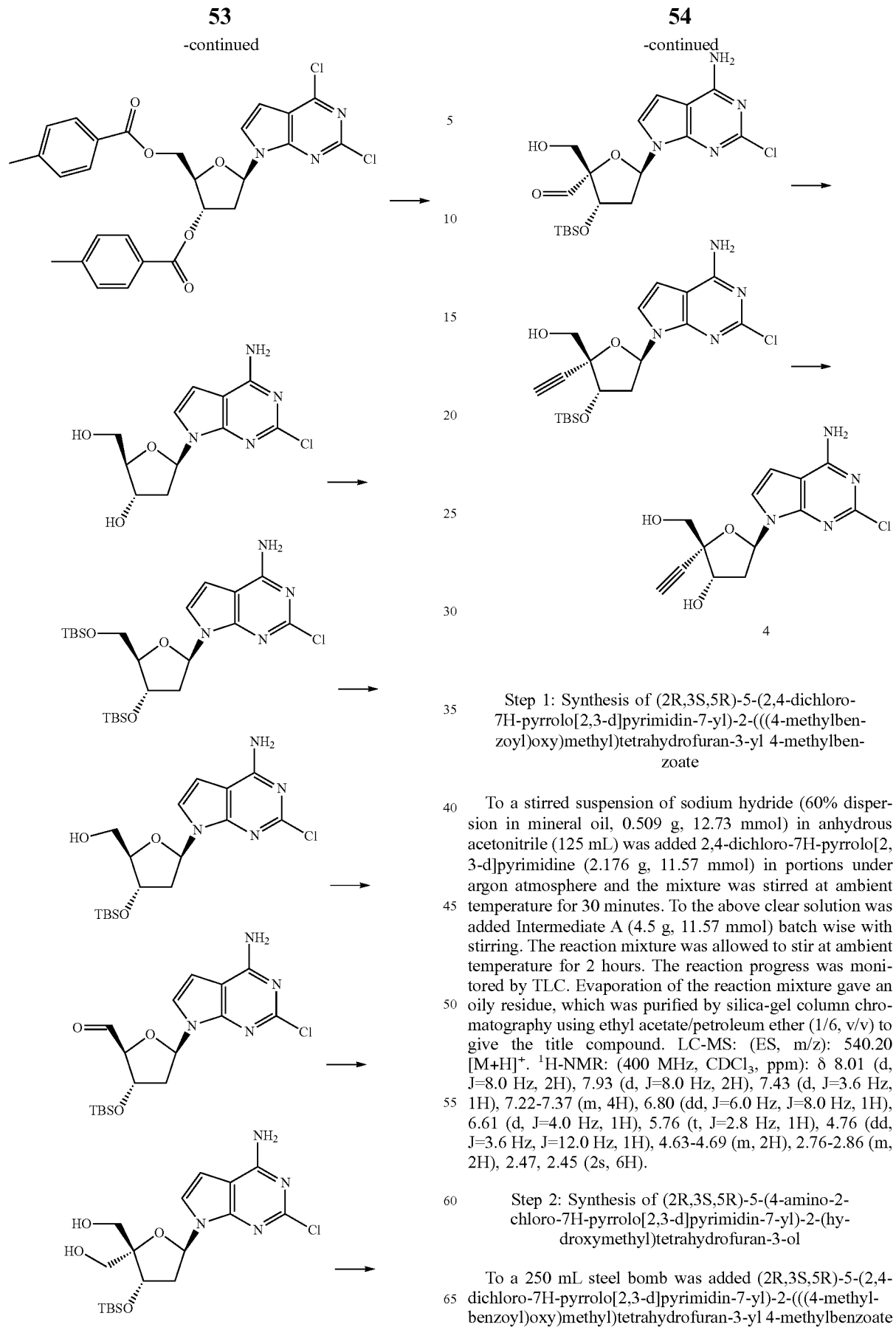

Step 1: Synthesis of (2R,3S,5R)-5-(2,4-dichloro-7H-pyrrolo[2,3-d]pyrimidin-7-yl)-2-(((4-methylbenzoyl)oxy)methyl)tetrahydrofuran-3-yl 4-methylbenzoate To a stirred suspension of sodium hydride (60% dispersion in mineral oil, 0.509 g, 12.73 mmol) in anhydrous acetonitrile (125 mL) was added 2,4-dichloro-7H-pyrrolo[2,3-d]pyrimidine (2.176 g, 11.57 mmol) in portions under argon atmosphere and the mixture was stirred at ambient temperature for 30 minutes. To the above clear solution was added Intermediate A (4.5 g, 11.57 mmol) batch wise with stirring. The reaction mixture was allowed to stir at ambient temperature for 2 hours. The reaction progress was monitored by TLC. Evaporation of the reaction mixture gave an oily residue, which was purified by silica-gel column chromatography using ethyl acetate/petroleum ether (1/6, v/v) to give the title compound. LC-MS: (ES, m/z): 540.20 [M+H]$^+$. $^1$H-NMR: (400 MHz, CDCl$_3$, ppm): δ 8.01 (d, J=8.0 Hz, 2H), 7.93 (d, J=8.0 Hz, 2H), 7.43 (d, J=3.6 Hz, 1H), 7.22-7.37 (m, 4H), 6.80 (dd, J=6.0 Hz, J=8.0 Hz, 1H), 6.61 (d, J=4.0 Hz, 1H), 5.76 (t, J=2.8 Hz, 1H), 4.76 (dd, J=3.6 Hz, J=12.0 Hz, 1H), 4.63-4.69 (m, 2H), 2.76-2.86 (m, 2H), 2.47, 2.45 (2s, 6H).

Step 2: Synthesis of (2R,3S,5R)-5-(4-amino-2-chloro-7H-pyrrolo[2,3-d]pyrimidin-7-yl)-2-(hydroxymethyl)tetrahydrofuran-3-ol To a 250 mL steel bomb was added (2R,3S,5R)-5-(2,4-dichloro-7H-pyrrolo[2,3-d]pyrimidin-7-yl)-2-(((4-methylbenzoyl)oxy)methyl)tetrahydrofuran-3-yl 4-methylbenzoate (5 g, 9.25 mmol). The medium was cooled to −40° C. To this was added isopropanolic ammonia (isopropanol/liquid ammonia=1/3, v/v, 150 mL). The medium was sealed, heated to 90° C. and stirred for 16 hours. The resulting mixture was cooled to room temperature and concentrated under vacuum. The residue was re-dissolved in MeOH (100 mL), followed by the addition of sodium methoxide MeOH solution (1.0 M, 16.89 mL, 16.89 mmol) dropwise at 0° C. The resulting mixture was warmed to 25° C. and stirred for 2 hours. After the reaction achieved to complete, the mixture was neutralized by the addition of acetic acid (0.01 mL) and concentrated under vacuum. The residue was suspended in DCM/MeOH (v/v, 100/1, 150 mL). After stirring for 20 minutes, a solid was precipitated. The solid was collected by filtration, washed with DCM and dried in vacuo to give the title compound. LC-MS: (ES, m/z): 285.20 [M+H]$^+$. $^1$H-NMR: (400 MHz, CD$_3$OD, ppm): δ 7.31 (d, J=2.8 Hz, 1H), 6.58 (d, J=2.8 Hz, 1H), 6.45 (t, J=6.8 Hz, 1H), 4.52-4.53 (m, 1H), 3.98-4.01 (m, 1H), 3.81 (dd, J=2.4 Hz, J=12.0 Hz, 1H), 3.73 (dd, J=3.2 Hz, J=12.0 Hz, 1H), 2.63-2.70 (m, 1H), 2.29-2.34 (m, 1H).

Step 3: Synthesis of 7-((2R,4S,5R)-4-((tert-butyldimethylsilyl)oxy)-5-(((tert-butyldimethylsilyl)oxy)methyl)tetrahydrofuran-2-yl)-2-chloro-7H-pyrrolo[2,3-d]pyrimidin-4-amine To a stirred solution of (2R,3S,5R)-5-(4-amino-2-chloro-7H-pyrrolo[2,3-d]pyrimidin-7-yl)-2-(hydroxymethyl)tetrahydrofuran-3-ol (3.2 g, 6.74 mmol) and imidazole (1.836 g, 27.0 mmol) in dry DMF (10 mL) under argon atmosphere was added TBS-Cl (3.05 g, 20.23 mmol) at ambient temperature. The resulting mixture was stirred overnight. The reaction mixture was diluted with ethyl acetate (100 mL), washed with water (2×20 mL), aqueous NaHCO$_3$ (saturated, 2×20 mL) and brine (2×20 mL) successively. The organic layer was dried over anhydrous Na$_2$SO$_4$, filtered and concentrated under vacuum. The residue was purified by silica gel column chromatography using ethyl acetate/petroleum ether (35% to 42% EA in PE) to give the title compound. LC-MS: (ES, m/z): 513.20 [M+H]$^+$. $^1$H-NMR: (400 MHz, CDCl$_3$, ppm): ϵ7.32 (s, 1H), 6.61 (t, J=6.8 Hz, 1H), 6.38 (s, 1H), 5.44 (br, 2H), 4.59-4.61 (m, 1H), 3.91-3.99 (m, 1H), 3.77-3.88 (m, 2H), 2.44-2.51 (m, 1H), 2.34-2.37 (m, 1H), 0.93-0.95 (m, 18H), 0.11-0.12 (m, 12H). $^1$H-NMR: (400 MHz, CD$_3$OD, ppm): δ 7.31 (d, J=2.8 Hz, 1H), 6.58 (d, J=2.8 Hz, 1H), 6.45 (t, J=6.8 Hz, 1H), 4.52-4.53 (m, 1H), 3.98-4.01 (m, 1H), 3.81 (dd, J=2.4 Hz, J=12.0 Hz, 1H), 3.73 (dd, J=3.2 Hz, J=12.0 Hz, 1H), 2.63-2.70 (m, 1H), 2.29-2.34 (m, 1H).

Step 4: Synthesis of ((2R,3S,5R)-5-(4-amino-2-chloro-7H-pyrrolo[2,3-d]pyrimidin-7-yl)-3-((tert-butyldimethylsilyl)oxy)tetrahydrofuran-2-yl)methanol To a stirred solution of 7-((2R,4S,5R)-4-((tert-butyldimethylsilyl)oxy)-5-(((tert-butyldimethylsilyl)oxy)methyl)tetrahydrofuran-2-yl)-2-chloro-7H-pyrrolo[2,3-d]pyrimidin-4-amine (2.3 g, 4.48 mmol) in THF (40 mL) was added a pre-cooled solution of trifluoroacetic acid/water (v/v, 1/1, 20 mL) dropwise with stirring at 0° C. in 10 minutes. The resulting mixture was stirred for 2 hours at 0° C. The reaction progress was monitored by TLC. The resulting solution was co-evaporated with toluene (3×60 mL) while maintain the inner temperature below 25° C. give a pink syrup. The residue was purified by silica gel column chromatography using ethyl acetate/dichloromethane (1/1) to give the title compound. LC-MS: (ES, m/z): 399.20 [M+H]$^+$. $^1$H-NMR: (400 MHz, d$_6$-DMSO, ppm): δ 7.53 (br, 2H), 7.35 (d, J=3.2 Hz, 1H), 6.60 (d, J=3.2 Hz, 1H), 6.35 (t, J=6.8 Hz, 1H), 4.95 (t, J=5.4 Hz, 1H), 4.51-4.54 (m, 1H), 3.73-3.79 (m, 1H), 3.46-3.55 (m, 2H), 2.54-2.59 (m, 1H), 2.16-2.20 (m, 1H), 0.90 (s, 9H), 0.11 (s, 6H). $^1$H-NMR: (400 MHz, d$_6$-DMSO, ppm): δ 7.53 (br, 2H), 7.35 (d, J=3.2 Hz, 1H), 6.60 (d, J=3.2 Hz, 1H), 6.35 (t, J=6.8 Hz, 1H), 4.95 (t, J=5.4 Hz, 1H), 4.51-4.54 (m, 1H), 3.73-3.79 (m, 1H), 3.46-3.55 (m, 2H), 2.54-2.59 (m, 1H), 2.16-2.20 (m, 1H), 0.90 (s, 9H), 0.11 (s, 6H).

Step 5: Synthesis of (2S,3S,5R)-5-(4-amino-2-chloro-7H-pyrrolo[2,3-d]pyrimidin-7-yl)-3-((tert-butyldimethylsilyl)oxy)tetrahydrofuran-2-carbaldehyde To a stirred solution of ((2R,3S,5R)-5-(4-amino-2-chloro-7H-pyrrolo[2,3-d]pyrimidin-7-yl)-3-((tert-butyldimethylsilyl)oxy)tetrahydrofuran-2-yl)methanol (600 mg, 1.504 mmol) in anhydrous DMSO (3 mL) and acetonitrile (15 mL) under argon atmosphere was added IBX (632 mg, 2.256 mmol). The mixture was stirred at ambient temperature for 2.5 hours. The reaction mixture was diluted with ethyl acetate (20 mL), washed with brine (2×10 mL), dried over anhydrous sodium sulfate and filtered. The filtrate was concentrated under vacuum to afford the title compound, which was used to the next step directly without further purification. LC-MS: (ES, m/z): 415.40 [M+H$_2$O]$^+$.

Step 6: Synthesis of ((3S,5R)-5-(4-amino-2-chloro-7H-pyrrolo[2,3-d]pyrimidin-7-yl)-3-((tert-butyldimethylsilyl)oxy)tetrahydrofuran-2,2-diyl)dimethanol To a stirred solution of (2S,3S,5R)-5-(4-amino-2-chloro-7H-pyrrolo[2,3-d]pyrimidin-7-yl)-3-((tert-butyldimethylsilyl)oxy)tetrahydrofuran-2-carbaldehyde (700 mg, crude) in 1,4-dioxane (28 mL) and water (7 mL) was added formaldehyde solution (7 mL, 93 mmol), followed by addition a aqueous solution of sodium hydroxide (7 mL, 2 N, 14.00 mmol) dropwise in 5 minutes. The resulting mixture was stirred at 25° C. for 3 hours. Upon the started nucleoside-aldehyde was all consumed, the reaction mixture was neutralized by the addition of acetic acid (0.5 mL). The mixture was diluted with ethyl acetate (100 mL) and washed successively with water (2×20 mL), saturated aqueous NaHCO$_3$ (20 mL) and brine (20 mL). The organic layer was dried over Na$_2$SO$_4$, filtered and concentrated under vacuum. The residue was re-dissolved in anhydrous EtOH (4 mL) and added sodium borohydride (133 mg, 3.53 mmol) under argon atmosphere in portions at 0° C. After stirring for 1 hour at 25° C., the mixture was neutralized by the addition of acetic acid (1.0 mL). The mixture was concentrated under vacuum. The residue was diluted with CHCl$_3$ (100 mL) and washed successively with water (2×20 mL) and brine (1×20 mL). The organic layer was dried over Na$_2$SO$_4$, filtered and concentrated under vacuum. The residue was purified by silica gel column chromatography using DCM/MeOH (30/1) to give the title compound. LC-MS: (ES, m/z): 429.30 [M+H]$^+$. $^1$H-NMR: (300 MHz, d$_6$-DMSO, ppm): δ 7.51 (br, 2H), 7.38 (d, J=3.9 Hz, 1H), 6.60 (d, J=3.6 Hz, 1H), 6.40 (t, J=6.9 Hz, 1H), 4.88 (t, J=5.5 Hz, 1H), 4.62 (dd, J=3.3 Hz, J=5.5 Hz, 1H), 4.39 (t, J=5.7 Hz, 1H), 3.43-3.63 (m, 4H), 2.61-2.70 (m, 1H), 2.21-2.29 (m, 1H), 0.90 (s, 9H), 0.10 (s, 6H).

Step 7: Synthesis of (2R,3S,5R)-5-(4-amino-2-chloro-7H-pyrrolo[2,3-d]pyrimidin-7-yl)-3-((tert-butyldimethylsilyl)oxy)-2-(hydroxymethyl)tetrahydrofuran-2-carbaldehyde To a stirred solution of ((3S,5R)-5-(4-amino-2-chloro-7H-pyrrolo[2,3-d]pyrimidin-7-yl)-3-((tert-butyldimethylsilyl)oxy)tetrahydrofuran-2,2-diyl)dimethanol (150 mg, 0.350 mmol) in dry acetonitrile (15 mL) was added IBX (294 mg, 1.049 mmol) under argon atmosphere. The resulting mixture was stirred at 30° C. for 2 hours. The mixture was filtered, washed with CHCl3 (3×15 mL). The filtrate was collected and then concentrated under vacuum to give the title compound, which was used to the next step directly without further purification. LC-MS: (ES, m/z): 427.30 [M+H]+.

Step 8: Synthesis of ((2R,3S,5R)-5-(4-amino-2-chloro-7H-pyrrolo[2,3-d]pyrimidin-7-yl)-3-((tert-butyldimethylsilyl)oxy)-2-ethynyltetrahydrofuran-2-yl)methanol (2R,3S,5R)-5-(4-amino-2-chloro-7H-pyrrolo[2,3-d]pyrimidin-7-yl)-3-((tert-butyldimethylsilyl)oxy)-2-(hydroxymethyl)tetrahydrofuran-2-carbaldehyde (200 mg, 0.468 mmol) was dissolved in anhydrous MeOH (9 mL) followed by the addition of potassium carbonate (162 mg, 1.171 mmol) at 0° C. under argon atmosphere. To the suspension was added a solution of dimethyl (1-diazo-2-oxopropyl)phosphonate (180 mg, 0.937 mmol) in MeOH (1 mL) dropwise with stirring in 1 minute. The resulting mixture was warmed to 30° C. and stirred for 16 hours. The reaction mixture was concentrated under vacuum. The residue was partitioned between ethyl acetate (30 mL) and water (10 mL). The organic layer was collected, washed with brine (2×10 mL), dried over anhydrous $Na_2SO_4$, filtered and concentrated under vacuum. The residue was then purified by preparative-TLC (MeOH/DCM=1/15) to afford the title compound. LC-MS: (ES, m/z): 423.60 [M+H]+. 1H-NMR: (400 MHz, d6-DMSO, ppm): δ 7.55 (br, 2H), 7.34 (d, J=3.6 Hz, 1H), 6.61 (d, J=3.6 Hz, 1H), 6.38 (t, J=6.4 Hz, 1H), 5.32 (t, J=6.0 Hz, 1H), 4.67 (t, J=6.0 Hz, 1H), 3.58-3.61 (m, 1H), 3.48-3.52 (m, 1H), 3.47 (s, 1H), 2.60-2.63 (m, 1H), 2.31-2.35 (m, 1H), 0.91 (s, 9H), 0.11 (d, J=3.6 Hz, 6H).

Step 9: Synthesis of (2R,3S,5R)-5-(4-amino-2-chloro-7H-pyrrolo[2,3-d]pyrimidin-7-yl)-2-ethynyl-2-(hydroxymethyl)tetrahydrofuran-3-ol To a stirred solution of ((2R,3S,5R)-5-(4-amino-2-chloro-7H-pyrrolo[2,3-d]pyrimidin-7-yl)-3-((tert-butyldimethylsilyl)oxy)-2-ethynyltetrahydrofuran-2-yl)methanol (60 mg, 0.142 mmol) in THF (1 mL) was added TBAF THF solution (1 M, 0.28 mL, 0.284 mmol) dropwise with stirring at ambient temperature. The resulting solution was stirred at ambient temperature for 2 hours. The mixture was concentrated under vacuum. The residue was then purified by Prep-HPLC with the following conditions (1#-Pre-HPLC-011(Waters)): Column, SunFire Prep C18 OBD Column, 5 um, 19*150 mm; mobile phase, water (with 10 mmol ammonium bicarbonate) and acetonitrile (8% acetonitrile up to 40% in 6 min, up to 95% in 1.5 min, down to 5% in 1 min); Detector, uv 254&220 nm. The product-containing fractions were collected and lyophilized to give compound 4 as a solid. LC-MS: (ES, m/z): 309.00 [M+H]+. 1H-NMR: (400 MHz, d6-DMSO, ppm): δ 7.54 (br, 2H), 7.33 (d, J=4.0 Hz, 1H), 6.60 (d, J=3.6 Hz, 1H), 6.41 (t, J=6.4 Hz, 1H), 5.52-5.53 (m, 1H), 5.26 (t, J=6.0 Hz, 1H), 4.47-4.48 (m, 1H), 3.61 (dd, J=5.2 Hz, J=11.6 Hz, 1H), 3.53 (dd, J=6.2 Hz, J=11.8 Hz, 1H), 3.48 (s, 1H), 2.41-2.50 (m, 1H), 2.32-2.38 (m, 1H)

Example 5

Synthesis of (2R,3S,5R)-5-(4-amino-5-bromo-7H-pyrrolo[2,3-d]pyrimidin-7-yl)-2-ethynyl-2-(hydroxymethyl)tetrahydrofuran-3-ol (5)

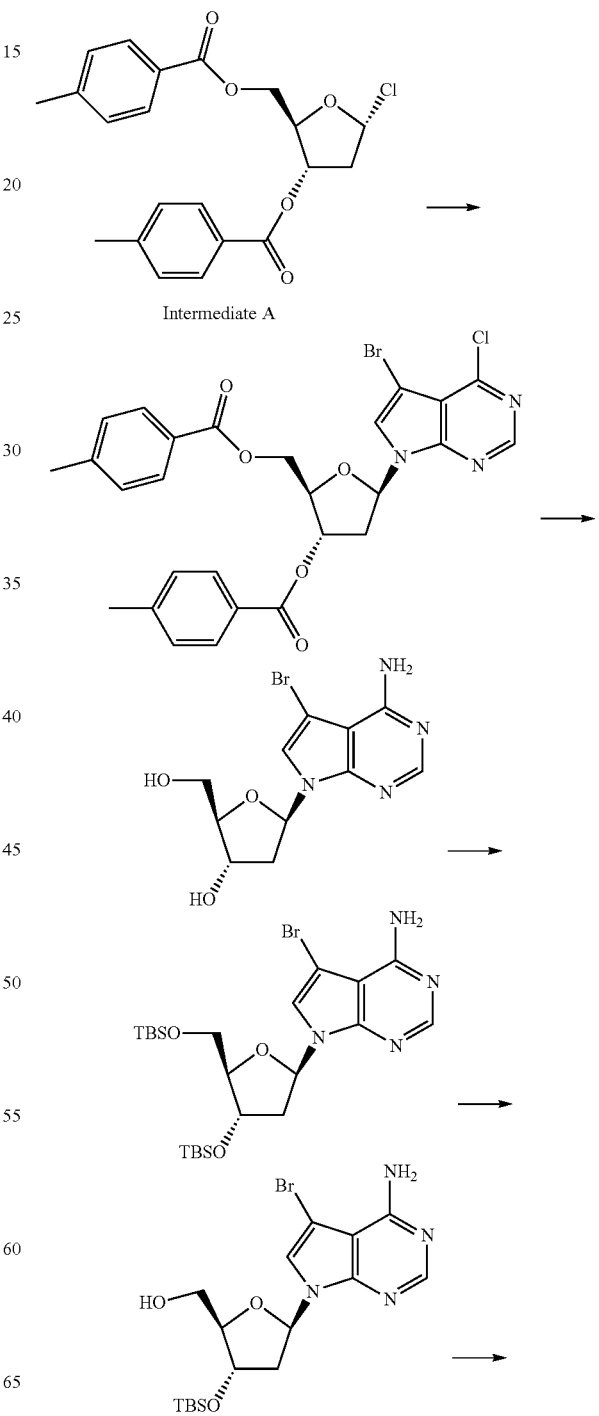

Intermediate A

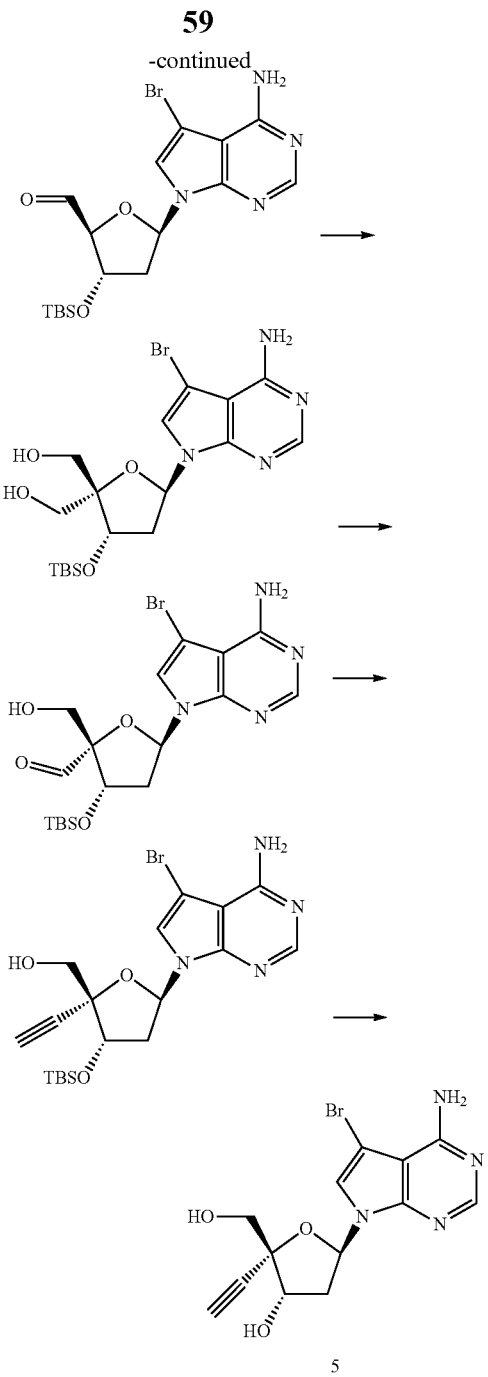

Step 1: Synthesis of (2R,3S,5S)-5-(5-bromo-4-chloro-7H-pyrrolo[2,3-d]pyrimidin-7-yl)-2-(((4-methylbenzoyl)oxy)methyl)tetrahydrofuran-3-yl 4-methylbenzoate Sodium hydride (0.479 g, 11.98 mmol) was added to a stirred solution of 5-bromo-4-chloro-7H-pyrrolo[2,3-d]pyrimidine (2.32 g, 9.98 mmol, synthesis described in Example 3, Step 1) in acetonitrile (30 mL). The resulting mixture was stirred for 30 minutes at 0° C., and then (2R,3S,5R)-5-chloro-2-(((4-methylbenzoyl)oxy)methyl)tetrahydrofuran-3-yl 4-methylbenzoate (4.27 g, 10.98 mmol) was added. After the resulting mixture was stirred at room temperature for 1 hour, it was diluted with 200 mL of ethyl acetate, washed with saturated aqueous sodium bicarbonate (60 mL) and saturated aqueous sodium chloride (60 mL), dried over anhydrous sodium sulfate, and concentrated under vacuum. The residue was purified by silica gel column chromatography with petroleum ether\ethyl acetate (1:2) to give the title compound: $^1$H-NMR (300 MHz, DMSO) δ 8.65 (s, 1H), 8.22 (s, 1H), 7.96 (d, J=8.4 Hz, 2H), 7.84 (d, J=8.1 Hz, 2H), 7.24-7.39 (m, 4H), 6.76-6.79 (m, 1H), 5.74-5.76 (m, 1H), 4.51-4.68 (m, 3H), 3.05-3.15 (m, 1H), 2.74-2.79 (m, 1H), 2.37 (d, J=1.8 Hz, 6H).

Step 2: Synthesis of (2R,3S,5R)-5-(4-amino-5-bromo-7H-pyrrolo[2,3-d]pyrimidin-7-yl)-2-(hydroxymethyl)tetrahydrofuran-3-ol (2R,3S,5R)-5-(5-bromo-4-chloro-7H-pyrrolo[2,3-d]pyrimidin-7-yl)-2-(((4-methylbenzoyl)oxy)methyl)tetrahydrofuran-3-yl 4-methylbenzoate (4.50 g, 7.69 mmol) was added to NH$_3$ saturated i-PrOH (15 mL) at −60° C. The resulting mixture was stirred at 80° C. for 12 hours, and then cooled down to room temperature and evaporated under vacuum to give (2R,3S,5R)-5-(4-amino-5-bromo-7H-pyrrolo[2,3-d]pyrimidin-7-yl)-2-(((4-methylbenzoyl)oxy)methyl)tetrahydrofuran-3-yl 4-methylbenzoate (4.2 g, 7.43 mmol) as a solid. This crude compound was dissolved in 30 mL MeOH, and then sodium methanolate (14.86 mL, 14.86 mmol) was added. After the resulting solution was stirred at room temperature for 2 hours, it was quenched with acetic acid (0.1 mL) and concentrated under vacuum. The crude product was purified by silica gel column chromatography by petroleum ether \ethyl acetate (1:2) to give the title compound: $^1$H-NMR (300 MHz, DMSO) δ 8.12 (s, 1H), 7.78 (s, 1H), 6.78 (s, 2H), 6.48-6.51 (m, 1H), 5.25 (s, 1H), 5.01 (s, 1H), 4.32 (s, 1H), 3.81 (s, 1H), 3.17 (s, 1H), 2.35-2.50 (m, 1H), 2.12-2.19 (m, 1H).

Step 3: Synthesis of 5-bromo-7-((2R,4S,5R)-4-((tert-butyldimethylsilyl)oxy)-5-(((tert-butyldimethylsilyl)oxy)methyl)tetrahydrofuran-2-yl)-7H-pyrrolo[2,3-d]pyrimidin-4-amine Tert-butylchlorodimethylsilane (1.786 g, 11.85 mmol) was added to a stirred solution of (2R,3S,5R)-5-(4-amino-5-bromo-7H-pyrrolo[2,3-d]pyrimidin-7-yl)-2-(hydroxymethyl)tetrahydrofuran-3-ol (1.3 g, 3.95 mmol), 1H-imidazole (1.076 g, 15.80 mmol) in DMF (8 mL). The resulting mixture was stirred at room temperature for 4 hours, and then diluted with 400 mL of ethyl acetate, washed with saturated aqueous sodium bicarbonate (80 mL) and saturated aqueous sodium chloride (80 mL), dried over anhydrous sodium sulfate and concentrated in vacuum. The residue was purified by silica gel column chromatography with ethyl acetate/petroleum ether (1:4) to give the title compound: $^1$H-NMR (300 MHz, DMSO) δ 8.10 (s, 1H), 7.55 (s, 1H), 6.79 (s, 2H), 6.48-6.53 (m, 1H), 4.50 (s, 1H), 3.62-3.76 (m, 3H), 2.43-2.50 (m, 1H), 2.17-2.16 (m, 1H), 0.88 (d, J=2.7 Hz, 18H), 0.10 (s, 6H), 0.05 (s, 6H).

Step 4: Synthesis of ((2R,3S,5R)-5-(4-amino-5-bromo-7H-pyrrolo[2,3-d]pyrimidin-7-yl)-3-((tert-butyldimethylsilyl)oxy)tetrahydrofuran-2-yl)

5-bromo-7-((2R,4S,5R)-4-((tertbutyldimethylsilyl)oxy)-5-(((tertbutyldimethylsilyl)oxy)methyl)tetrahydrofuran-2-yl)-7H-pyrrolo[2,3-d]pyrimidin-4-amine (1.55 g, 2.78 mmol) was dissolved in THF (4 mL) and then treated with a precooled solution of trifluoroacetic acid/water (v/v=1/1, 4 mL) dropwise with stirring at 0° C. in 10 minutes. After the resulting mixture was stirred at 0° C. for 2 hours, it was coevaporated with toluene below 25° C. to give a pink syrup. The residue was applied onto a silica gel column, eluted with ethyl acetate/dichloromethane (1/1) to give the title compound: $^1$H-NMR (300 MHz, DMSO) δ 8.19 (s, 1H), 7.74 (s, 1H), 7.28 (s, 2H), 6.50 (q, J=6.0 Hz, 2H), 4.51 (q, J=2.7 Hz, 1H), 3.81 (s, 1H), 3.47-3.57 (m, 2H), 2.49-2.58 (m, 1H), 2.17-2.22 (m, 1H), 0.85 (s, 9H), 0.09 (s, 6H).

Step 5: Synthesis of (2R,3S)-2-(((tert-butyldiphenylsilyloxy)methyl)-5-methoxy-2-phenyltetrahydrofuran-3-yl 4-methylbenzoate 2-Iodoxybenzoic acid (839 mg, 3.00 mmol) was added to a solution of ((2R,3S,5R)-5-(4-amino-5-bromo-7H-pyrrolo[2,3-d]pyrimidin-7-yl)-3-((tert-butyldimethylsilyl)oxy)tetrahydrofuran-2-yl)methanol (443 mg, 0.999 mmol) in acetonitrile (45 mL). The resulting solution was stirred at 80° C. for 2 hours, then cooled down to 0° C., filtered and concentrated under reducing pressure. This resulted in the title compound, which was used to the next step directly without further purification: MS(ES, m/z): 441.08[M+H]$^+$.

Step 6: Synthesis of ((2S,4R)-4-(4-amino-5-bromo-7H-pyrrolo[2,3-d]pyrimidin-7-yl)-2-((tert-butyldimethylsilyl)oxy)cyclopentane-1,1-diyl)dimethanol Sodium hydroxide (4.03 mL, 8.07 mmol) was added to a stirred solution of (2S,3S,5R)-5-(4-amino-5-bromo-7H-pyrrolo[2,3-d]pyrimidin-7-yl)-3-((tert-butyldimethylsilyl)oxy)tetrahydrofuran-2-carbaldehyde (445 mg, 1.008 mmol) and formaldehyde (1009 mg, 10.08 mmol) in dioxane (6 mL). The resulting mixture was stirred at room temperature for 3 hours, and then diluted with 150 mL of ethyl acetate, washed with saturated aqueous sodium bicarbonate (30 mL) and saturated aqueous sodium chloride (30 mL), dried over anhydrous sodium sulfate and concentrated under vacuum to give a solid. Sodium borohydride (109 mg, 2.88 mmol) was added to the solution of the prior solid in ethanol (15 mL) at 0° C. The resulting solution was stirred at room temperature for 2 hours, then quenched with acetic acid (0.1 mL) and concentrated under reducing pressure. The crude product was applied onto a silica gel column chromatography by petroleum ether \ethyl acetate (1:2) to give the title compound. MS(ES, m/z): 473.43 [M+H]$^+$.

Step 7: Synthesis of (2R,3S,5R)-5-(4-amino-5-bromo-7H-pyrrolo[2,3-d]pyrimidin-7-yl)-3-((tert-butyldimethylsilyl)oxy)-2-(hydroxymethyl)tetrahydrofuran-2-carbaldehyde 2-Iodoxybenzoic acid (302 mg, 1.077 mmol) was added to a solution of ((3S,5R)-5-(4-amino-5-bromo-7H-pyrrolo[2,3-d]pyrimidin-7-yl)-3-((tert-butyldimethylsilyl)oxy)tetrahydrofuran-2,2-diyl)dimethanol (170 mg, 0.359 mmol) in acetonitrile (40 mL). After the resulting solution was stirred at 0° C. for 12 hours, it was cooled down to 0° C. and then concentrated under reducing pressure to give the title compound, which was used to the next step directly without further purification. MS(ES, m/z): 471.43[M+H]$^+$.

Step 8: Synthesis of ((2R,3S,5R)-5-(4-amino-5-bromo-7H-pyrrolo[2,3-d]pyrimidin-7-yl)-3-((tert-butyldimethylsilyl)oxy)-2-ethynyltetrahydrofuran-2-yl)methanol Dimethyl (1-diazo-2-oxopropyl)phosphonate (139 mg, 0.721 mmol) was added to a solution of (2R,3S,5R)-5-(4-amino-5-bromo-7H-pyrrolo[2,3-d]pyrimidin-7-yl)-3-((tert-butyldimethylsilyl)oxy)-2-(hydroxymethyl)tetrahydrofuran-2-carbaldehyde (170 mg, 0.361 mmol), potassium carbonate (125 mg, 0.902 mmol) in methanol (8 mL) at 0° C. The resulting solution was stirred at room temperature for 12 hours, then filtered and concentrated under reducing pressure. The crude compound was purified by Prep-TLC by petroleum ether\ethyl acetate (1:2) to give the title compound. $^1$H-NMR (300 MHz, CD$_3$OD, ppm) δ 8.00 (s, 1H), 7.39 (s, 1H), 6.44-6.47 (m, 1H), 4.62-4.66 (m, 1H), 3.61-3.71 (m, 2H), 2.90 (s, 1H), 2.25-2.55 (m, 2H), 0.88 (s, 9H), 0.57 (d, J=3 Hz, 6H).

Step 9: Synthesis of (2R,3S,5R)-5-(4-amino-5-bromo-7H-pyrrolo[2,3-d]pyrimidin-7-yl)-2-ethynyl-2-(hydroxymethyl)tetrahydrofuran-3-ol ((2R,3S,5R)-5-(4-amino-5-bromo-7H-pyrrolo[2,3-d]pyrimidin-7-yl)-3-((tert-butyldimethylsilyl)oxy)-2-ethynyltetrahydrofuran-2-yl)methanol (40 mg, 0.086 mmol) and TBAF (0.086 mL, 0.086 mmol) was dissolved into THF (1 mL). The resulting solution was stirred for 2 hours at 30° C., then evaporated and purified as following condition: Column: X Bridge C18, 19*150 mm, 5 um; Mobile Phase A:Water/0.05% TFA, Mobile Phase B: ACN; Flow rate: 20 mL/min; Gradient: 30% B to 70% B in 10 min; 254 nm. This resulted in compound 5 as a solid: $^1$H-NMR (300 MHz, DMSO, ppm) δ 8.11 (s, 1H), 7.59 (s, 1H), 6.52 (t, J=6.6 Hz, 1H), 4.48 (t, J=6.6 Hz, 1H), 3.53-3.64 (m, 2H), 3.44 (s, 1H), 2.33-2.52 (m, 2H); MS (ES, m/z): 353.17 [M+H]$^+$.

Example 6

Synthesis of (2R,3S,5R)-5-(4-amino-5-chloro-7H-pyrrolo[2,3-d]pyrimidin-7-yl)-2-ethynyl-2-(hydroxymethyl)tetrahydrofuran-3-ol (6)

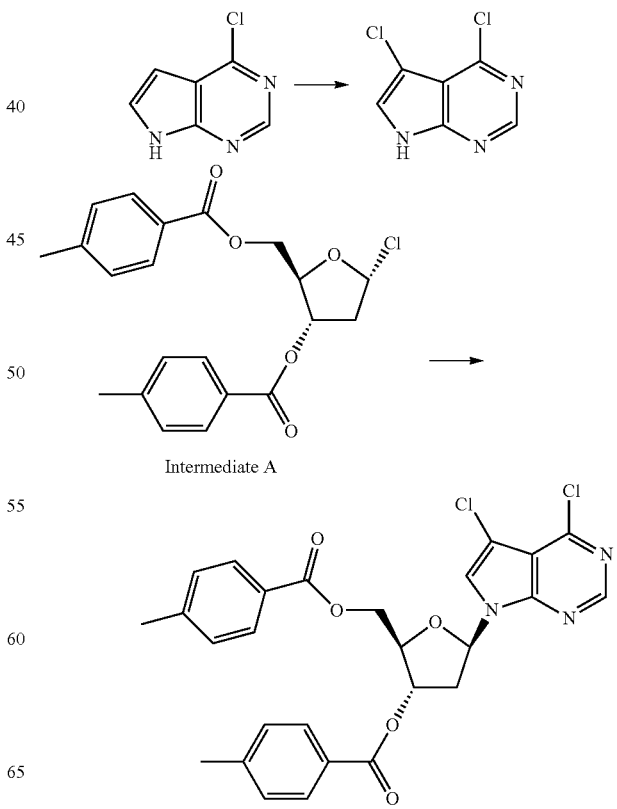

Intermediate A

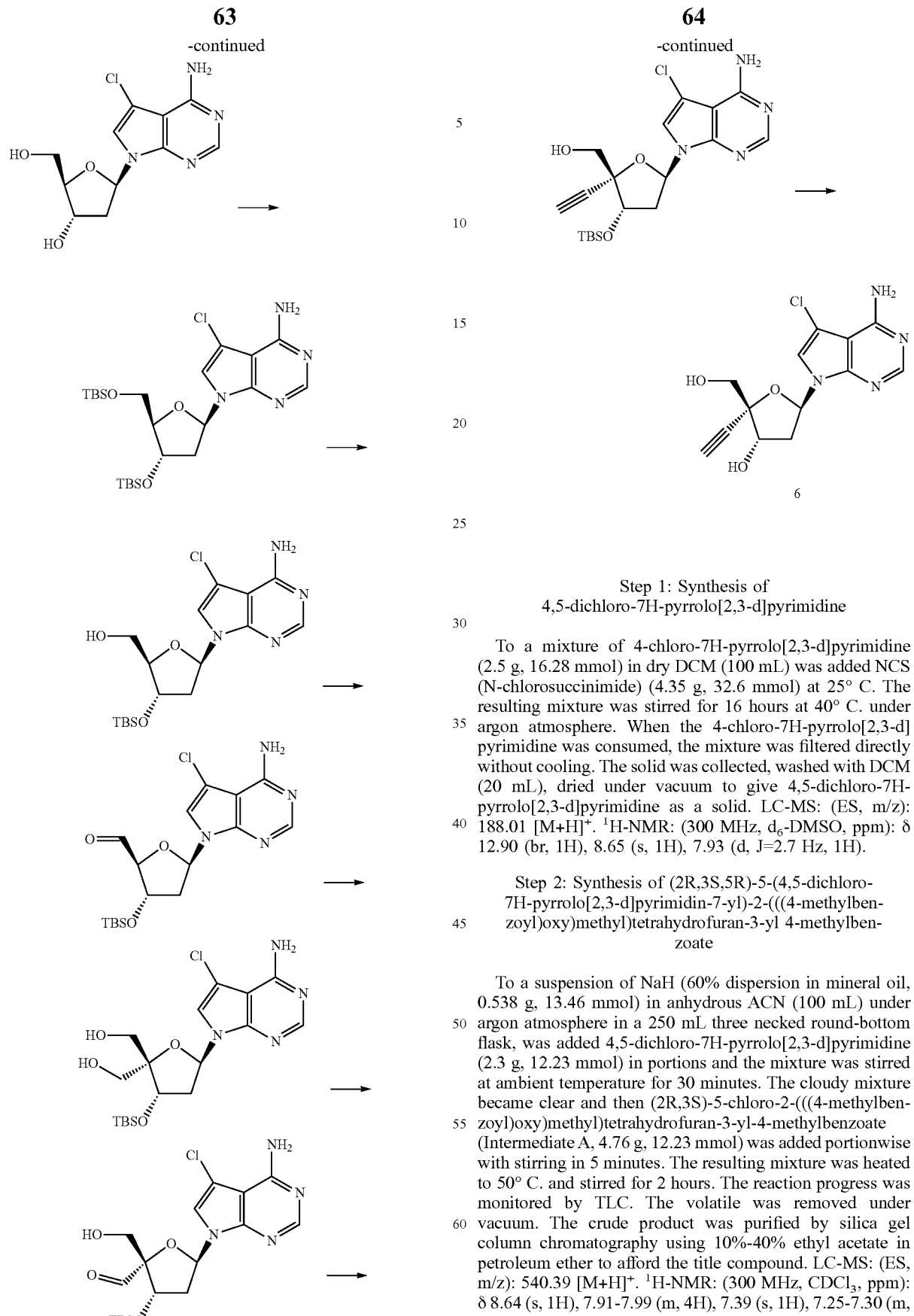

Step 1: Synthesis of 4,5-dichloro-7H-pyrrolo[2,3-d]pyrimidine

To a mixture of 4-chloro-7H-pyrrolo[2,3-d]pyrimidine (2.5 g, 16.28 mmol) in dry DCM (100 mL) was added NCS (N-chlorosuccinimide) (4.35 g, 32.6 mmol) at 25° C. The resulting mixture was stirred for 16 hours at 40° C. under argon atmosphere. When the 4-chloro-7H-pyrrolo[2,3-d] pyrimidine was consumed, the mixture was filtered directly without cooling. The solid was collected, washed with DCM (20 mL), dried under vacuum to give 4,5-dichloro-7H-pyrrolo[2,3-d]pyrimidine as a solid. LC-MS: (ES, m/z): 188.01 [M+H]$^+$. $^1$H-NMR: (300 MHz, d$_6$-DMSO, ppm): δ 12.90 (br, 1H), 8.65 (s, 1H), 7.93 (d, J=2.7 Hz, 1H).

Step 2: Synthesis of (2R,3S,5R)-5-(4,5-dichloro-7H-pyrrolo[2,3-d]pyrimidin-7-yl)-2-(((4-methylbenzoyl)oxy)methyl)tetrahydrofuran-3-yl 4-methylbenzoate To a suspension of NaH (60% dispersion in mineral oil, 0.538 g, 13.46 mmol) in anhydrous ACN (100 mL) under argon atmosphere in a 250 mL three necked round-bottom flask, was added 4,5-dichloro-7H-pyrrolo[2,3-d]pyrimidine (2.3 g, 12.23 mmol) in portions and the mixture was stirred at ambient temperature for 30 minutes. The cloudy mixture became clear and then (2R,3S)-5-chloro-2-(((4-methylbenzoyl)oxy)methyl)tetrahydrofuran-3-yl-4-methylbenzoate (Intermediate A, 4.76 g, 12.23 mmol) was added portionwise with stirring in 5 minutes. The resulting mixture was heated to 50° C. and stirred for 2 hours. The reaction progress was monitored by TLC. The volatile was removed under vacuum. The crude product was purified by silica gel column chromatography using 10%-40% ethyl acetate in petroleum ether to afford the title compound. LC-MS: (ES, m/z): 540.39 [M+H]$^+$. $^1$H-NMR: (300 MHz, CDCl$_3$, ppm): δ 8.64 (s, 1H), 7.91-7.99 (m, 4H), 7.39 (s, 1H), 7.25-7.30 (m, 4H), 6.80 (t, J=6.9 Hz, 1H), 5.75 (dd, J=3.6 Hz, J=6.0 Hz, 1H), 4.60-4.78 (m, 3H), 2.76-2.80 (m, 2H), 2.44 (d, J=4.8 Hz, 6H).

Step 3: Synthesis of (2R,3S,5R)-5-(4-amino-5-chloro-7H-pyrrolo[2,3-d]pyrimidin-7-yl)-2-(hydroxymethyl)tetrahydrofuran-3-ol To a 150 mL steel bomb, was placed (2R,3S,5R)-5-(4,5-dichloro-7H-pyrrolo[2,3-d]pyrimidin-7-yl)-2-(((4-methylbenzoyl)oxy)methyl)tetrahydrofuran-3-yl 4-methylbenzoate (3.6 g, 6.66 mmol). The medium was cooled to −40° C. To this was added isopropanolic ammonia (isopropanol/liquid ammonia=1/3, v/v, 120 mL). The medium was sealed, heated to 90° C. and stirred for 16 hours. TLC indicated that the started nucleoside was all consumed and target product was observed as a major product. The resulting mixture was concentrated under vacuum. The crude product was purified by silica gel column chromatography using 2%-10% methanol in dichloromethane to afford the title compound. LC-MS: (ES, m/z): 284.70 [M+H]$^+$. $^1$H-NMR: (300 MHz, d$_6$-DMSO, ppm): δ 8.09 (s, 1H), 7.58 (s, 1H), 6.87 (br, 2H), 6.51 (dd, J=6.3 Hz, J=7.8 Hz, 1H), 5.25 (d, J=4.2 Hz, 1H), 5.03 (t, J=5.6 Hz, 1H), 4.30-4.34 (m, 1H), 3.81 (dd, J=4.3 Hz, J=6.8 Hz, 1H), 3.46-3.60 (m, 2H), 2.40-2.48 (m, 1H), 2.13-2.20 (m, 1H).

Step 4. Synthesis of 7-((2R,4S,5R)-4-((tert-butyldimethylsilyl)oxy)-5-(((tert-butyldimethylsilyl)oxy)methyl)tetrahydrofuran-2-yl)-5-chloro-7H-pyrrolo[2,3-d]pyrimidin-4-amine To a stirred solution of (2R,3S,5R)-5-(4-amino-5-chloro-7H-pyrrolo[2,3-d]pyrimidin-7-yl)-2-(hydroxymethyl)tetrahydrofuran-3-ol (1.7 g, 5.97 mmol) in DMF (10 mL) was added 1H-imidazole (1.423 g, 20.90 mmol) and TBDMS-Cl (2.70 g, 17.91 mmol) successively at 0° C. under argon atmosphere. The resulting mixture was warmed to 25° C. and stirred for 2 hours. The resulting solution was diluted with ethyl acetate (100 mL), washed with water (100 mL). The aqueous layer was re-extracted with ethyl acetate (2×100 mL). The organic layers were combined, washed with saturated aq NaHCO$_3$ (2×100 mL) and brine (2×100 mL) successively, dried over anhydrous Na$_2$SO$_4$, filtered and concentrated under vacuum. The residue was purified by silica gel column chromatography using 2%-10% ethyl acetate in petroleum ether to afford the title compound. LC-MS: (ES, m/z): 513.22 [M+H]$^+$. $^1$H-NMR: (300 MHz, d$_6$-DMSO, ppm): ε 8.10 (s, 1H), 7.50 (s, 1H), 6.85 (br, 2H), 6.51 (t, J=6.8 Hz, 1H), 4.48-4.52 (m, 1H), 3.62-3.80 (m, 3H), 2.55-2.60 (m, 1H), 2.17-2.24 (m, 1H), 0.89 (s, 18H), 0.08 (d, J=13.6 Hz, 12H).

Step 5. Synthesis of ((2R,3S,5R)-5-(4-amino-5-chloro-7H-pyrrolo[2,3-d]pyrimidin-7-yl)-3-((tert-butyldimethylsilyl)oxy)tetrahydrofuran-2-yl)methanol To a stirred solution of ((2R,4S,5R)-4-((tert-butyldimethylsilyl)oxy)-5-(((tert-butyldimethylsilyl)oxy)methyl)tetrahydrofuran-2-yl)-5-chloro-7H-pyrrolo[2,3-d]pyrimidin-4-amine (2.42 g, 4.72 mmol) in THF (48 mL) was added a pre-cooled solution of trifluoroacetic acid/water (1/1, v/v, 24 mL) dropwise with stirring at 0° C. in 10 minutes. The resulting mixture was stirred at 0° C. for 4 hours. The reaction progress was monitored by TLC. The resulting solution was co-evaporated with toluene (3×100 mL) while maintain the inner temperature below 25° C. The resulting crude material was purified by silica gel column chromatography using 2%-10% methanol in dichloromethane to afford the title compound. LC-MS: (ES, m/z): 398.96 [M+H]$^+$. $^1$H-NMR: (300 MHz, d$_6$-DMSO, ppm): δ 8.28 (s, 1H), 7.86 (br, 2H), 7.78 (s, 1H), 6.52 (t, J=6.8 Hz, 1H), 4.53 (t, J=2.6 Hz, 1H), 3.83 (dd, J=4.5 Hz, J=6.9 Hz, 1H), 3.48-3.60 (m, 2H), 2.50-2.58 (m, 1H), 2.18-2.25 (m, 1H), 0.90 (s, 9H), 0.11 (s, 6H).

Step 6. Synthesis of (2S,3S,5R)-5-(4-amino-5-chloro-7H-pyrrolo[2,3-d]pyrimidin-7-yl)-3-((tert butyldimethylsilyl)oxy)tetrahydrofuran-2-carbaldehyde To a stirred solution of ((2R,3S,5R)-5-(4-amino-5-chloro-7H-pyrrolo[2,3-d]pyrimidin-7-yl)-3-((tert-butyldimethylsilyl)oxy)tetrahydrofuran-2-yl)methanol (300 mg, 0.752 mmol) in anhydrous ACN (30 mL) was added 2-Iodoxybenzoic acid (632 mg, 2.256 mmol) under argon atmosphere. The mixture was heated to 85° C. and stirred for 20 minutes. The solid was filtered out. The filtrate was concentrated in vacuo to afford the title compound, which was used to the next reaction step directly without further purification. LC-MS: (ES, m/z): 396.94 [M+H]$^+$.

Step 7. Synthesis of ((3S,5R)-5-(4-amino-5-chloro-7H-pyrrolo[2,3-d]pyrimidin-7-yl)-3-((tert-butyldimethylsilyl)oxy)tetrahydrofuran-2,2-diyl)dimethanol To a stirred solution of (2S,3S,5R)-5-(4-amino-5-chloro-7H-pyrrolo[2,3-d]pyrimidin-7-yl)-3-((tert-butyldimethylsilyl)oxy)tetrahydrofuran-2-carbaldehyde (434 mg, 0.820 mmol) in 1,4-dioxane (25 mL) in a 100 mL round-bottom flask, was added formaldehyde solution (5 mL), followed by the addition of sodium hydroxide solution (2 N, 5 mL, 10.00 mmol) dropwise at 0° C. in 5 minutes. The resulting mixture was warmed to 25° C. and stirred for 3 hours. Upon the started nucleoside-aldehyde was all consumed, the reaction mixture was neutralized by the addition of AcOH. The mixture was diluted with ethyl acetate (60 mL) and washed successively with water (2×20 mL), saturated aqueous NaHCO$_3$ (2×20 mL) and brine (2×20 mL). The organic layer was dried over Na$_2$SO$_4$ and evaporated under reduced pressure. The residue was re-dissolved in anhydrous EtOH (30 mL) and added sodium tetrahydroborate (62.0 mg, 1.640 mmol) in portions at 0° C. under argon atmosphere. After stirring for 16 hour at 25° C., the reaction mixture was neutralized by the addition of AcOH. The mixture was concentrated under vacuum. The residue was suspended in CHCl$_3$ (40 mL) and washed successively with water (2×15 mL) and brine (2×15 mL). The organic layer was dried over Na$_2$SO$_4$, filtered and concentrated under vacuum. The residue was purified by silica gel column chromatography with dichloromethane/methanol (30/1) to give the title compound. LC-MS: (ES, m/z): 428.99 [M+H]$^+$. $^1$H-NMR: (300 MHz, d$_6$-DMSO, ppm): δ 8.10 (s, 1H), 7.60 (s, 1H), 6.86 (br, 2H), 6.54 (t, J=6.9 Hz, 1H), 5.01 (t, J=5.3 Hz, 1H), 4.59 (dd, J=3.0 Hz, J=5.4 Hz, 1H), 4.40 (t, J=5.6 Hz, 1H), 3.42-3.61 (m, 4H), 2.60-2.69 (m, 1H), 2.18-2.25 (m, 1H), 0.89 (s, 9H), 0.09 (s, 6H).

Step 8. Synthesis of (2R,3S,5R)-5-(4-amino-5-chloro-7H-pyrrolo[2,3-d]pyrimidin-7-yl)-3-((tert-butyldimethylsilyl)oxy)-2-(hydroxymethyl)tetrahydrofuran-2-carbaldehyde ((3S,5R)-5-(4-amino-5-chloro-7H-pyrrolo[2,3-d]pyrimidin-7-yl)-3-((tert-butyldimethylsilyl)oxy)tetrahydrofuran-2,2-diyl)dimethanol (166 mg, 0.387 mmol) was dissolved in anhydrous ACN (20 mL) under argon atmosphere and then IBX (325 mg, 1.161 mmol) was added. The resulting mixture was warmed to 30° C. and stirred for 20 hours. The solid was filtered out. The filtrate was concentrated in vacuo to afford the title compound, which was used to the next reaction step directly without further purification. LC-MS: (ES, m/z): 426.97 [M+H]+.

Step 9: Synthesis of ((2R,3S,5R)-5-(4-amino-5-chloro-7H-pyrrolo[2,3-d]pyrimidin-7-yl)-3-((tert-butyldimethylsilyl)oxy)-2-ethynyltetrahydrofuran-2-yl)methanol To a stirred solution of (2R,3S,5R)-5-(4-amino-5-chloro-7H-pyrrolo[2,3-d]pyrimidin-7-yl)-3-((tert-butyldimethylsilyl)oxy)-2-(hydroxymethyl)tetrahydrofuran-2-carbaldehyde (160 mg, 0.375 mmol) in dry MeOH (8 mL) was added $K_2CO_3$ (129 mg, 0.937 mmol) followed by the addition of dimethyl (1-diazo-2-oxopropyl)phosphonate (144 mg, 0.749 mmol) at 0° C. dropwise with stirring under argon atmosphere. The resulting mixture was gradually warmed to 25° C. and stirred for 16 hours. The resulting mixture was concentrated under vacuum. The residue was purified by silica gel column chromatography using 30%-50% ethyl acetate in petroleum ether to afford the title compound. LC-MS: (ES, m/z): 422.98 [M+H]+. 1H-NMR: (300 MHz, $d_6$-DMSO, ppm): δ 8.10 (s, 1H), 7.58 (s, 1H), 6.90 (br, 2H), 6.52 (t, J=6.6 Hz, 1H), 5.42-5.46 (m, 1H), 4.64 (t, J=5.7 Hz, 1H), 3.59-3.67 (m, 1H), 3.50-3.54 (m, 1H), 3.48 (s, 1H), 2.59-2.64 (m, 1H), 2.27-2.31 (m, 1H), 0.91 (s, 9H), 0.12 (s, 6H).

Step 10: Synthesis of (2R,3S,5R)-5-(4-amino-5-chloro-7H-pyrrolo[2,3-d]pyrimidin-7-yl)-2-ethynyl-2-(hydroxymethyl)tetrahydrofuran-3-ol (6)

To a stirred solution of ((2R,3S,5R)-5-(4-amino-5-chloro-7H-pyrrolo[2,3-d]pyrimidin-7-yl)-3-((tert-butyldimethylsilyl)oxy)-2-ethynyltetrahydrofuran-2-yl)methanol (64 mg, 0.151 mmol) in THF (3 mL) was added TBAF solution (1.0 M, 151 μl, 0.151 mmol) dropwise with stirring under argon atmosphere. The resulting solution was stirred for 1 hour at 25° C. The resulting mixture was concentrated under vacuum. The residue was applied onto a silica gel column and eluted with DCM/MeOH (20/1 to 5/1) to give crude product. The crude product was further purified by Prep-HPLC with the following conditions (1#-Pre-HPLC-011 (Waters)): Column, SunFire Prep C18 OBD (Optimum Bed Density) Column, 5 um, 19*150 mm; mobile phase, water (with 10 mmol ammonium bicarbonate) and acetonitrile (10% acetonitrile up to 45% in 5 min, up to 95% in 1.5 min, down to 5% in 1 min); Detector, uv 254&220 nm. The product-containing fractions were collected and lyophilized to give compound 6 as a solid. LC-MS: (ES, m/z): 308.72 [M+H]+. 1H-NMR: (400 MHz, $d_6$-DMSO, ppm): δ 8.10 (s, 1H), 7.54 (s, 1H), 6.88 (br, 2H), 6.52 (t, J=6.4 Hz, 1H), 5.39-5.52 (m, 2H), 4.48 (t, J=6.6 Hz, 1H), 3.59 (dd, J=12.0 Hz, J=28.8 Hz, 2H), 3.48 (s, 1H), 2.47-2.54 (m, 1H), 2.31-2.37 (m, 1H).

Intermediate B

Synthesis of ((2R,3S,5R)-5-(4-amino-5-iodo-7H-pyrrolo[2,3-d]pyrimidin-7-yl)-3-((tert-butyldimethylsilyl)oxy)-2-ethynyltetrahydrofuran-2-yl)methanol Intermediate B

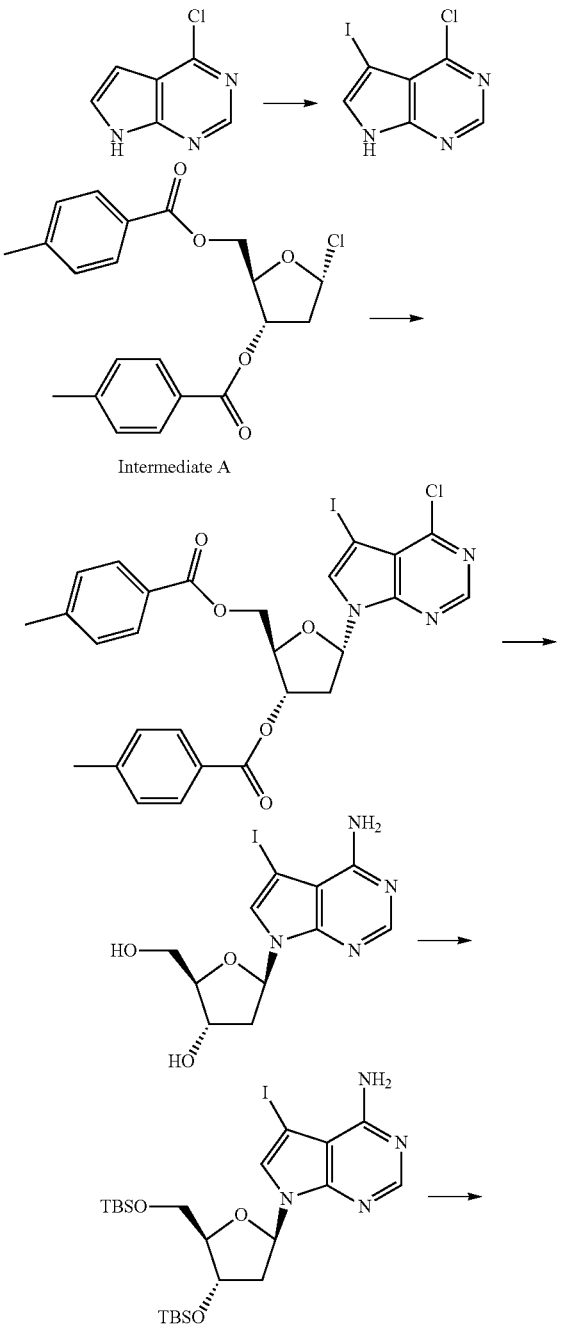

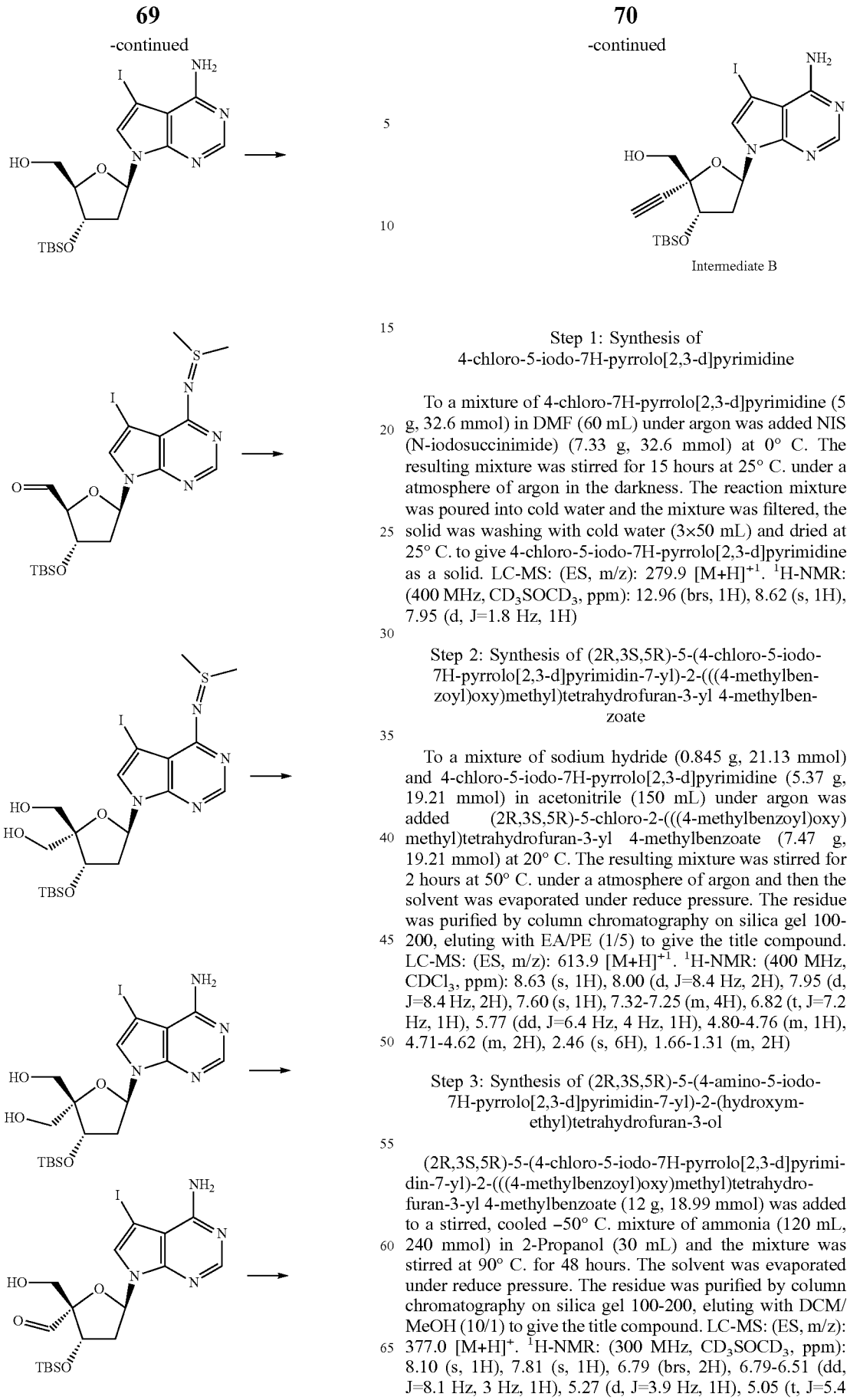

Intermediate B

Step 1: Synthesis of 4-chloro-5-iodo-7H-pyrrolo[2,3-d]pyrimidine

To a mixture of 4-chloro-7H-pyrrolo[2,3-d]pyrimidine (5 g, 32.6 mmol) in DMF (60 mL) under argon was added NIS (N-iodosuccinimide) (7.33 g, 32.6 mmol) at 0° C. The resulting mixture was stirred for 15 hours at 25° C. under a atmosphere of argon in the darkness. The reaction mixture was poured into cold water and the mixture was filtered, the solid was washing with cold water (3×50 mL) and dried at 25° C. to give 4-chloro-5-iodo-7H-pyrrolo[2,3-d]pyrimidine as a solid. LC-MS: (ES, m/z): 279.9 [M+H]$^{+1}$. $^1$H-NMR: (400 MHz, CD$_3$SOCD$_3$, ppm): 12.96 (brs, 1H), 8.62 (s, 1H), 7.95 (d, J=1.8 Hz, 1H)

Step 2: Synthesis of (2R,3S,5R)-5-(4-chloro-5-iodo-7H-pyrrolo[2,3-d]pyrimidin-7-yl)-2-(((4-methylbenzoyl)oxy)methyl)tetrahydrofuran-3-yl 4-methylbenzoate To a mixture of sodium hydride (0.845 g, 21.13 mmol) and 4-chloro-5-iodo-7H-pyrrolo[2,3-d]pyrimidine (5.37 g, 19.21 mmol) in acetonitrile (150 mL) under argon was added (2R,3S,5R)-5-chloro-2-(((4-methylbenzoyl)oxy)methyl)tetrahydrofuran-3-yl 4-methylbenzoate (7.47 g, 19.21 mmol) at 20° C. The resulting mixture was stirred for 2 hours at 50° C. under a atmosphere of argon and then the solvent was evaporated under reduce pressure. The residue was purified by column chromatography on silica gel 100-200, eluting with EA/PE (1/5) to give the title compound. LC-MS: (ES, m/z): 613.9 [M+H]$^{+1}$. $^1$H-NMR: (400 MHz, CDCl$_3$, ppm): 8.63 (s, 1H), 8.00 (d, J=8.4 Hz, 2H), 7.95 (d, J=8.4 Hz, 2H), 7.60 (s, 1H), 7.32-7.25 (m, 4H), 6.82 (t, J=7.2 Hz, 1H), 5.77 (dd, J=6.4 Hz, 4 Hz, 1H), 4.80-4.76 (m, 1H), 4.71-4.62 (m, 2H), 2.46 (s, 6H), 1.66-1.31 (m, 2H)

Step 3: Synthesis of (2R,3S,5R)-5-(4-amino-5-iodo-7H-pyrrolo[2,3-d]pyrimidin-7-yl)-2-(hydroxymethyl)tetrahydrofuran-3-ol (2R,3S,5R)-5-(4-chloro-5-iodo-7H-pyrrolo[2,3-d]pyrimidin-7-yl)-2-(((4-methylbenzoyl)oxy)methyl)tetrahydrofuran-3-yl 4-methylbenzoate (12 g, 18.99 mmol) was added to a stirred, cooled −50° C. mixture of ammonia (120 mL, 240 mmol) in 2-Propanol (30 mL) and the mixture was stirred at 90° C. for 48 hours. The solvent was evaporated under reduce pressure. The residue was purified by column chromatography on silica gel 100-200, eluting with DCM/MeOH (10/1) to give the title compound. LC-MS: (ES, m/z): 377.0 [M+H]$^+$. $^1$H-NMR: (300 MHz, CD$_3$SOCD$_3$, ppm): 8.10 (s, 1H), 7.81 (s, 1H), 6.79 (brs, 2H), 6.79-6.51 (dd, J=8.1 Hz, 3 Hz, 1H), 5.27 (d, J=3.9 Hz, 1H), 5.05 (t, J=5.4

Hz, 1H), 4.33 (brs, 1H), 3.81 (brs, 1H), 3.60-3.46 (m, 2H), 2.51-2.44 (m, 1H), 2.19-2.10 (m, 1H)

Step 4: Synthesis of 7-((2R,4S,5R)-4-((tert-butyldimethylsilyl)oxy)-5-(((tert-butyldimethylsilyl)oxy)methyl)tetrahydrofuran-2-yl)-5-iodo-7H-pyrrolo[2,3-d]pyrimidin-4-amine To a mixture of (2R,3S,5R)-5-(4-amino-5-iodo-7H-pyrrolo[2,3-d]pyrimidin-7-yl)-2-(hydroxymethyl)tetrahydrofuran-3-ol (6 g, 15.95 mmol) and imidazole (4.34 g, 63.8 mmol) in DMF (30 mL) under argon was added TBS-Cl (44.7 mL, 44.7 mmol) at 0° C. The resulting mixture was stirred for 2 hours at 23° C. under a atmosphere of argon. The reaction progress was monitored by LCMS. The reaction mixture was quenched with water (150 mL) and extracted with ethyl acetate (3×200 mL). The combined organic layers was washed with brine (5×200 mL), dried over anhydrous sodium sulfate and filtered. The filtrate was concentrated under reduced pressure, the residue was purified by a silica gel column, eluting with EA/PE (3:7) to afford the title compound. LC-MS: (ES, m/z): 605.3 [M+H]$^{+1}$. $^1$H-NMR: (400 MHz, CD$_3$SOCD$_3$, ppm): 8.10 (s, 1H), 7.58 (s, 1H), 6.67 (brs. 2H), 6.49 (t, J=6.8 Hz, 1H), 4.50 (t, J=2.4 Hz, 1H), 3.88-3.81 (m, 1H), 3.74 (dd, J=10.8 Hz, 5.6 Hz, 1H), 3.65 (dd, J=10.8 Hz, 4 Hz, 1H), 2.50-2.49 (m, 1H), 2.25-2.14 (m, 1H), 0.89 (s, 18H), 0.10-0.07 (m, 12H).

Step 5: Synthesis of ((2R,3S,5R)-5-(4-amino-5-iodo-7H-pyrrolo[2,3-d]pyrimidin-7-yl)-3-((tert-butyldimethylsilyl)oxy)tetrahydrofuran-2-yl)methanol To a mixture of 7-((2R,4S,5R)-4-((tert-butyldimethylsilyl)oxy)-5-(((tert-butyldimethylsilyl)oxy)methyl)tetrahydrofuran-2-yl)-5-iodo-7H-pyrrolo[2,3-d]pyrimidin-4-amine (6.6 g, 10.92 mmol) in THF (66 mL) was added a solution of TFA (16 mL, 208 mmol) in Water (16 mL) at 0° C. The resulting mixture was stirred for 4 hour at 0° C. The reaction progress was monitored by LCMS. The solvent was evaporated under reduced pressure. The residue was dissolved in DCM/MeOH (10/1, 150 mL) and the pH value of the solution was adjusted to 7 with sodium hydrogen carbonate (5.0 g), filtered and the solvent was evaporated under reduced pressure. The residue was purified by column chromatography on silica gel 100-200, eluting with 40-50% EA in PE to give the title compound. LC-MS: (ES, m/z): 491.1 [M+H]$^{+1}$. $^1$H-NMR: (400 MHz, CD$_3$SOCD$_3$, ppm): 8.14 (s, 1H), 7.71 (s, 1H), 6.88 (brs, 2H), 6.47 (dd, J=8.4 Hz, 6 Hz, 1H), 4.51 (t, J=2.4 Hz, 1H), 3.80-3.79 (m, 1H), 3.54-3.50 (m, 2H), 2.57-2.53 (m, 1H), 2.18-2.13 (m, 1H), 0.89 (s, 9H), 0.10 (s, 6H).

Step 6: Synthesis of (2S,3S,5R)-3-[(tert-butyldimethylsilyl)oxy]-5-{4-[(dimethyl-Si{4}-sulfanylidene)amino]-5-iodo-7H-pyrrolo[2,3-d]pyrimidin-7-yl}oxolane-2-carbaldehyde To a mixture of ((2R,3S,5R)-5-(4-amino-5-iodo-7H-pyrrolo[2,3-d]pyrimidin-7-yl)-3-((tert-butyldimethylsilyl)oxy)tetrahydrofuran-2-yl)methanol (4.682 g, 9.55 mmol) and DCC (N,N-dicyclohexylcarbodiimide) (6.1 g, 29.6 mmol) in DMSO (40 mL) under argon were added pyridine (0.850 mL, 10.51 mmol) and TFA (0.515 mL, 6.68 mmol) at 0° C. The resulting mixture was stirred for 14 hours at 20° C. under argon. The reaction progress was monitored by LCMS. The reaction mixture was quenched with water (150 mL) and extracted with ethyl acetate (3×100 mL). The combined organic layers was washed with brine (120 mL), dried over anhydrous sodium sulfate and filtered. The filtrate was concentrated under reduced pressure to afford crude title product as a solid. LC-MS: (ES, m/z): 567.0 [M+H$_2$O+H]$^+$

Step 7: Synthesis of mixture of [(3S,5R)-3-[(tert-butyldimethylsilyl)oxy]-5-{4-[(dimethyl-Si{4}-sulfanylidene)amino]-5-iodo-7H-pyrrolo[2,3-d]pyrimidin-7-yl}-2-(hydroxymethyl)oxolan-2-yl]methanol To a mixture of (2S,3S,5R)-3-[(tert-butyldimethylsilyl)oxy]-5-{4-[(dimethyl-Si{4}-sulfanylidene)amino]-5-iodo-7H-pyrrolo[2,3-d]pyrimidin-7-yl}oxolane-2-carbaldehyde (80 mg, 0.146 mmol) and formaldehyde (0.5 mL, 0.146 mmol) in 1,4-Dioxane (4 mL) was added 2 M sodium hydroxide (0.5 mL, 1.000 mmol) at 0° C. The resulting mixture was stirred for 4 hours at 20° C. The reaction progress was monitored by LCMS. The reaction mixture was quenched with acetic acid (0.2 mL) and extracted with ethyl acetate (3×40 mL). The combined organic layers was washed with sat. NaHCO$_3$ (30 mL) then brine (40 mL), dried over anhydrous sodium sulfate and filtered. The filtrate was concentrated under reduced pressure, the residue was dissolved in Ethanol (4 mL). This mixture was added sodium tetrahydroborate (20 mg, 0.529 mmol) under argon. This mixture was stirred for 36 hours at 20° C. The reaction progress was monitored by LCMS. The reaction mixture was quenched with acetic acid (0.05 mL) and extracted with CHCl$_3$ (3×40 mL). The combined organic layers was washed with sat. NaHCO$_3$ (30 mL) then brine (40 mL), dried over anhydrous sodium sulfate and filtered. The filtrate was concentrated under reduced pressure, purified by TLC, eluting with DCM/MeOH (12:1) to afford the title compound. LC-MS: (ES, m/z): 581.1 [M+H]$^{+1}$. $^1$H-NMR: (300 MHz, CD$_3$SOCD$_3$, ppm): 8.09 (s, 0.6H), 7.97 (s, 0.4H), 7.69 (s, 0.6H), 7.46 (s, 0.4H), 6.66 (brs, 0.8H), 6.53-6.42 (m, 1H), 5.10 (t, J=5.4 Hz, 0.4H), 5.02 (t, J=5.4 Hz, 0.6H), 4.58 (brs, 1H), 4.42-4.37 (m, 1H), 3.58-3.49 (m, 4H), 2.78 (d, J=2.7 Hz, 3H), 2.68-2.61 (m, 1H), 2.23-2.16 (m, 1H), 0.90 (s, 9H), 0.10 (s, 6H).

Step 8: Synthesis of ((3S,5R)-5-(4-amino-5-iodo-7H-pyrrolo[2,3-d]pyrimidin-7-yl)-3-((tert-butyldimethylsilyl)oxy)tetrahydrofuran-2,2-diyl)dimethanol To a solution of [(3S,5R)-3-[(tert-butyldimethylsilyl)oxy]-5-{4-[(dimethyl-Si {4}-sulfanylidene)amino]-5-iodo-7H-pyrrolo[2,3-d]pyrimidin-7-yl}-2-(hydroxymethyl)oxolan-2-yl]methanol (230 mg, 0.396 mmol) in DCM (2 mL) was added TFA (2 mL, 26.0 mmol) at 0° C. The resulting mixture was stirred for 3 hours at 20° C. under argon. The reaction progress was monitored by LCMS. The reaction mixture was concentrated under reduced pressure, the residue was purified by a silica gel column, eluting with DCM/MeOH (95:5) to afford the title compound. LC-MS: (ES, m/z): 521.2 [M+H]$^{+1}$. $^1$H-NMR: (400 MHz, CD$_3$SOCD$_3$, ppm): 8.12 (s, 1H), 7.71 (s, 1H), 7.10 (brs, 2H), 6.43 (t, J=6.8 Hz, 1H), 4.50 (dd, J=6 Hz, 3.2 Hz, 1H), 3.50-3.37 (m, 4H), 2.59-2.52 (m, 1H), 2.17-2.11 (m, 1H), 0.80 (s, 9H), 0.00 (s, 6H).

Step 9: Synthesis of (2R,3S,5R)-5-(4-amino-5-iodo-7H-pyrrolo[2,3-d]pyrimidin-7-yl)-3-((tert-butyldimethylsilyl)oxy)-2-(hydroxymethyl)tetrahydrofuran-2-carbaldehyde To a solution of ((3S,5R)-5-(4-amino-5-iodo-7H-pyrrolo[2,3-d]pyrimidin-7-yl)-3-((tert-butyldimethylsilyl)oxy)tetrahydrofuran-2,2-diyl)dimethanol (960 mg, 1.845 mmol) in Acetonitrile (25 mL) under argon was added IBX (1550 mg, 5.53 mmol) at 18° C. The resulting mixture was stirred for 18 hours at 18° C. under argon. The reaction progress was monitored by LCMS. The reaction mixture was filtered. The filtrate was concentrated under reduced pressure, to afford the crude product as a solid. This crude product was used for next step directly without further purification. LC-MS: (ES, m/z): 519.1 [M+H]$^+$ Step 10: Synthesis of ((2R,3S,5R)-5-(4-amino-5-iodo-7H-pyrrolo[2,3-d]pyrimidin-7-yl)-3-((tert-butyldimethylsilyl)oxy)-2-ethynyltetrahydrofuran-2-yl)methanol Intermediate B To a mixture of (2R,3S,5R)-5-(4-amino-5-iodo-7H-pyrrolo[2,3-d]pyrimidin-7-yl)-3-((tert-butyldimethylsilyl)oxy)-2-(hydroxymethyl)tetrahydrofuran-2-carbaldehyde (190 mg, 0.366 mmol) and K$_2$CO$_3$ (127 mg, 0.916 mmol) in MeOH (10 mL) under argon was added dimethyl (1-diazo-2-oxopropyl)phosphonate (141 mg, 0.733 mmol) at 0° C. The resulting mixture was stirred for 16 hours at 18° C. under argon. The color of the mixture turned from yellow to blue. The reaction progress was monitored by LCMS/TLC. The reaction mixture was concentrated under reduced pressure, the residue was purified by a silica gel column, eluting with DCM/MeOH (97:3) to afford the title compound. LC-MS: (ES, m/z): 515.1 [M+H]$^{+1}$. $^1$H-NMR: (400 MHz, CDCl$_3$, ppm): 8.22 (s, 1H), 7.12 (s, 1H), 6.25 (dd, J=8.8 Hz, 5.6 Hz, 1H), 5.84 (brs, 2H), 4.71 (dd, J=5.6 Hz, 2 Hz, 1H), 4.01 (d, J=12.4 Hz, 1H), 3.80 (d, J=16 Hz, 1H), 3.17-3.10 (m, 1H), 2.59 (s, 1H), 2.27-2.21 (m, 1H), 0.91 (s, 9H), 0.11 (s, 6H)

Example 7

Synthesis of (2R,3S,5R)-5-(4-amino-5-iodo-7H-pyrrolo[2,3-d]pyrimidin-7-yl)-2-ethynyl-2-(hydroxymethyl)tetrahydrofuran-3-ol (7)

To a solution of ((2R,3S,5R)-5-(4-amino-5-iodo-7H-pyrrolo[2,3-d]pyrimidin-7-yl)-3-((tert-butyldimethylsilyl)oxy)-2-ethynyltetrahydrofuran-2-yl)methanol (Intermediate B, 20 mg, 0.039 mmol) in tetrahydrofuran (3 mL) under argon was added TBAF (0.05 mL, 0.050 mmol) at 18° C. The resulting mixture was stirred for 0.5 hours at 18° C. under argon. The reaction progress was monitored by TLC. The reaction mixture was concentrated under reduced pressure, the residue was purified by a silica gel column, eluting with CH$_2$Cl$_2$/MeOH (7:1), to give crude product which was purified by Prep-HPLC with the following conditions: Instrument, Water-1 (26); Column: Xbridge RP18, 5 um, 19×150 mm; mobile phase: water (0.05% Ammonium bicarbonate+Carbon dioxide) and acetonitrile (10% acetonitrile up to 40% in 8 min, hold 100% for 2 min, down to 10% in 2 min); Detector, UV 220 and 254 nm. The collected fractions were combined and concentrated under reducing pressure to give compound 7 as a solid. LC-MS: (ES, m/z): 401.0[M+H]$^+$. $^1$H-NMR: (400 MHz, CD$_3$OD): δ8.10 (s, 1H), 7.63 (s, 1H), 6.68 (s, 2H), 6.49 (t, J=6.4 Hz, 1H), 5.52 (d, J=5.2 Hz, 1H), 4.48 (q, J=6.0 Hz, 1H), 3.64-3.60 (m, 1H), 3.57-3.52 (m, 1H), 3.48 (s, 1H), 2.53-2.47 (m, 1H), 2.35-2.29 (m, 1H).

Example 8

Synthesis of (2R,3S,5R)-5-(2,4-diamino-7H-pyrrolo[2,3-d]pyrimidin-7-yl)-2-ethynyl-2-(hydroxymethyl)tetrahydrofuran-3-ol (8)

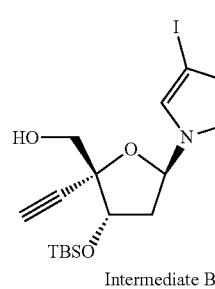

Intermediate B

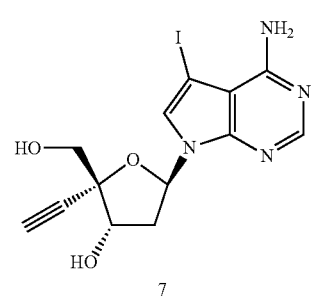

7

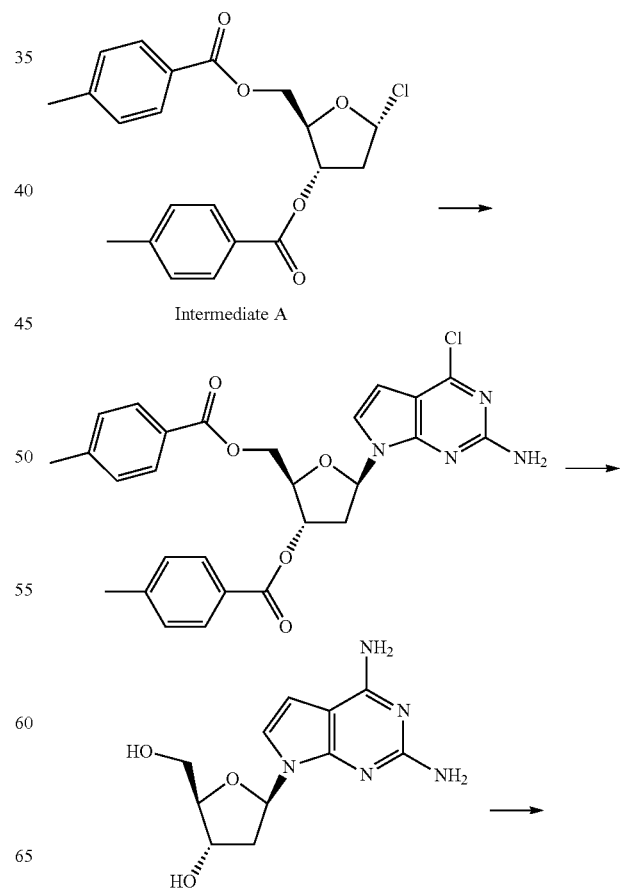

Intermediate A

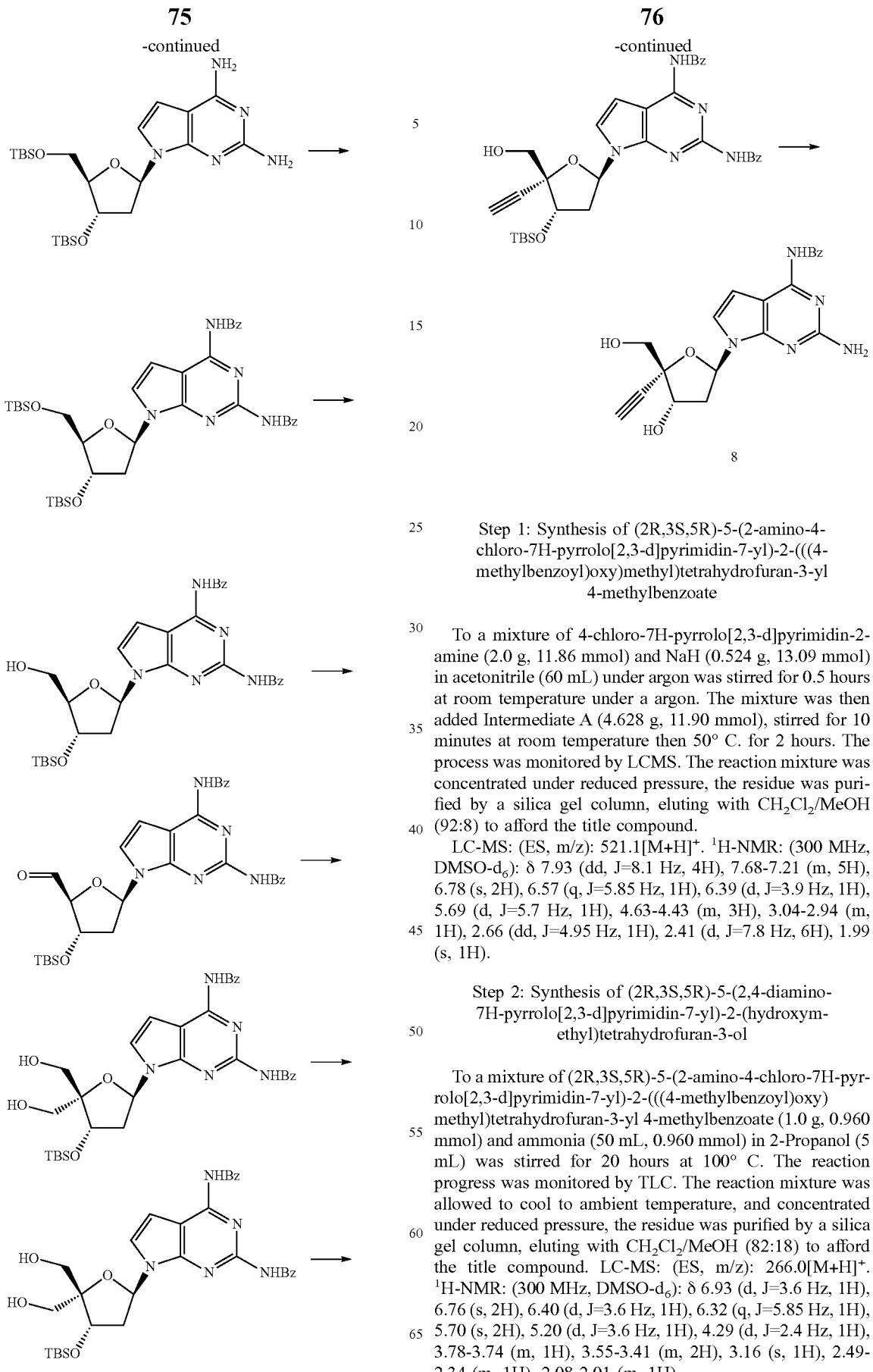

Step 1: Synthesis of (2R,3S,5R)-5-(2-amino-4-chloro-7H-pyrrolo[2,3-d]pyrimidin-7-yl)-2-(((4-methylbenzoyl)oxy)methyl)tetrahydrofuran-3-yl 4-methylbenzoate To a mixture of 4-chloro-7H-pyrrolo[2,3-d]pyrimidin-2-amine (2.0 g, 11.86 mmol) and NaH (0.524 g, 13.09 mmol) in acetonitrile (60 mL) under argon was stirred for 0.5 hours at room temperature under a argon. The mixture was then added Intermediate A (4.628 g, 11.90 mmol), stirred for 10 minutes at room temperature then 50° C. for 2 hours. The process was monitored by LCMS. The reaction mixture was concentrated under reduced pressure, the residue was purified by a silica gel column, eluting with $CH_2Cl_2$/MeOH (92:8) to afford the title compound.

LC-MS: (ES, m/z): 521.1[M+H]$^+$. $^1$H-NMR: (300 MHz, DMSO-$d_6$): δ 7.93 (dd, J=8.1 Hz, 4H), 7.68-7.21 (m, 5H), 6.78 (s, 2H), 6.57 (q, J=5.85 Hz, 1H), 6.39 (d, J=3.9 Hz, 1H), 5.69 (d, J=5.7 Hz, 1H), 4.63-4.43 (m, 3H), 3.04-2.94 (m, 1H), 2.66 (dd, J=4.95 Hz, 1H), 2.41 (d, J=7.8 Hz, 6H), 1.99 (s, 1H).

Step 2: Synthesis of (2R,3S,5R)-5-(2,4-diamino-7H-pyrrolo[2,3-d]pyrimidin-7-yl)-2-(hydroxymethyl)tetrahydrofuran-3-ol To a mixture of (2R,3S,5R)-5-(2-amino-4-chloro-7H-pyrrolo[2,3-d]pyrimidin-7-yl)-2-(((4-methylbenzoyl)oxy)methyl)tetrahydrofuran-3-yl 4-methylbenzoate (1.0 g, 0.960 mmol) and ammonia (50 mL, 0.960 mmol) in 2-Propanol (5 mL) was stirred for 20 hours at 100° C. The reaction progress was monitored by TLC. The reaction mixture was allowed to cool to ambient temperature, and concentrated under reduced pressure, the residue was purified by a silica gel column, eluting with $CH_2Cl_2$/MeOH (82:18) to afford the title compound. LC-MS: (ES, m/z): 266.0[M+H]$^+$. $^1$H-NMR: (300 MHz, DMSO-$d_6$): δ 6.93 (d, J=3.6 Hz, 1H), 6.76 (s, 2H), 6.40 (d, J=3.6 Hz, 1H), 6.32 (q, J=5.85 Hz, 1H), 5.70 (s, 2H), 5.20 (d, J=3.6 Hz, 1H), 4.29 (d, J=2.4 Hz, 1H), 3.78-3.74 (m, 1H), 3.55-3.41 (m, 2H), 3.16 (s, 1H), 2.49-2.34 (m, 1H), 2.08-2.01 (m, 1H).

Step 3: Synthesis of 7-((2R,4S,5R)-4-((tert-butyldimethylsilyl)oxy)-5-(((tert-butyldimethylsilyl)oxy)methyl)tetrahydrofuran-2-yl)-7H-pyrrolo[2,3-d]pyrimidine-2,4-diamine To a mixture of (2R,3S,5R)-5-(2,4-diamino-7H-pyrrolo[2,3-d]pyrimidin-7-yl)-2-(hydroxymethyl)tetrahydrofuran-3-ol (1.39 g, 5.24 mmol) and TBDMS-Cl (2.369 g, 15.72 mmol) in DMF (6 mL) under argon was added imidazole (1.784 g, 26.2 mmol). The resulting mixture was stirred for 16 hours at 20° C. under a argon atmosphere. The reaction progress was monitored by LCMS/TLC. The reaction mixture was concentrated under reduced pressure, the residue was purified by a silica gel column, eluting with $CH_2Cl_2$/MeOH (92:8) to afford the title compound as a solid. LC-MS: (ES, m/z): 494.4 [M+H]$^+$, $^1$H-NMR: (300 MHz, CDCl$_3$): δ 7.58 (s, 2H), 7.04 (d, J=3.9 Hz, 1H), 6.54 (d, J=3.9 Hz, 1H), 6.52 (s, 2H), 6.32 (dd, J=6.0 Hz, 1H), 4.45 (t, J=2.4 Hz, 1H), 3.78 (d, J=2.1 Hz, 1H), 3.68 (t, J=5.5 Hz, 2H), 3.17 (d, J=3.0 Hz, 1H), 2.49-2.42 (m, 1H), 2.17-2.10 (m, 1H), 0.89 (s, 18H), 0.10-0.09 (m, 12H).

Step 4: Synthesis of N,N'-(7-((2R,4S,5R)-4-((tert-butyldimethylsilyl)oxy)-5-(((tert-butyldimethylsilyl)oxy)methyl)tetrahydrofuran-2-yl)-7H-pyrrolo[2,3-d]pyrimidine-2,4-diyl)dibenzamide To a mixture of 7-((2R,4S,5R)-4-((tert-butyldimethylsilyl)oxy)-5-(((tert-butyldimethylsilyl)oxy)methyl)tetrahydrofuran-2-yl)-7H-pyrrolo[2,3-d]pyrimidine-2,4-diamine (138 mg, 0.279 mmol) and DMAP (5 mg, 0.041 mmol) in pyridine (5 mL) under argon was added benzoyl chloride (158 mg, 1.124 mmol). The resulting mixture was stirred for 4 hours at 0° C. under argon. The reaction progress was monitored by LCMS/TLC. The reaction mixture was quenched by water (50 mL) and extracted with ethyl acetate (3×30 mL). The combined organic layers was washed with brine (40 mL), dried over anhydrous sodium sulfate and filtered. The filtrate was concentrated under reduced pressure, the residue was purified by a silica gel column, eluting with PE/EA (2:1) to provide the title compound. LC-MS: (ES, m/z): 702.3[M+H]$^+$, $^1$H-NMR: (300 MHz, CDCl$_3$): δ 11.11 (s, 1H), 10.80 (s, 1H), 8.09 (d, J=7.2 Hz, 2H), 7.73 (d, J=7.2 Hz, 2H), 7.66-7.43 (m, 8H), 6.62-6.54 (m, 2H), 4.56 (s, 1H), 3.84-3.64 (m, 4H), 2.81-2.72 (m, 1H), 2.26-2.22 (m, 1H), 0.90-0.83 (m, 18H), 0.11-0.01 (m, 12H).

Step 5: Synthesis of N,N'-(7-((2R,4S,5R)-4-((tert-butyldimethylsilyl)oxy)-5-(hydroxymethyl)tetrahydrofuran-2-yl)-7H-pyrrolo[2,3-d]pyrimidine-2,4-diyl)dibenzamide To a mixture of N,N'-(7-((2R,4S,5R)-4-((tert-butyldimethylsilyl)oxy)-5-(((tert-butyldimethylsilyl)oxy)methyl)tetrahydrofuran-2-yl)-7H-pyrrolo[2,3-d]pyrimidine-2,4-diyl)dibenzamide (110 mg, 0.157 mmol) in THF (4 mL) was added a solution of TFA (0.5 mL, 6.49 mmol) in Water (0.5 mL) at 0° C. The resulting mixture was stirred for 4 hours at 0° C. The reaction progress was monitored by LCMS. The reaction mixture was concentrated under reduced pressure, the residue was purified by a silica gel column, eluting with $CH_2Cl_2$/MeOH (95:5) to afford the title compound. LC-MS: (ES, m/z): 588.6[M+H]$^+$, $^1$H-NMR: (300 MHz, CDCl$_3$): δ 11.11 (s, 1H), 10.81 (s, 1H), 8.09 (d, J=7.2 Hz, 2H), 7.97 (d, J=7.2 Hz, 2H), 7.65-7.46 (m, 8H), 6.62-6.56 (m, 2H), 4.96 (t, J=5.4 Hz, 1H), 4.58 (t, J=2.7 Hz, 1H), 3.82-3.77 (m, 2H), 3.56-3.51 (m, 2H), 2.72-2.67 (m, 1H), 2.27-2.21 (m, 1H), 0.88 (s, 9H), 0.09 (s, 6H).

Step 6: Synthesis of N,N'-(7-((2R,4S,5S)-4-((tert-butyldimethylsilyl)oxy)-5-formyltetrahydrofuran-2-yl)-7H-pyrrolo[2,3-d]pyrimidine-2,4-diyl)dibenzamide To a mixture of N,N'-(7-((2R,4S,5R)-4-((tert-butyldimethylsilyl)oxy)-5-(hydroxymethyl)tetrahydrofuran-2-yl)-7H-pyrrolo[2,3-d]pyrimidine-2,4-diyl)dibenzamide (35 mg, 0.060 mmol) in acetonitrile (5 mL) under argon was added IBX (42 mg, 0.150 mmol). The resulting mixture was stirred for 50 minutes at 50° C. under a argon. The reaction progress was monitored by LCMS. The reaction mixture was allowed to cool to ambient temperature and filtered. The filtrate was concentrated under reduced pressure, the crude product was used for next step directly without further purification. LC-MS: (ES, m/z): 618.3 [M+CH$_3$OH]$^+$

Step 7: Synthesis of N,N'-(7-((2R,4S)-4-((tert-butyldimethylsilyl)oxy)-5,5-bis(hydroxymethyl)tetrahydrofuran-2-yl)-7H-pyrrolo[2,3-d]pyrimidine-2,4-diyl)dibenzamide To a solution of N,N'-(7-((2R,4S,5S)-4-((tert-butyldimethylsilyl)oxy)-5-formyltetrahydrofuran-2-yl)-7H-pyrrolo[2,3-d]pyrimidine-2,4-diyl)dibenzamide (35 mg, 0.060 mmol) in 1,4-Dioxane (5 mL), was added formaldehyde (1 mL, 0.060 mmol), NaOH (1 mL, 2.000 mmol), the mixture was stirred for 4 hours at 20° C., cooled to 0° C., quenched with AcOH to pH 6, added water (40 mL) and extracted with ethyl acetate (3×40 mL). The combined organic layers was washed with brine (30 mL), dried over anhydrous sodium sulfate and filtered. The filtrate was concentrated under reduced pressure, the residue was dissovled in ethanol (5.00 mL), added NaBH$_4$ (5.65 mg, 0.149 mmol) under argon. The resulting mixture was stirred for 16 hours at 20° C. The reaction progress was monitored by LCMS. The reaction mixture was allowed to cool to ambient temperature, quenched with AcOH to PH 6, added water (40 mL) and extracted with ethyl acetate (3×40 mL). The organic layers were concentrated and purified by a silica gel column, eluting with $CH_2Cl_2$/MeOH (20:1) to afford the title product as a solid. LC-MS: (ES, m/z): 618.2 [M+H]$^+$, $^1$H-NMR: (400 MHz, CDCl$_3$): δ 11.11 (s, 1H), 10.80 (s, 1H), 8.09 (d, J=7.2 Hz, 2H), 7.73 (d, J=7.2 Hz, 2H), 7.66-7.43 (m, 8H), 6.62-6.54 (m, 2H), 4.56 (s, 1H), 3.84-3.64 (m, 4H), 2.81-2.72 (m, 1H), 2.26-2.22 (m, 1H), 0.90-0.83 (m, 18H), 0.11-0.01 (m, 12H).

Step 8: Synthesis of N,N'-(7-((2R,4S,5R)-4-((tert-butyldimethylsilyl)oxy)-5-formyl-5-(hydroxymethyl)tetrahydrofuran-2-yl)-7H-pyrrolo[2,3-d]pyrimidine-2,4-diyl)dibenzamide To a solution of N,N'-(7-((2R,4S)-4-((tert-butyldimethylsilyl)oxy)-5,5-bis(hydroxymethyl)tetrahydrofuran-2-yl)-

7H-pyrrolo[2,3-d]pyrimidine-2,4-diyl)dibenzamide (30 mg, 0.049 mmol) in acetonitrile (10 mL) under argon was added IBX (40 mg, 0.143 mmol) at 20° C. The resulting mixture was stirred for 3 hours at 25° C. under argon. The reaction progress was monitored by LCMS. The reaction mixture was allowed to cool to ambient temperature and filtered. The filtrate was concentrated under reduced pressure to afford crude product as a solid used for next step directly without further purification. LC-MS: (ES, m/z): 616.2 [M+H]$^+$

Step 9: Synthesis of N,N'-(7-((2R,4S,5R)-4-((tert-butyldimethylsilyl)oxy)-5-ethynyl-5-(hydroxymethyl)tetrahydrofuran-2-yl)-7H-pyrrolo[2,3-d]pyrimidine-2,4-diyl)dibenzamide To a mixture of N,N'-(7-((2R,4S,5R)-4-((tert-butyldimethylsilyl)oxy)-5-formyl-5-(hydroxymethyl)tetrahydrofuran-2-yl)-7H-pyrrolo[2,3-d]pyrimidine-2,4-diyl)dibenzamide (70 mg, 0.114 mmol) and K$_2$CO$_3$ (39.3 mg, 0.284 mmol) in MeOH (5 mL) under argon was added a solution of dimethyl (2-diazo-3-oxobutanoyl)phosphonate (50.0 mg, 0.227 mmol) in MeOH (0.25 mL) at 0° C. The resulting mixture was stirred for 16 hours at 25° C. under argon. The reaction progress was monitored by LCMS. The reaction mixture was concentrated under reduced pressure, the residue was purified by TLC, eluting with CH$_2$Cl$_2$/MeOH (20:1) to afford the title compound. LC-MS: (ES, m/z): 612.4[M+H]$^+$

Step 10: Synthesis of (2R,3S,5R)-5-(2,4-diamino-7H-pyrrolo[2,3-d]pyrimidin-7-yl)-2-ethynyl-2-(hydroxymethyl)tetrahydrofuran-3-ol (8)

To a solution of N,N'-(7-((2R,4S,5R)-4-((tert-butyldimethylsilyl)oxy)-5-ethynyl-5-(hydroxymethyl)tetrahydrofuran-2-yl)-7H-pyrrolo[2,3-d]pyrimidine-2,4-diyl)dibenzamide (40 mg, 0.065 mmol) in MeOH (4 mL) under argon was added a solution of NaOCH$_3$ in MeOH (0.065 mL, 0.065M) at 20° C. The resulting mixture was stirred for 48 hours at 40° C. under argon. The reaction progress was monitored by LCMS. The reaction mixture was allowed to cool to ambient temperature, and concentrated under reduced pressure, the residue was purified by TLC, eluting with CH$_2$Cl$_2$/MeOH (20:1) to afford crude intermediate (27 mg) as a solid which was diluted in THF (3 mL) under argon. Added a solution of TBAF (1M, 0.040 mL, 0.04 mmol) at 20° C. The resulting mixture was stirred for 0.5 hours at 20° C. under argon. The reaction progress was monitored by LCMS/TLC. The reaction mixture was concentrated under reduced pressure, the residue was purified by TLC, eluting with CH$_2$Cl$_2$/MeOH (5:1) to afford crude product (15 mg) then was purified by Prep-HPLC with the following conditions: Instrument, Waters-2767-Prep; Column: Xbridge RP18, 5 um, 19×150 mm; mobile phase: water (0.05% Ammonium bicarbonate (carbon dioxide) and acetonitrile (5% acetonitrile up to 40% in 8 min); Detector, UV 220 and 254 nm. The collected fractions were combined and concentrated under reducing pressure to give compound 8 as a solid. LC-MS: (ES, m/z): 618.2 [M+H]$^+$, $^1$H-NMR: (400 MHz, CDCl$_3$): δ 6.85 (d, J=3.6 Hz, 1H), 6.55 (s, 2H), 6.36 (d, J=4.0 Hz, 2H), 5.56 (s, 2H), 5.48-5.43 (m, 2H), 4.42 (q, J=5.6 Hz, 1H), 3.61-3.49 (m, 2H), 3.44 (s, 1H), 2.47-2.40 (m, 1H), 2.26-2.21 (m, 1H).

Example 9

Synthesis of (2R,3S,5R)-5-(4-amino-2-fluoro-7H-pyrrolo[2,3-d]pyrimidin-7-yl)-2-ethynyl-2-(hydroxymethyl)tetrahydrofuran-3-ol (9)

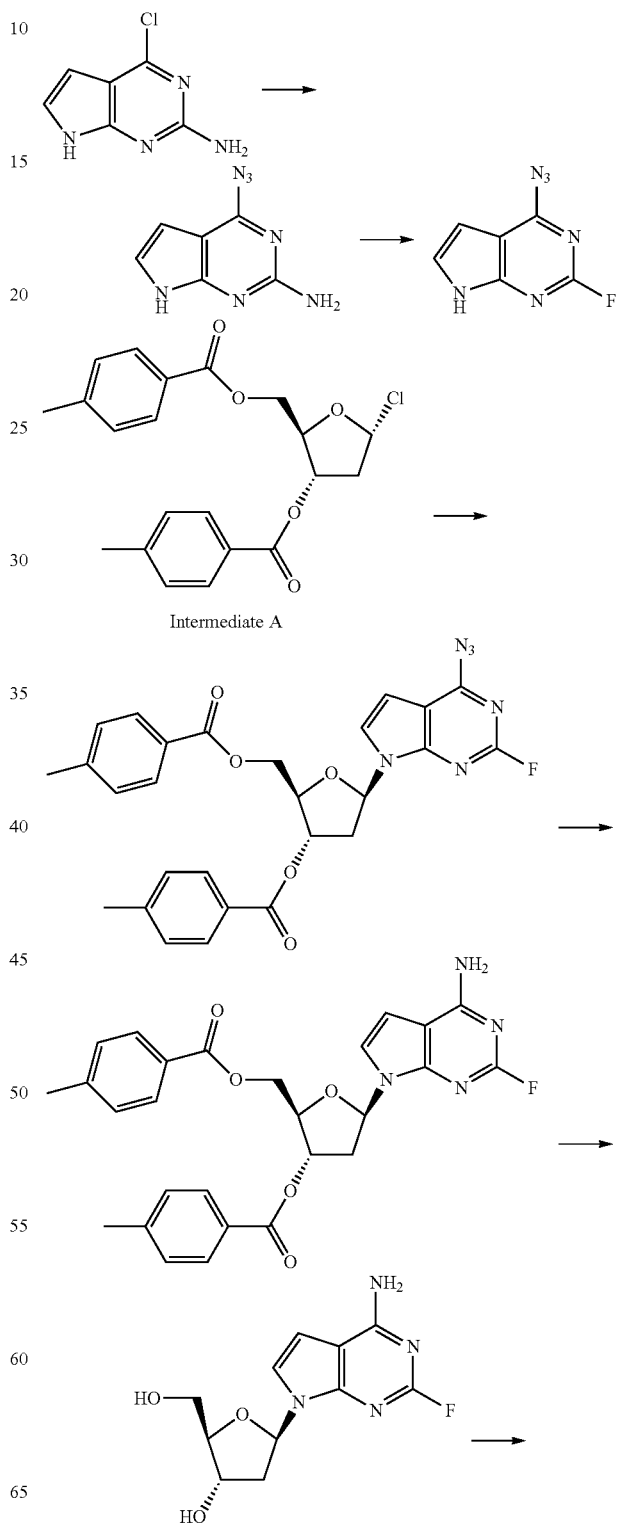

Intermediate A

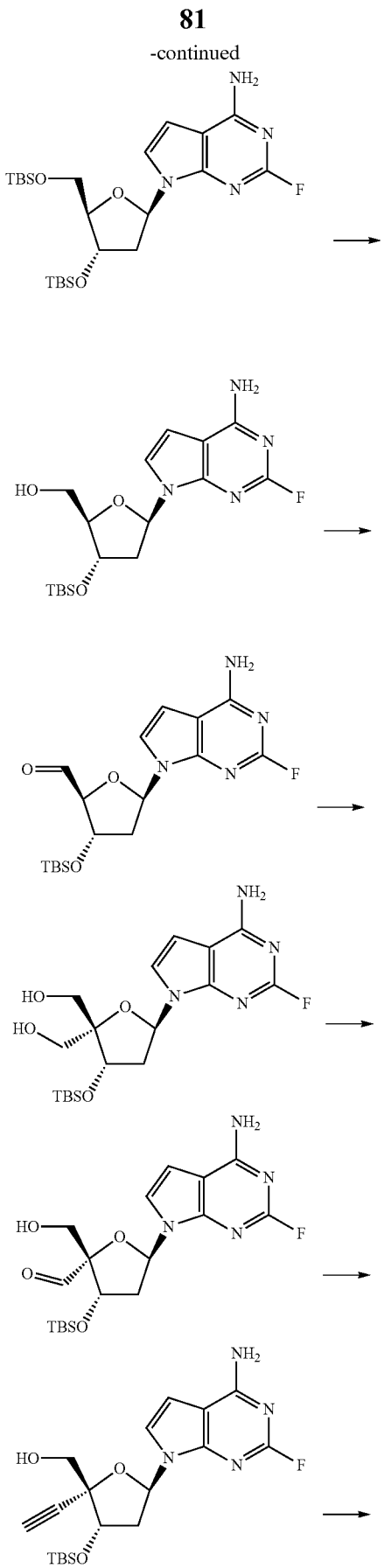

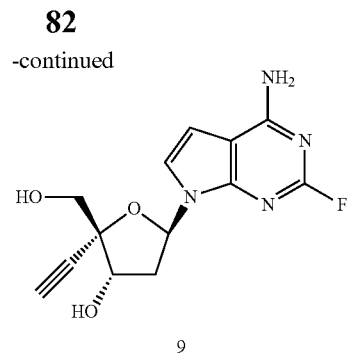

9

Step 1: Synthesis of
4-azido-7H-pyrrolo[2,3-d]pyrimidin-2-amine

To a stirred solution of 4-chloro-7H-pyrrolo[2,3-d]pyrimidin-2-amine (3.5 g, 20.76 mmol) in anhydrous DMSO (35 mL) under argon atmosphere, was added a solution of sodium azide (2.025 g, 31.1 mmol) in water (3.50 mL). The mixture was heated to 100° C. and stirred overnight. The reaction progress was monitored by TLC & LCMS. The resulting mixture was cooled to ambient temperature. 250 g crushed ice was added and the mixture was stirred at 0° C. for 30 minutes. A precipitate was formed. The precipitate was collected by filtration, washed with cold water and dried over $P_2O_5$ under vacuum overnight to give 4-azido-7H-pyrrolo[2,3-d]pyrimidin-2-amine as a solid, which was used to the next reaction step directly without further purification. $^1$H-NMR: (400 MHz, $d_6$-DMSO, ppm): δ 11.91 (brs, 1H), 7.96 (brs, 2H), 7.13 (t, J=3.0 Hz, 1H), 6.72 (dd, J=2.0 Hz, J=3.2 Hz, 1H). LC-MS: (ES, m/z): 176.00 [M+H]$^+$.

Step 2: Synthesis of
4-azido-2-fluoro-7H-pyrrolo[2,3-d]pyrimidine

Hydrogen fluoride-pyridine (70% HF in 30% Py) (12 mL, 133 mmol) was massed into a teflon bottle under argon atmosphere. To this was added 4-azido-7H-pyrrolo[2,3-d]pyrimidin-2-amine (3.1 g, 17.70 mmol). The mixture was stirred at ambient temperature until it became a clear solution, then cooled to −60° C., followed by the addition of tert-butyl nitrite (2.5 mL, 21.02 mmol) drop-wised in 10 minutes. The resulting mixture was stirred between −60° C. to −40° C. for 2 hours. The reaction progress was monitored by TLC & LCMS. The mixture was poured into cold aqueous NaHCO$_3$ (150 mL, saturated). The crude product was extracted with ethyl acetate (100 mL×3), washed with brine (100 mL×2), dried over anhydrous Na$_2$SO$_4$, filtered and the filtrate was concentrated under vacuum to give a residue. The residue was then purified by silica gel column chromatography using ethyl acetate/petroleum ether (¼) to give 4-azido-2-fluoro-7H-pyrrolo[2,3-d] as a solid. $^1$H-NMR: (300 MHz, $d_6$-DMSO, ppm): δ 12.43 (brs, 1H), 7.48 (d, J=3.9 Hz, 1H), 6.50 (d, J=3.6 Hz, 1H). F-NMR: (282 MHz, $d_6$-DMSO, ppm): δ −54.57 (s, 1F). LC-MS: (ES, m/z): 179.20 [M+H]$^+$.

Step 3: Synthesis of (2R,3S,5R)-5-(4-azido-2-fluoro-7H-pyrrolo[2,3-d]pyrimidin-7-yl)-2-(((4-methylbenzoyl)oxy)methyl)tetrahydrofuran-3-yl 4-methylbenzoate To a stirred suspension of sodium hydride 60% dispersion in mineral oil (0.272 g, 6.79 mmol) in anhydrous DMF (20 mL) under argon atmosphere in a 50 mL two necked round-bottom flask, was added 4-azido-2-fluoro-7H-pyrrolo[2,3-d]pyrimidine (1.1 g, 6.18 mmol) in portions at 0° C. and the mixture was stirred at this temperature for 5 minutes. Intermediate A (2.4 g, 6.17 mmol) was added with stirring. The reaction mixture was warmed to 25° C. and stirred for 2 hours. The reaction progress was monitored by TLC & LCMS. The mixture was diluted with ethyl acetate (100 mL), washed with water (70 mL). The aqueous layer was re-extracted with ethyl acetate (60 mL×2). The combined organic layer was washed with brine (100 mL×3), dried over anhydrous $Na_2SO_4$, filtered and concentrated under vacuum. The crude product was purified by silica gel column chromatography using ethyl acetate/petroleum ether (1/10) to give the title compound. $^1$H-NMR: (400 MHz, $CDCl_3$, ppm): δ 8.00 (d, J=8.4 Hz, 2H), 7.95 (d, J=8.0 Hz, 2H), 7.32-7.23 (m, 4H), 6.74 (dd, J=6.4 Hz, J=8.0 Hz, 1H), 6.49 (d, J=4.0 Hz, 1H), 5.75-5.74 (m, 1H), 4.75-4.54 (m, 3H), 2.85-2.74 (m, 2H), 2.47-2.43 (m, 6H). F-NMR: (376 MHz, $CDCl_3$, ppm): δ −52.26 (s, 1F, β isomer), −52.48 (s, 1F, α isomer). LC-MS: (ES, m/z): 531.42 $[M+H]^+$.

Step 4: Synthesis of (2R,3S,5R)-5-(4-amino-2-fluoro-7H-pyrrolo[2,3-d]pyrimidin-7-yl)-2-(((4-methylbenzoyl)oxy)methyl)tetrahydrofuran-3-yl 4-methylbenzoate To a stirred solution of (2R,3S,5R)-5-(4-azido-2-fluoro-7H-pyrrolo[2,3-d]pyrimidin-7-yl)-2-(((4-methylbenzoyl)oxy)methyl)tetrahydrofuran-3-yl 4-methylbenzoate (2.0 g, 3.77 mmol) in a mixture of MeOH (10 mL) and DCM (15 mL) under argon atmosphere, was added propane-1,3-dithiol (0.816 g, 7.54 mmol), followed by the addition of triethylamine (0.763 g, 7.54 mmol) dropwise with stirring in 10 minutes at 25° C. The mixture was stirred at 25° C. for 30 minutes. The reaction progress was monitored by TLC. The resulting mixture was concentrated under vacuum. The residue was then purified by silica gel column chromatography using ethyl acetate/petroleum ether (42% EA in PE) to give the title compound as a powder. $^1$H-NMR: (400 MHz, $CDCl_3$, ppm): δ 8.00 (d, J=8.0 Hz, 2H), 7.97 (d, J=8.0 Hz, 2H), 7.33-7.26 (m, 4H), 7.12 (d, J=4.0 Hz, 1H), 6.72 (dd, J=6.2 Hz, J=8.2 Hz, 1H), 6.38 (d, J=3.6 Hz, 1H), 5.75-5.72 (m, 1H), 5.36 (brs, 2H), 4.73-4.57 (m, 3H), 2.79-2.74 (m, 2H), 2.47 (s, 3H), 2.44 (s, 3H). F-NMR: (376 MHz, $CDCl_3$, ppm): δ −52.97 (s, 1F, β isomer), −53.10 (s, 1F, α isomer). LC-MS: (ES, m/z): 505.63 $[M+H]^+$.

Step 5: Synthesis of (2R,3S,5R)-5-(4-amino-2-fluoro-7H-pyrrolo[2,3-d]pyrimidin-7-yl)-2-(hydroxymethyl)tetrahydrofuran-3-ol To a stirred solution of (2R,3S,5R)-5-(4-amino-2-fluoro-7H-pyrrolo[2,3-d]pyrimidin-7-yl)-2-(((4-methylbenzoyl)oxy)methyl)tetrahydrofuran-3-yl 4-methylbenzoate (1.75 g, 3.47 mmol) in anhydrous MeOH (10 mL) under argon atmosphere, was injected sodium methoxide MeOH solution (1.0 M, 3.47 mL, 3.47 mmol) with stirring at 0° C. in 5 minutes. The resulting mixture was allowed to stir at 0° C. to 10° C. for 4 hours. The reaction progress was monitored by TLC & LCMS. The resulting mixture was neutralized by the addition of AcOH, then concentrated under reduced pressure. The residue was then purified by silica gel column chromatography using dichloromethane/methanol (6% MeOH in DCM) to give the title compound. $^1$H-NMR: (400 MHz, $d_6$-DMSO, ppm): δ 7.55 (brs, 2H), 7.31 (d, J=3.6 Hz, 1H), 6.61 (d, J=3.6 Hz, 1H), 6.34 (dd, J=6.4 Hz, J=8.0 Hz, 1H), 5.26 (d, J=3.6 Hz, 1H), 4.92 (t, J=5.0 Hz, 1H), 4.32 (d, J=2.4 Hz, 1H), 3.82-3.79 (m, 1H), 3.58-3.46 (m, 2H), 2.48-2.41 (m, 1H), 2.19-2.13 (m, 1H). F-NMR: (376 MHz, $d_6$-DMSO, ppm): δ −53.77 (s, 1F, β isomer), −53.98 (s, 1F, α isomer). LC-MS: (ES, m/z): 269.20 $[M+H]^+$.

Step 6: Synthesis of 7-((2R,4S,5R)-4-((tert-butyldimethylsilyl)oxy)-5-(((tert-butyldimethylsilyl)oxy)methyl)tetrahydrofuran-2-yl)-2-fluoro-7H-pyrrolo[2,3-d]pyrimidin-4-amine (2R,3S,5R)-5-(4-amino-2-fluoro-7H-pyrrolo[2,3-d]pyrimidin-7-yl)-2-(hydroxymethyl)tetrahydrofuran-3-ol (850 mg, 3.17 mmol) and imidazole (863 mg, 12.68 mmol) were massed into a 50 mL round bottom flask under argon atmosphere. To the flask was injected anhydrous DMF (10 mL), followed by the addition of TBS-Cl (1433 mg, 9.51 mmol) in portions. The mixture was stirred at 25° C. for 2 hours. After The reaction reached to complete, the mixture was diluted with ethyl acetate (60 mL), washed with water (30 mL×2), aqueous $NaHCO_3$ (saturated, 30 mL×2) and brine (30 mL×2) respectively. The organic layer was collected and dried over anhydrous $Na_2SO_4$, filtered and concentrated under reduced pressure to give crude product. The residue was then purified by silica gel column chromatography using ethyl acetate/petroleum ether (20% EA in PE) to give the title compound. $^1$H-NMR: (300 MHz, $d_6$-DMSO, ppm): δ 7.55 (brs, 2H), 7.26 (d, J=3.6 Hz, 1H), 6.60 (d, J=3.3 Hz, 1H), 6.31 (t, J=6.6 Hz, 1H), 4.55-4.50 (m, 1H), 3.80-3.61 (m, 4H), 2.64-2.55 (m, 1H), 2.23-2.17 (m, 1H), 0.90-0.87 (m, 18H), 0.11-0.06 (m, 12H). F-NMR: (282 MHz, $d_6$-DMSO, ppm): δ −53.64 (s, 1F, β isomer), −53.78 (s, 1F, α isomer). LC-MS: (ES, m/z): 497.58 $[M+H]^+$.

Step 7: ((2R,3S,5R)-5-(4-amino-2-fluoro-7H-pyrrolo[2,3-d]pyrimidin-7-yl)-3-((tert-butyldimethylsilyl)oxy)tetrahydrofuran-2-yl)methanol To a stirred solution of 7-((2R,4S,5R)-4-((tert-butyldimethylsilyl)oxy)-5-(((tert-butyldimethylsilyl)oxy)methyl)tetrahydrofuran-2-yl)-2-fluoro-7H-pyrrolo[2,3-d]pyrimidin-4-amine (1.4 g, 2.82 mmol) in THF (24 mL) was added aqueous TFA (TFA/$H_2O$=1/1, v/v, 12 mL) dropwise with stirring at 0° C. in 10 minutes. The reaction mixture was allowed to stir at 0° C. The reaction progress was monitored by TLC. After stirring for 5 hours, the started di-TBS protected nucleoside was all consumed, then the reaction mixture was co-evaporated with toluene (50 mL×3). The residue was re-dissolved in a mixture of MeOH/DCM (15% MeOH in DCM, 50 mL). Solid $NaHCO_3$ (2 g) was added at 0° C., followed by the addition of water (1 mL). The resulting mixture was stirred for 30 minutes. After the pH value was adjusted to 7, the solids were filtered out, the filtrate was collected and concentrated under reduced pressure. The residue was purified by silica gel column chromatography using ethyl acetate/petroleum ether (40% EA in PE) to give the title compound. $^1$H-NMR: (400 MHz, $d_6$-DMSO, ppm): δ 7.57 (brs, 2H), 7.32 (d, J=3.6 Hz, 1H), 6.61 (d, J=3.6 Hz, 1H), 6.32 (dd, J=6.0 Hz, J=8.0 Hz, 1H), 4.99-4.96 (m, 1H), 4.52 (t, J=2.8 Hz, 1H), 3.79 (q, J=2.4 Hz, 1H), 3.54-3.49 (m, 2H), 2.57-2.53 (m, 1H), 2.19-2.13 (m, 1H), 0.91-0.88 (m, 9H), 0.13-0.11 (m, 6H). F-NMR: (376 MHz, $d_6$-DMSO, ppm): δ −53.71 (s, 1F, β isomer), −53.89 (s, 1F, α isomer). LC-MS: (ES, m/z): 383.36 $[M+H]^+$.

Step 8: Synthesis of (2S,3S,5R)-5-(4-amino-2-fluoro-7H-pyrrolo[2,3-d]pyrimidin-7-yl)-3-((tert-butyldimethylsilyl)oxy)tetrahydrofuran-2-carbaldehyde TFA (0.051 mL, 0.659 mmol) was injected to a stirred solution of ((2R,3S,5R)-5-(4-amino-2-fluoro-7H-pyrrolo[2, 3-d]pyrimidin-7-yl)-3-((tert-butyldimethylsilyl)oxy)tetrahydrofuran-2-yl)methanol (360 mg, 0.941 mmol), DCC (N,N-dicyclohexylcarbodiimide) (602 mg, 2.92 mmol) and pyridine (0.084 mL, 1.035 mmol) in anhydrous DMSO (2 mL) under argon atmosphere at room temperature in 2 min, and the mixture was stirred overnight. The reaction progress was monitored by TLC & LCMS. The mixture was filtered to remove dicyclohexylurea, and the filtrate was partitioned with ethyl acetate (30 mL) and H$_2$O (30 mL). The organic layer was collected and washed with brine (20 mL×2), dried over anhydrous Na$_2$SO$_4$, filtered and the filtrate was evaporated under reduced pressure to give the title compound, which was used to the next reaction step directly without further purification. LC-MS: (ES, m/z): 381.20 [M+H]$^+$, 413.20 [M+MeOH+H]$^+$.

Step 9: Synthesis of ((4S,5R)-5-(4-amino-2-fluoro-7H-pyrrolo[2,3-d]pyrimidin-7-yl)-3-((tert-butyldimethylsilyl)oxy)tetrahydrofuran-2,2-diyl)dimethanol To a stirred solution of (2S,3S,5R)-5-(4-amino-2-fluoro-7H-pyrrolo[2,3-d]pyrimidin-7-yl)-3-((tert-butyldimethylsilyl)oxy)tetrahydrofuran-2-carbaldehyde (400 mg, 1.051 mmol) in 1,4-dioxane (8 mL) in a 50 mL round-bottom flask, was added formaldehyde solution (1.2 mL, 16.01 mmol), followed by the addition of sodium hydroxide solution (1.2 mL, 2.400 mmol) dropwise in 2 minutes. The resulting mixture was stirred at 25° C. for 7 hours. Upon the started nucleoside was all consumed, the reaction mixture was neutralized by addition of AcOH. The resulting mixture was diluted with AcOEt (100 mL) and washed successively with water (2×40 mL), saturated aq NaHCO$_3$ (2×40 mL) and brine (50 mL). The organic layer was dried over Na$_2$SO$_4$ and evaporated under reduced pressure. The residue was re-dissolved in EtOH (3 mL) and added sodium borohydride (199 mg, 5.26 mmol) in portions at 0° C. After stirring for 5 hours at 25° C., the reaction mixture was neutralized by addition of AcOH. The mixture was concentrated under reduced pressure, the residue was partitioned between CHCl$_3$ (100 mL) and water (50 mL). The organic layer was washed successively with water and brine, dried over Na$_2$SO$_4$, and evaporated under reduced pressure. The residue was purified by silica gel column chromatography using dichloromethane/methanol (30/1) to give the title compound. $^1$H-NMR: (400 MHz, d$_6$-DMSO, ppm): δ 7.55 (brs, 2H), 7.34 (d, J=3.6 Hz, 1H), 6.60 (d, J=3.6 Hz, 1H), 6.35 (t, J=7.0 Hz, 1H), 4.90 (t, J=3.6 Hz, 1H), 4.60 (q, J=2.8 Hz, 1H), 4.41 (t, J=3.6 Hz, 1H), 3.60-3.43 (m, 4H), 2.69-2.62 (m, 1H), 2.23-2.17 (m, 1H), 0.92 (s, 9H), 0.09 (s, 6H). F-NMR: (376 MHz, d$_6$-DMSO, ppm): δ −53.80 (s, 1F, (3 isomer). LC-MS: (ES, m/z): 413.32 [M+H]$^+$, 435.34 [M+Na]$^+$.

Step 10: Synthesis of (2R,3S,5R)-5-(4-amino-2-fluoro-7H-pyrrolo[2,3-d]pyrimidin-7-yl)-3-((tert-butyldimethylsilyl)oxy)-2-(hydroxymethyl)tetrahydrofuran-2-carbaldehyde To a stirred solution of ((3S,5R)-5-(4-amino-2-fluoro-7H-pyrrolo[2,3-d]pyrimidin-7-yl)-3-((tert-butyldimethylsilyl)oxy)tetrahydrofuran-2,2-diyl)dimethanol (180 mg, 0.436 mmol) in anhydrous acetonitrile (15 mL) and dry DMSO (1.5 mL) in a 50 mL round-bottom flask under argon atmosphere, was added IBX (367 mg, 1.309 mmol). The resulting mixture was stirred at 20° C. for 8 hours. The reaction mixture was filtered, washed with dichloromethane. The filtrate was collected and concentrated under reduced pressure. The residue was re-dissolved in ethyl acetate (40 mL), washed with water (3×15 mL) and brine (2×20 mL) successively, dried over anhydrous Na$_2$SO$_4$, filtered and the filtrate was concentrated under reduced pressure to give the title compound, which was used to the next reaction step directly without further purification.
$^1$H-NMR: (400 MHz, CDCl$_3$, ppm): δ 9.65 (s, 1H), 7.60 (d, J=3.6 Hz, 1H), 6.43 (dd, J=5.6 Hz, J=9.6 Hz, 1H), 6.39 (d, J=3.6 Hz, 1H), 5.56-5.43 (m, 3H), 4.96 (d, J=4.8 Hz, 1H), 4.08 (d, J=11.2 Hz, 1H), 3.81 (d, J=12.8 Hz, 1H), 3.27-3.19 (m, 1H), 2.25 (dd, J=5.4 Hz, J=13.0 Hz, 1H), 0.91 (s, 9H), 0.11 (d, J=5.2 Hz, 6H).
F-NMR: (376 MHz, CDCl$_3$, ppm): δ −53.14 (s, 1F). LC-MS: (ES, m/z): 411.21 [M+H]$^+$.

Step 11: Synthesis of ((2R,3S,5R)-5-(4-amino-2-fluoro-7H-pyrrolo[2,3-d]pyrimidin-7-yl)-3-((tert-butyldimethylsilyl)oxy)-2-ethynyltetrahydrofuran-2-yl)methanol To a stirred solution of (2R,3S,5R)-5-(4-amino-2-fluoro-7H-pyrrolo[2,3-d]pyrimidin-7-yl)-3-((tert-butyldimethylsilyl)oxy)-2-(hydroxymethyl)tetrahydrofuran-2-carbaldehyde (190 mg, 0.463 mmol) in anhydrous MeOH (8 mL) under argon atmosphere, was added potassium carbonate (160 mg, 1.157 mmol). The mixture was cooled to 0° C., then was added dimethyl (1-diazo-2-oxopropyl)phosphonate (178 mg, 0.926 mmol) dropwise in 1 minute. The resulting mixture was warmed to 25° C. and stirred overnight. The reaction mixture was concentrated under reduced pressure, and then purified by silica gel column chromatography using methanol/dichloromethane (4.8% MeOH in DCM) to give the title compound. $^1$H-NMR: (400 MHz, CDCl$_3$, ppm): δ 6.99 (d, J=3.6 Hz, 1H), 6.35 (d, J=3.6 Hz, 1H), 6.28 (dd, J=6.0 Hz, J=8.8 Hz, 1H), 5.45-5.33 (m, 3H), 4.76 (q, J=2.8 Hz, 1H), 4.03 (dd, J=2.0 Hz, J=12.4 Hz, 1H), 8.16-3.79 (m, 1H), 3.12-3.06 (m, 1H), 2.70 (s, 1H), 2.33-2.27 (m, 1H), 0.94 (s, 9H), 0.16 (d, J=8.0 Hz, 6H). F-NMR: (376 MHz, CDCl$_3$, ppm): δ −53.26 (s, 1F). LC-MS: (ES, m/z): 407.30 [M+H]$^+$.

Step 12: Synthesis of (2R,3S,5R)-5-(4-amino-2-fluoro-7H-pyrrolo[2,3-d]pyrimidin-7-yl)-2-ethynyl-2-(hydroxymethyl)tetrahydrofuran-3-ol (9)

To a stirred solution of ((2R,3S,5R)-5-(4-amino-2-fluoro-7H-pyrrolo[2,3-d]pyrimidin-7-yl)-3-((tert-butyldimethylsilyl)oxy)-2-ethynyltetrahydrofuran-2-yl)methanol (15 mg, 0.037 mmol) in anhydrous THF (1 mL) under argon atmosphere was added TBAF THF solution (0.037 mL, 0.037 mmol) dropwise with stirring in 1 minute at ambient temperature. The medium was stirred at ambient temperature for 2 hours. The reaction progress was monitored by TLC. Upon the started nucleoside was all consumed, the mixture was concentrated under vacuum, the residue was then purified by preparative-TLC (MeOH/DCM=1/15) to give a crude product (10 mg). The crude product was further purified by preparative-HPLC with the following conditions: (1#-Pre-HPLC-011(Waters)): Column, X-bridge C18 Column, 19*150 mm, 5um; mobile phase, water with 10 mmol ammonium bicarbonate and acetonitrile (5% acetonitrile up to 30% in 5 min, up to 95% in 2 min); Detector, uv 254&220 nm. The product-containing fractions were collected and lyophilized to give compound 9 as a solid. $^1$H-NMR: (400 MHz, d$_6$-DMSO, ppm): ε 7.57 (brs, 2H), 7.28 (d, J=3.6 Hz, 1H), 6.61 (d, J=3.6 Hz, 1H), 6.35 (t, J=6.4 Hz, 1H), 5.51 (d, J=5.6 Hz, 1H), 5.27 (t, J=6.0 Hz, 1H), 4.48 (dd, J=6.4 Hz, J=12.0 Hz, 1H), 3.61 (dd, J=5.6 Hz, J=11.6 Hz, 1H), 3.53 (dd, J=6.4 Hz, J=12.0 Hz, 1H), 3.48 (s, 1H), 2.50-2.46 (m, 1H), 2.37-2.31 (m, 1H). F-NMR: (376 MHz, $d_6$-DMSO, ppm): δ −53.67 (s, 1F). LC-MS: (ES, m/z): 293.15 [M+H]$^+$, 315.15 [M+Na]$^+$.

Example 10

Synthesis of (2R,3S,5R)-5-(4-amino-7H-pyrrolo[2,3-d]pyrimidin-7-yl)-3-hydroxy-2-(hydroxymethyl)tetrahydrofuran-2-carbonitrile (10)

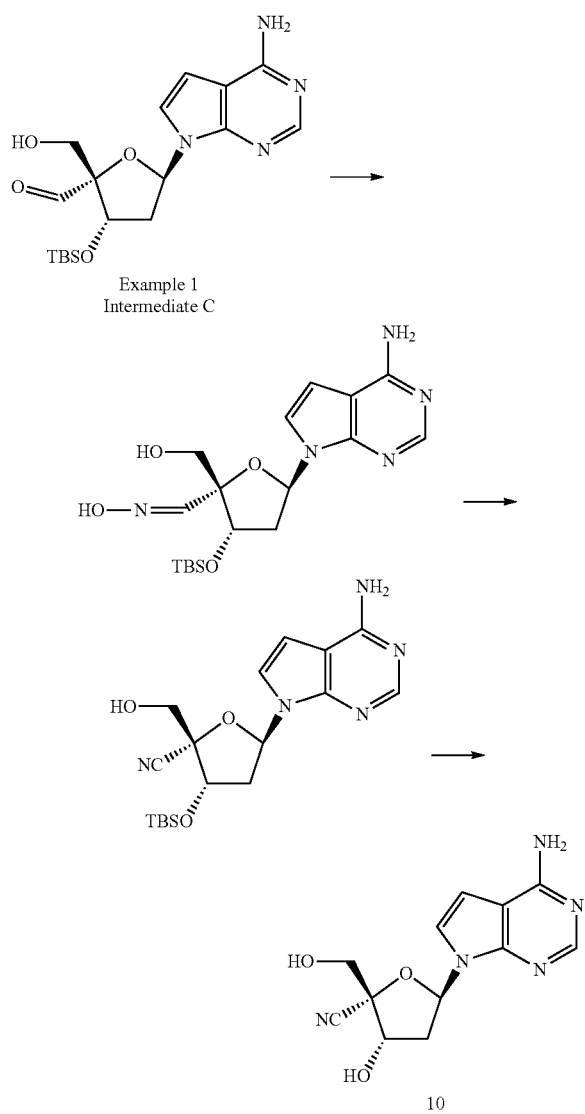

Step 1: Synthesis of 5-(4-amino-7H-pyrrolo[2,3-d]pyrimidin-7-yl)-3-((tert-butyldimethylsilyl)oxy)-2-(hydroxymethyl)tetrahydrofuran-2-carbaldehyde oxime To a stirred solution of (2R,3S,5R)-5-(4-amino-7H-pyrrolo[2,3-d]pyrimidin-7-yl)-3-((tert-butyldimethylsilyl)oxy)-2-(hydroxymethyl)tetrahydrofuran-2-carbaldehyde (Example 1, Intermediate C, 50 mg, 0.127 mmol, 1.0 eq) in dry pyridine (2.5 mL) was added hydroxylamine hydrochloride (26.6 mg, 0.382 mmol, 3.0 eq) under argon atmosphere. The resulting mixture was stirred at 30° C. for 2 hours. The reaction progress was monitored by LCMS. The reaction mixture was concentrated under vacuum, the residue then dissolved in ethyl acetate (50 mL), washed with water (2×30 mL) and brine (35 mL) successively, dried over anhydrous sodium sulfate, filtered and the filtrate was concentrated under vacuum. The residue was purified by preparative-TLC (DCM/MeOH=10/1) to afford the title compound. LC-MS: (ES, m/z): 408.20 [M+H]$^+$.

Step 2: Synthesis of (2R,3S,5R)-5-(4-amino-7H-pyrrolo[2,3-d]pyrimidin-7-yl)-3-((tert-butyldimethylsilyl)oxy)-2-(hydroxymethyl)tetrahydrofuran-2-carbonitrile To a stirred mixture of 5-(4-amino-7H-pyrrolo[2,3-d]pyrimidin-7-yl)-3-((tert-butyldimethylsilyl)oxy)-2-(hydroxymethyl)tetrahydrofuran-2-carbaldehyde oxime (40 mg, 0.098 mmol) and triethylamine (105 mg, 1.038 mmol) in dry DCM (5 mL) was added 2,2,2-trifluoroacetic anhydride (110 mg, 0.524 mmol) dropwise with stirring at 20° C. under argon atmosphere. The resulting mixture was stirred at 20° C. for 20 hours. The reaction progress was monitored by LCMS. The reaction mixture was diluted with DCM (30 mL), washed with saturated aqueous NaHCO$_3$ (25 mL) and brine (25 mL) successively, dried over anhydrous Na$_2$SO$_4$, filtered and the filtrate was concentrated under vacuum. The residue was purified by preparative-TLC (DCM/MeOH=10/1) to afford the title compound. LC-MS: (ES, m/z): 390.11 [M+H]$^+$. $^1$H-NMR: (300 MHz, CD3OD, ppm): δ 8.10 (s, 1H), 7.30 (d, J=3.6 Hz, 1H), 6.68 (t, J=6.9 Hz, 1H), 6.64 (d, J=3.6 Hz, 1H), 4.90 (t, J=6.3 Hz, 1H), 3.85 (dd, J=12.0 Hz, J=21.6 Hz, 2H), 2.85-2.94 (m, 1H), 2.42-2.49 (m, 1H), 1.02 (s, 9H), 0.26 (d, J=9.0 Hz, 6H).

Step 3: Synthesis of (2R,3S,5R)-5-(4-amino-7H-pyrrolo[2,3-d]pyrimidin-7-yl)-3-hydroxy-2-(hydroxymethyl)tetrahydrofuran-2-carbonitrile (10)

To a stirred solution of (2R,3S,5R)-5-(4-amino-7H-pyrrolo[2,3-d]pyrimidin-7-yl)-3-((tert-butyldimethylsilyl)oxy)-2-(hydroxymethyl)tetrahydrofuran-2-carbonitrile (35 mg, 0.090 mmol) in dry THF (5 mL) was added TBAF THF solution (1.0 M, 0.108 mL, 0.108 mmol) dropwise with stirring under argon atmosphere at 15° C. The resulting mixture was stirred at 15° C. for 0.5 hours. The reaction progress was monitored by LCMS and TLC. The reaction mixture was concentrated under vacuum. The residue was purified by preparative-TLC (DCM/MeOH=10/1) to give a syrup. The crude product was further purified by Prep-HPLC with the following conditions: (1#-Pre-HPLC-011(Waters)): Column, SunFire C18 reverse Column, 19*150 mm, 5 um; mobile phase, water with 10 mmol ammonium bicarbonate and acetonitrile (5% acetonitrile up to 20% in 7.5 min, up to 95% in 2 min, down to 5% in 1 min); Detector, uv 254&220 nm. The product-containing fractions were collected and lyophilized to give the title compound 10 as a solid. LC-MS: (ES, m/z): 276.10 [M+H]$^+$. $^1$H-NMR: (400 MHz, $d_6$-DMSO, ppm): δ 8.07 (s, 1H), 7.34 (d, J=3.6 Hz, 1H), 7.33 (br, 2H), 7.08 (s, 1H), 6.64 (t, J=7.0 Hz, 1H), 6.61 (d, J=3.6 Hz, 1H), 6.27 (d, J=4.8 Hz, 1H), 5.82 (t, J=6.0 Hz, 1H), 4.61 (dd, J=4.8 Hz, J=10.0 Hz, 1H), 3.75 (dd, J=5.6 Hz, J=12.0 Hz, 1H), 3.62 (dd, J=6.0 Hz, J=11.6 Hz, 1H), 2.74-2.81 (m, 1H), 2.33-2.38 (m, 1H).

Example 11
Synthesis of (2R,3S,5R)-5-(4-aminopyrrolo[2,1-f][1,2,4]triazin-7-yl)-2-ethynyl-2-(hydroxymethyl)tetrahydrofuran-3-ol (11)
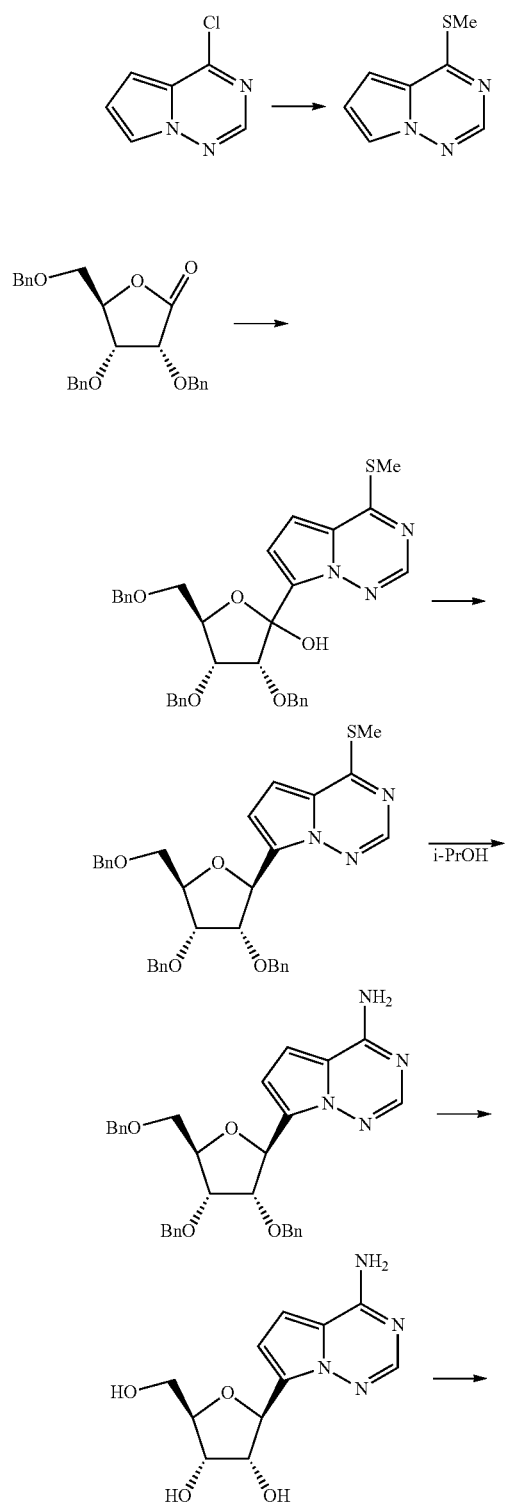
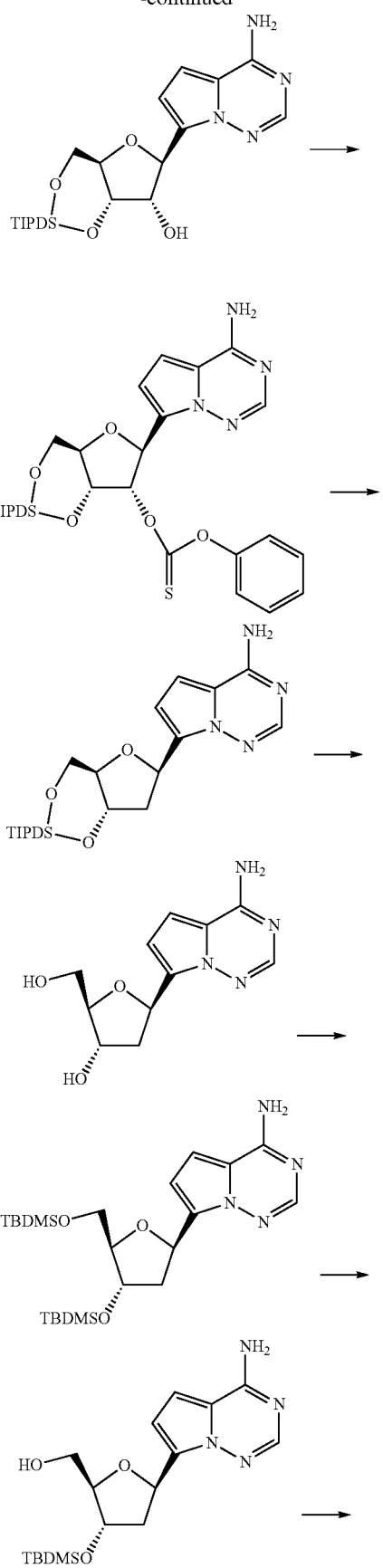

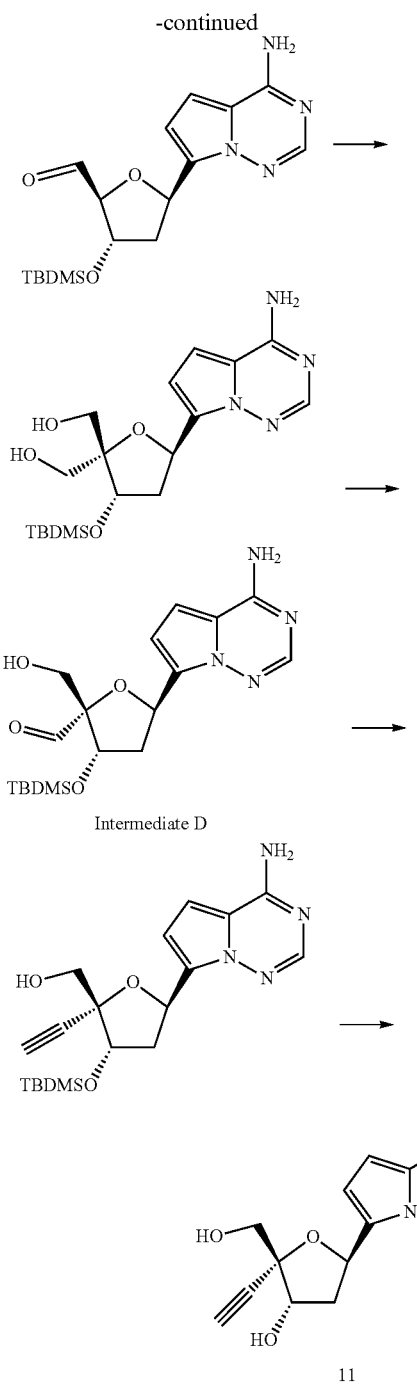

Intermediate D

11

Step 1: Synthesis of
4-(methylthio)pyrrolo[2,1-f][1,2,4]triazine

The synthesis of 4-chloropyrrolo[2,1-f][1,2,4]triazine is described in WO2011/150356A1, 2011. Into a 500-mL round-bottom flask, was placed a solution of 4-chloropyrrolo[2,1-f][1,2,4]triazine (17 g, 110.70 mmol) and (methylsulfanyl)sodium (15 g, 214.01 mmol in tetrahydrofuran (300 mL). The resulting solution was stirred for 1 overnight at room temperature. The solids were filtered out. The resulting mixture was concentrated in vacuo. The residue was applied onto a silica gel column with ethyl acetate/petroleum ether (1:10). This resulted in the title compound. LC-MS (ES, m/z): 166 [M+H]$^+$ Step 2: (3R,4R,5R)-3,4-bis(benzyloxy)-5-((benzyloxy)methyl)-2-(4-(methylthio)pyrrolo[2,1-f][1,2,4]triazin-7-yl)tetrahydrofuran-2-ol To a solution of 4-(methylthio)pyrrolo[2,1-f][1,2,4]triazine (1.650 g, 9.99 mmol) in THF (30 mL) was added lithium diisopropylamide (7.5 mL, 15.00 mmol) at −78° C. under argon atmosphere and the resulting mixture was stirred for 30 minutes at −78° C. After that, (3R,4R,5R)-3,4-bis(benzyloxy)-5-((benzyloxy)methyl)dihydrofuran-2(3H)-one (4.18 g, 9.99 mmol) in THF (10 mL) was added at −78° C. under argon atmosphere and stirred 120 minutes at −78 to −50° C. The reaction was quenched by additional of ammonium chloride (aq, 10 mL), and then extracted with ethyl acetate (300 mL). The organic layer was washed with (3×50 mL) brine, dried over sodium sulfate and concentrated under vacuum. The residue was applied on a silica gel column, eluted with ethyl acetate/petroleum ether (1:5) to give the title compound. LC-MS: 584.2 [M+H]$^+$ Step 3: Synthesis of 7-((2S,3S,4R,5R)-3,4-bis(benzyloxy)-5-((benzyloxy)methyl)tetrahydrofuran-2-yl)-4-(methylthio)pyrrolo[2,1-f][1,2,4]triazine To a solution of 3R,4R,5R)-3,4-bis(benzyloxy)-5-((benzyloxy)methyl)-2-(4-(methylthio)pyrrolo[2,1-f][1,2,4]triazin-7-yl)tetrahydrofuran-2-ol (3.00 g, 5.14 mmol) in DCM (30 mL) was added triethylsilane (2.390 g, 20.56 mmol) and trifluoroborane (0.697 g, 10.28 mmol) at 0° C. under argon atmosphere. The resulting solution was stirred for 30 minutes at 0° C. and then quenched by additional of sodium bicarbonate (aq, 20 mL), extracted by DCM (200 mL). The organic layer was washed with 3×50 mL brine, dried over sodium sulfate and concentrated under vacuum. The residue was applied on a silica gel column, eluted with ethyl acetate/petroleum ether (1:10) to give the title compound. LC-MS: 568.4 [M+H]$^+$. $^1$H-NMR: (300 MHz, CDCl$_3$, ppm): δ 8.21 (s, 1H), 7.23-7.36 (m, 15H), 6.81 (d, J=4.5 Hz, 1H), 6.70 (d, J=4.5 Hz, 1H), 5.69 (d, J=4.2 Hz, 1H), 4.37-4.62 (m, 7H), 4.22-4.26 (m, 1H), 4.10-4.13 (m, 1H), 3.66-3.67 (m, 1H), 3.62-3.63 (m, 1H), 2.75 (s, 3H).

Step 4: Synthesis of 7-((2S,3S,4R,5R)-3,4-bis(benzyloxy)-5-((benzyloxy)methyl)tetrahydrofuran-2-yl)pyrrolo[2,1-f][1,2,4]triazin-4-amine To a solution of 7-((2S,3S,4R,5R)-3,4-bis(benzyloxy)-5-((benzyloxy)methyl)tetrahydrofuran-2-yl)-4-(methylthio)pyrrolo[2,1-f][1,2,4]triazine (4.6 g, 8.10 mmol) in 2-propanol (5 mL) was flushed ammonia (1350 mg, 79 mmol) at −40.0° C. for 60 minutes in sealed tube. After the resulting mixture was stirred for 16 hours at 80° C., it was evaporated to give the title compound. LC-MS: 537.3 [M+H]$^+$. $^1$H-NMR: (300 MHz, DMSO, ppm): δ 7.80 (s, 1H), 7.69 (s, 2H), 7.24-7.36 (m, 15H), 6.88 (d, J=4.5 Hz, 1H), 6.80 (d, J=4.2 Hz, 1H), 5.44 (d, J=5.4 Hz, 1H), 4.49-4.62 (m, 6H), 4.31 (t, J=5.1 Hz, 1H), 4.15-4.18 (m, 1H), 4.09-4.12 (m, 1H), 3.29-3.67 (m, 2H).

Step 5: Synthesis of (2S,3R,4S,5R)-2-(4-aminopyrrolo[2,1-f][1,2,4]triazin-7-yl)-5-(hydroxymethyl)tetrahydrofuran-3,4-diol To a solution of 7-((2S,3S,4R,5R)-3,4-bis(benzyloxy)-5-((benzyloxy)methyl)tetrahydrofuran-2-yl)pyrrolo[2,1-f][1, 2,4]triazin-4-amine (100 mg, 0.186 mmol) in acetic acid (2 mL) was added Pd(OH)$_2$ (10 mol %)/C (100 mg, 0.130 mmol) under hydrogen at 25° C. for 4 hours. The mixture was filtered through a celite pad, and the filtrate was evaporated. The residue was applied on a silica gel column, eluted with MeOH/DCM (1:8) to give the title compound. LC-MS: 267.2 [M+H]$^+$. $^1$H-NMR: (300 MHz, DMSO, ppm): δ 7.79 (s, 1H), 7.77 (s, 2H), 6.84 (d, J=4.2 Hz, 1H), 6.68 (d, J=4.2 Hz, 1H), 5.10 (d, J=6.6 Hz, 1H), 4.95 (d, J=6.6 Hz, 1H), 4.84 (d, J=4.8 Hz, 1H), 4.76 (t, J=5.4 Hz, 1H), 4.20-4.25 (m, 1H), 3.94 (d, J=4.8 Hz, 1H), 3.78 (d, J=4.2 Hz, 1H), 3.41-3.64 (m, 2H).

Step 6: Synthesis of (6aR,8S,9S,9aS)-8-(4-aminopyrrolo[2,1-f][1,2,4]triazin-7-yl)-2,2,4,4-tetraisopropyltetrahydro-6H-furo[3,2-f][1,3,5,2,4]trioxadisilocin-9-ol (2S,3R,4S,5R)-2-(4-aminopyrrolo[2,1-f][1,2,4]triazin-7-yl)-5-(hydroxymethyl)tetrahydrofuran-3,4-diol (790 mg, 2.97 mmol) and 1H-imidazole (606 mg, 8.90 mmol) were dissolved in DMF (20 mL) under argon. 1,3-dichloro-1,1,3,3-tetraisopropyldisiloxane (936 mg, 2.97 mmol) was added by dropwise at 0° C. After the resulting mixture was stirred for 5 hours at 25° C. under argon, water (10 mL) was added and the resulting mixture was diluted with ethyl acetate (400 mL). The organic phase was washed with (3×60 mL) of water and 60 mL of brine, dried over Na$_2$SO$_4$ and concentrated under vacuum. The residue was applied on a silica gel, eluted with MeOH/DCM (1:20) to give the title compound. LC-MS: 509.3 [M+H]$^+$. $^1$H-NMR: (400 MHz, DMSO, ppm): δ 7.81 (s, 1H), 7.70 (s, 2H), 6.82 (d, J=4.8 Hz, 1H), 6.61 (d, J=4.4 Hz, 1H), 5.20 (d, J=4.8 Hz, 1H), 5.16 (d, J=1.6 Hz, 1H), 4.31-4.35 (m, 1H), 4.12-4.15 (m, 1H), 4.00-4.03 (m, 1H), 3.88-3.91 (m, 1H), 0.96-1.05 (m, 28H)

Step 7: Synthesis of O-((6aR,8S,9S,9aR)-8-(4-aminopyrrolo[2,1-f][1,2,4]triazin-7-yl)-2,2,4,4-tetraisopropyltetrahydro-6H-furo[3,2-f][1,3,5,2,4]trioxadisilocin-9-yl) O-phenyl carbonothioate (6aR,8S,9S,9aS)-8-(4-aminopyrrolo[2,1-f][1,2,4]triazin-7-yl)-2,2,4,4-tetraisopropyltetrahydro-6H-furo[3,2-f][1,3,5,2,4]trioxadisilocin-9-ol (210 mg, 0.413 mmol) and N,N-dimethylpyridin-4-amine (202 mg, 1.651 mmol) were dissolved in DCM (10 mL) under argon. O-phenyl carbonochloridothioate (143 mg, 0.826 mmol) were added by dropwise at 0° C. After the reaction was stirred at 25° C. under argon for 2 hours, the resulting mixture was diluted with DCM (100 mL), and then washed with 3×30 mL of water and 30 mL of brine. The organic layer was dried over Na$_2$SO$_4$ and concentrated under vacuum. The residue was applied on a silica gel column and eluted with ethyl acetate/petroleum ether (3:1) to give the title compound.

LC-MS: 645.2 [M+H]$^+$, $^1$H-NMR: (400 MHz, DMSO, ppm): δ 7.83 (s, 2H), 7.79 (s, 1H), 7.48 (t, J=8.0 Hz, 2H), 7.33 (t, J=7.2 Hz, 1H), 7.14 (d, J=7.6 Hz, 2H), 6.80 (d, J=4.4 Hz, 1H), 6.71 (d, J=4.4 Hz, 1H), 6.16 (dd, J=2.4 Hz, J=5.6 Hz, 1H), 5.46 (d, J=2.0 Hz, 1H), 4.90 (dd, J=5.6 Hz, J=8.8 Hz, 1H), 3.95-4.06 (m, 2H), 3.85-3.87 (m, 1H), 0.96-1.06 (m, 28H).

Step 8: Synthesis of 7-((6aR,8R,9aS)-2,2,4,4-tetraisopropyltetrahydro-6H-furo[3,2-f][1,3,5,2,4]trioxadisilocin-8-yl)pyrrolo[2,1-f][1,2,4]triazin-4-amine O-((6aR,8S,9S,9aR)-8-(4-aminopyrrolo[2,1-f][1,2,4]triazin-7-yl)-2,2,4,4-tetraisopropyltetrahydro-6H-furo[3,2-f][1,3,5,2,4]trioxadisilocin-9-yl) O-phenyl carbonothioate (1.45 g, 2.248 mmol), AIBN (0.738 g, 4.50 mmol) and tributylstannane (3.93 g, 13.49 mmol) were dissolved in toluene (20 mL) under argon. After the reaction was stirred at 80° C. under argon for 3 hours, the resulting solution was concentrated under vacuum. The residue was applied on a silica gel column and eluted with ethyl acetate/petroleum ether (2.5:1) to give the title compound. LC-MS: 493.4 [M+H]$^+$, $^1$H-NMR: (400 MHz, DMSO, ppm): δ 7.81 (s, 1H), 7.79 (s, 2H), 6.81 (d, J=4.4 Hz, 1H), 6.60 (d, J=4.4 Hz, 1H), 5.46 (t, 1H), 4.58-4.62 (m, 1H), 3.90-4.00 (m, 1H), 3.75-3.80 (m, 2H), 2.20-2.30 (m, 1H), 2.30-2.40 (m, 1H), 0.98-1.06 (m, 28H).

Step 9: Synthesis of (2R,3S,5R)-5-(4-aminopyrrolo[2,1-f][1,2,4]triazin-7-yl)-2-(hydroxymethyl)tetrahydrofuran-3-ol 7-((6aR,8R,9aS)-2,2,4,4-tetraisopropyltetrahydro-6H-furo[3,2-f][1,3,5,2,4]trioxadisilocin-8-yl)pyrrolo[2,1-f][1,2,4]triazin-4-amine (1.0 g, 2.029 mmol) was dissolved in THF (10 mL) under argon. TBAF (0.531 g, 2.029 mmol) was added to the reaction solution by dropwise at 20° C. After the resulting solution was stirred at 20° C. under argon for 2 hours, it was concentrated under vacuum. The residue applied on a silica gel column and eluted with DCM/MeOH (20:1) to give the title compound. LC-MS: 251.2 [M+H]$^+$, $^1$H-NMR: (400 MHz, DMSO, ppm): ε7.83 (s, 1H), 7.81 (s, 2H), 6.84 (d, J=4.8 Hz, 1H), 6.82 (d, J=4.4 Hz, 1H), 5.47-5.51 (m, 1H), 5.06 (d, J=4.0 Hz, 1H), 4.73 (t, J=6.0 Hz, 1H), 4.22 (m, 1H), 3.74-3.78 (m, 1H), 3.32-3.45 (m, 2H), 2.16-2.20 (m, 1H), 2.09-2.14 (m, 1H).

Step 10: Synthesis of 7-((2R,4S,5R)-4-((tert-butyldimethylsilyl)oxy)-5-(((tert-butyldimethylsilyl)oxy)methyl)tetrahydrofuran-2-yl)pyrrolo[2,1-f][1,2,4]triazin-4-amine (2R,3S,5R)-5-(4-aminopyrrolo[2,1-f][1,2,4]triazin-7-yl)-2-(hydroxymethyl)tetrahydrofuran-3-ol (300 mg, 1.199 mmol), 1H-imidazole (490 mg, 7.19 mmol) and tert-butylchlorodimethylsilane (723 mg, 4.80 mmol) were dissolved in DMF (4.0 mL) under argon. After the reaction mixture was stirred at 20° C. under argon for 5 hours, the resulting mixture was diluted with ethyl acetate (100 mL), washed with (3×30 mL) of water and 30 mL of brine. The organic layer was dried with Na$_2$SO$_4$ and concentrated under vacuum. The residue was applied on a silica gel column and eluted with ethyl acetate/petroleum ether (2:1) to give the title compound. LC-MS: 479.3 [M+H]$^+$, $^1$H-NMR: (300 MHz, DMSO, ppm): δ 7.82 (s, 1H), 7.75 (s, 2H), 6.82 (d, J=4.5 Hz, 1H), 6.61 (d, J=4.5 Hz, 1H), 5.48-5.53 (m, 1H), 4.42 (m, 1H), 3.78 (m, 1H), 3.48-3.62 (m, 2H), 2.22-2.27 (m, 1H), 2.04-2.10 (m, 1H), 0.78-0.89 (m, 18H), 0.00-0.10 (m, 12H)

Step 11: Synthesis of ((2R,3S,5R)-5-(4-aminopyrrolo[2,1-f][1,2,4]triazin-7-yl)-3-((tert-butyldimethylsilyl)oxy)tetrahydrofuran-2-yl)methanol 7-((2R,4S,5R)-4-((tert-butyldimethylsilyl)oxy)-5-(((tert-butyldimethylsilyl)oxy)methyl)tetrahydrofuran-2-yl)pyrrolo[2,1-f][1,2,4]triazin-4-amine (500 mg, 1.044 mmol) was dissolved in THF (8.0 mL), H$_2$O (2.0 mL) and TFA (2.0 mL) and stirred at 0° C. for 4 hours. The reaction mixture was adjusted to pH 7 with sodium bicarbonate and then extracted with ethyl acetate (30 mL×3), washed with (3×20 mL) of water and 20 mL of brine. The organic layer was dried over Na$_2$SO$_4$ and concentrated under vacuum. The residue was applied on a silica gel column and eluted with ethyl acetate/petroleum ether (2:1) to give the title compound. LC-MS: 365.3 [M+H]$^+$, $^1$H-NMR: (400 MHz, DMSO, ppm): δ 7.82 (s, 1H), 7.68 (s, 2H), 6.82 (d, J=4.4 Hz, 1H), 6.65 (d, J=4.4 Hz, 1H), 5.46-5.50 (m, 1H), 4.80 (t, J=5.6 Hz, 1H), 4.42 (d, J=4.2 Hz, 1H), 3.74-3.78 (m, 1H), 3.32-3.44 (m, 2H), 2.24-2.28 (m, 1H), 2.02-2.06 (m, 1H), 0.85-0.90 (m, 9H), 0.00-0.10 (m, 6H).

Step 12: Synthesis of (2S,3S,5R)-5-(4-aminopyrrolo[2,1-f][1,2,4]triazin-7-yl)-3-((tert-butyldimethylsilyl)oxy)tetrahydrofuran-2-carbaldehyde ((2R,3S,5R)-5-(4-aminopyrrolo[2,1-f][1,2,4]triazin-7-yl)-3-((tert-butyldimethylsilyl)oxy)tetrahydrofuran-2-yl)methanol (270 mg, 0.741 mmol) and IBX (270 mg, 0.963 mmol) was dissolved in acetonitrile (20.0 mL) under argon. After the reaction mixture was stirred at 80° C. under argon for 1 hour, the solid was filtered out and the filtrate was concentrated under vacuum to give the title compound which was used for next step directly. LC-MS: 363.2 [M+H]$^+$, $^1$H-NMR: (400 MHz, DMSO, ppm): δ 9.59 (s, 1H), 7.84 (s, 1H), 7.73 (s, 2H), 6.86 (d, J=4.4 Hz, 1H), 6.64 (d, J=4.4 Hz, 1H), 5.67-5.71 (m, 1H), 4.71 (d, J=4.4 Hz, 1H), 4.25 (s, 1H), 2.25-2.32 (m, 1H), 2.12-2.17 (m, 2H), 0.84-0.91 (m, 9H), 0.00-0.13 (m, 6H).

Step 13: Synthesis of ((4S,5R)-5-(4-aminopyrrolo[2,1-f][1,2,4]triazin-7-yl)-3-((tert-butyldimethylsilyl)oxy)tetrahydrofuran-2,2-diyl)dimethanol (2S,3S,5R)-5-(4-aminopyrrolo[2,1-f][1,2,4]triazin-7-yl)-3-((tert-butyldimethylsilyl)oxy)tetrahydrofuran-2-carbaldehyde (200 mg, 0.552 mmol) was dissolved in 1,4-dioxane (10 mL) at 20° C. Then formaldehyde (2.0 mL, 0.552 mmol) and sodium hydroxide (2.0 mL, 4.00 mmol) were added. After the resulting mixture was stirred at 20° C. for 4 hours, it was adjusted to pH 7 with acetic acid. The mixture was diluted with ethyl acetate (150 mL), then washed with 3×30 mL of water and 30 mL of brine. The organic layer was dried over Na$_2$SO$_4$, and concentrated under vacuum. The residue was dissolved in ethanol (10 mL) at 0° C., and then NaBH$_4$ (41.7 mg, 1.103 mmol) was added at 0° C. After the resulting mixture was stirred at 20° C. for 16 hours, it was adjusted to pH=7 with acetic acid and the mixture was extracted with ethyl acetate (150 mL), then washed with (3×30 mL) of water and 30 mL of brine. The organic layer was dried over Na$_2$SO$_4$ and concentrated under vacuum. The residue was applied to a silica gel column and eluted with DCM/MeOH (10:1) to give the title compound. LC-MS: 395.2 [M+H]$^+$, $^1$H-NMR: (400 MHz, DMSO, ppm): ϵ7.82 (s, 1H), 7.70 (s, 2H), 6.82 (d, J=4.4 Hz, 1H), 6.66 (d, J=4.4 Hz, 1H), 5.50-5.60 (m, 1H), 4.68 (t, 1H), 4.52 (d, J=4.4 Hz, 1H), 4.22 (t, 1H), 3.53-3.60 (m, 2H), 2.35-2.45 (m, 1H), 2.00-2.10 (m, 1H), 0.90 (s, 9H), 0.08-0.09 (m, 6H).

Step 14: Synthesis of (2R,3S,5R)-5-(4-aminopyrrolo[2,1-f][1,2,4]triazin-7-yl)-3-((tert-butyldimethylsilyl)oxy)-2-(hydroxymethyl)tetrahydrofuran-2-carbaldehyde ((3S,5R)-5-(4-aminopyrrolo[2,1-f][1,2,4]triazin-7-yl)-3-((tert-butyldimethylsilyl)oxy)tetrahydrofuran-2,2-diyl)dimethanol (90 mg, 0.228 mmol) and IBX (256 mg, 0.912 mmol) were dissolved in acetonitrile (15.0 mL) under argon. After the reaction mixture was stirred at 30° C. under argon for 48 hours, the solid was filtered out. The filtrate was concentrated under vacuum to give the title compound, which was used for next step directly.

Step 15: Synthesis of ((2R,3S,5R)-5-(4-aminopyrrolo[2,1-f][1,2,4]triazin-7-yl)-3-((tert-butyldimethylsilyl)oxy)-2-ethynyltetrahydrofuran-2-yl)methanol (2R,3S,5R)-5-(4-aminopyrrolo[2,1-f][1,2,4]triazin-7-yl)-3-((tert-butyldimethylsilyl)oxy)-2-(hydroxymethyl)tetrahydrofuran-2-carbaldehyde (80 mg, 0.204 mmol) and K$_2$CO$_3$ (85 mg, 0.611 mmol) were dissolved in methanol (10 mL) under argon. Dimethyl (1-diazo-2-oxopropyl)phosphonate (78 mg, 0.408 mmol) was added to the reaction mixture dropwise at 0° C. After the reaction mixture was stirred at 25° C. under argon for 16 hours, it was filtrated and concentrated under vacuum. The residue was applied to a silica gel column and eluted with DCM/MeOH (10:1) to give the title compound. LC-MS: 389.3 [M+H]$^+$ Step 16: Synthesis of (2R,3S,5R)-5-(4-aminopyrrolo[2,1-f][1,2,4]triazin-7-yl)-2-ethynyl-2-(hydroxymethyl)tetrahydrofuran-3-ol (11)

((2R,3S,5R)-5-(4-aminopyrrolo[2,1-f][1,2,4]triazin-7-yl)-3-((tert-butyldimethylsilyl)oxy)-2-ethynyltetrahydrofuran-2-yl)methanol (50 mg, 0.129 mmol) and TBAF (33.6 mg, 0.129 mmol) were dissolved in THF (5.0 mL) under argon. After the resulting solution was stirred at 25° C. under argon for 2 hours, the reaction mixture was concentrated under vacuum. The residue was purified by Prep-HPLC with the following conditions (1#-Pre-HPLC-011(Waters)): Column, Xbridge Prep C18 Column, 19*150 mm; mobile phase, water (10 mmoL/L NH$_4$HCO$_3$) and acetonitrile (5.0% acetonitrile up to 25.0% in 8 min, up to 95.0% in 1.5 min, down to 5.0% in 1.5 min); Detector, UV254 & 220 nm) to give the title compound 11 as a solid. LC-MS: 275.1 [M+H]$^+$, $^1$H-NMR: (400 MHz, DMSO, ppm): ϵ7.82 (s, 1H), 7.69 (s, 2H), 6.82 (d, J=4.4 Hz, 1H), 6.69 (d, J=4.0 Hz, 1H), 5.60 (t, J=7.6 Hz, 1H), 5.28 (d, J=4.2 Hz, 1H), 5.06 (d, J=6.8 Hz, J=6.0 Hz, 1H), 4.30-4.34 (m, 1H), 3.45-3.56 (m, 2H), 3.38 (s, 1H), 2.30-2.37 (m, 1H), 2.17-2.13 (m, 1H).

Example 12

Synthesis of (2R,3S,5R)-5-(4-aminopyrrolo[2,1-f][1,2,4]triazin-7-yl)-3-hydroxy-2-(hydroxymethyl)tetrahydrofuran-2-carbonitrile (12)

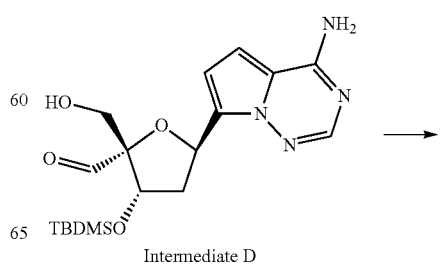

Intermediate D

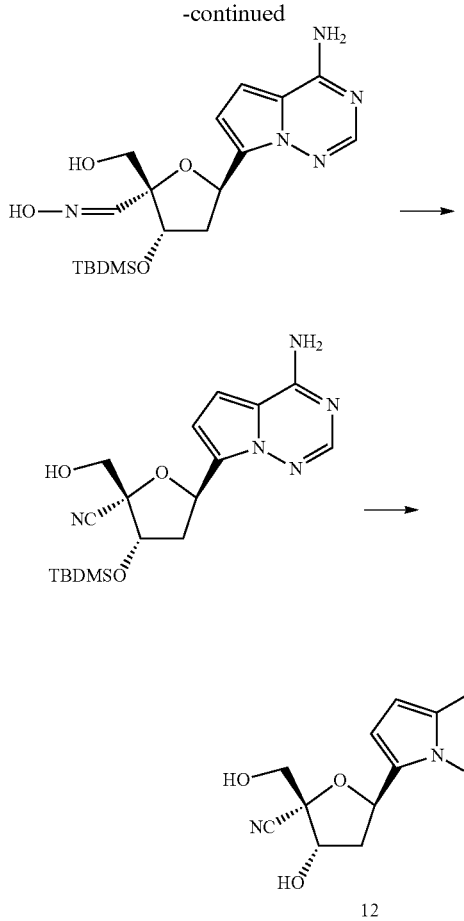

Step 1: Synthesis of 5-(4-aminopyrrolo[2,1-f][1,2,4]triazin-7-yl)-3-((tert-butyldimethylsilyl)oxy)-2-(hydroxymethyl)tetrahydrofuran-2-carbaldehyde oxime To a mixture of Intermediate D (see Example 11) (70 mg, 0.178 mmol) in pyridine (5 mL) under argon was added hydroxylamine hydrochloride (37.17 mg, 0.543 mmol) at 25° C. After the resulting mixture was stirred for 2 hours at 25° C., the reaction mixture was concentrated under reduced pressure. The residue was diluted with ethyl acetate (100 mL), washed with water (3×20 mL) and brine (20 mL), dried over anhydrous sodium sulfate and concentrated under reduced pressure to afford the title compound that was used without purification. LC-MS: 408.2 [M+H]$^+$

Step 2: Synthesis of (2R,3S,5R)-5-(4-aminopyrrolo[2,1-f][1,2,4]triazin-7-yl)-3-((tert-butyldimethylsilyl)oxy)-2-(hydroxymethyl)tetrahydrofuran-2-carbonitrile To a mixture of 5-(4-aminopyrrolo[2,1-f][1,2,4]triazin-7-yl)-3-((tert-butyldimethylsilyl)oxy)-2-(hydroxymethyl)tetrahydrofuran-2-carbaldehyde oxime (70 mg, 0.172 mmol) in DCM (15 mL) under argon was added Et$_3$N (69.5 mg, 0.687 mmol) and 2,2,2-trifluoroacetic anhydride (72.2 mg, 0.344 mmol) at 25° C. The resulting mixture was stirred for 16 hours at 25° C. and then the reaction mixture was diluted with DCM (100 mL), washed with sat aqueous sodium bicarbonate (3×20 mL) and brine (20 mL), dried over anhydrous sodium sulfate and concentrated under reduced pressure. The residue was purified by a silica gel column, eluting with DCM/MeOH (15:1) to afford the title compound. LC-MS: 309.2 [M+H]$^+$.

Step 3: Synthesis of (2R,3S,5R)-5-(4-aminopyrrolo[2,1-f][1,2,4]triazin-7-yl)-3-hydroxy-2-(hydroxymethyl)tetrahydrofuran-2-carbonitrile (12)

To a mixture of (2R,3S,5R)-5-(4-aminopyrrolo[2,1-f][1,2,4]triazin-7-yl)-3-((tert-butyldimethylsilyl)oxy)-2-(hydroxymethyl)tetrahydrofuran-2-carbonitrile (50 mg, 0.128 mmol) in THF (10 mL) under argon was added TBAF (33.6 mg, 0.128 mmol) at 25° C. The resulting mixture was stirred for 2 hours at 25° C. and then concentrated under reduced pressure. The crude product was purified by Prep-HPLC with the following conditions: Instrument, (1#-Pre-HPLC-011(waters)); Column: Xbridge C18, 5 um, 19×150 mm; mobile phase: water (0.05% NH$_4$CO$_3$) and ACN (5.0% ACN up to 40% in 10 min, hold 95% for 2 minutes, down to 5% in 2 minutes); Detector, UV 220 and 254 nm. The collected fractions were combined and concentrated under reducing pressure to give the title compound 12 as a solid. LC-MS: 276.0 [M+H]$^+$, $^1$H-NMR: (400 MHz, DMSO, ppm): ∈7.86 (s, 1H), 7.74-7.84 (s, 2H), 6.88 (d, J=4.4 Hz, 1H), 6.84 (d, J=4.4 Hz, 1H), 6.10 (d, J=4.4 Hz, 1H), 5.72-5.79 (m, 1H), 5.62-5.63 (m, 1H), 4.44-4.61 (s, 1H), 3.53-3.62 (m, 2H), 2.42-2.49 (m, 1H), 2.19-2.24 (m, 1H).

Example 13 ammonium ((2R,3S,5R)-5-(4-amino-7H-pyrrolo[2,3-d]pyrimidin-7-yl)-2-ethynyl-3-hydroxytetrahydrofuran-2-yl)methyl triphosphate (13)

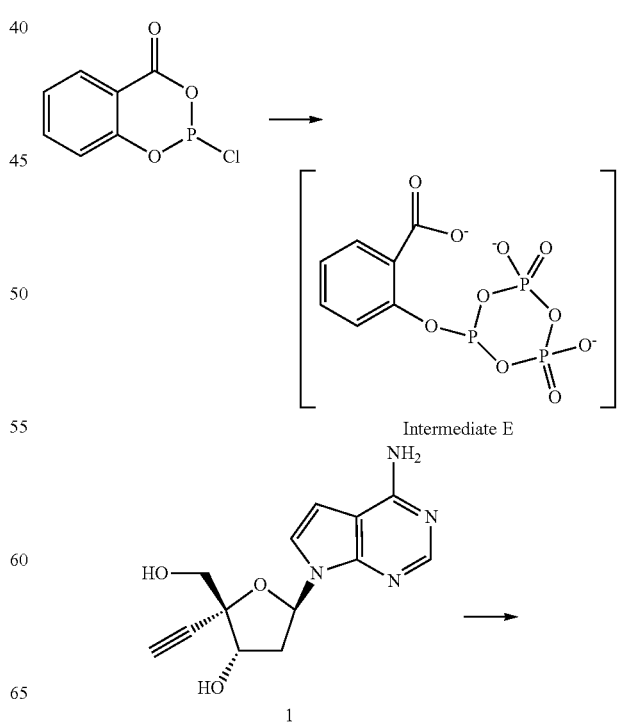

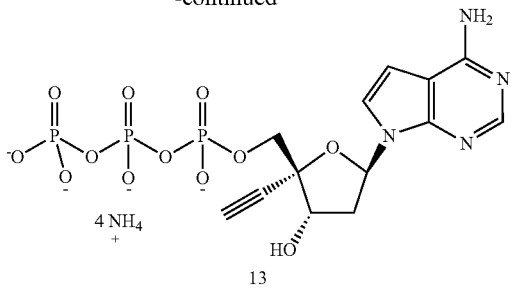

13

Step 1: 2-((4,4,6,6-tetraoxido-1,3,5,2,4,6-trioxatriphosphinan-2-yl)oxy)benzoate Intermediate E In a glove box under an argon atmosphere, dry tributylamine (0.4 mL, 1.679 mmol) was added to the flask containing tributylammonium pyrophosphate (112 mg, 0.205 mmol) dissolved in 0.4 mL dimethylformamide (DMF) to give a clear solution. The clear solution was then injected into the flask containing dry 2-chloro-4H-benzo[d][1,3,2]dioxaphosphinin-4-one (27.6 mg, 0.136 mmol) in dimethylformamide (0.4 mL) under vigorous stirring. The resulting mixture was stirred at 30° C. for 30 minutes to give a solution of Intermediate E which was used to the next reaction directly without any work-up.

Step 2: Synthesis of ammonium ((2R,3S,5R)-5-(4-amino-7H-pyrrolo[2,3-d]pyrimidin-7-yl)-2-ethynyl-3-hydroxytetrahydrofuran-2-yl)methyl triphosphate (13)

(2R,3S,5R)-5-(4-amino-7H-pyrrolo[2,3-d]pyrimidin-7-yl)-2-ethynyl-2-(hydroxymethyl)tetrahydrofuran-3-ol (Compound 1, 8 mg, 0.029 mmol) was placed into a round-bottom flask (10 mL) and then dried over $P_2O_5$ under high vacuum overnight. To this flask was added activated molecular sieves 4 Å (100 mg). The medium was charged with argon and then a solution of Intermediate E (2.0 eq, freshly prepared) in dry DMF (0.15 mL) was transferred into the above flask by syringes and the mixture was stirred at 25° C. for 3 hours. The reaction progress was monitored by TLC (acetonitrile:0.1 M ammonium chloride=7:3). Upon most of the started nucleoside was consumed, the mixture was cooled down to 0° C., iodine solution [3% in 0.1 mL of pyridine/water (9:1)] was then injected into the reaction mixture. As the iodine was consumed, dropwise addition of the iodine solution was continued until a permanent brown color of iodine was maintained. After 15 minutes, triethylammonium bicarbonate buffer (1.0 M, 2 mL) was added with stirring at 10° C. for another 15 minutes. The volatile was removed under vacuum (inner temperature not exceed 25° C.). The residue was re-dissolved in water (2 mL) and extracted with chloroform (2×2 mL). The collected aqueous layer which containing crude product was then purified by preparative-HPLC with the following conditions (1#-Pre-HPLC-011(Waters)): Column, XBridge™ Prep OBD (Optimum Bed Density) T3 Column, 19*150 mm, 5um; mobile phase, water with 50 mmol ammonium bicarbonate and acetonitrile (2% acetonitrile up to 5.2% in 5 min, up to 95% in 2 min, down to 5% in 1.5 min); Detector, UV 254 & 220 nm. The product-containing fractions were collected and lyophilized to give the title compound 13 as a solid. LC-MS: (ES, m/z): 512.90 [M−H-4NH$_3$]$^-$. $^1$H-NMR: (400 MHz, D$_2$O, ppm): δ 8.06 (s, 1H), 7.38 (d, J=3.6 Hz, 1H), 6.63 (t, J=7.6 Hz, 1H), 6.58 (d, J=3.6 Hz, 1H), 4.06-4.14 (m, 2H), 2.67-2.72 (m, 1H), 2.54-2.59 (m, 1H). P-NMR: (161 MHz, D$_2$O, ppm): δ −5.86 (s, 1P), −11.49--11.39 (d, J=15.13 Hz, 1P), −19.29 (s, 1P).

The following compounds 14-21 were synthesized using the method described in Example 13:

Example 14 ammonium ((2R,3S,5R)-5-(4-amino-5-fluoro-7H-pyrrolo[2,3-d]pyrimidin-7-yl)-2-ethynyl-3-hydroxytetrahydrofuran-2-yl)methyl triphosphate (14)

LC-MS: (ES, m/z): 530.85 [M−H-4NH$_3$]$^-$. $^1$H-NMR: (400 MHz, D$_2$O, ppm): δ 8.00 (s, 1H), 7.14 (s, 1H), 6.62 (dd, J=4.8 Hz, J=6.0 Hz, 1H), 4.13 (dd, J=5.6 Hz, J=11.2 Hz, 1H), 4.06 (dd, J=5.0 Hz, J=11.4 Hz, 1H), 2.48-2.64 (m, 2H). P-NMR: (161 MHz, D$_2$O, ppm): δ −5.97--5.89 (d, J=13.85 Hz, 1P), −11.52--11.43 (d, J=14.81 Hz, 1P), −19.31 (s, 1P).

Example 15 ammonium (2R,3S,5R)-5-(4-amino-5-methyl-7H-pyrrolo[2,3-d]pyrimidin-7-yl)-2-ethynyl-3-hydroxytetrahydrofuran-2-yl)methyl triphosphate (15)

LC-MS: (ES, m/z): 527.00 [M−H-4NH$_3$]$^-$. $^1$H-NMR: (400 MHz, D$_2$O, ppm): δ 7.96 (s, 1H), 7.07 (s, 1H), 6.55 (t, J=6.6 Hz, 1H), 4.11 (dd, J=6.2 Hz, J=11.4 Hz, 1H), 4.05 (dd, J=5.8 Hz, J=12.0 Hz, 1H), 2.59-2.66 (m, 1H), 2.48-2.53 (m, 1H), 2.78 (s, 3H). P-NMR: (161 MHz, D$_2$O, ppm): δ −5.90 (s, 1P), −11.48--11.39 (d, J=14.49 Hz, 1P), −19.32 (s, 1P).

Example 16 bis-triethylammonium ((2R,3S,5R)-5-(4-amino-2-chloro-7H-pyrrolo[2,3-d]pyrimidin-7-yl)-2-ethynyl-3-hydroxytetrahydrofuran-2-yl)methyl triphosphate (16)

LC-MS: (ES, m/z): 546.95 [M−H-2TEA]$^-$. $^1$H-NMR: (400 MHz, D$_2$O, ppm): δ 7.31 (d, J=4.0 Hz, 1H), 6.53 (d, J=4.0 Hz, 1H), 6.50 (t, J=6.4 Hz, 1H), 4.15 (dd, J=5.8 Hz, J=10.6 Hz, 1H), 4.08 (dd, J=4.8 Hz, J=11.2 Hz, 1H), 2.62-2.67 (m, 1H), 2.53-2.58 (m, 1H). P-NMR: (161 MHz, D$_2$O, ppm): δ −5.86--5.77 (d, J=14.81 Hz, 1P), −11.45--11.35 (d, J=15.13 Hz, 1P), −19.24 (s, 1P).

Example 17 ammonium ((2R,3S,5R)-5-(4-amino-5-chloro-7H-pyrrolo[2,3-d]pyrimidin-7-yl)-2-ethynyl-3-hydroxytetrahydrofuran-2-yl)methyl triphosphate (17)

LC-MS: (ES, m/z): 546.70 [M−H-4NH$_3$]$^-$. $^1$H-NMR: (400 MHz, D$_2$O, ppm): δ 7.97 (s, 1H), 7.34 (s, 1H), 6.54 (t, J=6.0 Hz, 1H), 4.01-4.13 (m, 2H), 2.52-2.62 (m, 2H). P-NMR: (161 MHz, D$_2$O, ppm): δ −5.81 (s, 1P), −11.42 (s, 1P), −19.25 (s, 1P).

Example 18 bis-triethylammonium ((2R,3S,5R)-5-(4-amino-7H-pyrrolo[2,3-d]pyrimidin-7-yl)-2-cyano-3-hydroxytetrahydrofuran-2-yl)methyl triphosphate (18)

LC-MS: (ES, m/z): 514.35 [M–H-2TEA]⁻. ¹H-NMR: (400 MHz, D$_2$O, ppm): δ 8.04 (s, 1H), 7.29 (d, J=3.2 Hz, 1H), 6.70 (t, J=6.8 Hz, 1H), 6.55 (d, J=3.2 Hz, 1H), 4.87 (t, J=6.0 Hz, 1H), 4.21-4.16 (m, 2H), 2.99 (q, J=7.2 Hz, 15H), 2.80-2.76 (m, 1H), 2.58-2.54 (m, 1H), 1.12 (t, J=7.2 Hz, 26H). P-NMR: (161 MHz, D$_2$O, ppm): δ −5.85 (s, 1P), −11.84 (d, J=15.30 Hz, 1P), −19.38 (s, 1P).

Example 19 ammonium ((2R,3S,5R)-5-(4-aminopyrrolo[2,1-f][1,2,4]triazin-7-yl)-2-ethynyl-3-hydroxytetrahydrofuran-2-yl)methyl triphosphate (19)

LC-MS: (ES, m/z): 512.90 [M–H-4NH$_3$]⁻. ¹H-NMR: (400 MHz, D$_2$O, ppm): δ 7.73 (s, 1H), 6.77 (dd, J=4.4 Hz, J=7.4 Hz, 2H), 5.73 (t, J=7.4 Hz, 1H), 4.52-4.56 (m, 1H), 3.98-4.03 (m, 2H), 2.56-2.63 (m, 1H), 2.34-2.40 (m, 1H). P-NMR: (161 MHz, D$_2$O, ppm): δ −5.79 (s, 1P), −11.24 (s, 1P), −19.21 (s, 1P).

Example 20 ammonium ((2R,3S,5R)-5-(4-aminopyrazolo[1,5-a][1,3,5]triazin-8-yl)-2-ethynyl-3-hydroxytetrahydrofuran-2-yl)methyl triphosphate (20)

LC-MS: (ES, m/z): 513.95 [M–H-4 NH$_3$]⁻. ¹H-NMR: (400 MHz, D$_2$O, ppm): δ 8.22 (s, 1H), 7.99 (s, 1H), 5.53 (t, J=7.6 Hz, 1H), 4.60-4.57 (m, 1H), 4.12-4.03 (m, 2H), 2.56-2.49 (m, 1H), 2.35-2.29 (m, 1H). P-NMR: (161 MHz, D$_2$O, ppm): δ −5.82 (s, 1P), −11.32-11.23 (d, J=13.69 Hz, 1P), −19.24 (s, 1P).

Example 21 ammonium ((2R,3S,5R)-5-(4-aminoimidazo[2,1-f][1,2,4]triazin-7-yl)-2-ethynyl-3-hydroxytetrahydrofuran-2-yl)methyl triphosphate (21)

LC-MS: (ES, m/z): 513.95 [M–H-4NH$_3$]⁻. ¹H-NMR: (400 MHz, D$_2$O, ppm): δ 8.23 (s, 1H), 7.98 (s, 1H), 5.66 (t, J=7.6 Hz, 1H), 4.61-4.58 (m, 1H), 4.05 (brs, 2H), 2.68-2.61 (m, 1H), 2.46-2.42 (m, 1H). P-NMR: (161 MHz, D$_2$O, ppm): δ −5.81 (s, 1P), −11.33-11.24 (d, J=13.85 Hz, 1P), −19.19 (s, 1P).

The names of the corresponding salt-free form of compounds 13-21 are, respectively:

13) ((2R,3S,5R)-5-(4-amino-7H-pyrrolo[2,3-d]pyrimidin-7-yl)-2-ethynyl-3-hydroxytetrahydrofuran-2-yl)methyl tetrahydrogen triphosphate;
14) ((2R,3S,5R)-5-(4-amino-5-fluoro-7H-pyrrolo[2,3-d]pyrimidin-7-yl)-2-ethynyl-3-hydroxytetrahydrofuran-2-yl)methyl tetrahydrogen triphosphate;
15) ((2R,3S,5R)-5-(4-amino-5-methyl-7H-pyrrolo[2,3-d]pyrimidin-7-yl)-2-ethynyl-3-hydroxytetrahydrofuran-2-yl)methyl tetrahydrogen triphosphate;
16) ((2R,3S,5R)-5-(4-amino-2-chloro-7H-pyrrolo[2,3-d]pyrimidin-7-yl)-2-ethynyl-3-hydroxytetrahydrofuran-2-yl)methyl tetrahydrogen triphosphate;
17) ((2R,3S,5R)-5-(4-amino-5-chloro-7H-pyrrolo[2,3-d]pyrimidin-7-yl)-2-ethynyl-3-hydroxytetrahydrofuran-2-yl)methyl tetrahydrogen triphosphate;
18) ((2R,3S,,5R)-5-(4-amino-7H-pyrrolo[2,3-d]pyrimidin-7-yl)-2-cyano-3-hydroxytetrahydrofuran-2-yl)methyl tetrahydrogen triphosphate;
19) ((2R,3S,,5R)-5-(4-aminopyrrolo[2,1-f][1,2,4]triazin-7-yl)-2-ethynyl-3-hydroxytetrahydrofuran-2-yl)methyl tetrahydrogen triphosphate;
20) ((2R,3S,5R)-5-(4-aminopyrazolo[1,5-a][1,3,5]triazin-8-yl)-2-ethynyl-3-hydroxytetrahydrofuran-2-yl)methyl tetrahydrogen triphosphate; and
21) ((2R,3S,5R)-5-(4-aminoimidazo[2,1-f][1,2,4]triazin-7-yl)-2-ethynyl-3-hydroxytetrahydrofuran-2-yl)methyl tetrahydrogen triphosphate.

Example 22

Synthesis of (2R,3S,5R)-5-(4-aminoimidazo[2,1-f][1,2,4]triazin-7-yl)-2-ethynyl-2-(hydroxymethyl)tetrahydrofuran-3-ol (22)

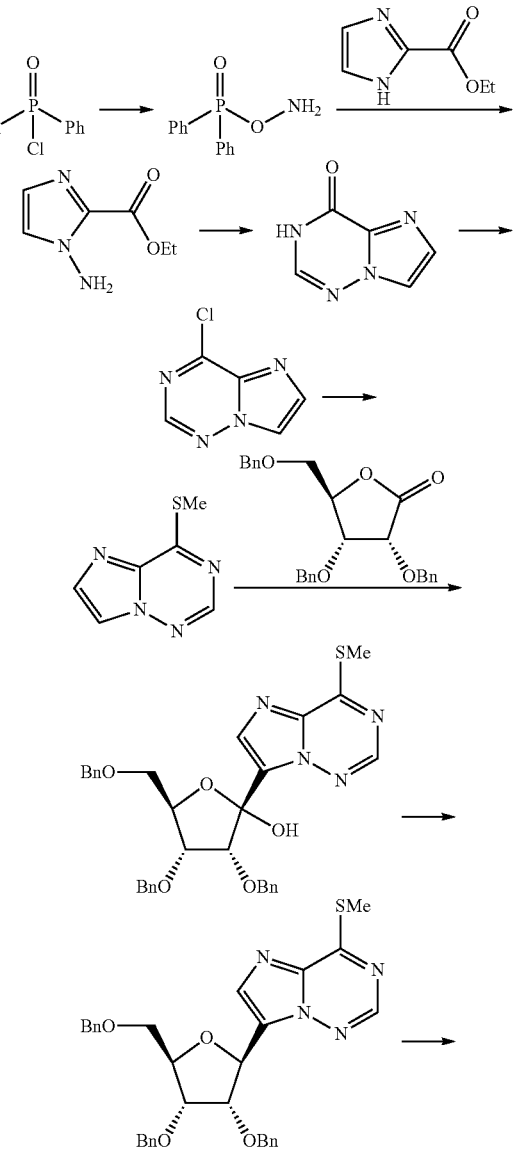

103
-continued
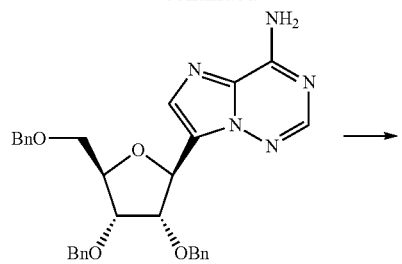
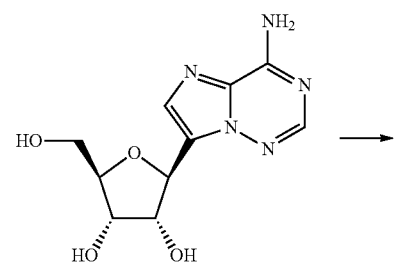
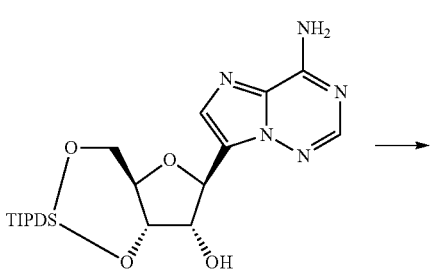
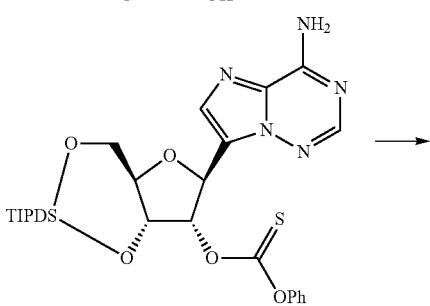
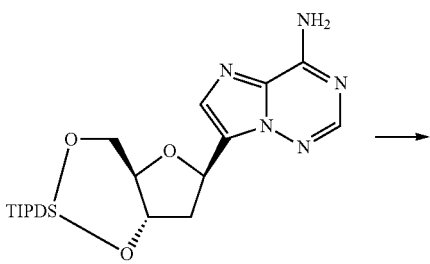
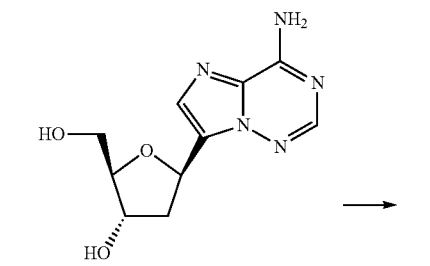
104
-continued
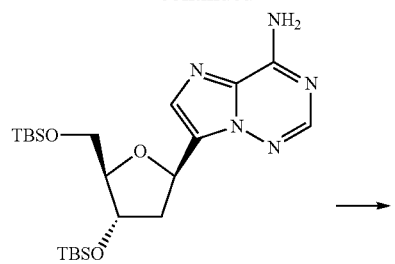
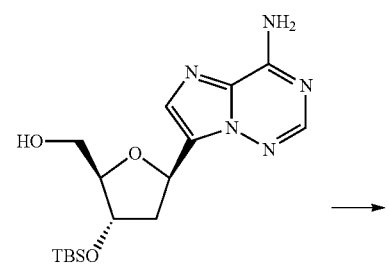
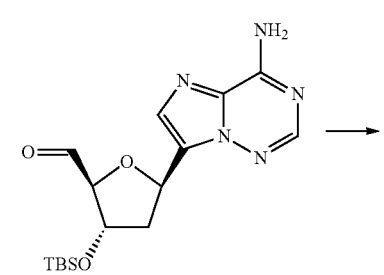
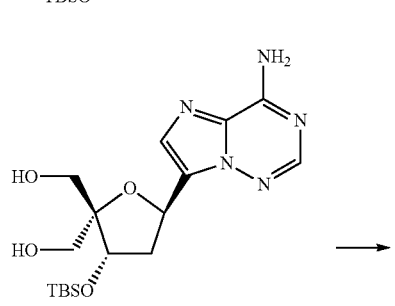
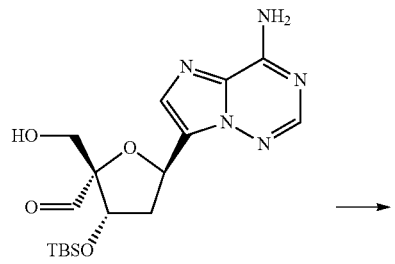
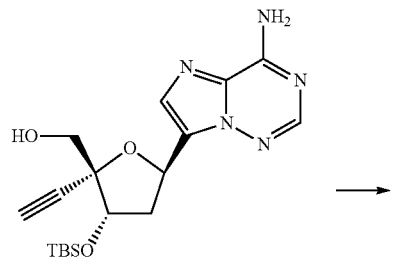

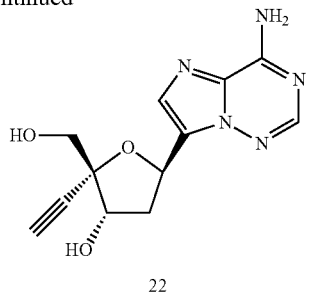

22

Step 1: Synthesis of (aminooxy)diphenylphosphine oxide

To a stirred solution of hydroxylamine hydrochloride (70 g, 1007 mmol) in a mixture of 1,4-dioxane (100 mL) and water (100 mL) was added a solution of NaOH (38.3 g, 957 mmol) in water (400 mL) dropwise with stirring at 0° C. in 30 minutes. The resulting solution was stirred at 0° C. for 20 minutes. To the above was injected a solution of diphenylphosphinic chloride (77 mL, 403 mmol) in 1,4-dioxane (100 mL) quickly at 0° C. The resulting mixture was stirred vigorously at ambient temperature for 10 minutes. A precipitate was formed and collected by filtration. The solid was re-suspended in aq NaOH (0.25 N, 1000 mL) and stirred at 4° C. for 1.5 hours. The mixture was filtered and the filter cake was washed with water (3×1000 mL) and ether (2×500 mL) successively. The solid was dried under vacuum overnight to give (aminooxy)diphenylphosphine oxide. LC-MS: (ES, m/z): 233.9 [M+H]$^+$. $^1$H-NMR: (400 MHz, d$_6$-DMSO, ppm): δ 7.82-7.69 (m, 4H), 7.58-7.40 (m, 6H) P-NMR: (121 MHz, d$_6$-DMSO, ppm): δ 21.53 (s, 1P).

Step 2: Synthesis of ethyl 1-amino-1H-imidazole-2-carboxylate

To a stirred solution of ethyl 1H-imidazole-2-carboxylate (6 g, 30.9 mmol) in DMF (250 mL) under argon atmosphere was added LiHMDS THF solution (93 mL, 93 mmol, 1 M) dropwise at −10° C. for 60 minutes. The resulting mixture was stirred at −10° C. for additional 30 min, and then (aminooxy)diphenylphosphine oxide (21.63 g, 93 mmol) was added in portions for 30 minutes while maintained the temperature between 0° C. to 10° C. The resulting mixture was warmed to room temperature and stirred vigorously for 16 hours. The reaction was quenched with ice water (600 mL) and extracted with EtOAc (2×800 mL). The combined organic layers was dried over anhydrous Na$_2$SO$_4$, filtered and the filtrate was concentrated under reduced pressure to give ethyl 1-amino-1H-imidazole-2-carboxylate which was used for the next reaction step directly without further purification. LC-MS: (ES, m/z): 156.1 [M+H]$^+$. $^1$H-NMR: (400 MHz, d$_6$-DMSO, ppm): δ 7.37 (d, J=0.8 Hz, 1H), 6.96 (d, J=0.8 Hz, 1H), 6.57 (br s, 2H), 4.33-4.27 (m, 2H), 1.31 (t, J=7.2 Hz, 3H).

Step 3: Synthesis of imidazo[2,1-f][1,2,4]triazin-4(3H)-one

To a stirred mixture of ethyl 1-amino-1H-imidazole-2-carboxylate (6 g, 30.9 mmol) in EtOH (60 mL) under argon atmosphere was added formamidine acetate (17.71 g, 170 mmol). The resulting mixture was heated to reflux and stirred overnight. The reaction mixture was cooled to ambient temperature and filtered. The filter cake was washed with water (3×10 mL) and EtOAc (2×10 mL) successively. The collected solid was dried under high vacuum overnight to give imidazo[2,1-f][1,2,4]triazin-4(3H)-one. LC-MS: (ES, m/z): 136.9 [M+H]$^+$. $^1$H-NMR: (400 MHz, d$_6$-DMSO, ppm): δ 12.31 (br s, 1H), 8.09 (s, 1H), 7.98 (d, J=0.8 Hz, 1H), 7.50 (d, J=0.8 Hz, 1H).

Step 4: Synthesis of 4-chloroimidazo[2,1-f][1,2,4]triazine

Imidazo[2,1-f][1,2,4]triazin-4(3H)-one (2.4 g, 17.63 mmol) was massed into a 100 mL round-bottom flask under argon atmosphere followed by the injection of POCl$_3$ (20 mL) at room temperature. The mixture was heated to reflux and stirred for 16 h. The volatile was removed under reduce pressure. The residue was partitioned between EtOAc (100 mL) and water (30 mL). The organic layer was washed with cold aq NaHCO$_3$ (saturated, 3×20 mL) and brine (20 mL) successively, dried over anhydrous Na$_2$SO$_4$, filtered and the filtrate was concentrated under reduced pressure. The residue was purified by silica gel column chromatography using pet. ether/EtOAc (5/1) to afford 4-chloroimidazo[2,1-f][1,2,4]triazine. LC-MS: (ES, m/z): 155.0 [M+H]$^+$. $^1$H-NMR: (400 MHz, d$_6$-DMSO, ppm): δ 8.81 (s, 1H), 8.65 (d, J=1.2 Hz, 1H), 8.08 (d, J=0.8 Hz, 1H).

Step 5. Synthesis of 4-(methylthio)imidazo[2,1-f][1,2,4]triazine

To a stirred solution of 4-chloroimidazo[2,1-f][1,2,4]triazine (20 g, 129 mmol) in THF (500 mL) under argon atmosphere was added NaSMe (13.60 g, 194 mmol) at room temperature. The resulting mixture was stirred at room temperature for 72 hours. The reaction mixture was quenched with aqueous NH$_4$Cl (saturated, 200 mL) and extracted with EtOAc (2×500 mL). The combined organic layers was washed with brine (2×200 mL), dried over anhydrous Na$_2$SO$_4$, filtered and the filtrate was concentrated under reduced pressure. The residue was purified by silica gel column chromatography using pet. ether/EtOAc (1/1) to afford 4-(methylthio)imidazo[2,1-f][1,2,4]triazine. LC-MS: (ES, m/z): 167.2 [M+H]$^+$. $^1$H-NMR: (400 MHz, CDCl$_3$, ppm): δ 8.47 (s, 1H), 7.90 (d, J=0.8 Hz, 1H), 7.76 (d, J=0.4 Hz, 1H), 2.73 (s, 3H).

Step 6: Synthesis of (3R,4R,5R)-3,4-bis(benzyloxy)-5-((benzyloxy)methyl)-2-(4-(methylthio)imidazo[2,1-f][1,2,4]triazin-7-yl)tetrahydrofuran-2-ol To a stirred solution of 4-(methylthio)imidazo[2,1-f][1,2,4]triazine (1 g, 6.02 mmol) in THF (25 mL) under argon atmosphere was injected LDA THF solution (4.5 mL, 9.0 mmol, 2 M) at −78° C. in 5 minutes. The resulting mixture was maintained at −78° C. for 30 minutes, and then a solution of (3R,4R,5R)-3,4-bis(benzyloxy)-5-((benzyloxy)methyl)dihydrofuran-2(3H)-one (commercial, 3.27 g, 7.82 mmol) in THF (15 mL) was injected and the resulting mixture was stirred between −78° C. to −50° C. for 2 hours. The reaction was quenched with aqueous NH$_4$Cl (saturated, 20 mL) and extracted with EtOAc (2×50 mL). The combined organic layers was washed with brine (2×20 mL), dried over anhydrous Na$_2$SO$_4$, filtered and the filtrate was concentrated under reduced pressure. The residue was purified by silica gel column chromatography using pet. ether/EtOAc (5/1) to give (3R,4R,5R)-3,4-bis(benzyloxy)-5-

((benzyloxy)methyl)-2-(4-(methylthio)imidazo[2,1-f][1,2,4]triazin-7-yl)tetrahydrofuran-2-ol. LC-MS: (ES, m/z): 585.1 [M+H]$^+$.

Step 7: Synthesis of 7-((2S,3S,4R,5R)-3,4-bis(benzyloxy)-5-((benzyloxy)methyl)tetrahydrofuran-2-yl)-4-(methylthio)imidazo[2,1-f][1,2,4]triazine To a stirred solution of (3R,4R,5R)-3,4-bis(benzyloxy)-5-((benzyloxy)methyl)-2-(4-(methylthio)imidazo[2,1-f][1,2,4]triazin-7-yl)tetrahydrofuran-2-ol (1.7 g, 2.91 mmol) in DCM (30 mL) under argon atmosphere were injected boron trifluoride-diethyl etherate (825.3 mg, 5.82 mmol) and triethylsilane (1.35 g, 11.63 mmol) at 0° C. successively. The resulting mixture was stirred at 0° C. for additional 16 hours. The reaction was quenched with aqueous NaHCO$_3$ (saturated, 20 mL) and extracted with DCM (2×30 mL). The combined organic layers was washed with brine (30 mL), dried over anhydrous Na$_2$SO$_4$, filtered and the filtrate was concentrated under reduced pressure. The residue was purified by silica gel column chromatography using pet. ether/EtOAc (10/1) to give 7-((2S,3S,4R,5R)-3,4-bis(benzyloxy)-5-((benzyloxy)methyl)tetrahydrofuran-2-yl)-4-(methylthio)imidazo[2,1-f][1,2,4]triazine. LC-MS: (ES, m/z): 570.0 [M+H]$^+$. $^1$H-NMR: (300 MHz, CDCl$_3$, ppm): δ 8.38 (s, 1H), 7.66 (s, 1H), 7.37-7.26 (m, 15H), 5.56 (d, J=5.4 Hz, 1H), 4.70-4.49 (m, 6H), 4.39 (q, J=4.2 Hz, 1H), 4.34 (t, J=5.4 Hz, 1H), 4.15 (t, J=5.1 Hz, 1H), 3.70 (dd, J=3.6 Hz, J=10.5 Hz, 1H), 3.60 (dd, J=3.9 Hz, J=10.8 Hz, 1H), 2.70 (s, 3H).

Step 8: Synthesis of 7-((2S,3S,4R,5R)-3,4-bis(benzyloxy)-5-((benzyloxy)methyl)tetrahydrofuran-2-yl)imidazo[2,1-f][1,2,4]triazin-4-amine To a 80 mL steel bomb, was massed 7-((2S,3S,4R,5R)-3,4-bis(benzyloxy)-5-((benzyloxy)methyl)tetrahydrofuran-2-yl)-4-(methylthio)imidazo[2,1-f][1,2,4]triazine (1.4 g, 2.462 mmol). The medium was cooled to −60° C. To this was added isopropanolic ammonia (isopropanol/liquid ammonia=2/3, mixed at −60° C., 50 mL). The resulting mixture was heated to 90° C. and stirred for 16 hours. The reaction mixture was cooled to room temperature and then concentrated under reduced pressure. The residue was purified by silica gel column chromatography using pet. ether/EtOAc (1/1) to give 7-((2S,3S,4R,5R)-3,4-bis(benzyloxy)-5-((benzyloxy)methyl)tetrahydrofuran-2-yl)imidazo[2,1-f][1,2,4]triazin-4-amine LC-MS: (ES, m/z): 538.3 [M+H]$^+$. $^1$H-NMR: (400 MHz, d$_6$-DMSO, ppm): δ 8.24 (br s, 1H), 8.15 (br s, 1H), 8.05 (s, 1H), 7.49 (s, 1H), 7.36-7.28 (m, 15H), 5.35 (d, J=5.2 Hz, 1H), 4.63 (s, 2H), 4.56 (d, J=4.8 Hz, 2H), 4.52 (d, J=2.0 Hz, 2H), 4.45 (t, J=5.2 Hz, 1H), 4.22-4.16 (m, 2H), 3.65 (dd, J=3.2 Hz, J=10.8 Hz, 1H), 3.58 (dd, J=4.4 Hz, J=10.8 Hz, 1H).

Step 9: Synthesis of (2S,3R,4S,5R)-2-(4-aminoimidazo[2,1-f][1,2,4]triazin-7-yl)-5-(hydroxymethyl)tetrahydrofuran-3,4-diol To a stirred solution of 7-((2S,3S,4R,5R)-3,4-bis(benzyloxy)-5-((benzyloxy)methyl)tetrahydrofuran-2-yl)imidazo[2,1-f][1,2,4]triazin-4-amine (1.2 g, 2.232 mmol) in AcOH (10 mL) was added 20% Pd(OH)$_2$/C (1.2 g). The medium was charged with hydrogen (2 atm) and stirred at 25° C. for 24 hours. The solid was filtered out and washed with AcOH (2×15 mL). The combined filtrate was concentrated under reduced pressure. The residue was purified by silica gel column chromatography using DCM/MeOH (8/1) to afford (2S,3R,4S,5R)-2-(4-aminoimidazo[2,1-f][1,2,4]triazin-7-yl)-5-(hydroxymethyl)tetrahydrofuran-3,4-diol. LC-MS: (ES, m/z): 290.0 [M+Na]$^+$. $^1$H-NMR: (400 MHz, d$_6$-DMSO, ppm): δ 8.22 (br s, 1H), 8.15 (br s, 1H), 8.07 (s, 1H), 7.64 (s, 1H), 5.13-5.09 (m, 2H), 5.03 (d, J=6.4 Hz, 1H), 4.78 (br s, 1H), 4.32 (t, J=6.0 Hz, 1H), 3.99 (t, J=4.8 Hz, 1H), 3.81 (q, J=4.4 Hz, 1H), 3.56 (dd, J=3.2 Hz, J=11.2 Hz, 1H), 3.46 (dd, J=3.6 Hz, J=11.2 Hz, 1H).

Step 10: Synthesis of (6aR,8S,9S,9aS)-8-(4-aminoimidazo[2,1-f][1,2,4]triazin-7-yl)-2,2,4,4-tetraisopropyltetrahydro-6H-furo[3,2-f][1,3,5,2,4]trioxadisilocin-9-ol To a stirred solution of (2S,3R,4S,5R)-2-(4-aminoimidazo[2,1-f][1,2,4]triazin-7-yl)-5-(hydroxymethyl)tetrahydrofuran-3,4-diol (3.2 g, 11.97 mmol) and 1H-imidazole (3.26 g, 47.9 mmol) in DMF (65 mL) under argon atmosphere was injected 1,3-dichloro-1,1,3,3-tetraisopropyldisiloxane (3.97 g, 12.57 mmol) at 0° C. The resulting mixture was warmed to 30° C. and stirred for 5 hours. The reaction was quenched with water (70 mL) and extracted with EtOAc (3×100 mL). The combined organic layer was washed with brine (3×100 mL), dried over anhydrous Na$_2$SO$_4$, filtered and the filtrate was concentrated under reduced pressure. The residue was purified by silica gel column chromatography using pet. ether/EtOAc (3/1) to give (6aR,8S,9S,9aS)-8-(4-aminoimidazo[2,1-f][1,2,4]triazin-7-yl)-2,2,4,4-tetraisopropyltetrahydro-6H-furo[3,2-f][1,3,5,2,4] trioxadisilocin-9-ol. LC-MS: (ES, m/z): 510.4 [M+H]$^+$. $^1$H-NMR: (400 MHz, CDCl$_3$, ppm): δ 8.12 (s, 1H), 7.62 (s, 1H), 7.03 (br s, 1H), 6.39 (br s, 1H), 5.31 (d, J=3.2 Hz, 1H), 4.68 (dd, J=6.0 Hz, J=7.0 Hz, 1H), 4.47 (q, J=2.8 Hz, 1H), 4.10-4.05 (m, 3H), 3.20 (br s, 1H), 1.15-1.05 (m, 28H).

Step 11: Synthesis of O-((6aR,8S,9S,9aR)-8-(4-aminoimidazo[2,1-f][1,2,4]triazin-7-yl)-2,2,4,4-tetraisopropyltetrahydro-6H-furo[3,2-f][1,3,5,2,4]trioxadisilocin-9-yl) O-phenyl carbonothioate To a stirred solution of (6aR,8S,9S,9aR)-8-(4-aminoimidazo[2,1-f][1,2,4]triazin-7-yl)-2,2,4,4-tetraisopropyltetrahydro-6H-furo[3,2-f][1,3,5,2,4]trioxadisilocin-9-ol (4.0 g, 7.85 mmol) and DMAP (3.83 g, 31.4 mmol) in DCM (160 mL) under argon atmosphere was injected O-phenyl carbonochloridothioate (2.71 g, 15.69 mmol) at 0° C. The resulting mixture was stirred at 0° C. for additional 3 hours. The reaction mixture was concentrated under reduced pressure. The residue was purified by silica gel column chromatography using pet. ether/EtOAc (1/3) to give O-((6aR,8S,9S,9aR)-8-(4-aminoimidazo[2,1-f][1,2,4]triazin-7-yl)-2,2,4,4-tetraisopropyltetrahydro-6H-furo[3,2-f][1,3,5,2,4]trioxadisilocin-9-yl) O-phenyl carbonothioate. LC-MS: (ES, m/z): 646.3 [M+H]$^+$. $^1$H-NMR: (400 MHz, d$_6$-DMSO, ppm): δ 8.37 (br s, 1H), 8.28 (br s, 1H), 8.02 (s, 1H), 7.67 (s, 1H), 7.49 (t, J=8.0 Hz, 2H), 7.34 (t, J=7.4 Hz, 1H), 7.15 (d, J=8.4 Hz, 2H), 6.22 (dd, J=2.0 Hz, J=5.2 Hz, 1H), 5.49 (d, J=2.0 Hz, 1H), 4.95 (dd, J=5.2 Hz, J=8.8 Hz, 1H), 4.07-3.96 (m, 2H), 3.91-3.88 (m, 1H), 1.07-1.04 (m, 28H).

Step 12: Synthesis of 7-((6aR,8R,9aS)-2,2,4,4-tetraisopropyltetrahydro-6H-furo[3,2-f][1,3,5,2,4]trioxadisilocin-8-yl)imidazo[2,1-f][1,2,4]triazin-4-amine To a stirred solution of O-((6aR,8S,9S,9aR)-8-(4-aminoimidazo[2,1-f][1,2,4]triazin-7-yl)-2,2,4,4-tetraisopropyltetrahydro-6H-furo[3,2-f][1,3,5,2,4]trioxadisilocin-9-yl) O-phenyl carbonothioate (350 mg, 0.542 mmol) and AIBN (133 mg, 0.813 mmol) in degassed toluene (10 mL) under argon atmosphere was injected tri-n-butyltin hydride (314 mg, 1.084 mmol) at room temperature. The mixture was heated to 80° C. and stirred for 3 hours. The reaction mixture was concentrated under reduced pressure. The residue was purified by silica gel column chromatography using pet. ether/EtOAc (1/3) to give 7-((6aR,8R,9aS)-2,2,4,4-tetraisopropyltetrahydro-6H-furo[3,2-f][1,3,5,2,4]trioxadisilocin-8-yl)imidazo[2,1-f][1,2,4]triazin-4-amine LC-MS: (ES, m/z): 494.5 [M+H]$^+$. $^1$H-NMR: (400 MHz, d$_6$-DMSO, ppm): δ 8.23 (br s, 1H), 8.16 (br s, 1H), 8.05 (s, 1H), 7.56 (s, 1H), 5.42 (t, J=7.0 Hz, 1H), 4.63 (dd, J=5.8 Hz, J=13.0 Hz, 1H), 3.95 (dd, J=3.2 Hz, J=11.6 Hz, 1H), 3.83 (dd, J=6.8 Hz, J=12.0 Hz, 1H), 3.78-3.75 (m, 1H), 2.55-2.51 (m, 1H), 2.37-2.32 (m, 1H), 1.07-1.01 (m, 28H).

Step 13: Synthesis of (2R,3S,5R)-5-(4-aminoimidazo[2,1-f][1,2,4]triazin-7-yl)-2-(hydroxymethyl) tetrahydrofuran-3-ol To a stirred solution of 7-((6aR,8R,9aS)-2,2,4,4-tetraisopropyltetrahydro-6H-furo[3,2-f][1,3,5,2,4]trioxadisilocin-8-yl)imidazo[2,1-f][1,2,4]triazin-4-amine (2.7 g, 5.47 mmol) in THF (60 mL) was injected hydrogen fluoride-pyridine (5.42 g, 54.7 mmol) at 0° C. The mixture was warmed to ambient temperature and stirred for 20 hours. The reaction mixture was cooled to 0° C., neutralized with solid NaHCO$_3$ and then diluted with MeOH (50 mL). The solid was filtered out and the filtrate was concentrated under reduced pressure. The residue was treated with DCM/MeOH (20 mL, 100/1, v/v) and stirred for 30 minutes. The white precipitate was collected and dried under vacuum overnight to give (2R,3S,5R)-5-(4-aminoimidazo[2,1-f][1,2,4]triazin-7-yl)-2-(hydroxymethyl)tetrahydrofuran-3-ol. $^1$H-NMR: (400 MHz, d$_6$-DMSO, ppm): δ 8.20 (br s, 1H), 8.13 (br s, 1H), 8.06 (s, 1H), 7.60 (s, 1H), 5.42 (dd, J=5.8 Hz, J=10.2 Hz, 1H), 5.12 (d, J=4.0 Hz, 1H), 4.74 (t, J=5.6 Hz, 1H), 4.28-4.25 (m, 1H), 3.81-3.78 (m, 1H), 3.42 (t, J=5.4 Hz, 2H), 2.33-2.26 (m, 1H), 2.13-2.09 (m, 1H).

Step 14: Synthesis of 7-((2R,4S,5R)-4-((tert-butyldimethylsilyl)oxy)-5-(((tert-butyldimethylsilyl) oxy)methyl)tetrahydrofuran-2-yl)imidazo[2,1-f][1,2,4]triazin-4-amine (2R,3S,5R)-5-(4-aminoimidazo[2,1-f][1,2,4]triazin-7-yl)-2-(hydroxymethyl)tetrahydrofuran-3-ol (200 mg, 0.796 mmol) and 1H-imidazole (217 mg, 3.18 mmol) were massed into a 10 mL flask under argon atmosphere. To the mixture was injected anhydrous DMF (2.5 mL), followed by the addition of tert-butylchlorodimethylsilane (360 mg, 2.388 mmol) at 0° C. The mixture was stirred at 25° C. for 3 h. The resulting mixture was diluted with EtOAc (50 mL), washed with aqueous NaHCO$_3$ (saturated, 2×15 mL) and brine (20 mL) respectively. The organic layer was collected and dried over anhydrous Na$_2$SO$_4$, filtered and concentrated under reduced pressure. The residue was purified by silica gel column chromatography using pet. ether/EtOAc (35%-52% EtOAc in pet. ether) to give 7-((2R,4S,5R)-4-((tert-butyldimethylsilyl)oxy)-5-(((tert-butyldimethylsilyl)oxy) methyl)tetrahydrofuran-2-yl)imidazo[2,1-f][1,2,4]triazin-4-amine LC-MS: (ES, m/z): 480.1 [M+H]$^+$. $^1$H-NMR: (300 MHz, d$_6$-DMSO, ppm): δ 8.20 (br s, 1H), 8.13 (br s, 1H), 8.06 (s, 1H), 7.57 (s, 1H), 5.43 (dd, J=5.6 Hz, J=10.0 Hz, 1H), 4.46-4.44 (m, 1H), 3.81 (t, J=4.5 Hz, 1H), 3.63-3.51 (m, 2H), 2.45-2.36 (m, 1H), 2.16-2.10 (m, 1H), 0.89 (s, 9H), 0.86 (s, 9H), 0.10 (s, 6H), 0.02 (d, J=3.6 Hz, 6H).

Step 15: Synthesis of ((2R,3S,5R)-5-(4-aminoimidazo[2,1-f][1,2,4]triazin-7-yl)-3-((tert-butyldimethylsilyl)oxy)tetrahydrofuran-2-yl)methanol 7-((2R,4S,5R)-4-((tert-butyldimethylsilyl)oxy)-5-(((tert-butyldimethylsilyl)oxy)methyl)tetrahydrofuran-2-yl)imidazo[2,1-f][1,2,4]triazin-4-amine (350 mg, 0.730 mmol) was massed into a 25 mL round-bottom flask, followed by the injection of THF (4 mL). The medium was cooled to 0° C. To this was added a precooled solution of trifluoroacetic acid/water (1/1, v/v, 2 mL) dropwise with stirring at 0° C. in 10 min. The resulting mixture was stirred at 0° C. for 2 hours. The reaction progress was monitored by TLC & LCMS. The resulting solution was co-evaporated with toluene (3×20 mL) and the residue was re-suspended in aq NaHCO$_3$ (saturated, 4 mL) and then evaporated to dryness. The residue was purified by silica gel column chromatography with EtOAc/DCM (1/1) to give ((2R,3S,5R)-5-(4-aminoimidazo[2,1-f][1,2,4]triazin-7-yl)-3-((tert-butyldimethylsilyl)oxy)tetrahydrofuran-2-yl)methanol. LC-MS: (ES, m/z): 366.2 [M+H]$^+$. $^1$H-NMR: (300 MHz, d$_6$-DMSO, ppm): δ 8.09 (br s, 1H), 8.03 (br s, 1H), 7.96 (s, 1H), 7.51 (s, 1H), 5.31 (q, J=5.4 Hz, 1H), 4.70 (t, J=5.7 Hz, 1H), 4.34 (d, J=5.1 Hz, 1H), 3.69 (t, J=4.5 Hz, 1H), 3.33-3.28 (m, 2H), 2.34-2.24 (m, 1H), 2.01-1.96 (m, 1H), 0.79 (s, 9H), 0.01 (s, 6H).

Step 16: Synthesis of (2S,3S,5R)-5-(4-aminoimidazo[2,1-f][1,2,4]triazin-7-yl)-3-((tert-butyldimethylsilyl)oxy)tetrahydrofuran-2-carbaldehyde To a stirred solution of ((2R,3S,5R)-5-(4-aminoimidazo [2,1-f][1,2,4]triazin-7-yl)-3-((tert-butyldimethylsilyl)oxy) tetrahydrofuran-2-yl)methanol (280 mg, 0.766 mmol) in anhydrous acetonitrile (20 mL) under argon atmosphere was added IBX (644 mg, 2.298 mmol) at room temperature. The mixture was heated to 80° C. and stirred for 25 minutes. LCMS indicated that the started nucleoside was all consumed. The resulting mixture was cooled to room temperature. The solids were filtered out and the filtrate was concentrated under reduced pressure to give (2S,3S,5R)-5-(4-aminoimidazo[2,1-f][1,2,4]triazin-7-yl)-3-((tert-butyldimethylsilyl)oxy)tetrahydrofuran-2-carbaldehyde, which was used for the next reaction step directly without further purification. LC-MS: (ES, m/z): 363.7 [M+H]$^+$.

Step 17: Synthesis of ((3S,5R)-5-(4-aminoimidazo [2,1-f][1,2,4]triazin-7-yl)-3-((tert-butyldimethylsilyl) oxy)tetrahydrofuran-2,2-diyl)dimethanol To a stirred solution of (2S,3S,5R)-5-(4-aminoimidazo[2, 1-f][1,2,4]triazin-7-yl)-3-((tert-butyldimethylsilyl)oxy)tetrahydrofuran-2-carbaldehyde (300 mg, crude) in 1,4-dioxane (4 mL) in a 25 mL round-bottom flask, was injected 37% aq formaldehyde (1.0 mL), followed by aq NaOH (1.0 mL, 2.0 mmol, 2 N) at 0° C. The resulting mixture was warmed to ambient temperature and stirred for 16 hours. Upon the started nucleoside was all consumed, the reaction mixture was neutralized with AcOH (~0.2 mL). The mixture was diluted with EtOAc (100 mL) and washed successively with water (2×25 mL), aqueous NaHCO$_3$ (saturated, 25 mL) and brine (20 mL). The organic layer was dried over anhydrous Na$_2$SO$_4$, filtered and the filtrate was concentrated under reduced pressure give a crude product. The crude product was re-dissolved in EtOH (5 mL) under argon atmosphere and was added sodium borohydride (153 mg, 4.04 mmol) in portions at 0° C. After stirring at ambient temperature for 16 hours, the reaction mixture was neutralized with AcOH (~0.2 mL) and evaporated to dryness. The residue was partitioned between CHCl$_3$ (50 mL) and water (25 mL). The aqueous layer was re-extracted with CHCl$_3$ (2×25 mL). The combined organic layer was washed brine (40 mL), dried over anhydrous Na$_2$SO$_4$, filtered and the filtrate was concentrated under reduced pressure. The residue was purified by silica gel column chromatography using DCM/MeOH (30/1) to give ((3S,5R)-5-(4-aminoimidazo[2,1-f][1,2,4]triazin-7-yl)-3-((tert-butyldimethylsilyl)oxy)tetrahydrofuran-2,2-diyl)dimethanol. LC-MS: (ES, m/z): 395.8 [M+H]$^+$. $^1$H-NMR: (400 MHz, d$_6$-DMSO, ppm): ϵ 8.18 (br s, 1H), 8.12 (br s, 1H), 8.07 (s, 1H), 7.62 (s, 1H), 5.47 (q, J=5.2 Hz, 1H), 4.68 (t, J=5.6 Hz, 1H), 4.53 (d, J=3.6 Hz, 1H), 4.27 (t, J=5.6 Hz, 1H), 3.60-3.55 (m, 1H), 3.53-3.51 (m, 2H), 3.34-3.31 (m, 1H), 2.56-2.53 (m, 1H), 2.11-2.07 (m, 1H), 0.90 (s, 9H), 0.09 (d, J=2.8 Hz, 6H).

Step 18: Synthesis of (2R,3S,5R)-5-(4-aminoimidazo[2,1-f][1,2,4]triazin-7-yl)-3-((tert-butyldimethylsilyl)oxy)-2-(hydroxymethyl)tetrahydrofuran-2-carbaldehyde To a stirred mixture of ((3S,5R)-5-(4-aminoimidazo[2,1-f][1,2,4]triazin-7-yl)-3-((tert-butyldimethylsilyl)oxy)tetrahydrofuran-2,2-diyl)dimethanol (180 mg, 0.455 mmol) in acetonitrile (20 mL) and DMSO (2 mL) under argon atmosphere was added IBX (382 mg, 1.365 mmol) at room temperature. The resulting mixture was warmed to 30° C. and stirred for 2 hours. The solid was filtered out, washed with CHCl$_3$ (2×20 mL) and the combined filtrate was concentrated under reduced pressure. The residue was re-dissolved in EtOAc (30 mL), washed successively with aqueous NaHCO$_3$ (saturated, 2×15 mL) and brine (20 mL), dried over anhydrous Na$_2$SO$_4$, filtered and the filtrate was concentrated under reduced pressure to give (2R,3S,5R)-5-(4-aminoimidazo[2,1-f][1,2,4]triazin-7-yl)-3-((tert-butyldimethylsilyl)oxy)-2-(hydroxymethyl)tetrahydrofuran-2-carbaldehyde, which was used for the next reaction step directly without further purification. LC-MS: (ES, m/z): 393.8 [M+H]$^+$.

Step 19: Synthesis of ((2R,3S,5R)-5-(4-amino-7aH-pyrrolo[3,2-d]pyrimidin-7-yl)-3-((tert-butyldimethylsilyl)oxy)-2-ethynyltetrahydrofuran-2-yl)methanol To a stirred mixture of (2R,3S,5R)-5-(4-aminoimidazo[2,1-f][1,2,4]triazin-7-yl)-3-((tert-butyldimethylsilyl)oxy)-2-(hydroxymethyl)tetrahydrofuran-2-carbaldehyde (250 mg, 0.286 mmol, crude) and K$_2$CO$_3$ (120 mg, 0.86 mmol) in MeOH (10 mL) under argon atmosphere was injected a solution of dimethyl (1-diazo-2-oxopropyl)phosphonate (110 mg, 0.58 mmol) in MeOH (1 mL) at 0° C. The resulting mixture was warmed to 30° C. and stirred for 16 hours. The reaction mixture was concentrated under reduced pressure. The residue was purified by silica gel column chromatography using DCM/MeOH (30/1) to give ((2R,3S,5R)-5-(4-amino-7aH-pyrrolo[3,2-d]pyrimidin-7-yl)-3-((tert-butyldimethylsilyl)oxy)-2-ethynyltetrahydrofuran-2-yl)methanol. LC-MS: (ES, m/z): 390.2 [M+H]$^+$. $^1$H-NMR: (400 MHz, d$_6$-DMSO, ppm): δ 8.23 (br s, 1H), 8.08 (s, 1H), 7.67 (s, 1H), 5.54 (t, J=7.8 Hz, 1H), 5.16 (t, J=6.2 Hz, 1H), 4.53 (dd, J=4.6 Hz, J=6.2 Hz, 1H), 3.55 (dd, J=5.2 Hz, J=11.6 Hz, 1H), 3.45 (dd, J=7.0 Hz, J=11.8 Hz, 1H), 3.42 (s, 1H), 2.56-2.53 (m, 1H), 2.23-2.17 (m, 1H), 0.91 (s, 9H), 0.10 (d, J=3.2 Hz, 6H).

Step 20. Synthesis of (2R,3S,5R)-5-(4-aminoimidazo[2,1-f][1,2,4]triazin-7-yl)-2-ethynyl-2-(hydroxymethyl)tetrahydrofuran-3-ol (22)

To a stirred solution of ((2R,3S,5R)-5-(4-aminoimidazo[2,1-f][1,2,4]triazin-7-yl)-3-((tert-butyldimethylsilyl)oxy)-2-ethynyltetrahydrofuran-2-yl)methanol (150 mg, 0.385 mmol) in anhydrous THF (5 mL) under argon atmosphere was injected TBAF THF solution (0.385 mL, 0.385 mmol, 1 M) at 0° C. The mixture was warmed to room temperature and stirred for 16 hours. The reaction progress was monitored by TLC & LCMS. The resulting mixture was concentrated under reduced pressure. The residue was purified by silica gel column chromatography using DCM/MeOH (24/1) to give the title compound 22. LC-MS: (ES, m/z): 309.00 [M+H]$^+$. $^1$H-NMR: (400 MHz, d$_6$-DMSO, ppm): δ 8.21 (br s, 1H), 8.14 (br s, 1H), 8.07 (s, 1H), 7.64 (s, 1H), 5.53 (t, J=7.6 Hz, 1H), 5.34 (d, J=5.2 Hz, 1H), 5.07 (t, J=6.4 Hz, 1H), 4.35 (q, J=6.0 Hz, 1H), 3.56 (dd, J=5.6 Hz, J=12.0 Hz, 1H), 3.48 (dd, J=7.0 Hz, J=11.8 Hz, 1H), 3.41 (s, 1H), 2.46-2.41 (m, 1H), 2.28-2.21 (m, 1H).

Example 23

Synthesis of (2R,3S,5R)-5-(4-aminopyrazolo[1,5-a][1,3,5]triazin-8-yl)-2-ethynyl-2-(hydroxymethyl)tetrahydrofuran-3-ol (23)

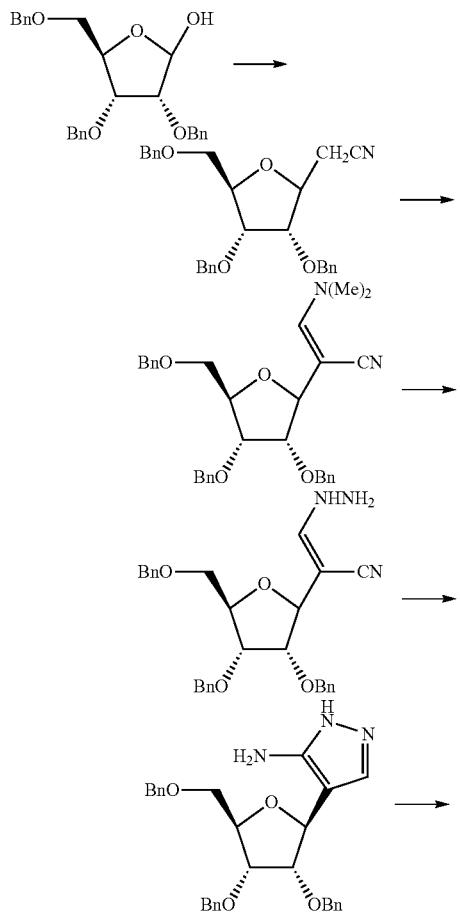

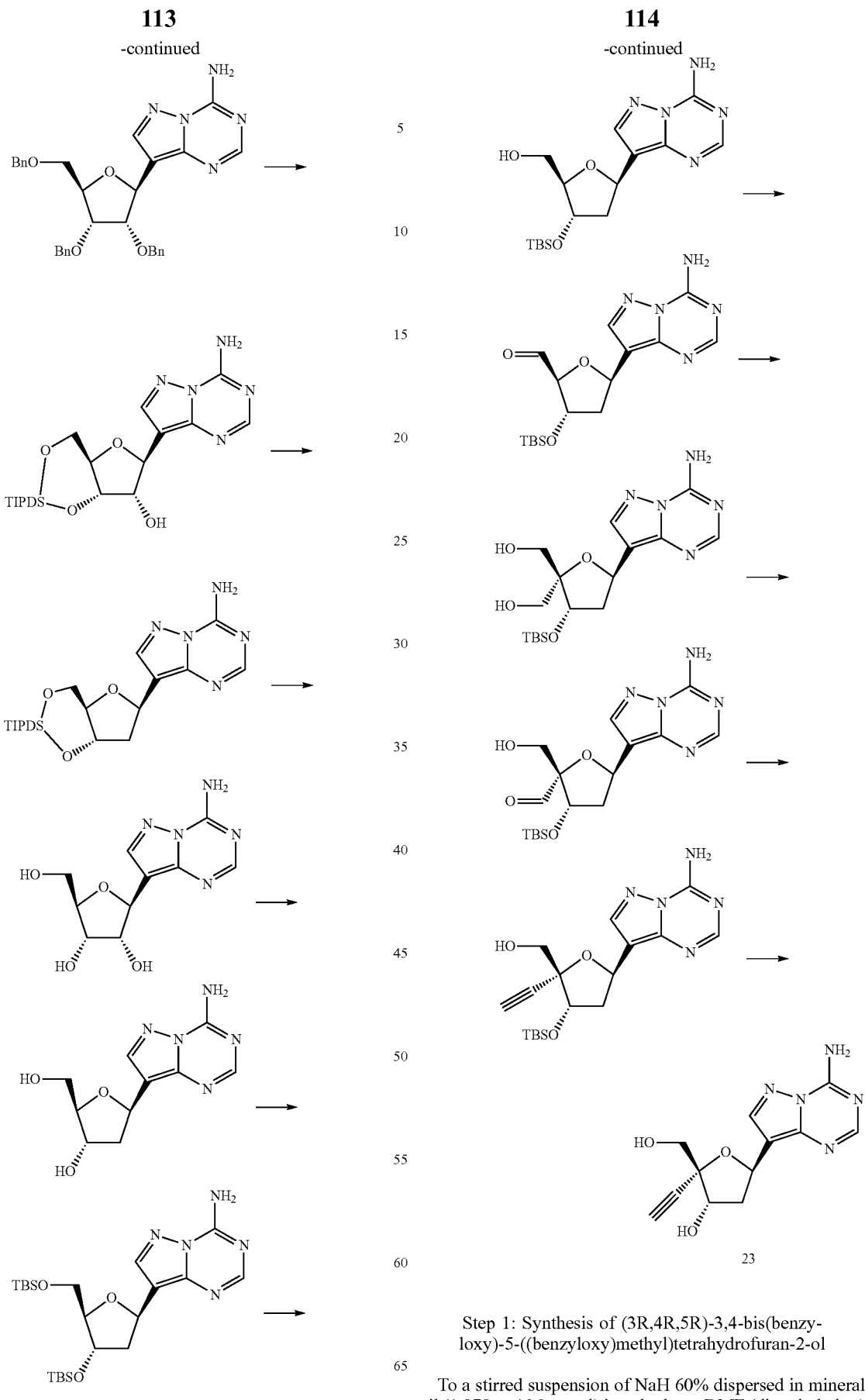
Step 1: Synthesis of (3R,4R,5R)-3,4-bis(benzyloxy)-5-((benzyloxy)methyl)tetrahydrofuran-2-ol
To a stirred suspension of NaH 60% dispersed in mineral oil (1.878 g, 46.9 mmol) in anhydrous DME (dimethylether)

(150 mL) under argon atmosphere was injected diethyl (cyanomethyl)phosphonate (11.88 g, 67.1 mmol) at 0° C. over 10 minutes. The mixture was warmed to 25° C. and maintained for 0.5 h and then a solution of (3R,4R,5R)-3,4-bis(benzyloxy)-5-((benzyloxy)methyl)tetrahydrofuran-2-ol (14.1 g, 33.5 mmol) in dry DME (100 mL) was added drop-wise with stirring at 0° C. over 30 minutes. The resulting mixture was warmed to 25° C. again and maintained for 2 hours. The resulting mixture was diluted with H$_2$O (300 mL) and extracted with Et$_2$O (3×500 mL). The combined organic layers was washed with brine (500 mL), dried over anhydrous Na$_2$SO$_4$, filtered and the filtrate was concentrated under reduced pressure. The residue was purified by flash silica gel column chromatography using EtOAc/pet. ether (5%-20% EtOAc in pet. ether) to afford 2-((3S,4R,5R)-3,4-bis(benzyloxy)-5-((benzyloxy)methyl)tetrahydrofuran-2-yl)acetonitrile. LC-MS: (ES, m/z): 444.21 [M+H]$^+$. $^1$H-NMR: (300 MHz, CDCl$_3$, ppm): δ 7.33-7.31 (m, 15H), 4.63-4.43 (m, 6H), 4.25-4.13 (m, 2H), 3.95 (dd, J=3.0 Hz, J=4.8 Hz, 1H), 3.77 (dd, J=5.4 Hz, J=6.9 Hz, 1H), 3.53-3.45 (m, 2H), 2.78-2.75 (m, 0.4H), 2.66 (dd, J=4.8 Hz, J=16.8 Hz, 0.8H), 2.50 (dd, J=4.8 Hz, J=16.8 Hz, 0.8H).

Step 2: Synthesis of 2-((3S,4R,5R)-3,4-bis(benzyloxy)-5-((benzyloxy)methyl)tetrahydrofuran-2-yl)-3-(dimethylamino)acrylonitrile To a stirred solution of 2-((3S,4R,5R)-3,4-bis(benzyloxy)-5-((benzyloxy)methyl)tetrahydrofuran-2-yl)acetonitrile (12.6 g, 28.4 mmol) in DCM (90 mL) under argon atmosphere were injected dry DMF (2.54 mL, 32.8 mmol) followed by 1-tert-butoxy-N,N,N',N'-tetramethylmethanediamine (19.80 g, 114 mmol) at 0° C. over 5 minutes. The resulting mixture was warmed to 25° C. and stirred for 16 hours. The resulting mixture was concentrated under reduced pressure. The residue was purified by flash silica gel column chromatography using EtOAc/pet. ether (15%-35% EtOAc in pet. ether) to afford 2-((3S,4R,5R)-3,4-bis(benzyloxy)-5-((benzyloxy)methyl)tetrahydrofuran-2-yl)-3-(dimethylamino)acrylonitrile. LC-MS: (ES, m/z): 499.25 [M+H]$^+$. $^1$H-NMR: (300 MHz, CDCl$_3$, ppm): δ 7.33-7.30 (m, 15H), 6.47 (s, 1H), 4.65-4.53 (m, 6H), 4.32 (d, J=7.2 Hz, 1H), 4.19-4.15 (m, 1H), 4.00-3.90 (m, 2H), 3.59-3.46 (m, 2H), 3.04 (s, 6H).

Step 3. Synthesis of 2-((3S,4R,5R)-3,4-bis(benzyloxy)-5-((benzyloxy)methyl)tetrahydrofuran-2-yl)-3-hydrazinylacrylonitrile To a stirred solution of 2-((3S,4R,5R)-3,4-bis(benzyloxy)-5-((benzyloxy)methyl)tetrahydrofuran-2-yl)-3-(dimethylamino)acrylonitrile (12.9 g, 25.9 mmol) in MeOH (90 mL) were added hydrazine hydrate (21.15 g, 647 mmol), H$_2$O (3.0 mL, 167 mmol) and hydrazine hydrochloride (2.66 g, 38.8 mmol) successively at room temperature. The resulting mixture was heated to 65° C. and stirred for 16 hours. The final mixture was concentrated under reduced pressure. The residue was diluted with H$_2$O (500 mL) and extracted with EtOAc (3×500 mL). The combined organic layers was washed with brine (500 mL), dried over anhydrous Na$_2$SO$_4$, filtered and the filtrate was concentrated under reduced pressure to afford 2-((3 S,4R,5R)-3,4-bis(benzyloxy)-5-((benzyloxy)methyl)tetrahydrofuran-2-yl)-3-hydrazinylacrylonitrile, which was used for the next reaction step directly without further purification. LC-MS: (ES, m/z): 486.23 [M+H]$^+$.

Step 4: Synthesis of 4-[(2S,3S,4R,5R)-3,4-bis(benzyloxy)-5-[(benzyloxy)methyl]oxolan-2-yl]-1H-pyrazol-5-amine 2-((3S,4R,5R)-3,4-bis(benzyloxy)-5-((benzyloxy)methyl)tetrahydrofuran-2-yl)-3-hydrazinylacrylonitrile (18 g, 37.1 mmol) was put into a 1000-mL round-bottom flask followed by the injection of ACN (200 mL). The mixture was refluxed for 48 hours. The resulting mixture was concentrated under reduced pressure. The residue was purified by flash silica gel column chromatography using MeOH/DCM (2% to 10% MeOH in DCM) to afford 4-[(2S,3S,4R,5R)-3,4-bis(benzyloxy)-5-[(benzyloxy)methyl]oxolan-2-yl]-1H-pyrazol-5-amine LC-MS: (ES, m/z): 486.23 [M+H]$^+$. $^1$H-NMR: (400 MHz, CDCl$_3$, ppm): δ 7.40-7.24 (m, 16H), 4.97 (d, J=6.8 Hz, 1H), 4.68 (d, J=12.0 Hz, 1H), 4.62-4.44 (m, 5H), 4.24-4.22 (m, 1H), 4.10-4.04 (m, 2H), 3.71 (dd, J=3.0 Hz, J=10.2 Hz, 1H), 3.63-3.50 (m, 1H).

Step 5. Synthesis of 8-((2S,3S,4R,5R)-3,4-bis(benzyloxy)-5-((benzyloxy)methyl)tetrahydrofuran-2-yl)pyrazolo[1,5-a][1,3,5]triazin-4-amine To a stirred mixture of cyanamide (50 g, 1189 mmol) was added trimethoxymethane (505 g, 4757 mmol) and the mixture was heated to 105° C. and stirred for 5 minutes. To the above was injected formic acid (4.38 g, 95 mmol) at 105° C. over 5 minutes. After the resulting solution was stirred at 105° C. for 5 hours, the reaction mixture was cooled down to room temperature. The solids were filtered out and the filtrate was concentrated under reduced pressure. The product was collected by distillation (0.1 mm Hg, 60° C. to 70° C.) to give (E)-methyl N-cyanoformimidate (50 g, 0.595 mol).

To a stirred solution of (E)-methyl N-cyanoformimidate (21.82 g, 259 mmol) in toluene (150 mL) under argon atmosphere was added a solution of 4-((3S,4R,5R)-3,4-bis(benzyloxy)-5-((benzyloxy)methyl)tetrahydrofuran-2-yl)-1H-pyrazol-5-amine (21 g, 43.2 mmol) in toluene (30 mL) at room temperature. The resulting mixture was heated to 90° C. and stirred for 20 hours. The resulting solution was concentrated under reduced pressure. The residue was purified by flash silica gel column chromatography using EtOAc/pet. ether (30% to 50% EtOAc in pet. ether) to afford 8-((2S,3S,4R,5R)-3,4-bis(benzyloxy)-5-((benzyloxy)methyl)tetrahydrofuran-2-yl)pyrazolo[1,5-a][1,3,5]triazin-4-amine LC-MS: (ES, m/z): 538.24 [M+H]$^+$. $^1$H-NMR: (300 MHz, CDCl$_3$, ppm): δ 8.05 (s, 1H), 7.99 (s, 1H), 7.31-7.23 (m, 15H), 6.67 (br s, 2H), 5.33 (d, J=5.4 Hz, 1H), 4.67-4.50 (m, 6H), 4.35-4.29 (m, 2H), 4.15-4.11 (m, 1H), 3.72 (dd, J=3.9 Hz, J=10.5 Hz, 1H), 3.62 (dd, J=4.2 Hz, J=10.8 Hz, 1H).

Step 6: Synthesis of (2S,3R,4S,5R)-2-(4-aminopyrazolo[1,5-a][1,3,5]triazin-8-yl)-5-(hydroxymethyl)tetrahydrofuran-3,4-diol To a stirred mixture of 8-((2S,3S,4R,5R)-3,4-bis(benzyloxy)-5-((benzyloxy)methyl)tetrahydrofuran-2-yl)pyrazolo[1,5-a][1,3,5]triazin-4-amine (10 g, 18.60 mmol) in AcOH (250 mL) was added palladium hydroxide 20% on carbon. The mixture was charged with hydrogen (1.5-2 atm) and stirred at 25° C. for 14 hours. The solids were filtered out. The filtrate was concentrated under reduced pressure. The residue was triturated with DCM (150 mL) to form a white precipitate. The precipitate was collected by filtration, washed with DCM and dried in vacuo overnight to give (2S,3R,4S,5R)-2-(4-aminopyrazolo[1,5-a][1,3,5]triazin-8-yl)-5-(hydroxymethyl)tetrahydrofuran-3,4-diol. LC-MS: (ES, m/z): 268.10 [M+H]⁺. ¹H-NMR: (300 MHz, d₆-DMSO, ppm): δ 8.76 (br s, 1H), 8.41 (br s, 1H), 8.19 (s, 1H), 8.06 (s, 1H), 4.96-4.91 (m, 2H), 4.86-4.81 (m, 2H), 4.20 (q, J=6.0 Hz, 1H), 3.98 (q, J=4.5 Hz, 1H), 3.78 (q, J=3.9 Hz, 1H), 3.61-3.55 (m, 1H), 3.49-3.43 (m, 1H).

Step 7: Synthesis of (6aR,8S,9S,9aS)-8-(4-aminopyrazolo[1,5-a][1,3,5]triazin-8-yl)-2,2,4,4-tetraisopropyltetrahydro-6H-furo[3,2-f][1,3,5,2,4]trioxadisilocin-9-ol To a stirred solution of (2S,3R,4S,5R)-2-(4-aminopyrazolo[1,5-a][1,3,5]triazin-8-yl)-5-(hydroxymethyl)tetrahydrofuran-3,4-diol (2.2 g, 8.23 mmol) and 1H-imidazole (1.681 g, 24.70 mmol) in dry DMF (100 mL) under argon atmosphere was injected 1,3-dichloro-1,1,3,3-tetraisopropyldisiloxane (2.86 g, 9.06 mmol) at 0° C. over 4 minutes. The resulting mixture was warmed to 25° C. and stirred for 3 hours. The residue was diluted with H₂O (50 mL) and extracted with EtOAc (3×50 mL). The combined organic layers was washed with brine (2×50 mL), dried over anhydrous Na₂SO₄, filtered and the filtrate was concentrated under reduced pressure. The residue was purified by flash silica gel column chromatography using EtOAc/pet. ether (30%-50% EtOAc in pet. ether) to afford (6aR,8S,9S,9aS)-8-(4-aminopyrazolo[1,5-a][1,3,5]triazin-8-yl)-2,2,4,4-tetraisopropyltetrahydro-6H-furo[3,2-f][1,3,5,2,4]trioxadisilocin-9-ol. LC-MS: (ES, m/z): 510.25 [M+H]⁺. ¹H-NMR: (300 MHz, d₆-DMSO, ppm): δ 8.72 (br s, 1H), 8.42 (br s, 1H), 8.08 (s, 1H), 8.02 (s, 1H), 5.08 (d, J=4.8 Hz, 1H), 4.91 (d, J=1.8 Hz, 1H), 4.41 (dd, J=5.4 Hz, J=8.1 Hz, 1H), 4.30-4.28 (m, 1H), 3.99-3.86 (m, 3H), 1.04-1.00 (m, 28H).

Step 8: Synthesis of 8-((6aR,8R,9aS)-2,2,4,4-tetraisopropyltetrahydro-6H-furo[3,2-f][1,3,5,2,4]trioxadisilocin-8-yl)pyrazolo[1,5-a][1,3,5]triazin-4-amine To a stirred solution of (6aR,8S,9S,9aS)-8-(4-aminopyrazolo[1,5-a][1,3,5]triazin-8-yl)-2,2,4,4-tetraisopropyltetrahydro-6H-furo[3,2-f][1,3,5,2,4]trioxadisilocin-9-ol (3.90 g, 7.65 mmol) in dry DCE (120 mL) under argon atmosphere was added 1,1'-thiocarbonyldiimidazole (1.704 g, 9.56 mmol) at room temperature. The resulting mixture was heated to 85° C. and stirred for 1.5 hours. TLC indicated the starting nucleoside was all consumed. The resulting solution was concentrated under reduced pressure to give crude imidazolyl intermediate which was immediately re-dissolved in degassed toluene (120 mL) under argon atmosphere. To the above was added AIBN (1.88 g, 11.48 mmol) followed by the injection of tributylstannane (4.45 g, 15.30 mmol) at 25° C. over 2 minutes. The resulting mixture was heated to 80° C. and stirred for 3 hours. The resulting solution was concentrated under reduced pressure. The crude residue was purified by flash silica gel column chromatography using EtOAc/pet. ether (30%-50% EtOAc in pet. ether) to afford 8-((6aR,8R,9aS)-2,2,4,4-tetraisopropyltetrahydro-6H-furo[3,2-f][1,3,5,2,4]trioxadisilocin-8-yl)pyrazolo[1,5-a][1,3,5]triazin-4-amine LC-MS: (ES, m/z): 494.25 [M+H]⁺. ¹H-NMR: (300 MHz, CDCl₃, ppm): δ 8.18 (s, 1H), 8.06 (s, 1H), 6.61 (br s, 2H), 5.40 (t, J=7.5 Hz, 1H), 4.70-4.65 (m, 1H), 4.10 (dd, J=3.0 Hz, J=10.8 Hz, 1H), 3.95-3.81 (m, 2H), 2.52-2.38 (m, 2H), 1.08-1.05 (m, 28H).

Step 9: Synthesis of (2R,3S,5R)-5-(4-aminopyrazolo[1,5-a][1,3,5]triazin-8-yl)-2-(hydroxymethyl)tetrahydrofuran-3-ol To a stirred solution of 8-((6aR,8R,9aS)-2,2,4,4-tetraisopropyl tetrahydro-6H-furo[3,2-f][1,3,5,2,4]trioxadisilocin-8-yl)pyrazolo[1,5-a][1,3,5]triazin-4-amine (1.5 g, 3.04 mmol) in anhydrous THF (35 mL) under argon atmosphere was injected HF-Pyridine solution (1.5 mL, 11.65 mmol) at 0° C. over 5 minutes. The mixture was warmed to 25° C. and stirred for 4 hours. The resulting mixture was neutralized by the addition of solid NaHCO₃ and then diluted with MeOH (30 mL). The un-dissolved solid was filtered out. The filtrate was concentrated under reduced pressure and then triturated with EtOAc (20 mL). A white precipitate was formed and collected by filtration then dried in vacuo overnight to afford (2R,3S,5R)-5-(4-aminopyrazolo[1,5-a][1,3,5]triazin-8-yl)-2-(hydroxymethyl)tetrahydrofuran-3-ol. LC-MS: (ES, m/z): 252.10 [M+H]⁺. ¹H-NMR: (300 MHz, d₆-DMSO, ppm): δ 8.71 (br s, 1H), 8.39 (br s, 1H), 8.19 (s, 1H), 8.05 (s, 1H), 5.25 (q, J=5.4 Hz, 1H), 5.03 (d, J=3.9 Hz, 1H), 4.87 (t, J=6.0 Hz, 1H), 4.26-4.24 (m, 1H), 3.76-3.74 (m, 1H), 3.52-3.40 (m, 2H), 2.32-2.22 (m, 1H), 2.04-1.98 (m, 1H)

Step 10: Synthesis of 8-((2R,4S,5R)-4-((tert-butyldimethylsilyl)oxy)-5-(((tert-butyldimethylsilyl)oxy)methyl)tetrahydrofuran-2-yl)pyrazolo[1,5-a][1,3,5]triazin-4-amine To a stirred solution of (2R,3S,5R)-5-(4-aminopyrazolo[1,5-a][1,3,5]triazin-8-yl)-2-(hydroxymethyl)tetrahydrofuran-3-ol (540 mg, 2.149 mmol) and 1H-imidazole (512 mg, 7.52 mmol) in DMF (10 mL) under argon atmosphere was added TBS-Cl (972 mg, 6.45 mmol) at 0° C. over 1 minutes. The resulting mixture was warmed to 25° C. and stirred for 2 hours. The resulting solution was diluted with H₂O (50 mL) and extracted with EtOAc (3×50 mL). The combined organic layers was washed with brine (2×50 mL), dried over anhydrous Na₂SO₄, filtered and the filtrate was concentrated under reduced pressure. The residue was purified by flash silica gel column chromatography using EtOAc/pet. ether (20% EtOAc in pet. ether) to afford 8-((2R,4S,5R)-4-((tert-butyldimethylsilyl)oxy)-5-(((tert-butyldimethylsilyl)oxy)methyl)tetrahydrofuran-2-yl)pyrazolo[1,5-a][1,3,5]triazin-4-amine LC-MS: (ES, m/z): 480.27 [M+H]⁺. ¹H-NMR: (400 MHz, CDCl₃, ppm): δ 8.18 (s, 1H), 8.10 (s, 1H), 6.80 (br s, 2H), 5.49 (q, J=5.2 Hz, 1H), 4.51 (d, J=5.2 Hz, 1H), 3.98 (t, J=4.0 Hz, 1H), 3.74 (dd, J=3.8 Hz, J=10.6 Hz, 1H), 3.63 (dd, J=6.4 Hz, J=10.8 Hz, 1H), 2.39-2.32 (m, 1H), 2.22-2.17 (m, 1H), 0.93-0.92 (m, 18H), 0.11-0.05 (m, 12H).

Step 11: Synthesis of ((2R,3S,5R)-5-(4-aminopyrazolo[1,5-a][1,3,5]triazin-8-yl)-3-((tert-butyldimethylsilyl)oxy)tetrahydrofuran-2-yl)methanol To a stirred solution of 8-((2R,4S,5R)-4-((tert-butyldimethylsilyl)oxy)-5-(((tert-butyldimethylsilyl)oxy)methyl)tetrahydrofuran-2-yl)pyrazolo[1,5-a][1,3,5]triazin-4-amine (800 mg, 1.667 mmol) in THF (16 mL) was injected a pre-cooled solution of TFA/H₂O (8 mL, v/v, 1/1) at 0° C. over 5 minutes. The resulting mixture was stirred at 0° C. for 1.5 hours. The reaction progress was monitored by TLC. The resulting solution was co-evaporated with toluene (3×50 mL) below 25° C. and the residue was re-dissolved in MeOH/DCM (20 mL, v/v, 1/2) and the mixture was neutralized with solid NaHCO₃. The solid was filtered out and the filtrate was concentrated under reduced pressure. The crude product was purified by flash silica gel column chromatography using MeOH/DCM (2% to 10% MeOH in DCM) to afford ((2R,3S,5R)-5-(4-aminopyrazolo[1,5-a][1,3,5]triazin-8-yl)-3-((tert-butyldimethylsilyl)oxy)tetrahydrofuran-2-yl)methanol. LC-MS: (ES, m/z): 366.19 [M+H]⁺.

$^1$H-NMR: (300 MHz, d$_6$-DMSO, ppm): δ 8.70 (br s, 1H), 8.38 (br s, 1H), 8.19 (s, 1H), 8.05 (s, 1H), 5.24 (q, J=5.4 Hz, 1H), 4.92 (t, J=6.0 Hz, 1H), 4.42 (d, J=4.8 Hz, 1H), 3.75 (dd, J=3.6 Hz, J=4.8 Hz, 1H), 3.46-3.43 (m, 2H), 2.39-2.30 (m, 1H), 2.00-1.94 (m, 1H), 0.90 (s, 9H), 0.11 (s, 6H).

Step 12: Synthesis of (2S,3S,5R)-5-(4-aminopyrazolo[1,5-a][1,3,5]triazin-8-yl)-3-((tert-butyldimethylsilyl)oxy)tetrahydrofuran-2-carbaldehyde To a stirred suspension of ((2R,3S,5R)-5-(4-aminopyrazolo[1,5-a][1,3,5]triazin-8-yl)-3-((tert-butyldimethylsilyl)oxy)tetrahydrofuran-2-yl)methanol (350 mg, 0.958 mmol) in anhydrous ACN (40 mL) under argon atmosphere was added IBX (804 mg, 2.87 mmol) at 25° C. The resulting mixture was heated to 80° C. and stirred for 1 hour. The solid was filtered out. The filtrate was concentrated under reducing pressure to afford (2S,3S,5R)-5-(4-aminopyrazolo[1,5-a][1,3,5]triazin-8-yl)-3-((tert-butyldimethylsilyl)oxy)tetrahydrofuran-2-carbaldehyde, which was used for the next reaction step directly without further purification. LC-MS: (ES, m/z): 364.17 [M+H]$^+$.

Step 13: Synthesis of ((3S,5R)-5-(4-aminopyrazolo[1,5-a][1,3,5]triazin-8-yl)-3-((tert-butyldimethylsilyl)oxy)tetrahydrofuran-2,2-diyl)dimethanol To a stirred solution of (2S,3S,5R)-5-(4-aminopyrazolo[1,5-a][1,3,5]triazin-8-yl)-3-((tert-butyldimethylsilyl)oxy)tetrahydrofuran-2-carbaldehyde (349 mg, 0.960 mmol) in 1,4-dioxane (25 mL) in a 100 mL round-bottom flask, was injected formaldehyde 37% aqueous solution (5 mL), followed by the injection of NaOH aqueous solution (5 mL, 2 N) at room temperature over 5 minutes. The resulting mixture was stirred at room temperature for 5 hours. Upon the started nucleoside was all consumed, the reaction mixture was neutralized with AcOH (~0.5 mL). The mixture was diluted with EtOAc (50 mL) and washed successively with H$_2$O (2×20 mL), aq NaHCO$_3$ (saturated, 2×20 mL) and brine (20 mL). The organic layer was dried over Na$_2$SO$_4$, filtered and the filtrate was concentrated under reduced pressure. The residue was re-dissolved in anhydrous EtOH (40 mL) and added sodium tetrahydroborate (72.6 mg, 1.920 mmol) in portions at 0° C. under argon atmosphere. After stirring at 25° C. for 16 hours, the reaction mixture was neutralized with AcOH (~0.2 mL) and concentrated under reduced pressure. The residue was partitioned between CHCl$_3$ (30 mL) and H$_2$O (15 mL). The aqueous layer was re-extracted with CHCl$_3$ (2×15 mL). The combined organic layer was washed with brine (20 mL), dried over Na$_2$SO$_4$, filtered and the filtrate was concentrated under reduced pressure. The residue was purified by flash silica gel column chromatography using MeOH/DCM (3.5% MeOH in DCM) to give ((3S,5R)-5-(4-aminopyrazolo[1,5-a][1,3,5]triazin-8-yl)-3-((tert-butyldimethylsilyl)oxy)tetrahydrofuran-2,2-diyl)dimethanol. LC-MS: (ES, m/z): 396.20 [M+H]$^+$. $^1$H-NMR: (300 MHz, d$_6$-DMSO, ppm): δ 8.70 (br s, 1H), 8.38 (br s, 1H), 8.20 (s, 1H), 8.05 (s, 1H), 5.30 (dd, J=5.1 Hz, J=11.1 Hz, 1H), 4.84 (t, J=6.0 Hz, 1H), 4.50 (d, J=4.2 Hz, 1H), 4.22 (dd, J=5.1 Hz, J=6.3 Hz, 1H), 3.62-3.48 (m, 3H), 3.41-3.31 (m, 1H), 2.57-2.50 (m, 1H), 1.95 (dd, J=5.1 Hz, J=12.6 Hz, 1H), 0.90 (s, 9H), 0.11 (s, 6H).

Step 14: Synthesis of (2R,3S,5R)-5-(4-aminopyrazolo[1,5-a][1,3,5]triazin-8-yl)-3-((tert-butyldimethylsilyl)oxy)-2-(hydroxymethyl)tetrahydrofuran-2-carbaldehyde To a stirred suspension of ((3S,5R)-5-(4-aminopyrazolo[1,5-a][1,3,5]triazin-8-yl)-3-((tert-butyldimethylsilyl)oxy)tetrahydrofuran-2,2-diyl)dimethanol (190 mg, 0.480 mmol) in ACN/DMSO (8 mL, v/v, 10/1) under argon atmosphere was added IBX (404 mg, 1.441 mmol) at 25° C. The resulting mixture was stirred at 30° C. for 7 hours. The solid was filtered out. The filtrate was concentrated under reduced pressure to give (2R,3S,5R)-5-(4-aminopyrazolo[1,5-a][1,3,5]triazin-8-yl)-3-((tert-butyldimethylsilyl)oxy)-2-(hydroxymethyl)tetrahydrofuran-2-carbaldehyde which was used for the next reaction step directly without further purification. LC-MS: (ES, m/z): 394.18 [M+H]$^+$.

Step 15: Synthesis of ((2R,3S,5R)-5-(4-aminopyrazolo[1,5-a][1,3,5]triazin-8-yl)-3-((tert-butyldimethylsilyl)oxy)-2-ethynyltetrahydrofuran-2-yl)methanol To a stirred solution of (2R,3S,5R)-5-(4-aminopyrazolo[1,5-a][1,3,5]triazin-8-yl)-3-((tert-butyldimethylsilyl)oxy)-2-(hydroxymethyl)tetrahydrofuran-2-carbaldehyde (189 mg, 0.480 mmol) in dry MeOH (6 mL) under argon atmosphere was added K$_2$CO$_3$ (199 mg, 1.441 mmol) followed by the injection of a solution of dimethyl (1-diazo-2-oxopropyl)phosphonate (185 mg, 0.961 mmol) in MeOH (1.5 mL) at 0° C. over 3 minutes. The reaction mixture was warmed slowly to 25° C. and then stirred at 25° C. for 16 hours. The resulted mixture was concentrated under reduced pressure. The residue was purified by flash silica gel column chromatography using MeOH/DCM (2% to 10% MeOH in DCM) to afford ((2R,3S,5R)-5-(4-aminopyrazolo[1,5-a][1,3,5]triazin-8-yl)-3-((tert-butyldimethylsilyl)oxy)-2-ethynyltetrahydrofuran-2-yl)methanol. LC-MS: (ES, m/z): 390.19 [M+H]$^+$. $^1$H-NMR: (300 MHz, CDCl$_3$, ppm): δ 8.17 (s, 1H), 7.98 (s, 1H), 6.43 (br s, 2H), 5.54 (dd, J=5.7 Hz, J=10.5 Hz, 1H), 4.61 (d, J=4.2 Hz, 1H), 3.97 (d, J=12.3 Hz, 1H), 3.76 (d, J=12.0 Hz, 1H), 2.70-2.61 (m, 1H), 2.54 (s, 1H), 2.20-2.14 (m, 1H), 0.95 (s, 9H), 0.12 (d, J=6.0 Hz, 6H).

Step 16: (2R,3S,5R)-5-(4-aminopyrazolo[1,5-a][1,3,5]triazin-8-yl)-2-ethynyl-2-(hydroxymethyl)tetrahydrofuran-3-ol (23)

To a stirred solution of ((2R,3S,5R)-5-(4-aminopyrazolo[1,5-a][1,3,5]triazin-8-yl)-3-((tert-butyldimethylsilyl)oxy)-2-ethynyltetrahydrofuran-2-yl)methanol (120 mg, 0.308 mmol) in THF (5 mL) under argon atmosphere was injected TBAF THF solution (0.462 mL, 0.462 mmol, 1.0 M) at 0° C. over 2 minutes. The mixture was stirred at 20° C. for 26 hours. The resulting mixture was concentrated under reduced pressure. The residue was purified by flash silica gel column chromatography using MeOH/DCM (5% to 10% MeOH in DCM) to give crude product. The crude product (90 mg) was further purified by Prep-HPLC with the following conditions (1#-Pre-HPLC-011(Waters)): Column, X-bridge C18 19×150 mm; mobile phase, water with NH$_4$HCO$_3$ (10 mmol/L) and ACN (4% ACN up to 9% in 6 min, hold 95% for 2 minutes, down to 5% in 2 minutes); Detector, UV 254 & 220 nm. The product-containing fractions were collected and lyophilized overnight to give (2R, 3S,5R)-5-(4-aminopyrazolo[1,5-a][1,3,5]triazin-8-yl)-2-ethynyl-2-(hydroxymethyl)tetrahydrofuran-3-ol. LC-MS: (ES, m/z): 276.10 [M+H]$^+$. $^1$H-NMR: (400 MHz, d$_6$-DMSO, ppm): δ 8.71 (br s, 1H), 8.43 (br s, 1H), 8.20 (s, 1H), 8.05 (s, 1H), 5.36 (t, J=7.6 Hz, 1H), 5.26-5.22 (m, 2H), 4.34 (dd, J=4.8 Hz, J=11.2 Hz, 1H), 3.58 (dd, J=5.2 Hz, J=11.6 Hz, 1H), 3.49 (dd, J=7.6 Hz, J=11.6 Hz, 1H), 3.37 (s, 1H), 2.44-2.37 (m, 1H), 2.16-2.12 (m, 1H).

RT Polymerase Assay

Full-length wild-type and 2 mutant RT proteins were expressed in *Escherichia coli* BL21(DE3) cells and purified.

Briefly, the heterodimeric nucleic acid substrate used in the HIV-1 RT polymerase reactions was generated by annealing biotinylated DNA primer to a 500 nucleotide RNA template. The HIV-1 RT enzyme (final concentration of 50 pM) was combined with an inhibitor compound or DMSO (10% DMSO in the final reaction mixture) in assay buffer (62.5 mM Tris-HCl, pH 7.8, 1.25 mM dithiothreitol, 7.5 mM MgCl$_2$, 100 mM KCl, 0.03% CHAPS, 0.125 mM EGTA). This mixture was pre-incubated for 30 minutes at room temperature in microtiter plates. The polymerization reaction was initiated by the addition of template/primer substrate (final concentration: 16.6 nM) and dNTPs (final concentration: 2 μM dCTP, dGTP, dATP, and 66.6 nM Ru-dUTP). After 90 min of incubation at 37° C., reactions were quenched by the addition of EDTA (25 mM). The resulting mixture was incubated for an additional 5 minutes at room temperature followed by transferring the solution (50 μL) to blocked avidin plate from Meso Scale Discovery (MSD). The mixtures were incubated at room temperature for 60 min prior to the quantification of the reaction product via an ECL 6000 imager instrument. The resulting data is shown in Table 2.

TABLE 2

| Example No. | Structure | dNTP IC$_{50}$ (nM) |
|---|---|---|
| 13 | 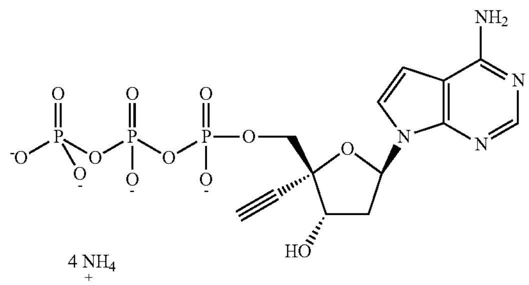 | 933 |
| 14 | 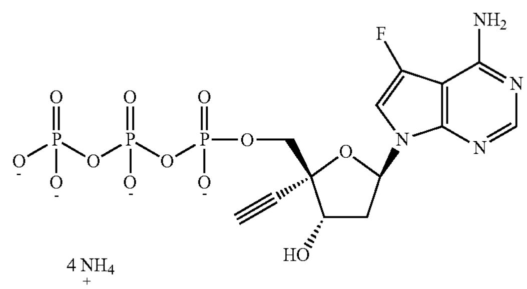 [SMILES: C#C[C@]1(COP(=O)(O)OP(=O)(O)OP(=O)(O)O)O[C@@H](n2cc(F)c3c(N)ncnc32)C[C@@H]1O] | 210 |
| 15 | 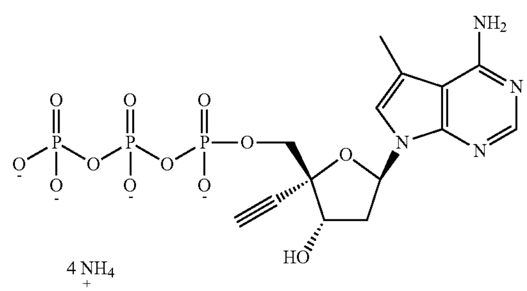 [SMILES: C#C[C@]1(COP(=O)(O)OP(=O)(O)OP(=O)(O)O)O[C@@H](n2cc(C)c3c(N)ncnc32)C[C@@H]1O] | 6237 |
| 16 | 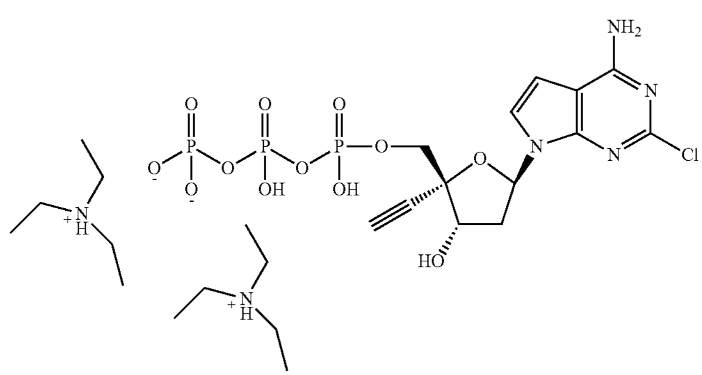 | 1820 |

TABLE 2-continued
| Example No. | Structure | dNTP IC$_{50}$ (nM) |
|---|---|---|
| 17 | 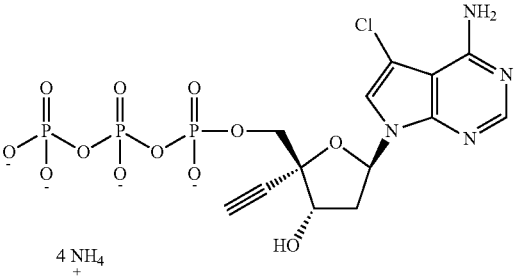 [SMILES: C#C[C@]1(COP(=O)(O)OP(=O)(O)OP(=O)(O)O)O[C@@H](n2cc(Cl)c3c(N)ncnc32)C[C@@H]1O] | 842 |
| 18 | 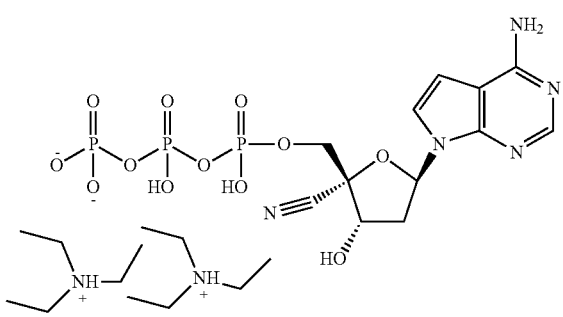 | 4150 |
| 19 | 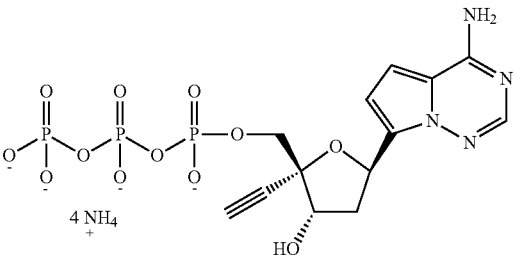 [SMILES: C#C[C@]1(COP(=O)(O)OP(=O)(O)OP(=O)(O)O)O[C@@H](c2ccc3c(N)ncnn23)C[C@@H]1O] | 3542 |
| 20 | 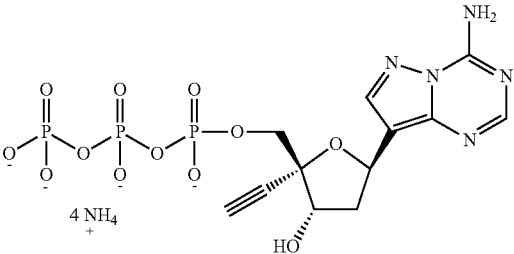 [SMILES: C#C[C@]1(COP(=O)(O)OP(=O)(O)OP(=O)(O)O)O[C@@H](c2cnn3c(N)ncnc23)C[C@@H]1O] | 1292 |
| 21 | 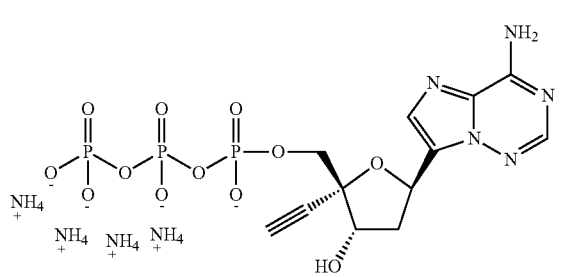 | 905 |

Viking Assay/CTG

Viking Assay:

Assessing Antiviral Potency in a Multiple Round HIV-1 Infection Assay.

HIV-1 replication was monitored using MT4-gag-GFP clone D3 (hereafter designate MT4-GFP), which are MT-4 cells modified to harbor a GFP reporter gene, the expression of which is dependent on the HIV-1 expressed proteins tat and rev. Productive infection of an MT4-GFP cell with HIV-1 results in GFP expression approximately 24 h post-infection.

MT4-GFP cells were maintained at 37° C./5% $CO_2$/90% relative humidity in RPMI 1640 supplemented with 10% fetal bovine serum, 100 U/mL penicillin/streptomycin, and 400 µg/mL G418 to maintain the reporter gene. For infections, MT4-GFP cells were placed in the same medium lacking G418 and infected overnight with H9IIIB virus at an approximate multiplicity of infection of 0.01 in the same incubation conditions. Cells were then washed and re-suspended in either RPMI 1640 containing 10% or 50% normal human serum at $1.6 \times 10^5$ cells/mL (10% or 50% NHS conditions) or in 100% normal human serum at $2 \times 10^5$ cells/mL (100% NHS conditions). Compound plates were prepared by dispensing compounds dissolved in DMSO into wells of 384 well poly D lysine-coated plates (0.2 µl/well) using an ECHO acoustic dispenser. Each compound was tested in a 10 point serial 3-fold dilution (typical final concentrations: 8.4 µM-0.43 nM). Controls included no inhibitor (DMSO only) and a combination of three antiviral agents (efavirenz, indinavir, and an integrase strand transfer inhibitor at final concentrations of 4 µM each). Cells were added (50 µL/well) to compound plates and the infected cells were maintained at 37° C./5% $CO_2$/90% relative humidity.

Infected cells were quantified at two time points, ~48 h and ~72 h post-infection, by counting the number of green cells in each well using an Acumen eX3 scanner. The increase in the number of green cells over ~24 h period gives the reproductive ratio, $R_0$, which is typically 5-15 and has been shown experimentally to be in logarithmic phase (data not shown). Inhibition of $R_0$ is calculated for each well, and $IC_{50}$s determined by non-linear 4-parameter curve fitting.

CTG Assay:

Assessing Cytotoxicity in CellTiter-Glo Luminescent Cell Viability Assay (CTG).

MT4-GFP cells were seeded in RPMI 1640 supplemented with 10% fetal bovine serum, 100 U/mL penicillin/streptomycin overnight at 37° C./5% $CO_2$/90% relative humidity. Cells were then washed and resuspended in RPMI 1640 containing 10% normal human serum at a density of $0.8 \times 10^5$ cells/mL. Compound plates were prepared by dispensing compounds dissolved in DMSO into wells of 384 well solid black plates (Corning 3571) using an ECHO acoustic dispenser (0.2 µl/well). Each compound was tested in a 10 point serial 3-fold dilution (final concentrations: 8.4 µM-0.43 nM). Controls included DMSO. Cells were added (50 µL/well) to compound plates and were maintained at 37° C./5% $CO_2$/90% relative humidity. CTG reagent (Promega, G7573) was added to the cell plates after 48 h incubation according to the manufacturer's description Luminescence signals were recorded on EnVision plate reader (Perkin-Elmer). $LD_{50}$s were determined by non-linear 4-parameter curve fitting. The resulting data is shown in Table 3 with the marketed HIV nucleoside reverse transcriptase inhibitor AZT (azidothymidine, zidovudine) included as a control.

TABLE 3

| | Structure | Viking, $IC_{50}$ (10% NHS) (nM) | CTG (µM) |
|---|---|---|---|
| AZT | 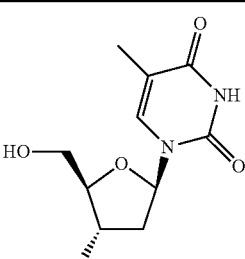 | 37 | >8.4 |

| Example No. | Structure | Viking, $IC_{50}$ (10% NHS) (nM) | CTG (µM) |
|---|---|---|---|
| 1 | 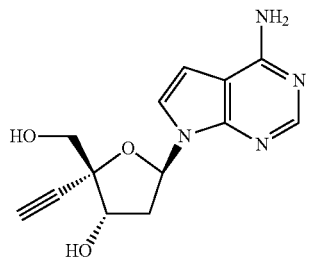 [SMILES: C#C[C@]1(CO)O[C@@H](n2ccc3c(N)ncnc32)C[C@@H]1O] | 1.3 | >8.4 |
| 2 | 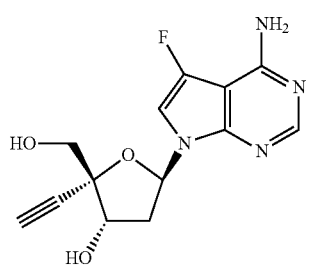 [SMILES: C#C[C@]1(CO)O[C@@H](n2cc(F)c3c(N)ncnc32)C[C@@H]1O] | 1.6 | >8.4 |
| 3 | 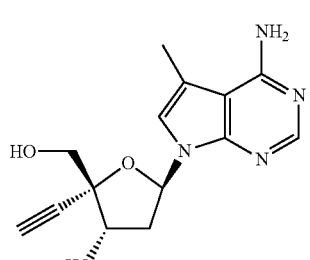 | 485 | >8.4 |
| 4 | 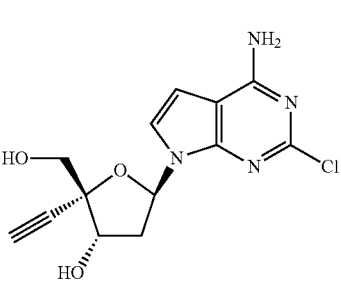 [SMILES: C#C[C@]1(CO)O[C@@H](n2ccc3c(N)nc(Cl)nc32)C[C@@H]1O] | 4.0 | >8.4 |

TABLE 3-continued

| # | Structure | Val1 | Val2 |
|---|---|---|---|
| 5 | 5-Br-7-deaza-adenine with 4'-ethynyl-2'-deoxyribose | 209 | >8.4 |
| 6 | 5-Cl-7-deaza-adenine with 4'-ethynyl-2'-deoxyribose | 128 | >8.4 |
| 7 | 5-I-7-deaza-adenine with 4'-ethynyl-2'-deoxyribose | 1030 | >8.4 |
| 8 | 2-amino-7-deaza-adenine with 4'-ethynyl-2'-deoxyribose | 194 | >8.4 |
| 9 | 2-F-7-deaza-adenine with 4'-ethynyl-2'-deoxyribose | 10.2 | >8.4 |
| 10 | 7-deaza-adenine with 4'-cyano-2'-deoxyribose | 128 | >8.4 |
| 11 | pyrrolo-triazine-amine with 4'-ethynyl-2'-deoxyribose | 17.2 | >8.4 |
| 12 | pyrrolo-triazine-amine with 4'-cyano-2'-deoxyribose | 735 | >8.4 |
| 22 | imidazo-triazine-amine with 4'-ethynyl-2'-deoxyribose | 38 | >8.4 |
| 23 | pyrazolo-triazine-amine with 4'-ethynyl-2'-deoxyribose | 64 | >8.4 |

Antiviral Persistence

HIV-1 replication was monitored using MT4-gag-GFP clone D3 (hereafter designate MT4-GFP), which are MT-4 cells modified to harbor a GFP reporter gene, the expression of which is dependent on the HIV-1 expressed proteins tat and rev. Productive infection of an MT4-GFP cell with HIV-1 results in GFP expression approximately 24 h post-infection. MT4-GFP cells were maintained at 37° C./5% $CO_2$/90% relative humidity in RPMI 1640 supplemented with 10% fetal bovine serum, 100 U/mL penicillin/streptomycin, and 400 µg/mL G418 to maintain the reporter gene. For 72 hour time point persistence assay (72 h plate) and 24 hour time point control assay (24 h plate), MT4-GFP cells were washed and re-suspended in RPMI 1640 containing 10% normal human serum at either $1.6 \times 10^5$ or $2.4 \times 10^5$ cells/mL (10% NHS). Compound plates were prepared by dispensing compounds dissolved in DMSO into wells of 384 well cell culture plates (0.205 µl/well) using an ECHO acoustic dispenser. Each compound was tested in a 10 point serial 3-fold dilution (typical final concentrations: 4.2 µM-0.21 nM). Controls included no inhibitor (DMSO only) and a combination of three antiviral agents (efavirenz, indinavir, and an integrase strand transfer inhibitor at final concentrations of 4 µM each). Cells were added (50 µL/well) to compound plates and were incubated at 37° C./5% $CO_2$/90% relative humidity for 24 hours. The cells were washed with 5×40 uL of RPMI 1640 supplemented with 10% NHS and 100 U/mL penicillin/streptomycin. 72 h plate was return back to 37° C. incubator for additional 48 hour incubation. 40 uL of the cells from each well of the 24 h plate or the 72 h plate (after 48 hour incubation post wash) were transferred to a poly-D-lysine coated plate. The cells were then infected with H9IIIB virus at an approximate multiplicity of infection of 0.1 in the same incubation conditions.

Infected cells were quantified at ~24 h post-infection, by counting the number of green cells in each well using an Acumen eX3 scanner. IC50s for the compounds in Table 4 were determined by non-linear 4-parameter curve fitting.

The antiviral persistence assay is meant to assess for the persistence of antiviral activity upon removal of the nucleoside. The data in Table 4 demonstrates the antiviral persistence of compounds of this invention in comparison to the marketed nucleoside AZT. The publication *AIDS Research and Therapy*, 2009, 6:5, highlights the value of antiviral persistence.

TABLE 4

| | Structure | $IC_{50}$ 24 h (nM) | $IC_{50}$ 72 h (nM) | Fold shift $IC_{50}$ 72 h/24 h |
|---|---|---|---|---|
| AZT | | 37 | 4713 | 127 |

| EXAMPLE No. | Structure | $IC_{50}$ 24 h (nM) | $IC_{50}$ 72 h (nM) | Fold Shift $IC_{50}$ 72 h/24 h |
|---|---|---|---|---|
| 1 | 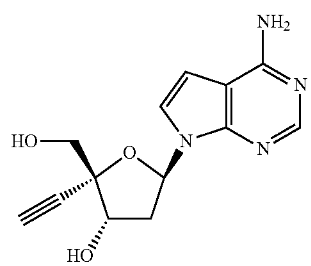 | 0.8 | 36 | 45 |
| 2 | 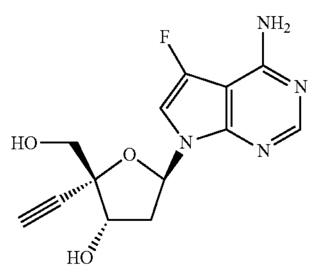 [SMILES: C#C[C@]1(CO)O[C@@H](n2cc(I)c3c(N)ncnc32)C[C@@H]1O] | 6.6 | 193 | 29 |
| 3 | 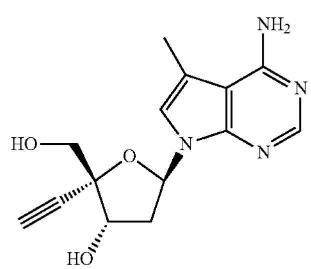 [SMILES: C#C[C@]1(CO)O[C@@H](n2cc(C)c3c(N)ncnc32)C[C@@H]1O] | 470 | 2500 | 5.3 |

TABLE 4-continued

| # | Structure | | | |
|---|---|---|---|---|
| 4 | (2-Cl, 4-NH₂ pyrrolopyrimidine nucleoside with 4'-ethynyl-2'-deoxyribose) | 9.6 | 360 | 37.5 |
| 5 | (5-Br, 4-NH₂ pyrrolopyrimidine nucleoside with 4'-ethynyl-2'-deoxyribose) | 22000 | >42000 | >1.9 |
| 6 | (5-Cl, 4-NH₂ pyrrolopyrimidine nucleoside with 4'-ethynyl-2'-deoxyribose) | 99 | 970 | 9.8 |
| 7 | (5-I, 4-NH₂ pyrrolopyrimidine nucleoside with 4'-ethynyl-2'-deoxyribose) | 17000 | 17000 | 1 |
| 8 | (2,4-diNH₂ pyrrolopyrimidine nucleoside with 4'-ethynyl-2'-deoxyribose) | 840 | 29000 | 34.5 |

TABLE 4-continued

| # | Structure | | | |
|---|---|---|---|---|
| 9 | (4-amino-2-fluoro-pyrrolopyrimidine with 4'-ethynyl-2'-deoxyribose) | 37 | 270 | 7.3 |
| 10 | (4-amino-pyrrolopyrimidine with 4'-cyano-2'-deoxyribose) | 170 | 1800 | 10.5 |
| 11 | (4-amino-pyrrolotriazine with 4'-ethynyl-2'-deoxyribose) | 12.4 | 1950 | 157 |
| 12 | (4-amino-pyrrolotriazine with 4'-cyano-2'-deoxyribose) | 880 | 25000 | 28 |
| 22 | (4-amino-imidazotriazine with 4'-ethynyl-2'-deoxyribose) | 38 | 350 | 9.2 |
| 23 | (4-amino-pyrazolotriazine with 4'-ethynyl-2'-deoxyribose) | 64 | 700 | 10.9 |

Adenosine Deaminase (ADA) Half-Life

The data in Table 5 was generated by reacting a substrate compound with human ADA type 1 in the presence of Tris-HCl buffer (pH 7.5) at 40° C. and monitoring by LCMS for consumption of starting material. The time necessary for 50% conversion to the corresponding inosine product is noted as the $T_{1/2}$ in Table 5. It is known that deamination by adenosine deaminase decreases the therapeutic potential of adenosine-like nucleoside inhibitors especially in vivo (see references below). The compounds shown in Table 5 have been shown to have varying degrees of stability to adenosine deaminase when compared to EDA ((2R,3S,5R)-5-(6-amino-9H-purin-9-yl)-2-ethynyl-2-(hydroxymethyl)tetrahydrofuran-3-ol) and natural deoxyadenosine. It is possible that compounds that are more resistant to ADA will have better pharmacokinetic properties.

REFERENCES

Journal of Medicinal Chemistry 1996, 39, 19, 3847; Chemical Pharmaceutical Bulletin. 1994, 42, 8, 1688-1690; Antimicrobial Agents and Chemotherapy (2013), 57(12), 6254-6264; Collection of Czechoslovak Chemical Communications (2006), 71(6), 769-787 Microbiologica (1995), 18(4), 359-70; J Antivir Antiretrovir S10.doi:10.4172/jaa.S10-002.

Conversion of Compound 2 to Inosine Product 2A 7-((2R,4S,5R)-5-ethynyl-4-hydroxy-5-(hydroxymethyl)tetrahydrofuran-2-yl)-5-fluoro-3H-pyrrolo[2,3-d]pyrimidin-4(7H)-one (2A)

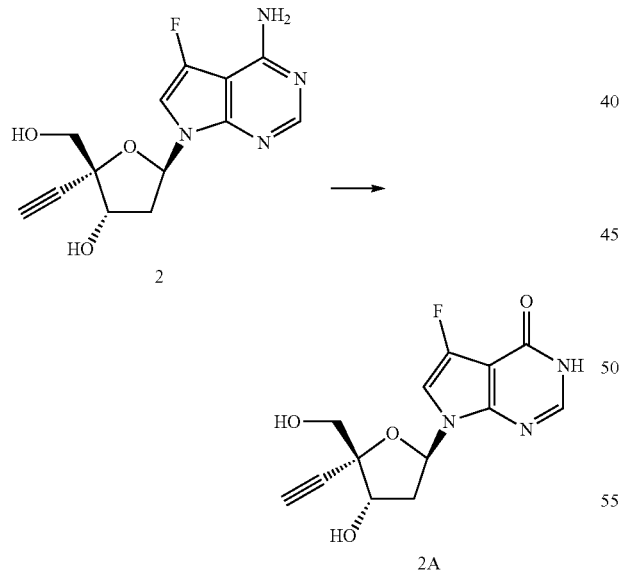

Tris-HCl buffer (pH 7.5, 5 mL) was injected into a 25-mL round-bottom flask. The mixture was heated to reflux for 30 minutes. Then the mixture was cooled to 30° C. and (2R,3S,5R)-5-(4-amino-5-fluoro-7H-pyrrolo[2,3-d]pyrimidin-7-yl)-2-ethynyl-2-(hydroxymethyl)tetrahydrofuran-3-ol (Example compound 2, 7 mg, 0.024 mmol) was added, followed by the addition of adenosine deaminase (3 mg, ~33 units). The resulting mixture was stirred at 40° C. and stirred for 4 days. The reaction mixture was concentrated under vacuum and the residue was purified by preparative-HPLC with the following conditions: Column: X-Bridge C18, 19*150 mm, 5 um; mobile phase, water with 10 mmol ammonium bicarbonate and acetonitrile (6% acetonitrile up to 30% in 5 min, hold 95% for 2 min, down to 40% in 2 min); Detector, uv 254&220 nm. The product-containing fractions were collected and lyophilized to give the title compound 2A as a solid. $^1$H-NMR: (400 MHz, d$_6$-DMSO, ppm): δ 11.58 (brs, 1H), 7.86 (s, 1H), 7.22 (d, J=1.6 Hz, 1H), 6.44 (t, J=5.8 Hz, 1H), 5.47 (d, J=4.8 Hz, 1H), 5.26-5.22 (m, 1H), 4.39-4.35 (m, 1H), 3.55-3.45 (m, 2H), 3.42 (s, 1H), 2.41-2.24 (m, 2H). $^{19}$F-NMR: (376 MHz, d$_6$-DMSO, ppm): δ −165.50 (s, 1F). LC-MS: (ES, m/z): 294.15 [M+H]$^+$.

The general procedures described above for conversion of compound 2 to 2A were applied to each of the substrate compounds in Table 5, and resulted in production of the inosine products shown for Deoxy-adenosine and EDA, as well as inosine products 1A, 2A, 11A, 22A, and 23A. Using the described procedures, conversion of compounds 4, 8 and 9 to 4A, 8A and 9A, respectively, was not detected (NA=substrate insensitive to adenosine deaminase).

Compound 1A: 7-((2R,4S,5R)-5-ethynyl-4-hydroxy-5-(hydroxymethyl)tetrahydrofuran-2-yl)-3H-pyrrolo[2,3-d]pyrimidin-4(7H)-one $^1$H-NMR: (400 MHz, CD$_3$OD, ppm): δ 8.31 (s, 1H), 7.37 (d, J=3.6 Hz, 1H), 6.68 (d, J=3.6 Hz, 1H), 6.62 (t, J=6.4 Hz, 1H), 4.69 (t, J=7.0 Hz, 1H), 3.80 (dd, J=12.0 Hz, J=30.0 Hz, 2H), 3.09 (s, 1H), 2.67-2.54 (m, 2H). LC-MS: (ES, m/z): 276.00 [M+H]$^+$.

Compound 11A: 7-((2R,4S,5R)-5-ethynyl-4-hydroxy-5-(hydroxymethyl)tetrahydrofuran-2-yl)pyrrolo[2,1-f][1,2,4]triazin-4(3H)-one $^1$H-NMR: (400 MHz, d$_6$-DMSO, ppm): δ 10.25 (brs, 1H), 7.86 (s, 1H), 6.83 (d, J=4.5 Hz, 1H), 6.63 (d, J=4.2 Hz, 1H), 5.53 (t, J=7.5 Hz, 1H), 5.31-5.25 (m, 1H), 5.09-5.05 (m, 1H), 4.31-4.27 (m, 1H), 3.55-3.45 (m, 2H), 3.33 (s, 1H), 2.35-2.18 (m, 2H). LC-MS: (ES, m/z): 298.00 [M+Na]$^+$.

Compound 22A: 7-((2R,4S,5R)-5-ethynyl-4-hydroxy-5-(hydroxymethyl)tetrahydrofuran-2-yl)imidazo[2,1-f][1,2,4]triazin-4(3H)-one $^1$H-NMR: (400 MHz, d$_6$-DMSO, ppm): δ 8.12 (s, 1H), 7.56 (s, 1H), 5.45 (t, J=7.4 Hz, 1H), 5.35 (d, J=4.0 Hz, 1H), 5.06 (brs, 1H), 4.33 (brs, 1H), 3.56-3.46 (m, 2H), 3.32 (s, 1H), 2.42-2.33 (m, 1H), 2.28-2.22 (m, 1H). LC-MS: (ES, m/z): 277.10 [M+H]$^+$.

Compound 23A: 8-((2R,4S,5R)-5-ethynyl-4-hydroxy-5-(hydroxymethyl)tetrahydrofuran-2-yl)pyrazolo[1,5-a][1,3,5]triazin-4(3H)-one $^1$H-NMR: (400 MHz, d$_6$-DMSO, ppm): δ 8.08 (s, 1H), 7.98 (s, 1H), 5.30 (t, J=7.4 Hz, 1H), 5.25 (d, J=5.2 Hz, 1H), 5.24-5.11 (m, 1H), 4.32 (q, J=5.2 Hz, 1H), 3.53 (dd, J$_1$=11.6 Hz, J$_2$=32.0 Hz, 2H), 3.36 (s, 1H), 2.36-2.29 (m, 1H), 2.16-2.10 (m, 1H). LC-MS: (ES, m/z): 274.80 [M−H]$^−$.

TABLE 5

| | Structure (Substrate) | Inosine Product | $T_{1/2}$ |
|---|---|---|---|
| Deoxy-adenosine | [structure: 2'-deoxyadenosine] | [structure: 2'-deoxyinosine] | <10 min |
| EDA | [structure: 4'-ethynyl-2'-deoxyadenosine] | [structure: 4'-ethynyl-2'-deoxyinosine] | <60 min |

| Example No. | Structure (Substrate) | Inosine No. | Inosine Product | $T_{1/2}$ |
|---|---|---|---|---|
| 1 | [structure: 7-deazaadenosine analog with 4'-ethynyl] | 1A | [structure: 7-deazainosine analog] | 12 days |
| 2 | [structure: 7-fluoro-7-deazaadenosine analog] | 2A | [structure: 7-fluoro-7-deazainosine analog] | 16 h |
| 4 | [structure: 2-chloro-7-deazaadenosine analog] | 4A | [structure: 2-chloro-7-deazainosine analog] | NA |

TABLE 5-continued

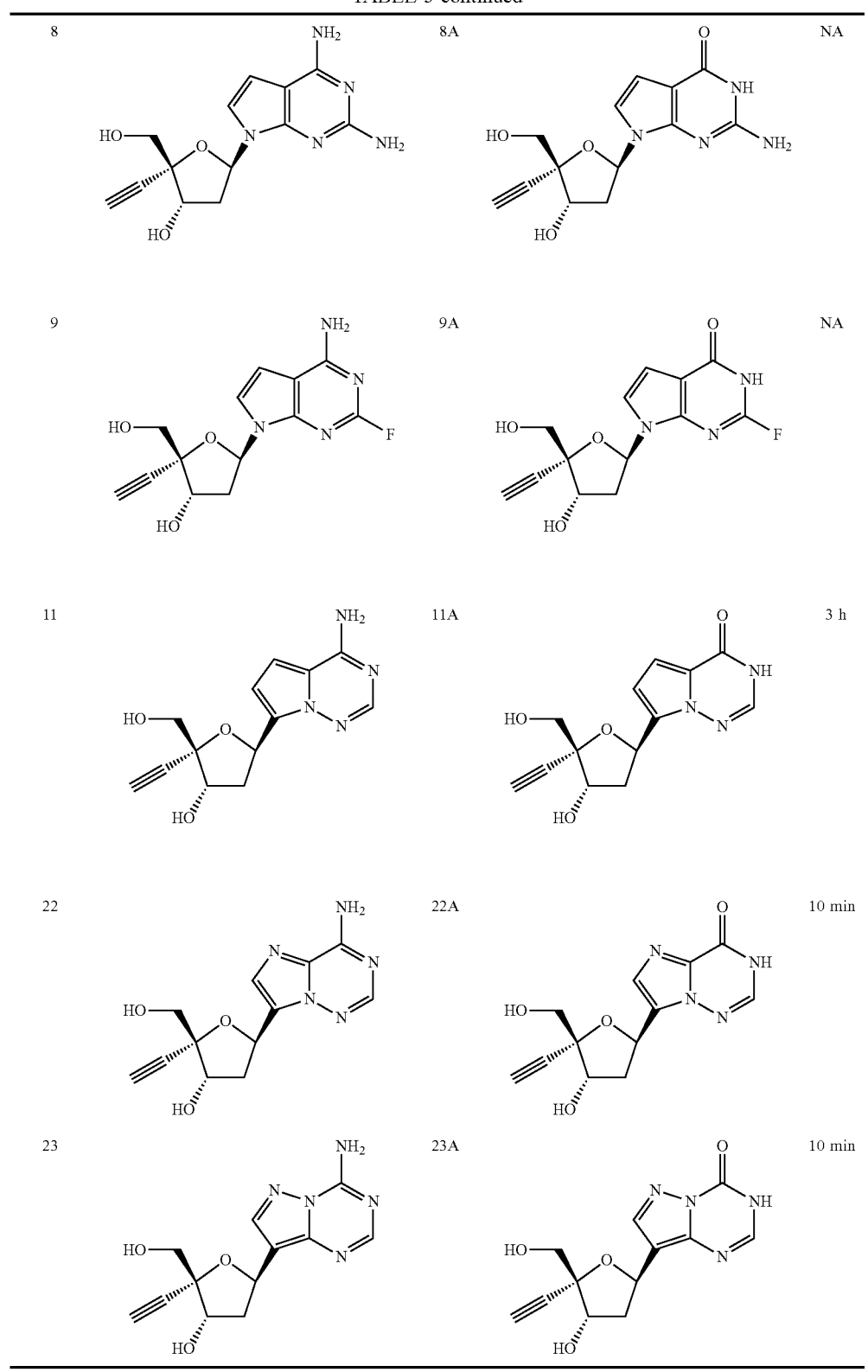

While the foregoing specification teaches the principles of the present invention, with examples provided for the purpose of illustration, the practice of the invention encompasses all of the usual variations, adaptations and/or modifications that come within the scope of the following claims.

Recitation or depiction of a specific compound in the claims (i.e., a species) without a specific stereoconfiguration designation, or with such a designation for less than all chiral centers, is intended to encompass the racemate, racemic mixtures, each individual enantiomer, a diastereoisomeric mixture and each individual diastereomer of the compound where such forms are possible due to the presence of one or more asymmetric centers. All publications, patents and patent applications cited herein are incorporated by reference in their entirety into the disclosure.

What is claimed:

1. A compound of structural Formula I

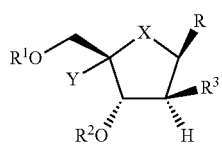

or a pharmaceutically acceptable salt thereof, wherein:
R is

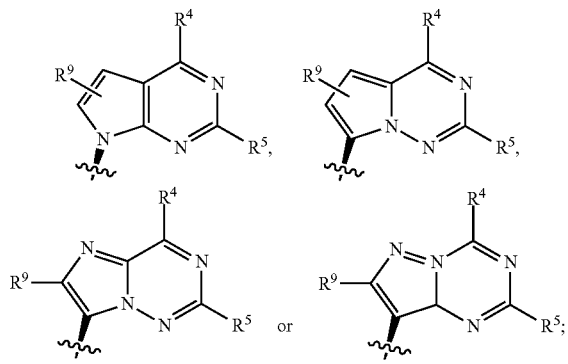

X is O, S, $CH_2$ or $CF_2$;
Y is —C≡C—$R^8$ or —C≡N;
$R^1$ is —H, —C(O)$R^6$, —C(O)O$R^6$, —C(O)N($R^6$)$_2$,

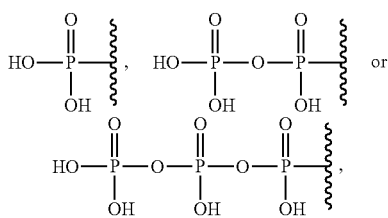

or a pro-drug modification of the mono-, di- or triphosphate;
$R^2$ is —H, —C(O)$R^{6a}$, —C(O)O$R^{6a}$ or —C(O)N($R^{6a}$)$_2$;
$R^3$ is —H;
$R^4$ is —H, —$C_1$-$C_6$ alkyl, —$C_2$-$C_6$ alkenyl, —$C_2$-$C_6$ alkynyl, —$C_1$-$C_6$ haloalkyl, —$C_3$-$C_7$ cycloalkyl, 5- or 6-membered monocyclic heteroaryl, a 9- or 10-membered bicyclic heteroaryl, halo, —CN, —$NO_2$, —N($R^X$)$_2$, —NH($C_1$-$C_6$alkylene)-(5- or 6-membered monocyclic heteroaryl), —NH($C_1$-$C_6$ alkylene)-(9- or 10-membered bicyclic heteroaryl), aryl, —NHC(O)O$R^{6b}$, —N(C(O)O$R^{6b}$)$_2$, —NHC(O)N($R^{6b}$)$_2$, or —NHC(O)$R^{6b}$, wherein each of said —$C_1$-$C_6$ alkyl group, said —$C_2$-$C_6$ alkenyl group or said —$C_2$-$C_6$ alkynyl group can be optionally substituted with halo;
$R^5$ is —H, —$C_1$-$C_6$ alkyl, —$C_2$-$C_6$ alkenyl, —$C_2$-$C_6$ alkynyl, —$C_1$-$C_6$ haloalkyl, —$C_3$-$C_7$ cycloalkyl, 5- or 6-membered monocyclic heteroaryl, a 9- or 10-membered bicyclic heteroaryl, halo, —$OR^X$, —CN, —$NO_2$, —N($R^X$)$_2$, —NH($C_1$-$C_6$alkylene)-(5- or 6-membered monocyclic heteroaryl), —NH($C_1$-$C_6$ alkylene)-(9- or 10-membered bicyclic heteroaryl), aryl, —NHC(O)O$R^{6b}$, —N(C(O)O$R^{6b}$)$_2$, —NHC(O)N($R^{6b}$)$_2$, or —NHC(O)$R^{6b}$, wherein each of said —$C_1$-$C_6$ alkyl group, said —$C_2$-$C_6$ alkenyl group or said —$C_2$-$C_6$ alkynyl group can be optionally substituted with halo;
$R^6$, $R^{6a}$ and $R^{6b}$ are each independently selected at each occurrence from —H, —$C_1$-$C_6$ alkyl, —$C_1$-$C_6$ haloalkyl, —($C_1$-$C_3$ alkylene)$_m$-($C_3$-$C_7$ cycloalkyl), —($C_1$-$C_3$ alkylene)$_m$-(aryl), —($C_1$-$C_3$ alkylene)$_m$-(4 to 7-membered heterocycloalkyl), —($C_1$-$C_3$ alkylene)$_m$-(5- or 6-membered monocyclic heteroaryl) or —($C_1$-$C_3$ alkylene)$_m$-(9- or 10-membered bicyclic heteroaryl), wherein each of said —$C_1$-$C_6$ alkyl, said $C_3$-$C_7$ cycloalkyl group, said aryl group, said 4 to 7-membered heterocycloalkyl group, said -(5- or 6-membered monocyclic heteroaryl group or said 9- or 10-membered bicyclic heteroaryl group can be optionally substituted with $R^7$;
m is an integer selected from 0 (zero) or 1;
$R^7$ represents from one to five substituent groups, each independently selected from —$C_1$-$C_6$alkyl, $C_2$-$C_6$ alkenyl, $C_2$-$C_6$ alkynyl, $C_1$-$C_6$ haloalkyl, aryl, or a 5-6-member heteroaryl;
$R^8$ is —H, —$C_1$-$C_6$ alkyl, —$C_1$-$C_6$ haloalkyl, —$C_3$-$C_7$ cycloalkyl, aryl, 5- or 6-membered monocyclic heteroaryl or 9- or 10-membered bicyclic heteroaryl;
$R^9$ is —H, halo, —$C_1$-$C_6$ alkyl, —$C_1$-$C_6$ haloalkyl, —CN, —$OR^Y$ or —N($R^Y$)$_2$;
$R^X$ is independently selected at each occurrence from —H, —$C_1$-$C_6$ alkyl, —$C_1$-$C_6$ haloalkyl, aryl, or 5- or 6-membered monocyclic heteroaryl;
or when either or both of $R^4$ or $R^5$ is —N($R^X$)$_2$, each $R^X$ may optionally be joined together with the nitrogen to which they are both attached to form a 5- or 6-membered monocyclic heteroaryl or 9- or 10-membered bicyclic heteroaryl; and
$R^Y$ is —H, —$C_1$-$C_6$ alkyl or —$C_1$-$C_6$ haloalkyl.

2. The compound of claim 1 or a pharmaceutically acceptable salt thereof wherein R is

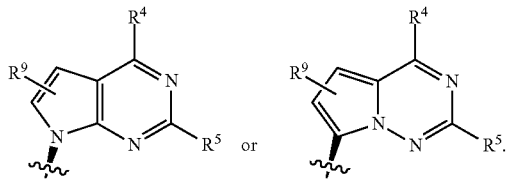

3. The compound of claim 1 or a pharmaceutically acceptable salt thereof wherein: $R^1$ is —H, —C(O)$R^6$, —C(O)O$R^6$, —C(O)N($R^6$)$_2$, or a pro-drug modification of

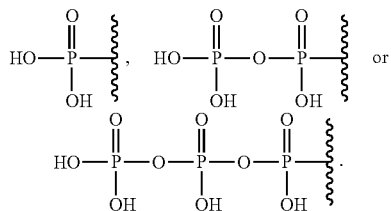

4. The compound of claim 1 or a pharmaceutically acceptable salt thereof wherein $R^1$ is

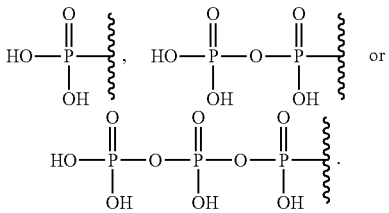

5. The compound of claim 1 or a pharmaceutically acceptable salt thereof wherein:
X is O, S, $CH_2$ or $CF_2$;
Y is —C≡C—$R^8$ or —C≡N;
$R^1$ is —H,

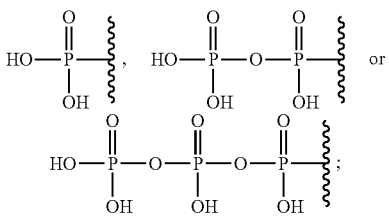

$R^2$ is —H;
$R^3$ is —H;
$R^4$ is —H, —$C_1$-$C_6$ alkyl, —$C_2$-$C_6$ alkenyl, —$C_2$-$C_6$ alkynyl, —$C_1$-$C_6$ haloalkyl, —$C_3$-$C_7$ cycloalkyl, 5- or 6-membered monocyclic heteroaryl, a 9- or 10-membered bicyclic heteroaryl, halo, —CN, —$NO_2$, —N($R^X$)$_2$, —NH($C_1$-$C_6$alkylene)-(5- or 6-membered monocyclic heteroaryl), —NH($C_1$-$C_6$ alkylene)-(9- or 10-membered bicyclic heteroaryl), aryl, —NHC(O)OR$^{6b}$, —N(C(O)OR$^{6b}$)$_2$, —NHC(O)N($R^{6b}$)$_2$, or —NHC(O)$R^{6b}$, wherein each of said —$C_1$-$C_6$ alkyl group, said —$C_2$-$C_6$ alkenyl group or said —$C_2$-$C_6$ alkynyl group can be optionally substituted with halo;
$R^5$ is —H, —$C_1$-$C_6$ alkyl, —$C_2$-$C_6$ alkenyl, —$C_2$-$C_6$ alkynyl, —$C_1$-$C_6$ haloalkyl, —$C_3$-$C_7$ cycloalkyl, a 5- or 6-membered monocyclic heteroaryl, a 9- or 10-membered bicyclic heteroaryl, halo, —OR$^X$, —CN, —$NO_2$, —N($R^X$)$_2$, —NH($C_1$-$C_6$alkylene)-(5- or 6-membered monocyclic heteroaryl), —NH($C_1$-$C_6$ alkylene)-(9- or 10-membered bicyclic heteroaryl) or aryl,
wherein each of said —$C_1$-$C_6$ alkyl group, said —$C_2$-$C_6$ alkenyl group or said —$C_2$-$C_6$ alkynyl group can be optionally substituted with halo;
$R^8$ is —H, —$C_1$-$C_6$ alkyl, —$C_1$-$C_6$ haloalkyl, —$C_3$-$C_7$ cycloalkyl, aryl, 5- or 6-membered monocyclic heteroaryl or 9- or 10-membered bicyclic heteroaryl;
$R^9$ is —H, halo, —$C_1$-$C_6$ alkyl, —$C_1$-$C_6$ haloalkyl, —CN, —OR$^Y$, or —N($R^Y$)$_2$;
$R^X$ is independently selected at each occurrence from —H, —$C_1$-$C_6$ alkyl, —$C_1$-$C_6$ haloalkyl, aryl, or 5- or 6-membered monocyclic heteroaryl;
or when either or both of $R^4$ or $R^5$ is —N($R^X$)$_2$, each $R^X$ may optionally be joined together with the nitrogen to which they are both attached to form a 5- or 6-membered monocyclic heteroaryl or 9- or 10-membered bicyclic heteroaryl; and
$R^Y$ is —H, —$C_1$-$C_6$ alkyl or —$C_1$-$C_6$ haloalkyl.

6. The compound of claim 1 or a pharmaceutically acceptable salt thereof wherein:
$R^1$ is —H, —C(O)$R^6$, —C(O)OR$^6$, —C(O)N($R^6$)$_2$,

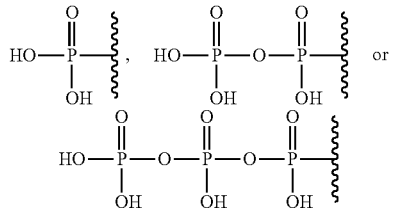

or a pro-drug modification of the mono-, di- or triphosphate;
$R^2$ is —H, —C(O)$R^{6a}$, —C(O)OR$^{6a}$ or —C(O)N($R^{6a}$)$_2$; and
$R^4$ is —H, —$C_1$-$C_6$ alkyl, —$C_2$-$C_6$ alkenyl, —$C_2$-$C_6$ alkynyl, —$C_1$-$C_6$ haloalkyl, —$C_3$-$C_7$ cycloalkyl, 5- or 6-membered monocyclic heteroaryl, a 9- or 10-membered bicyclic heteroaryl, halo, —CN, —$NO_2$, —N($R^X$)$_2$, —NH($C_1$-$C_6$alkylene)-(5- or 6-membered monocyclic heteroaryl), —NH($C_1$-$C_6$ alkylene)-(9- or 10-membered bicyclic heteroaryl), aryl, —NHC(O)OR$^{6b}$, —N(C(O)OR$^{6b}$)$_2$, —NHC(O)N($R^{6b}$)$_2$, or —NHC(O)$R^{6b}$, wherein each of said —$C_1$-$C_6$ alkyl group, said —$C_2$-$C_6$ alkenyl group or said —$C_2$-$C_6$ alkynyl group can be optionally substituted with halo;
$R^5$ is —H, —$C_1$-$C_6$ alkyl, —$C_2$-$C_6$ alkenyl, —$C_2$-$C_6$ alkynyl, —$C_1$-$C_6$ haloalkyl, —$C_3$-$C_7$ cycloalkyl, 5- or 6-membered monocyclic heteroaryl, a 9- or 10-membered bicyclic heteroaryl, halo, —OR$^X$, —CN, —$NO_2$, —N($R^X$)$_2$, —NH($C_1$-$C_6$alkylene)-(5- or 6-membered monocyclic heteroaryl), —NH($C_1$-$C_6$ alkylene)-(9- or 10-membered bicyclic heteroaryl), aryl, —NHC(O)OR$^{6b}$, —N(C(O)OR$^{6b}$)$_2$, —NHC(O)N($R^{6b}$)$_2$, or —NHC(O)$R^{6b}$, wherein each of said —$C_1$-$C_6$ alkyl group, said —$C_2$-$C_6$ alkenyl group or said —$C_2$-$C_6$ alkynyl group can be optionally substituted with halo;
provided that one or more of $R^1$, $R^2$, $R^4$ or $R^5$ is selected as follows:
$R^1$ is —C(O)$R^6$, —C(O)OR$^6$, —C(O)N($R^6$)$_2$ or a pro-drug modification of the mono-, di- or triphosphate; and/or
$R^2$ is —C(O)$R^{6a}$, —C(O)OR$^{6a}$ or —C(O)N($R^{6a}$)$_2$; and/or
$R^4$ is —NHC(O)OR$^{6b}$, —N(C(O)OR$^{6b}$)$_2$, —NHC(O)N($R^{6b}$)$_2$, or —NHC(O)$R^{6b}$; and/or
$R^5$ is —NHC(O)OR$^{6b}$, —N(C(O)OR$^{6b}$)$_2$, —NHC(O)N($R^{6b}$)$_2$, or —NHC(O)$R^{6b}$.

7. The compound of claim 1 or a pharmaceutically acceptable salt thereof wherein X is O.

8. The compound of claim 1 or a pharmaceutically acceptable salt thereof wherein Y is —C≡C—$R^8$.

9. The compound of claim 1 or a pharmaceutically acceptable salt thereof wherein $R^4$ is —N($R^X$)$_2$, —NHC(O)OR$^{6b}$, —N(C(O)OR$^{6b}$)$_2$, —NHC(O)N($R^{6b}$)$_2$, or —NHC(O)$R^{6b}$.

10. The compound of claim for a pharmaceutically acceptable salt thereof wherein $R^4$ is —N($R^X$)$_2$.

11. The compound of claim 1 or a pharmaceutically acceptable salt thereof wherein $R^5$ is —H, halo, —$C_1$-$C_6$ alkyl, —OR$^X$, —N($R^X$)$_2$, —NHC(O)OR$^{6b}$, —N(C(O)OR$^{6b}$)$_2$, —NHC(O)N($R^{6b}$)$_2$, or —NHC(O)$R^{6b}$.

12. The compound of claim 1 or a pharmaceutically acceptable salt thereof wherein $R^8$ is —H.

13. The compound of claim 1 or a pharmaceutically acceptable salt thereof wherein $R^9$ is —H, halo, —$C_1$-$C_3$ alkyl, —$C_1$-$C_3$ haloalkyl, —CN, —$OR^Y$ or —$N(R^Y)_2$.

14. The compound of claim 1 or a pharmaceutically acceptable salt thereof wherein $R^1$ is —H, $$\text{HO}-\overset{\overset{O}{\|}}{\underset{\underset{OH}{|}}{P}}-\xi, \quad \text{HO}-\overset{\overset{O}{\|}}{\underset{\underset{OH}{|}}{P}}-O-\overset{\overset{O}{\|}}{\underset{\underset{OH}{|}}{P}}-\xi \quad \text{or}$$

$$\text{HO}-\overset{\overset{O}{\|}}{\underset{\underset{OH}{|}}{P}}-O-\overset{\overset{O}{\|}}{\underset{\underset{OH}{|}}{P}}-O-\overset{\overset{O}{\|}}{\underset{\underset{OH}{|}}{P}}-\xi.$$

15. The compound of claim 1 or a pharmaceutically acceptable salt thereof wherein:

X is O;
Y is —C≡C—$R^8$;
$R^3$ is —H;
$R^4$ is —$N(R^X)_2$, —NHC(O)$OR^{6b}$, —N(C(O)$OR^{6b})_2$, —NHC(O)N($R^{6b})_2$, or —NHC(O)$R^{6b}$;
$R^5$ is —H, halo, —$C_1$-$C_6$ alkyl, —$OR^X$, —$N(R^X)_2$, —NHC(O)$OR^{6b}$, —N(C(O)$OR^{6b})_2$, —NHC(O)N($R^{6b})_2$, or —NHC(O)$R^{6b}$;
$R^8$ is —H; and
$R^9$ is —H, halo, —$C_1$-$C_3$ alkyl, —$C_1$-$C_3$ haloalkyl, —CN, —$OR^Y$ or —$N(R^Y)_2$.

16. The compound of claim 15 or a pharmaceutically acceptable salt thereof wherein $R^4$ is —$N(R^X)_2$.

17. The compound of claim 16 or a pharmaceutically acceptable salt thereof wherein $R^1$ is —H.

18. The compound of claim 1 having structural Formula II, III, IV or V,

II

III

IV

V or a pharmaceutically acceptable salt thereof, wherein:
X is O;
Y is —C≡CH or —C≡N;
$R^1$ is —H, —C(O)$R^6$, —C(O)$OR^6$, —C(O)N($R^6)_2$, $$\text{HO}-\overset{\overset{O}{\|}}{\underset{\underset{OH}{|}}{P}}-\xi, \quad \text{HO}-\overset{\overset{O}{\|}}{\underset{\underset{OH}{|}}{P}}-O-\overset{\overset{O}{\|}}{\underset{\underset{OH}{|}}{P}}-\xi \quad \text{or}$$

$$\text{HO}-\overset{\overset{O}{\|}}{\underset{\underset{OH}{|}}{P}}-O-\overset{\overset{O}{\|}}{\underset{\underset{OH}{|}}{P}}-O-\overset{\overset{O}{\|}}{\underset{\underset{OH}{|}}{P}}-\xi$$

or a pro-drug modification of the mono-, di- or triphosphate;
$R^2$ is H, —C(O)$R^{6a}$, —C(O)$OR^{6a}$ or —C(O)N($R^{6a})_2$;
$R^3$ is —H;
$R^4$ is —$N(R^X)_2$, —NHC(O)$OR^{6b}$ or —NHC(O)N($R^{6b})_2$;
$R^5$ is —H, halo, —$C_1$-$C_6$ alkyl, —$OR^X$ or —$N(R^X)_2$;
$R^6$, $R^{6a}$, and $R^{6b}$ are each independently selected at each occurrence from —H, —$C_1$-$C_6$ alkyl, —$C_1$-$C_6$ haloalkyl, or a 5- or 6-membered monocyclic heteroaryl, wherein $R^6$, $R^{6a}$, and $R^{6b}$ are each optionally substituted with $R^7$;
$R^7$ is —$C_1$-$C_6$ alkyl, aryl or 5-6 member monocyclic heteroaryl;
$R^9$ is —H, halo, —$C_1$-$C_3$ alkyl, —$C_1$-$C_3$ haloalkyl, —CN, —$OR^Y$, or —$N(R^Y)_2$;
$R^X$ is independently selected at each occurrence from —H, —$C_1$-$C_6$ alkyl, —$C_1$-$C_6$ haloalkyl, aryl, or 5- or 6-membered monocyclic heteroaryl;
or when either or both of $R^4$ or $R^5$ is —$N(R^X)_2$, each $R^X$ may optionally be joined together with the nitrogen to which they are both attached to form a 5- or 6-membered monocyclic heteroaryl or 9- or 10-membered bicyclic heteroaryl; and
$R^Y$ is —H, —$C_1$-$C_6$ alkyl or —$C_1$-$C_6$ haloalkyl.

19. The compound of claim 18, or a pharmaceutically acceptable salt thereof, wherein:
R¹ is —H,

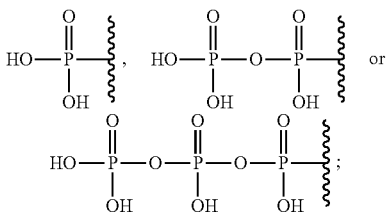

R² is H;
R⁴ is —NH₂;
R⁵ is —H, —Cl, —F or —NH₂; and
R⁹ is —H, —F, —Cl, —I, —Br or —CH₃.

20. The compound of claim 18 having structural Formula II,

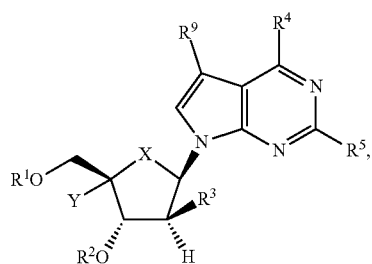

or a pharmaceutically acceptable salt thereof.

21. The compound of claim 20, or a pharmaceutically acceptable salt thereof, wherein:
R¹ is —H,

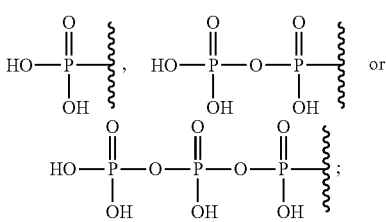

R² is H;
R⁴ is —NH₂;
R⁵ is —H, —Cl, —F or —NH₂; and
R⁹ is —H, —F, —Cl, —I, —Br or —CH₃.

22. The compound of claim 1 that is:

1) (2R,3S,5R)-5-(4-amino-7H-pyrrolo[2,3-d]pyrimidin-7-yl)-2-ethynyl-2-(hydroxymethyl)tetrahydrofuran-3-ol;
2) (2R,3S,5R)-5-(4-amino-5-fluoro-7H-pyrrolo[2,3-d]pyrimidin-7-yl)-2-ethynyl-2-(hydroxymethyl)tetrahydrofuran-3-ol;
3) (2R,3S,5R)-5-(4-amino-5-methyl-7H-pyrrolo[2,3-d]pyrimidin-7-yl)-2-ethynyl-2-(hydroxymethyl)tetrahydrofuran-3-ol;
4) (2R,3S,5R)-5-(4-amino-2-chloro-7H-pyrrolo[2,3-d]pyrimidin-7-yl)-2-ethynyl-2-(hydroxymethyl)tetrahydrofuran-3-ol;
5) (2R,3S,5R)-5-(4-amino-5-bromo-7H-pyrrolo[2,3-d]pyrimidin-7-yl)-2-ethynyl-2-(hydroxymethyl)tetrahydrofuran-3-ol;
6) (2R,3S,5R)-5-(4-amino-5-chloro-7H-pyrrolo[2,3-d]pyrimidin-7-yl)-2-ethynyl-2-(hydroxymethyl)tetrahydrofuran-3-ol;
7) (2R,3S,5R)-5-(4-amino-5-iodo-7H-pyrrolo[2,3-d]pyrimidin-7-yl)-2-ethynyl-2-(hydroxymethyl)tetrahydrofuran-3-ol;
8) (2R,3S,5R)-5-(2,4-diamino-7H-pyrrolo[2,3-d]pyrimidin-7-yl)-2-ethynyl-2-(hydroxymethyl)tetrahydrofuran-3-ol;
9) (2R,3S,5R)-5-(4-amino-2-fluoro-7H-pyrrolo[2,3-d]pyrimidin-7-yl)-2-ethynyl-2-(hydroxymethyl)tetrahydrofuran-3-ol;
10) (2R,3S,5R)-5-(4-amino-7H-pyrrolo[2,3-d]pyrimidin-7-yl)-3-hydroxy-2-(hydroxymethyl)tetrahydrofuran-2-carbonitrile ;
11) (2R,3S,5R)-5-(4-aminopyrrolo[2,1-f][1,2,4]triazin-7-yl)-2-ethynyl-2-(hydroxymethyl)tetrahydrofuran-3-ol;
12) (2R,3S,5R)-5-(4-aminopyrrolo[2,1-f][1,2,4]triazin-7-yl)-3-hydroxy-2-(hydroxymethyl)tetrahydrofuran-2-carbonitrile ;
13) ((2R,3S,5R)-5-(4-amino-7H-pyrrolo[2,3-d]pyrimidin-7-yl)-2-ethynyl-3-hydroxytetrahydrofuran-2-yl)methyl tetrahydrogen triphosphate;
14) ((2R,3S,5R)-5-(4-amino-5-fluoro-7H-pyrrolo[2,3-d]pyrimidin-7-yl)-2-ethynyl-3-hydroxytetrahydrofuran-2-yl)methyl tetrahydrogen triphosphate;
15) ((2R,3S,5R)-5-(4-amino-5-methyl-7H-pyrrolo[2,3-d]pyrimidin-7-yl)-2-ethynyl-3-hydroxytetrahydrofuran-2-yl)methyl tetrahydrogen triphosphate;
16) ((2R,3S,5R)-5-(4-amino-2-chloro-7H-pyrrolo[2,3-d]pyrimidin-7-yl)-2-ethynyl-3-hydroxytetrahydrofuran-2-yl)methyl tetrahydrogen triphosphate;
17) ((2R,3S,5R)-5-(4-amino-5-chloro-7H-pyrrolo[2,3-d]pyrimidin-7-yl)-2-ethynyl-3-hydroxytetrahydrofuran-2-yl)methyl tetrahydrogen triphosphate;
18) ((2R,3S,5R)-5-(4-amino-7H-pyrrolo[2,3-d]pyrimidin-7-yl)-2-cyano-3-hydroxytetrahydrofuran-2-yl)methyl tetrahydrogen triphosphate;
19) ((2R,3S,5R)-5-(4-aminopyrrolo[2,1-f][1,2,4]triazin-7-yl)-2-ethynyl-3-hydroxytetrahydrofuran-2-yl)methyl tetrahydrogen triphosphate;
20) ((2R,3S,5R)-5-(4-aminopyrazolo[1,5-a][1,3,5]triazin-8-yl)-2-ethynyl-3-hydroxytetrahydrofuran-2-yl)methyl tetrahydrogen triphosphate;
21) ((2R,3S,5R)-5-(4-aminoimidazo[2,1-f][1,2,4]triazin-7-yl)-2-ethynyl-3-hydroxytetrahydrofuran-2-yl)methyl tetrahydrogen triphosphate;
22) (2R,3S,5R)-5-(4-aminoimidazo[2,1-f] [1,2,4]triazin-7-yl)-2-ethynyl-2-(hydroxymethyl)tetrahydrofuran-3-ol;
23) (2R,3S,5R)-5-(4-aminopyrazolo[1,5-a][1,3,5]triazin-8-yl)-2-ethynyl-2-(hydroxymethyl)tetrahydrofuran-3-ol;

or a pharmaceutically acceptable salt thereof.

23. A pharmaceutical composition comprising an effective amount of a compound of claim 1, or a pharmaceutically acceptable salt thereof, and a pharmaceutically acceptable carrier.

24. A pharmaceutical composition comprising an effective amount of a compound of claim 1, or a pharmaceutically acceptable salt thereof, and a pharmaceutically acceptable carrier and further comprising an effective amount of an anti-HIV agent selected from an anti-HIV antiviral agent, an immunomodulator, or anti-infective agent.

25. The pharmaceutical composition of claim 24 wherein the anti-HIV antiviral agent is an HIV protease inhibitor, HIV reverse transcriptase inhibitor, HIV integrase inhibitor, HIV fusion inhibitor, HIV entry inhibitor, or HIV maturation inhibitor.

26. A method for the treatment of infection by HIV or for the treatment of AIDS in a subject in need thereof, which comprises administering to the subject an effective amount of the compound of claim 1, or a pharmaceutically acceptable salt thereof.

27. A method for the prophylaxis of infection by HIV or for the prophylaxis or delay in the onset of AIDS in a subject in need thereof, which comprises administering to the subject an effective amount of the compound of claim 1, or a pharmaceutically acceptable salt thereof.

28. A compound that is:

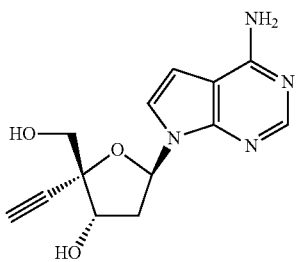 [SMILES: C#C[C@]1(CO)O[C@@H](n2ccc3c(N)ncnc32)C[C@@H]1O]

or a compound that is a pharmaceutically acceptable salt thereof.

29. The compound of claim 28 that is a pharmaceutically acceptable salt of:

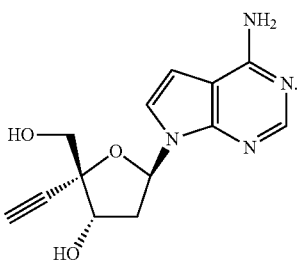 [SMILES: C#C[C@]1(CO)O[C@@H](n2ccc3c(N)ncnc32)C[C@@H]1O]

30. The compound of claim 28 that is:

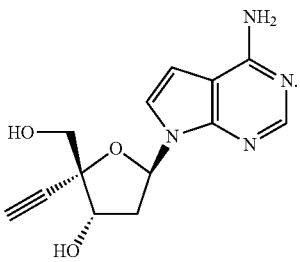 [SMILES: C#C[C@]1(CO)O[C@@H](n2ccc3c(N)ncnc32)C[C@@H]1O]

31. A pharmaceutical composition comprising an effective amount of a compound of claim 28 and a pharmaceutically acceptable carrier.

32. A pharmaceutical composition comprising an effective amount of a compound of claim 28 and a pharmaceutically acceptable carrier and further comprising an effective amount of an anti-HIV agent selected from an anti-HIV antiviral agent, an immunomodulator, or anti-infective agent.

33. The pharmaceutical composition of claim 32 wherein the anti-HIV antiviral agent is an HIV protease inhibitor, HIV reverse transcriptase inhibitor, HIV integrase inhibitor, HIV fusion inhibitor, HIV entry inhibitor, or HIV maturation inhibitor.

34. A method for the treatment of infection by HIV or for the treatment of AIDS in a subject in need thereof, which comprises administering to the subject an effective amount of the compound of claim 28.

35. A method for the prophylaxis of infection by HIV or for the prophylaxis or delay in the onset of AIDS in a subject in need thereof, which comprises administering to the subject an effective amount of the compound of claim 28.

36. A compound that is:

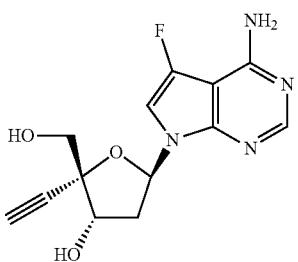 [SMILES: C#C[C@]1(CO)O[C@@H](n2cc(F)c3c(N)ncnc32)C[C@@H]1O]

or a compound that is a pharmaceutically acceptable salt thereof.

37. The compound of claim 36 that is a pharmaceutically acceptable salt of:

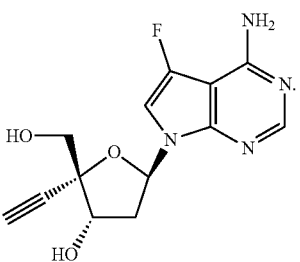 [SMILES: C#C[C@]1(CO)O[C@@H](n2cc(F)c3c(N)ncnc32)C[C@@H]1O]

38. The compound of claim 36 that is:

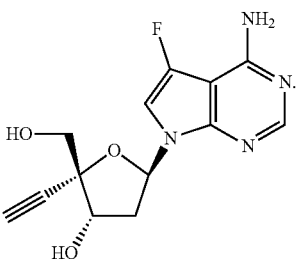 [SMILES: C#C[C@]1(CO)O[C@@H](n2cc(F)c3c(N)ncnc32)C[C@@H]1O]

39. A pharmaceutical composition comprising an effective amount of a compound of claim 36 and a pharmaceutically acceptable carrier.

40. A pharmaceutical composition comprising an effective amount of a compound of claim 36 and a pharmaceutically acceptable carrier and further comprising an effective amount of an anti-HIV agent selected from an anti-HIV antiviral agent, an immunomodulator, or anti-infective agent.

41. The pharmaceutical composition of claim 40 wherein the anti-HIV antiviral agent is an HIV protease inhibitor, HIV reverse transcriptase inhibitor, HIV integrase inhibitor, HIV fusion inhibitor, HIV entry inhibitor, or HIV maturation inhibitor.

42. A method for the treatment of infection by HIV or for the treatment of AIDS in a subject in need thereof, which comprises administering to the subject an effective amount of the compound of claim 36.

43. A method for the prophylaxis of infection by HIV or for the prophylaxis or delay in the onset of AIDS in a subject in need thereof, which comprises administering to the subject an effective amount of the compound of claim 36.

44. A compound that is:

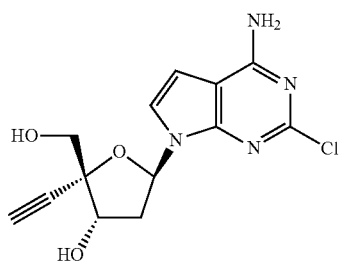 [SMILES: C#C[C@]1(CO)O[C@@H](n2ccc3c(N)nc(Cl)nc32)C[C@@H]1O]

or compound that is a pharmaceutically acceptable salt thereof.

45. The compound of claim 44 that is a pharmaceutically acceptable salt of:

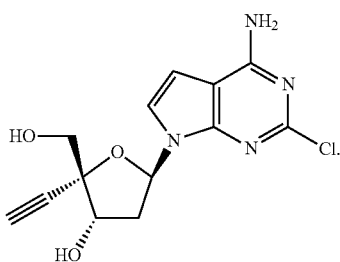 [SMILES: C#C[C@]1(CO)O[C@@H](n2ccc3c(N)nc(Cl)nc32)C[C@@H]1O]

46. The compound of claim 44 that is:

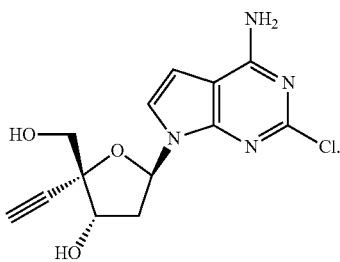 [SMILES: C#C[C@]1(CO)O[C@@H](n2ccc3c(N)nc(Cl)nc32)C[C@@H]1O]

47. A pharmaceutical composition comprising an effective amount of a compound of claim 44 and a pharmaceutically acceptable carrier.

48. A pharmaceutical composition comprising an effective amount of a compound of claim 44 and a pharmaceutically acceptable carrier and further comprising an effective amount of an anti-HIV agent selected from an anti-HIV antiviral agent, an immunomodulator, or anti-infective agent.

49. The pharmaceutical composition of claim 48 wherein the anti-HIV antiviral agent is an HIV protease inhibitor, HIV reverse transcriptase inhibitor, HIV integrase inhibitor, HIV fusion inhibitor, HIV entry inhibitor, or HIV maturation inhibitor.

50. A method for the treatment of infection by HIV or for the treatment of AIDS in a subject in need thereof, which comprises administering to the subject an effective amount of the compound of claim 44.

51. A method for the prophylaxis of infection by HIV, or for the prophylaxis or delay in the onset of AIDS in a subject in need thereof, which comprises administering to the subject an effective amount of the compound of claim 44.

52. The compound of claim 1 that is:

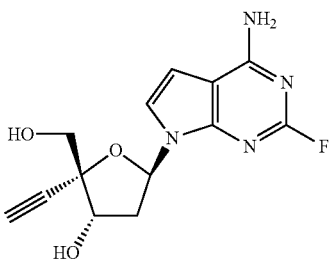 [SMILES: C#C[C@]1(CO)O[C@@H](n2ccc3c(N)nc(F)nc32)C[C@@H]1O]

or a compound that is a pharmaceutically acceptable salt thereof.

53. The compound of claim 52 that is a pharmaceutically acceptable salt of:

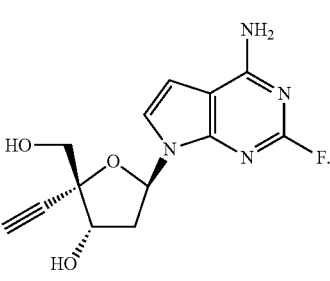 [SMILES: C#C[C@]1(CO)O[C@@H](n2ccc3c(N)nc(F)nc32)C[C@@H]1O]

54. A compound that is:

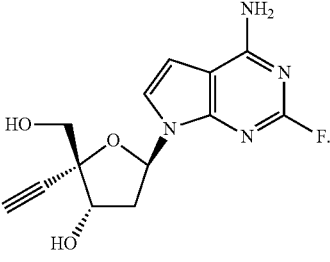 [SMILES: C#C[C@]1(CO)O[C@@H](n2ccc3c(N)nc(F)nc32)C[C@@H]1O]

55. A pharmaceutical composition comprising an effective amount of a compound of claim 52 and a pharmaceutically acceptable carrier.

56. A pharmaceutical composition comprising an effective amount of a compound of claim 52 and a pharmaceutically acceptable carrier and further comprising an effective amount of an anti-HIV agent selected from an anti-HIV antiviral agent, an immunomodulator, or anti-infective agent.

57. The pharmaceutical composition of claim 56 wherein the anti-HIV antiviral agent is an HIV protease inhibitor, HIV reverse transcriptase inhibitor, HIV integrase inhibitor, HIV fusion inhibitor, HIV entry inhibitor, or HIV maturation inhibitor.

58. A method for the treatment of infection by HIV or for the treatment of AIDS in a subject in need thereof, which comprises administering to the subject an effective amount of the compound of claim 52.

59. A method for the prophylaxis of infection by HIV or for the prophylaxis or delay in the onset of AIDS in a subject in need thereof, which comprises administering to the subject an effective amount of the compound of claim 52.

* * * * *